US012735472B2

(12) United States Patent
Fischer et al.

(10) Patent No.: US 12,735,472 B2
(45) **Date of Patent: *Sep. 15, 2026**

(54) TNFR2 AGONISTS WITH IMPROVED STABILITY

(71) Applicant: Universitat Stuttgart, Stuttgart (DE)

(72) Inventors: Roman Fischer, Nuremberg (DE); Martin Siegemund, Stuttgart (DE); Klaus Pfizenmaier, Tiefenbronn (DE); Roland Kontermann, Nurtingen (DE)

(73) Assignee: UNIVERSITÄT STUTTGART, Stuttgart (DE)

(*) Notice: Subject to any disclaimer, the term of this patent is extended or adjusted under 35 U.S.C. 154(b) by 1300 days.

This patent is subject to a terminal disclaimer.

(21) Appl. No.: 17/617,137

(22) PCT Filed: Jun. 24, 2020

(86) PCT No.: PCT/EP2020/067656

§ 371 (c)(1),
(2) Date: Dec. 7, 2021

(87) PCT Pub. No.: WO2020/260368

PCT Pub. Date: Dec. 30, 2020

(65) Prior Publication Data

US 2022/0267410 A1 Aug. 25, 2022

(30) Foreign Application Priority Data

Jun. 24, 2019 (EP) .................................... 19182102

(51) Int. Cl.
*C07K 14/525* (2006.01)
*A61K 38/19* (2006.01)
*C07K 14/705* (2006.01)
*C07K 19/00* (2006.01)
*A61K 38/00* (2006.01)

(52) U.S. Cl.
CPC ...... *C07K 14/70575* (2013.01); *A61K 38/191* (2013.01); *C07K 14/525* (2013.01); *C07K 19/00* (2013.01); *A61K 38/00* (2013.01); *C07K 2319/30* (2013.01); *C07K 2319/70* (2013.01); *C07K 2319/74* (2013.01)

(58) Field of Classification Search
CPC .. C07K 14/525; C07K 19/00; C07K 2319/00; C07K 2319/30; C07K 2319/74; C07K 2319/70; A61K 38/191; A61K 38/19
See application file for complete search history.

(56) References Cited

U.S. PATENT DOCUMENTS 4,588,585 A 5/1986 Mark
4,737,462 A 4/1988 Mark
4,879,111 A 11/1989 Chong
4,959,314 A 9/1990 Mark
5,017,691 A 5/1991 Lee
5,116,943 A 5/1992 Koths
5,597,899 A 1/1997 Banner
6,399,857 B1 * 6/2002 Kloti .................. C12N 15/8241 800/278
6,730,303 B1 5/2004 Feng
7,754,208 B2 7/2010 Ledbetter
8,927,205 B2 1/2015 Pfizenmaier
8,980,266 B2 3/2015 Eckelman
10,301,368 B2 5/2019 Sahin
10,875,928 B2 12/2020 Kontermann
11,142,558 B2 10/2021 Fischer
12,065,472 B2 * 8/2024 Fischer ................ C07K 14/525
12,173,046 B2 * 12/2024 Fischer ............ C07K 14/70575
2003/0069395 A1 4/2003 Sato
2004/0018170 A1 1/2004 Shirwan
2005/0152872 A1 7/2005 Gaide
2006/0171942 A1 8/2006 Saxon
2007/0286843 A1 12/2007 Pfizenmaier
2008/0050374 A1 2/2008 Cho
2010/0233079 A1 9/2010 Jakob
2011/0162095 A1 6/2011 Hill
2012/0134984 A1 5/2012 Lubman
2012/0276099 A1 11/2012 Poppe (Continued)

FOREIGN PATENT DOCUMENTS

DE 102004014983 A1 10/2005
DE 10247755 B4 1/2006
JP S5944399 A 3/1984

(Continued)

OTHER PUBLICATIONS

Bachman, J. Reverse-Transcription PCR (RT-PCR). Meth Enzymol 530: 67-74, 2013.*

Jaye et al. Isolation of a human anti-haemophilic factor IX cDNA clone using a unique 52-base synthetic oligonucleotide probe deduced from the amino acid sequence of bovine factor IX. Nucl Acids Res 11(8): 2325-2355, 1983.*

Lewin, B. Genes IV, Oxford: Oxford University Press, 1990; pp. 118-120.*

(Continued)

*Primary Examiner* — Bridget E Bunner
(74) *Attorney, Agent, or Firm* — McDonnell Boehnen Hulbert Berghoff, LLP

(57) ABSTRACT

The present invention relates to polypeptide consisting of three TNF homology domains of TNF-ligand family members proteins (THD) that specifically bind to the extracellular part of TNFR2, wherein C-terminal and N-terminal reference points are defined by consensus sequences. The THDs are linked by short stretches of further C-terminal and/or N-terminal amino acids of the THD or variants thereof as well as by peptide linkers. These peptides have an improved stability. Furthermore the invention relates to polypeptide multimers comprising several of the polypeptides of the present invention.

16 Claims, 26 Drawing Sheets

Figure 1:
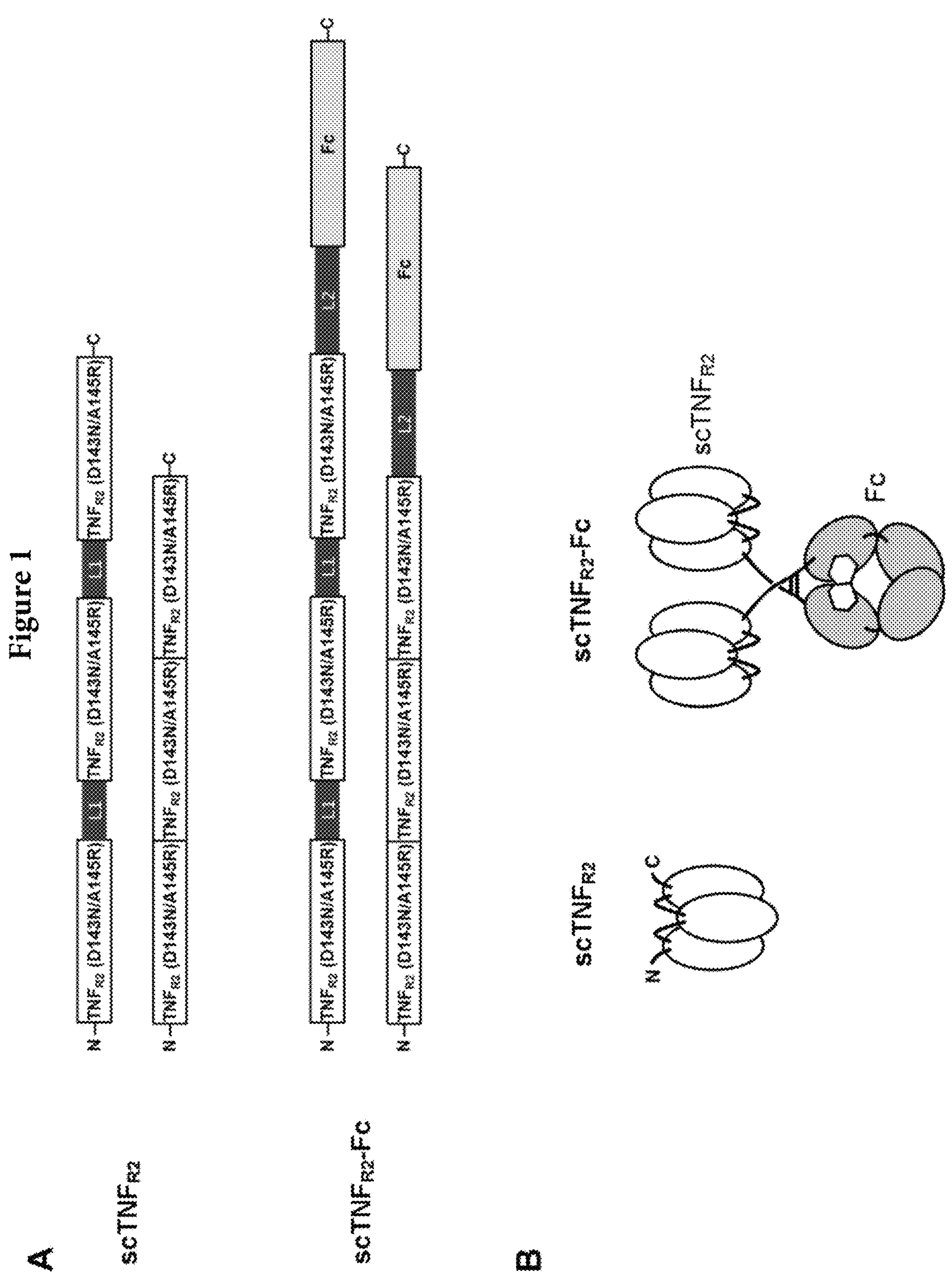
Figure 1C:
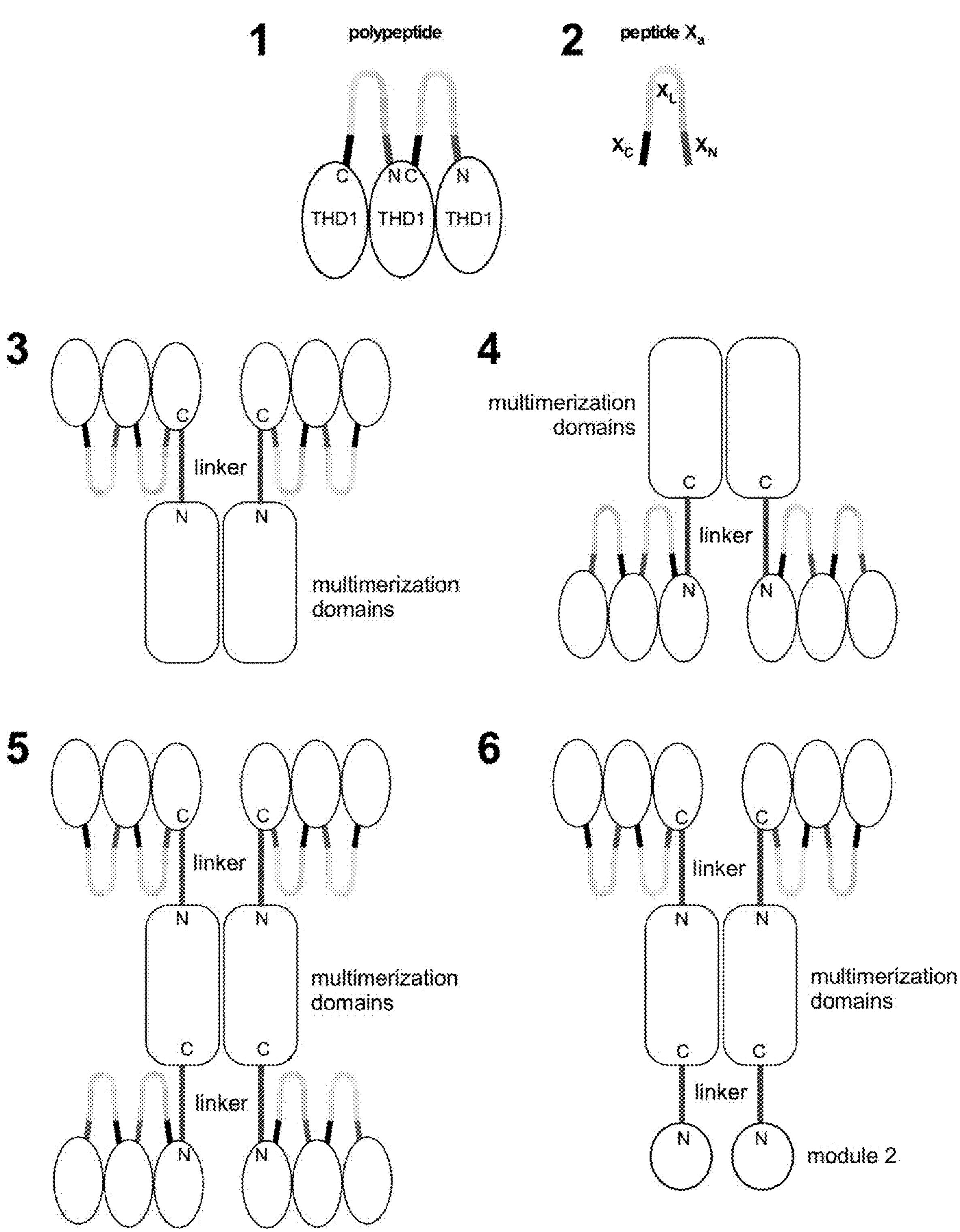

Specification includes a Sequence Listing.

(56) References Cited

U.S. PATENT DOCUMENTS

| | | | |
|---|---|---|---|
| 2013/0224145 | A1 | 8/2013 | Wang |
| 2014/0342994 | A1 | 11/2014 | Yang |

FOREIGN PATENT DOCUMENTS

| | | | |
|---|---|---|---|
| JP | 2009538120 | A | 11/2009 |
| WO | 9203569 | W | 3/1992 |
| WO | 2000025722 | A2 | 5/2000 |
| WO | 2000047740 | A2 | 8/2000 |
| WO | 2001025277 | A1 | 4/2001 |
| WO | 2001042298 | A1 | 6/2001 |
| WO | 2001087982 | A2 | 11/2001 |
| WO | 2002022680 | A2 | 3/2002 |
| WO | 2002072605 | A2 | 9/2002 |
| WO | 2002088317 | A2 | 11/2002 |
| WO | 2004035794 | A1 | 4/2004 |
| WO | 2005017148 | A1 | 2/2005 |
| WO | 2005103077 | A1 | 11/2005 |
| WO | 2006115800 | A2 | 11/2006 |
| WO | 2007014744 | A2 | 2/2007 |
| WO | 2007124283 | A2 | 11/2007 |
| WO | 2008012543 | A1 | 1/2008 |
| WO | 2008151088 | A2 | 12/2008 |
| WO | 2009007120 | A2 | 1/2009 |
| WO | 2010010051 | A1 | 1/2010 |
| WO | 2010051502 | A2 | 5/2010 |
| WO | 2011064257 | A2 | 6/2011 |
| WO | 2011109789 | A2 | 9/2011 |
| WO | 2016029043 | A1 | 2/2016 |
| WO | 2016112983 | A1 | 7/2016 |
| WO | 2016113395 | A1 | 7/2016 |
| WO | 2016118641 | A1 | 7/2016 |
| WO | 2016126781 | A1 | 8/2016 |
| WO | WO2016/146818 | | 9/2016 |
| WO | 2017040312 | A1 | 3/2017 |
| WO | 2018185247 | A1 | 10/2018 |
| WO | WO2018/226750 | | 12/2018 |

OTHER PUBLICATIONS

Murray, E.J. "Cloning Genes in Mammalian Cell-lines" in Molecular Biology and Biotechnology. Great Britain: The Royal Society of Chemistry, 2000, pp. 177-201.*

Sambrook et al. Molecular Cloning A Laboratory Manual, 2nd edition, Cold Spring Harbor, N.Y., 1989, p. 2.43-2.84.*

Abe, et al. (2011). "Fine tuning of receptor-selectivity for tumor necrosis factor-α using a phage display system with one-step competitive panning." Biomaterials 32, 5498-5504.

Ablamunits, et al. (2010). "Acquisition of regulatory function by human CD8+ T cells treated with anti-CD3 antibody requires TNF." Eur. J. Immunol. 40, 2891-2901.

Ando, et al. (2016). "Creation of mouse TNFR2-selective agonistic TNF mutants using a phage display technique." Biochem. Biophys. Rep. 7, 309-315.

Armour, et al. (1999). "Recombinant human IgG molecules lacking Fcy receptor I binding and monocyte triggering activities." Eur. J. Immunol. 29, 2613-2624.

Ban, et al. (2015). "Strategic internal covalent cross-linking of TNF produces a stable TNF trimer with improved TNFR2 signaling." Mol. Cell. Ther. 3, 7.

Bodmer, et al. (2002). "The molecular architecture of the TNF superfamily." Trends Biochem. Sci. 27, 19-26.

Boschert, et al. (2010). "Single chain TNF derivatives with individually mutated receptor binding sites reveal differential stoichiometry of ligand receptor complex formation for TNFR1 and TNER2." Cell. Signal. 22, 1088-1096.

Chen, et al. (2007). "Interaction of TNF with TNF Receptor Type 2 Promotes Expansion and Function of Mouse CD4+ CD25+ T Regulatory Cells." J. Immunol. 179, 154-161.

Chen, et al. (2013). "Fusion protein linkers: property, design and functionality." Adv. Drug. Deliv. Rev. 65, 1357-1369.

Chen, et al. (2013). "TNFR2 is Critical for the Stabilization of the CD4+Foxp3+ Regulatory T Cell Phenotype in the Inflammatory Environment." J. Immunol. 190, 1076-1084.

Colman (1994). "Effects of amino acid sequence changes on antibody-antigen interactions." Res. Immunol. 145, 33-36.

Deyev and Lebedenko (2008). "Multivalency: the hallmark of antibodies used for optimization of tumor targeting by design." BioEssays 30, 904-918.

Dong, et al. (2016). "Essential protective role of tumor necrosis factor receptor 2 in neurodegeneration." Proc. Natl. Acad. Sci. U.S.A. 113, 12304-12309.

Fesik (2000). "Insights into programmed cell death through structural biology." Cell 103, 273-282.

Fischer, et al. (2011). "A Tnf Receptor 2 Selective Agonist Rescues Human Neurons from Oxidative Stress-Induced Cell Death." PLoS ONE 6, e27621.

Fischer, et al. (2014). "Astrocyte-specific activation of TNFR2 promotes oligodendrocyte maturation by secretion of leukemia inhibitory factor." Glia 62, 272-283.

Fischer, et al. (2015). "Targeting sTNF/TNFR1 Signaling as a New Therapeutic Strategy." Antibodies 4, 48-70.

Fischer, et al. (2017). "Novel strategies to mimic transmembrane tumor necrosis factor-dependent activation of tumor necrosis factor receptor 2." Sci. Rep. 7, 6607.

Fischer, et al. (2018). "Selective Activation of Tumor Necrosis Factor Receptor II Induces Antiinflammatory Responses and Alleviates Experimental Arthritis." Arthritis Rheumatol. 70, 722-735.

Fischer, et al. (2019). "TNFR2 promotes Treg-mediated recovery from neuropathic pain across sexes." Proc. Natl. Acad. Sci. U.S.A. 116, 17045-17050.

Ha, et al. (2016). "Immunoglobulin Fc Heterodimer Platform Technology: From Design to Applications in Therapeutic Antibodies and Proteins." Front. Immunol. 7, 394.

Hellman (1994). "Profound reduction in allergen sensitivity following treatment with a novel allergy vaccine." Eur. J. Immunol. 24, 415-420.

Imperiali & O'Connor (1999). "Effect of N-linked glycosylation on glycopeptide and glycoprotein structure." Curr. Opin. Chem. Biol. 3, 643-649.

Kalliolias & Ivashkiv (2016). "TNF biology, pathogenic mechanisms and emerging therapeutic strategies." Nat. Rev. Rheumatol. 12, 49-62.

Klein, et al. (2014). "Design and characterization of structured protein linkers with differing flexibilities." Protein Eng. Des. Sel. 27, 325-330.

Krippner-Heidenreich, et al. (2002). "Control of Receptor-induced Signaling Complex Formation by the Kinetics of Ligand/Receptor Interaction." J. Biol. Chem. 277, 44155-44163.

Krippner-Heidenreich, et al. (2008). "Single-Chain TNF, a TNF Derivative with Enhanced Stability and Antitumoral Activity." J. Immunol. 180, 8176-8183.

Leuenberger, H.G.W, Nagel, B. & Kölbl, H., eds. (1995). "A multilingual glossary of biotechnological terms: IUPAC recommendations." Helvetica Chimica Acta, CH-4010 Basel, Switzerland, p. 9.

Liu, et al. (2017). "Fc Engineering for Developing Therapeutic Bispecific Antibodies and Novel Scaffolds." Front. Immunol. 8, 38.

Locksley, et al. (2001). "The TNF and TNF receptor superfamilies: integrating mammalian biology." Cell 104, 487-501.

Loetscher, et al. (1993). "Human tumor necrosis factor alpha (TNF alpha) mutants with exclusive specificity for the 55-kDa or 75-kDa TNF receptors." J. Biol. Chem. 268, 26350-26357.

MacCallum, et al. (1996). "Antibody-antigen interactions: contact analysis and binding site topography." J. Mol. Biol. 262, 732-745.

Maier, et al. (2013). "TNF receptor 2 protects oligodendrocyte progenitor cells against oxidative stress." Biochem. Biophys. Res. Commun. 440, 336-341.

Monaco, et al. (2015). "Anti-TNF therapy: past, present and future." Int. Immunol. 27, 55-62.

Mühlenbeck, et al. (2000). "The Tumor Necrosis Factor-related Apoptosis-inducing Ligand Receptors TRAIL-R1 and TRAIL-R2

(56) References Cited

OTHER PUBLICATIONS

Have Distinct Cross-linking Requirements for Initiation of Apoptosis and are Non-redundant in JNK Activation." J. Biol., Chem. 275, 32208-32213.
Probert (2015). "TNF and its receptors in the CNS: the essential, the desirable and the deleterious effects." Neuroscience 302, 2-22.
Richter, et al. (2012). "The Tumor Necrosis Factor Receptor Stalk Regions Define Responsiveness to Soluble versus Membrane-Bound Ligand." Mol. Cell. Biol. 32, 2515-2529.
Rudikoff, et al. (1982). "Single amino acid substitution altering antigen-binding specificity." Proc. Natl. Acad. Sci. USA 79, 1979-1983.
Sayers and Murphy (2005). "Combining proteasome inhibition with TNF-related apoptosis-inducing ligand (Apo2L/TRAIL) for cancer therapy." Cancer Immunol. Immunother. 55, 76-84.
Schlothauer, et al. (2016). "Novel human IgG1 and IgG4 Fc-engineered antibodies with completely abolished immune effector functions." Protein Eng. Des. Sel. 29, 457-466.
Seifert, et al. (2012). "The IgM CH2 domain as covalently linked homodimerization module for the generation of fusion proteins with dual specificity." Protein Eng. Des. Sel. 25, 603-612.
Shibata, et al. (2009). "The treatment of established murine collagen-induced arthritis with a TNFR1-selective antagonistic mutant TNF." Biomaterials 30, 6638-6647.
Steed, et al. (2003). "Inactivation of TNF Signaling by Rationally Designed Dominant-Negative TNF Variants." Science 301, 1895-1898.
Vafa, et al. (2014). "An engineered Fc variant of an IgG eliminates all immune effector functions via structural perturbations." Methods 65, 114-126.
Van Ostade, et al. (1993). "Human TNF mutants with selective activity on the p55 receptor." Nature 361, 266-269.
Vernersson, et al. (2002). "Generation of therapeutic antibody responses against IgE through vaccination." FASEB J. 16, 875-877.
Vie, et al. (1992). "Human fusion proteins between interleukin 2 and IgM heavy chain are cytotoxic for cells expressing the interleukin 2 receptor." Proc. Natl. Acad. Sci. USA 89, 11337-11341.
Wajant, et al. (2001). "Differential activation of TRAIL-R1 and -2 by soluble and membrane TRAIL allows selective surface antigen-directed activation of TRAIL-R2 by a soluble TRAIL derivative." Oncogene 20, 4101-4106.
Wang, et al. (2018). "IgG Fc engineering to modulate antibody effector functions." Protein Cell 9, 63-73.
Wu, et al. (1999). "Humanization of a murine monoclonal antibody by simultaneous optimization of framework and CDR residues." J. Mol. Biol. 294, 151-162.
Savelieff, et al., (2019) "Development of Multifunctional Molecules as Potential Therapeutic Candidates for Alzheimer's Disease, Parkinson's disease, and amyotrophic lateral sclerosis in the last decade." Chemical Reviews, 119:1221-1322.
Williams, et al., (2016) "Phenotypic screening revels TNFR2 as a promising target for cancer immunotherapy." Oncotarget, 7(42): 68278-68291.
Elgert, Immunology: Understanding the Immune System, Published 1996, pp. 323-326.
Fischer, et al., (2020) "Selective Targeting of TNF Receptors as a novel therapeutic approach." Frontiers in Cell and Developmental Biology, vol. 8, article 401, pp. 1-21.
"Fibroblast activation protein." In MeSH Database, National Center for Biotechnology Information, Bethesda, Maryland, USA [online]. Retrieved from the Internet: <http://www.ncbi.nlm.nih.gov/mesh/67087522>. no date provided.
Bork (2000). "Powers and pitfalls in sequence analysis: the 70% hurdle." Genome Res. 10, 398-400.
Bork and Bairoch (1996). "Go hunting in sequence databases but watch out for the traps." Trends Genet. 12, 425-427.
Brenner (1999). "Errors in genome annotation." Trends Genet. 15, 132-133.
Cuesta, et al. (2010). "Multivalent antibodies: when design surpasses evolution." Trends Biotechnol. 28, 355-362.
Doerks, et al. (1998). "Protein annotation: detective work for function prediction." Trends Genet. 14, 248-250.
Dorrington and Bennich (1978). "Structure-function relationships in human immunoglobulin E." Immunol. Rev. 41, 3-25.
Edwards, et al. (2003). "The Remarkable Flexibility of the Human Antibody Repertoire; Isolation of Over One Thousand Different Antibodies to a Single Protein, BLyS." J. Mol. Biol. 334, 103-118.
Fu, et al. (2016). "Structural Basis and Functional Role of Intramembrane Trimerization of the Fas/CD95 Death Receptor." Mol. Cell 61, 602-613.
Genbank Accession No. NM_00311. Aug. 9, 2001. <http://www.ncbi.nlm.nih.gov/nuccore/NM_003811.1>.
Gieffers, et al. (2012). "Dimerized single chain TRAIL-receptor agonists do not depend on Fc-gamma-receptor cross-linking for anti-tumor efficacy in vivo." Cancer Res. 72, 3856.
Hofmann, et al. (2018). "Activity of Tumor Necrosis Factor aα is Modulated by Dynamic Conformational Rearrangements." J. Am. Chem. Soc. 140, 167-175.
Holliger, et al. (1993). "Diabodies': small bivalent and bispecific antibody fragments." Proc. Natl. Acad. Sci. USA 90, 6444-6448.
International Search Report + Written Opinion of the International Searching Authority for PCT/EP2018/058786, mailed Oct. 11, 2018.
International Search Report for PCT/EP2012/001426, mailed Oct. 4, 2012.
International Search Report for PCT/EP2013/001126, mailed Oct. 24, 2013.
English translation of Office Action for JP 2019-554841, mailed Mar. 1, 2022.
Kortt, et al. (2001). "Dimeric and trimeric antibodies: high avidity scFvs for cancer targeting." Biomol. Eng. 18, 95-108.
Lloyd, et al. (2009). "Modelling the human immune response: performance of a 1011 human antibody repertoire against a broad panel of therapeutically relevant antigens." Protein Eng. Des. Sel. 22, 159-168.
Medler, et al. (2022). "Tumor necrosis factor receptor 2 (TNFR2): An emerging target in cancer therapy." Cancers 14, 2603, 22 pages.
Müller, et al. (2008). "A novel antibody-4-1BBL fusion protein for targeted costimulation in cancer immunotherapy." J. Immunother. 31, 714-722.
Müller, et al. (2008). "Activity of soluble OX40 ligand is enhanced by oligomerization and cell surface immobilization." Febs J. 275, 2296-2304.
Ngo, et al. (1994). "Computational complexity, protein structure prediction, and the Levinthal paradox." In the Protein Folding Problem and Tertiary Structure Prediction, 492-495. Boston, MA: Birkhäuser Boston.
Piche-Nicholas, et al. (2018). "Changes in complementarity-determining regions significantly alter IgG binding to the neonatal Fc receptor (FcRn) and pharmacokinetics." mAbs 10, 81-94.
Plückthun and Pack (1997). "New protein engineering approaches to multivalent and bispecific antibody fragments." Immunotechnology 3, 83-105.
Quazi (2022). "TNFR2 antagonist and agonist: a potential therapeutics in cancer immunotherapy." Med. Oncol. 39, 215, 15 pages.
Rossin, et al. (2019). "TRAIL and FasL Functions in Cancer and Autoimmune Diseases: Towards an Increasing Complexity." Cancers 11, 639, 18 pages.
Schneider, et al. (2010). "Potent antitumoral activity of TRAIL through generation of tumor-targeted single-chain fusion proteins." Cell Death Dis. 1, e68, 1-10.
Seifert, et al. (2014). "Tetravalent Antibody-scTRAIL Fusion Proteins with Improved Properties." Mol. Cancer Ther. 13, 101-111.
Siegemund, et al. (2012). "Superior antitumoral activity of dimerized targeted single-chain TRAIL fusion proteins under retention of tumor selectivity." Cell Death Dis. 3, e295, 1-11.
Skolnick and Fetrow (2000). "From genes to protein structure and function: novel applications of computational approaches in the genomic era." Trends Biotechnol. 18, 34-39.
Smith and Zhang (1997). "The challenges of genome sequence annotation or 'The devil is in the details.'" Nat. Biotechnol. 15, 1222-1223.

(56) References Cited

OTHER PUBLICATIONS

Stone, et al. (2006). "Multimeric Soluble CD40 Ligand and GITR Ligand as Adjuvants for Human Immunodeficiency Virus DNA Vaccines." J. Virol. 80, 1762-1772.

Tokuriki and Tawfik (2009). "Stability effects of mutations and protein evolvability." Curr. Opin. Struct. Biol. 19, 596-604.

Valliere-Douglass, et al. (2010). "Glutamine-linked and non-consensus asparagine-linked oligosaccharides present in human recombinant antibodies define novel protein glycosylation motifs." J. Biol. Chem. 285, 16012-16022.

Wajant (2015). "Principles of antibody-mediated TNF receptor activation." Cell Death Differ. 22, 1727-1741.

Wajant, et al. (2005). "Tumor therapeutics by design: targeting and activation of death receptors." Cytokine Growth Factor Rev. 16, 55-76.

Wang, et al. (2003). "Synthetic IgE peptide vaccine for immunotherapy of allergy." Vaccine 21, 1580-1590.

Wells (1990). "Additivity of mutational effects in proteins." Biochemistry 29, 8509-8517.

Wyzgol, et al. (2009). "Trimer stabilization, oligomerization, and antibody-mediated cell surface immobilization improve the activity of soluble trimers of CD27L, CD40L, 41 BBL, and glucocorticoid-induced TNF receptor ligand." J. Immunol. 183, 1851-1861.

Zhang, et al. (1992). "Site-directed Mutational Analysis of Human Tumor Necrosis Factor-a Receptor Binding Site and Structure-Functional Relationship." J. Biol. Chem. 267, 24069-24075.

Zhang, et al. (2007). "Targeted and untargeted CD137L fusion proteins for the immunotherapy of experimental solid tumors." Clin. Cancer Res. 13, 2758-2767.

International Search Report dated Sep. 3, 2020 for International Application No. PCT/EP2020067656, 2 pages.

* cited by examiner

A
scTNFR2
scTNFR2-Fc
N
C
TNFR2 (D143N/A145R)
L1
L2
Fc
B
scTNFR2
scTNFR2-Fc
Fc

Figure 1D

7 linker

8 linker linker

9

Protein

Figure 1E

| $scTNF_{R2}$ mutant | Sequence human $scTNF_{R2}$: C-Terminus $TNF_{R2}$ domain | Peptide linker | N-Terminus $TNF_{R2}$ domain | hu TNF aa positions | Length of $scTNF_{R2}$ (aa res.) | $T_m$ (°C) | $EC_{50}$ (+80M2) on Kym-1 (pM) |
|---|---|---|---|---|---|---|---|
| 118 (SIN:65) | ...GIIAL | GGGGS | SSRTPSDKPVAHV (SIN:58) | 80-233 | 472 | 62 | 130 |
| 127 (SIN: 66) | ...GIIAL | | SSRTPSDKPVAHV (SIN:59) | 80-233 | 462 | 67 | 151 |
| 130 (SIN: 70) | ...GIIAL | | RTPSDKPVAHV (SIN:60) | 82-233 | 456 | 60 | 100 |
| 129 (SIN: 67) | ...GIIAL | | PSDKPVAHV (SIN:61) | 84-233 | 450 | 72 | 759 |
| 139 (SIN: 68) | ...GIIAL | GGGG | SDKPVAHV (SIN:62) | 85-233 | 455 | 67 | 224 |
| 131 (SIN: 71) | ...GIIAL | | DKPVAHV (SIN:63) | 86-233 | 444 | 58 | - |
| 138 (SIN: 69) | ...GIIAL | GGGSGGGS | PVAHV (SIN:64) | 88-233 | 454 | 62 | 119 |

| $scTNF_{R2}$ FcΔab | Variant $scTNF_{R2}$ | Tm (°C) | $EC_{50}$ of binding to TNF-R2-Fc (pM) | $EC_{50}$ of binding to TNF-R2-Fc (pM) | $EC_{50}$ of binding to TNF-R2-Fc (pM) | $EC_{50}$ of NF-kB activation in HeLa-TNF-R2 (pM) |
|---|---|---|---|---|---|---|
| 745 (SIN:72) | 118 | 71 | 419±14 | 62 | 14.9±3.3 | 2.1±0.8 |
| 742 (SIN:73) | 127 | 74 | 365±31 | 59 | 20.5±4.5 | 3.1±1.2 |
| 743 (SIN:74) | 129 | 80 | 180±11 | 168 | ~3400*) | 199±110 |
| 744 (SIN:75) | 139 | 74 | 309±15 | 62 | 59.5±3.8 | 3.4±0.4 |

*) extrapolated scTNF$_{R2}$ 118

Viability (%)

[Protein] (nM)

○ 118 ■ 118 + 80M2 scTNF$_{R2}$ 127

Viability (%)

[Protein] (nM)

○ 127 ■ 127 + 80M2

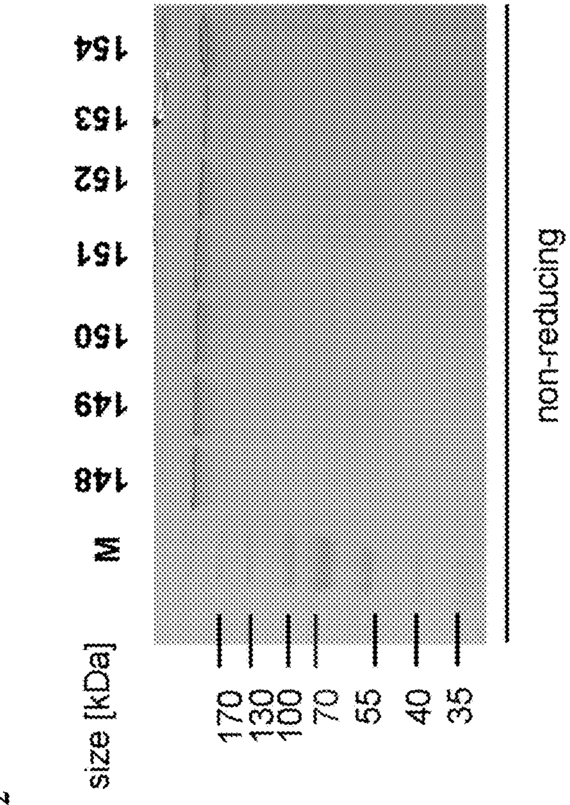
Figure 12
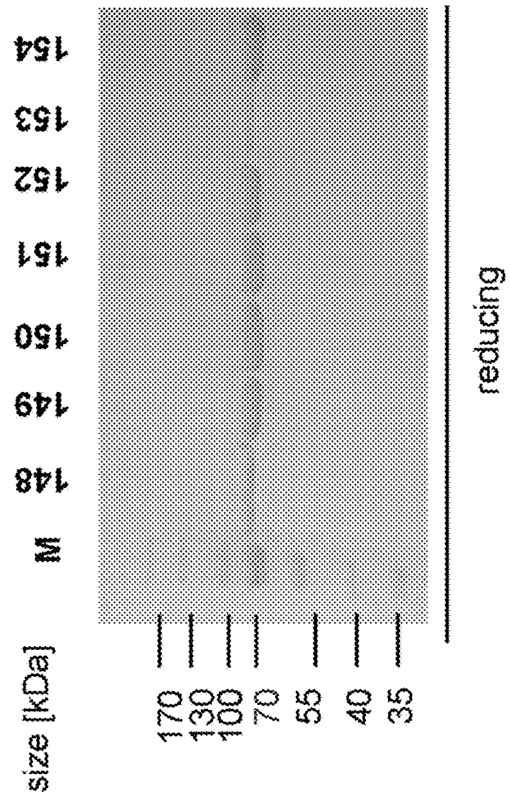

TNFR2 AGONISTS WITH IMPROVED STABILITY

CROSS REFERENCE TO RELATED APPLICATION(S)

This application is a U.S. National Phase of International Application No. PCT/EP2020/067656, filed on Jun. 24, 2020, which claims priority to European Patent Application No. 19182102.4, filed Jun. 24, 2019 all of which are incorporated by reference herein in their entirety.

SEQUENCE LISTING STATEMENT

A computer readable form of the Sequence Listing is filed with this application by electronic submission and is incorporated into this application by reference in its entirety. The Sequence Listing is contained in the file created on Dec. 7, 2021 having the file name "21-1548-WO-US_SequenceListing.txt" and is 158,063 bytes in size.

The present invention relates to a polypeptide consisting of three TNF homology domains of TNF-ligand family members proteins (THD) that specifically bind to the extracellular part of TNFR2, wherein C-terminal and N-terminal reference points are defined by consensus sequences. The THDs are linked by short stretches of further C-terminal and/or N-terminal amino acids of the THD or variants thereof as well as by peptide linkers. These polypeptides have an improved stability. Furthermore, the invention relates to polypeptide multimers comprising several of the polypeptides of the present invention. Further the invention relates to a nucleic acid molecule encoding said polypeptide or polypeptide multimer, a vector comprising said nucleic acid molecule and a pharmaceutical composition comprising said polypeptide, polypeptide multimer, nucleic acid molecule or vector. Further, the present invention relates to said polypeptide, polypeptide multimer, nucleic acid molecule or vector for use as a medicament or for the use in the prophylaxis or treatment of hyperproliferative disorders, inflammatory disorders or metabolic disorders.

BACKGROUND OF THE INVENTION

The tumor necrosis factor (TNF) superfamily is a family of structurally related cytokines with various functions. The structural hallmark defining the TNF ligand family is the carboxy-terminal TNF homology domain (THD) which is composed of two stacked β-pleated sheets that adopt a conserved jellyroll-like tertiary fold (Bodmer et al., 2000, Trends Biochem. Sci. 27, 19-26; Fesik, 2000, Cell 103, 273-282; Locksley et al., 2001, Cell 104, 487-501). This structural composition leads to the self-association of THD monomers into trimers and is necessary for receptor binding. Due to the carboxy-terminal localization of the THD, both the transmembrane form as well as soluble TNF ligands assemble into trimers.

Tumor necrosis factor (TNF) itself is a multifunctional cytokine with pleiotropic functions. It is a master regulator of the immune system and a key player in the initiation and orchestration of inflammation and immunity. TNF, like most ligands of the superfamily, is synthesized as a trimeric type 2 transmembrane protein (tmTNF) that can be proteolytically processed into soluble circulating TNF homotrimers (sTNF). Interestingly, sTNF and tmTNF differ in their capability to activate the two distinct TNF receptors (TNFRs): TNFR1 and TNFR2. Whereas TNFR1 is activated by both sTNF and tmTNF, TNFR2 is dependent on tmTNF to be robustly activated (Mühlenbeck et al., 2000, J. Biol., Chem. 275, 32208-32213; Wajant et al., 2001, Oncogene 20, 4101-4106).

Deregulated TNF expression and signaling can cause chronic inflammation, which may result in the development of autoimmune diseases and tissue damage (Fischer et al., 2015, Antibodies 4, 48-70; Kalliolias & Ivashkiv, 2016, Nat. Rev. Rheumatol. 12, 49-62). Indeed, elevated TNF levels have been associated with several inflammatory diseases, such as rheumatoid arthritis (RA), psoriasis, and inflammatory bowel disease; therapeutic agents that neutralize TNF are being successfully used to treat these diseases (Monaco et al., 2015, Int. Immunol. 27, 55-62). Surprisingly, however, a clinical trial with an anti-TNF drug that blocks both sTNF and tmTNF in multiple sclerosis patients resulted in disease exacerbation and had to be stopped. Moreover, the approved TNF inhibitors can cause severe side effects, including opportunistic infections, reactivation of tuberculosis, development of autoimmune disease, increased susceptibility to the development of lymphoma, and demyelinating diseases (Fischer et al., 2015, Antibodies 4, 48-70; Monaco et al., 2015, Int. Immunol. 27, 55-62). These unwanted clinical reactions most likely depend on the different biologic actions of TNF that are mediated via its two receptors.

Recent research has revealed that the TNF receptors induce opposing biologic responses. Whereas TNFR1 signaling promotes inflammation and tissue degeneration, TNFR2 contributes to immune suppression as well as tissue homeostasis and regeneration (Probert et al., 2015, Neuroscience 302, 2-22). Therefore, next-generation therapeutic approaches targeting the TNF system were developed, including blocking of sTNF-TNFR1 interaction or signaling and selective activation of TNFR2 (Shibata et al., 2009, Biomaterials 30, 6638-6647; Steed et al., 2003, Science 301, 1895-1898; Dong et al., 2016, PNAS 113, 12304-12309). The immunosuppressive activity mediated through TNFR2 is of particular interest for potential therapeutic application in autoimmune diseases. The immunosuppressive properties of TNFR2 are attributed to its prominent role in expansion and stabilization of Treg cells (Chen et al., 2007, J. Immunol. 179, 154-161; Chen et al., 2013, J. Immunol. 190, 1076-1084), a highly specialized subpopulation of T cells that function to suppress immune responses. According to the prevailing view, Treg cells regulate the self-tolerance of the immune system and help to prevent the development of autoimmune diseases. In addition to CD4+ Treg cells, additional T cell subpopulations with regulatory activity exist (i.e., CD8+ Treg cells). Similar to CD4+ Treg cells, the most potent CD8+ suppressors are characterized by the expression of TNFR2 (Ablamunits et al., 2010, Eur. J. Immunol. 40, 2891-2901).

To scrutinize the impact of selective activation of TNFR2 on Treg cell expansion and function, the inventors recently developed soluble, multivalent TNFR2-selective TNF derivatives that mimic the activity of tmTNF. These molecules are based on a single-chain derivative of TNF (scTNF) combined with mutations in the THD of TNF conferring selectivity for TNFR2 (Krippner-Heidenreich et al., 2008, J. Immunol. 180, 8176-8183), and fusion of the scTNF to di- or multimerization modules. These modules include a trimerizing tenascin domain, resulting in a nonavalent molecule (binding of up to 9 TNFR2) (Fischer et al., 2011, PLOS ONE 6:e27621; Fischer et al., 2014, Glia 62, 272-283), the dimerizing heavy chain domain 2 of IgE (EHD2) (Dong et al., 2016, PNAS 113, 12304-12309), homotetramerization domains of p53, GCN4 (Fischer et al., 2017, Sci. Rep. 7, 6607), and VASP and fusion of scTNF to the N- and C-terminus of an immunoglobulin Fc region (PCT/EP2018/058786).

In all these studies the inventors applied TNF subunits (domains) composed of amino acids 80-233, comprising the TNF homology domain (THD), with three subunits connected by flexible linkers of 12 or 16 residues (L1: $(GGGS)_3$ (SEQ ID NO 53); L2: $(GGGS)_4$ (SEQ ID NO 54); Krippner-Heidenreich et al., 2008, J. Immunol. 180, 8176-8183). In a subsequent study the linkers were reduced to a GGGGS (SEQ ID NO 26) sequence connecting the C-terminus of the first and second THD with the N-terminus of the second and third THD, respectively (all THDs composed of aa 80-233 of human TNF) (Fischer et al., 2011, PLOS ONE 6:e27621).

Furthermore, mutations were introduced conferring receptor selectivity for human TNFR2 (the TNFR2-selective scTNF D143N/A145R) (Loetscher et al., 1993, J. Biol. Chem. 268, 26350-26357), or human TNFR1 (the TNFR1-selective scTNF R32W/S86T) (van Ostade et al., 1993, Nature 361, 266-269) with the corresponding substitutions in all three subunits (Krippner-Heidenreich et al., 2008, J. Immunol. 180, 8176-8183). Functionally corresponding mutations (D221N/A223R) were also introduced into mouse TNF for selective binding to TNFR2 (Fischer et al., 2014, Glia 62, 272-283). Mutations can also be introduced in only one or two of the three THD subunits (Boschert et al., 2010, Cell Signal. 22, 1088-1096).

TNFR2-selective TNF muteins were also selected by phage display from a library of TNF mutants (Abe et al., 2011, Biomaterials 32, 5498-5504; Ando et al., 2016, Biochem. Biophys. Reports 7, 309-315). Furthermore, TNF molecules with improved TNFR2 signaling were generated by the introduction of internal covalent cross-linking by mutating two residues at the THD interface to cysteines (S95C/G148C) (Ban et al., 2015, Mol. Cell. Ther. 3:7).

Previously, the inventors demonstrated that oligomerized, covalently stabilized TNFR2-selective scTNF mimics tmTNF and efficiently activates TNFR2. These TNFR2-selective TNF muteins were shown to induce anti-inflammatory responses and to alleviate symptoms of experimental arthritis, to rescue neurons and oligodendrocytes from oxidative stress, and to be protective in a mouse model of NMDA-induced acute neurodegeneration (Fischer et al., 2011, PLOS One 6, e27621; Maier et al., 2013, Biochem. Biophys. Res. Commun. 440, 336-341; Fischer et al., 2018, Arthritis Reumatol. 70, 722-735; Dong et al., 2016, PNAS 113, 12304-12309).

Recently, the inventors demonstrated that the stability of single-chain members of the TNF superfamily can be improved by shortening the linker between the three subunits and reducing the subunit sequence to the minimal THD domain (WO 2016/146818).

Applying this strategy to scTNF, i.e. direct linkage of the C-terminus of first/second domain to the N-terminus of the second/third domain, the inventors found that the stability is increased by shorting the THD domain to positions (84-233) while further reduction (86-233) reduced stability. The scTNF derivative with a THD formed by aa 84-233 directly connected with each other showed an increase in thermal stability by 10° C., as determined by dynamic light scattering, however, exhibited an about 6-fold decreased bioactivity. It has surprisingly been shown by the present invention that an increased thermal stability (67° C. vs 62° C.) under full retention of bioactivity was observed for molecules composed either of 3 THDs (aa 80-233) directly connected without linker, or 3 shortened THDs (aa 85-233) connected with a 4 amino acid linker (GGGG; SEQ ID NO 16), compared to the reference scTNF molecule composed of 3 THDs (aa 80-233) connected by a GGGGS (SEQ ID NO 26) linker.

SUMMARY OF THE INVENTION

In a first aspect, the present invention provides a polypeptide, comprising a binding domain consisting of three peptide TNF homology domains of TNF-ligand family member proteins (THD) that specifically bind to the extracellular part of TNFR2, wherein the C-terminus of the first and second THD, respectively, which is in each case defined by the C-terminal consensus sequence V-F/Y-F-G-A/I-$X_1$ (SEQ ID NO: 1), is linked to the N-terminus of the second and third THD, respectively, which is in each case defined by the N-terminal consensus sequence P-V/A-A-H-V/L (SEQ ID NO: 2) through a peptide $X_a$, which is in each case independently selected and has a length of 9 to 12 amino acids, preferably 9 to 11, more preferably 9 to 10, preferably wherein $X_a$ does not comprise the amino acid sequence S-S-R-T-P-S-D-K (SEQ ID NO: 10); wherein $X_1$ is a non-polar/hydrophobic or polar/neutral amino acid, preferably selected from the group consisting of F and I.

In a second aspect, the present invention provides a polypeptide multimer comprising at least two polypeptides according to the first aspect of the invention that are (a) linked together, preferably linked together by an amino acid linker that has a length of between 1 to 30 amino acids, preferably 7 to 15 amino acids; or (b) linked to a protein, preferably selected from the group consisting of: a multimerization domain, a serum protein, a cytokine, a targeting moiety or a toxin, preferably a multimerization domain;

optionally wherein said polypeptides are linked to said protein by an amino acid linker that has a length of between 1 to 30 amino acids, preferably 7 to 15 amino acids.

In a third aspect, the present invention provides a nucleic acid molecule encoding the polypeptide according to the first aspect of the invention or the polypeptide multimer according to the second aspect of the invention.

In a fourth aspect, the present invention provides a vector encoding the nucleic acid molecule according to the third aspect of the invention.

In a fifth aspect, the present invention provides a polypeptide according to the first aspect of the invention, a polypeptide multimer according to the second aspect of the invention, a nucleic acid according to the third aspect of the invention or a vector according to the fourth aspect of the invention for use as a medicament.

In a sixth aspect, the present invention provides a pharmaceutical composition comprising as an active agent a polypeptide according to the first aspect of the invention, a polypeptide multimer according to the second aspect of the invention, a nucleic acid according to the third aspect of the invention or a vector according to the fourth aspect of the invention.

In a seventh aspect, the present invention provides a polypeptide according to the first aspect of the invention, a polypeptide multimer according to the second aspect of the invention, a nucleic acid according to the third aspect of the invention, a vector according to the fourth aspect of the invention or a pharmaceutical composition according to the fifth aspect of the invention for use in the diagnosis, prophylaxis or treatment of hyperproliferative disorders or inflammatory disorders, preferably cancer or malignancies of the hematologic system, autoimmune disorders and metabolic diseases, cardiovascular diseases, neuropathic diseases and neurological insults.

LIST OF FIGURES

In the following, the content of the figures comprised in this specification is described. In this context please also refer to the detailed description of the invention above and/or below.

Figure 1D:
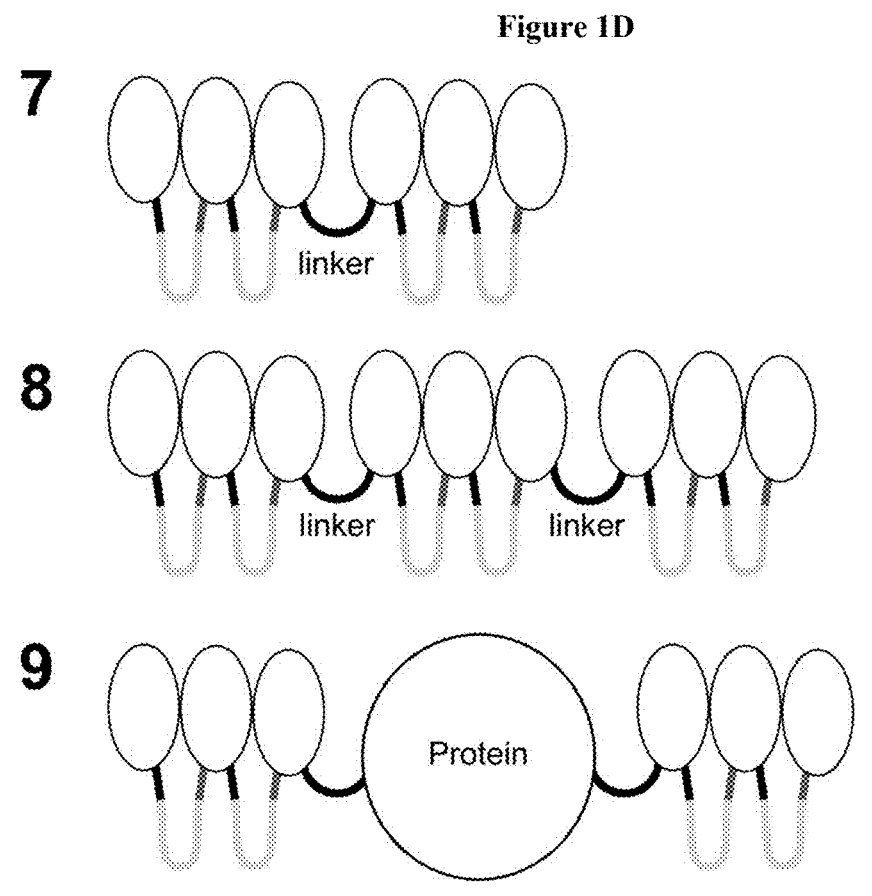

FIG. 1A-1E: Schematic representations of the $scTNF_{R2}$ mutant proteins and dimerized complexes thereof of the present invention. (A) Schematic polypeptide chains of $SCTNF_{R2}$ and the dimeric complex thereof $scTNF_{R2}$-Fc. $TNF_{R2}$ subunits were either genetically fused with a peptide linker L1 or without peptide linker, yielding $scTNF_{R2}$. The dimerization domain Fc was genetically fused at the C-terminal end of $scTNF_{R2}$ by using a peptide linker L2. (B) Schematic drawings of the tertiary/quaternary structures of $scTNF_{R2}$ and $scTNF_{R2}$-Fc. (C) & (D) Schematic drawings of embodiments of the (1) polypeptide and (3)-(6) examples of polypeptide multimers. Optionally, the polypeptides comprise a further module 2 (6), which, for example, allows organ or tissue-specific delivery and/or transport through tissue barriers such as the blood brain barrier. (2) depicts a schematic drawing of the linker polypeptide $X_a$. (E) Upper panel: Exemplary polypeptides according to the present invention (127, 139 and 138) and reference polypeptides (each row from top to bottom: SEQ ID NOs: 65, 66, 70, 67, 68, 71, 69). Lower panel exemplary polypeptide multimers of the present invention (742, 744) and reference polypeptide multimers.

Figure 2:
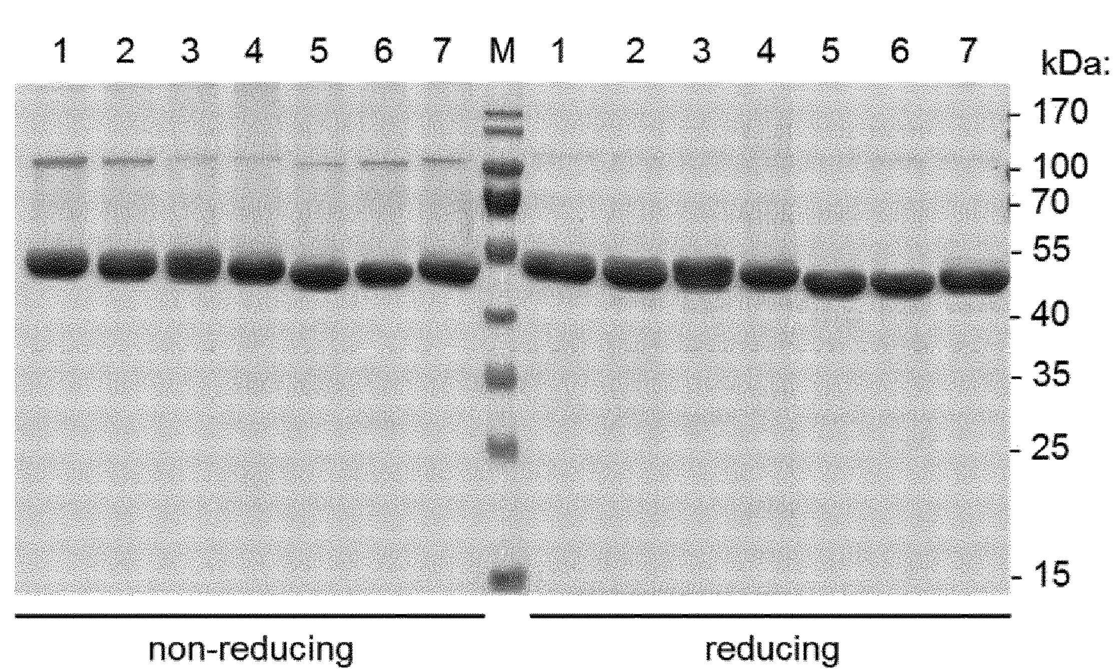
Figure 2:
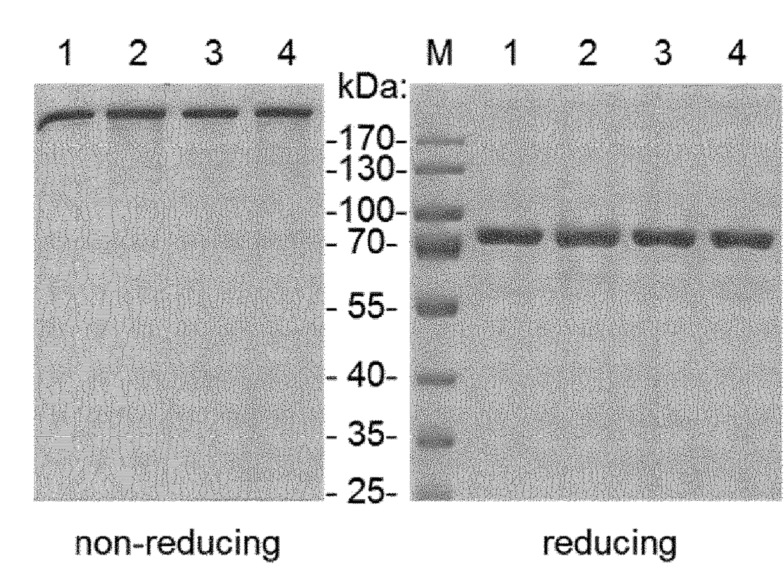

FIG. 2: Comparative SDS-PAGE analysis of $scTNF_{R2}$ mutant proteins and dimerized complexes thereof of the present invention. Fusion proteins were produced in HEK293-6E cells and purified by affinity chromatography. (A) $ScTNF_{R2}$ mutants were separated on 12% SDS-PAGE under non-reducing and reducing conditions and stained with Coomassie. 1, $scTNF_{R2}$(118); 2, $scTNF_{R2}$(127); 3, $scTNF_{R2}$(129); 4, $scTNF_{R2}$(130); 5, $SCTNF_{R2}$(131); 6, $scTNF_{R2}$(138); 7, $scTNF_{R2}$(139), M, molecular weight marker. (B) $ScTNF_{R2}$-Fc(Δab) complexes were separated on 10% SDS-PAGE under non-reducing and reducing conditions and stained with Coomassie. 1, $scTNF_{R2}$(127)-Fc(Δab) 742; 2, $scTNF_{R2}$(129)-Fc(Δab) 743; 3, $scTNF_{R2}$(139)-Fc (Δab)744; 4, $scTNF_{R2}$(118)-Fc(Δab) 745; M, molecular weight marker.

Figure 3A:
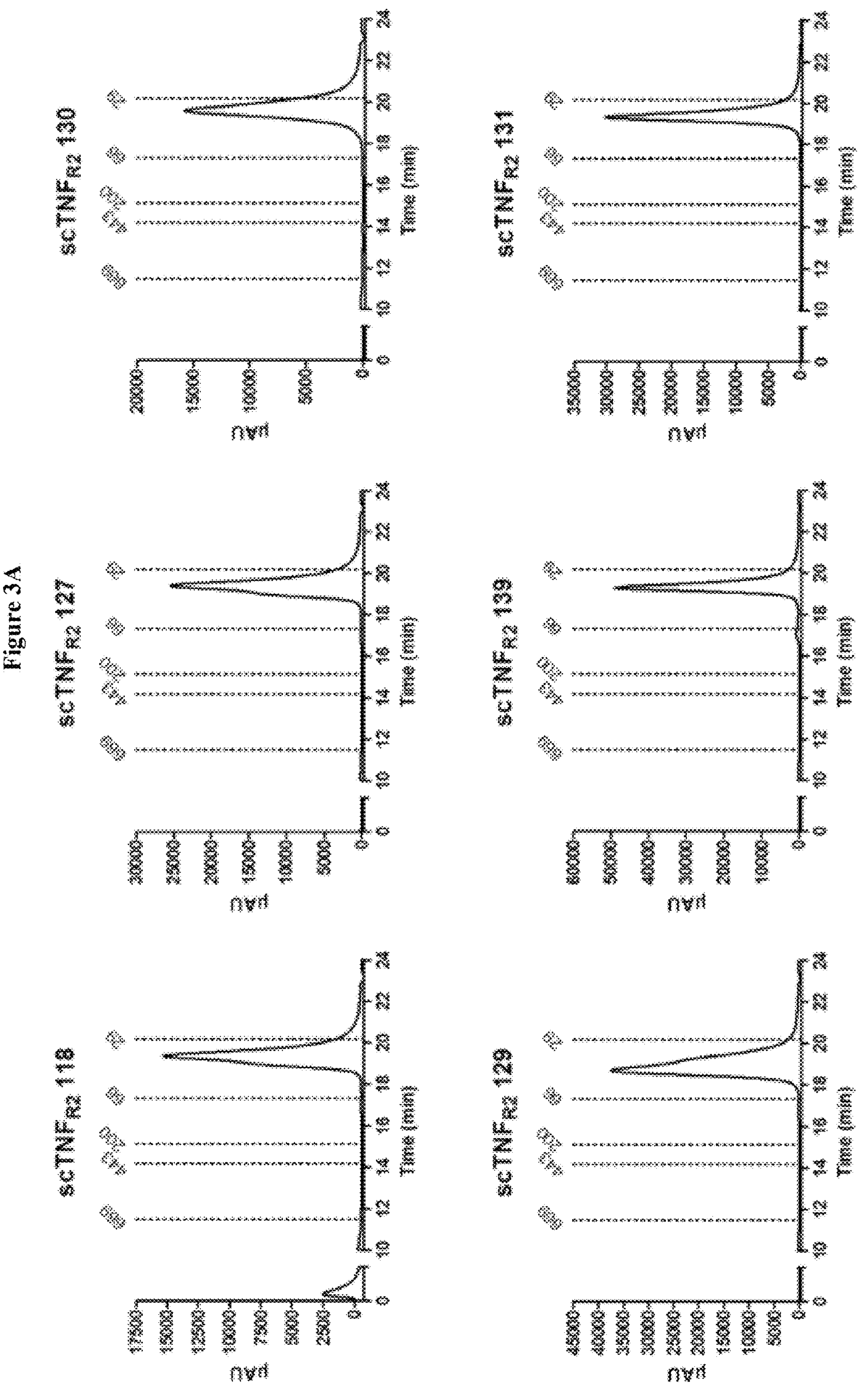
Figure 3B:
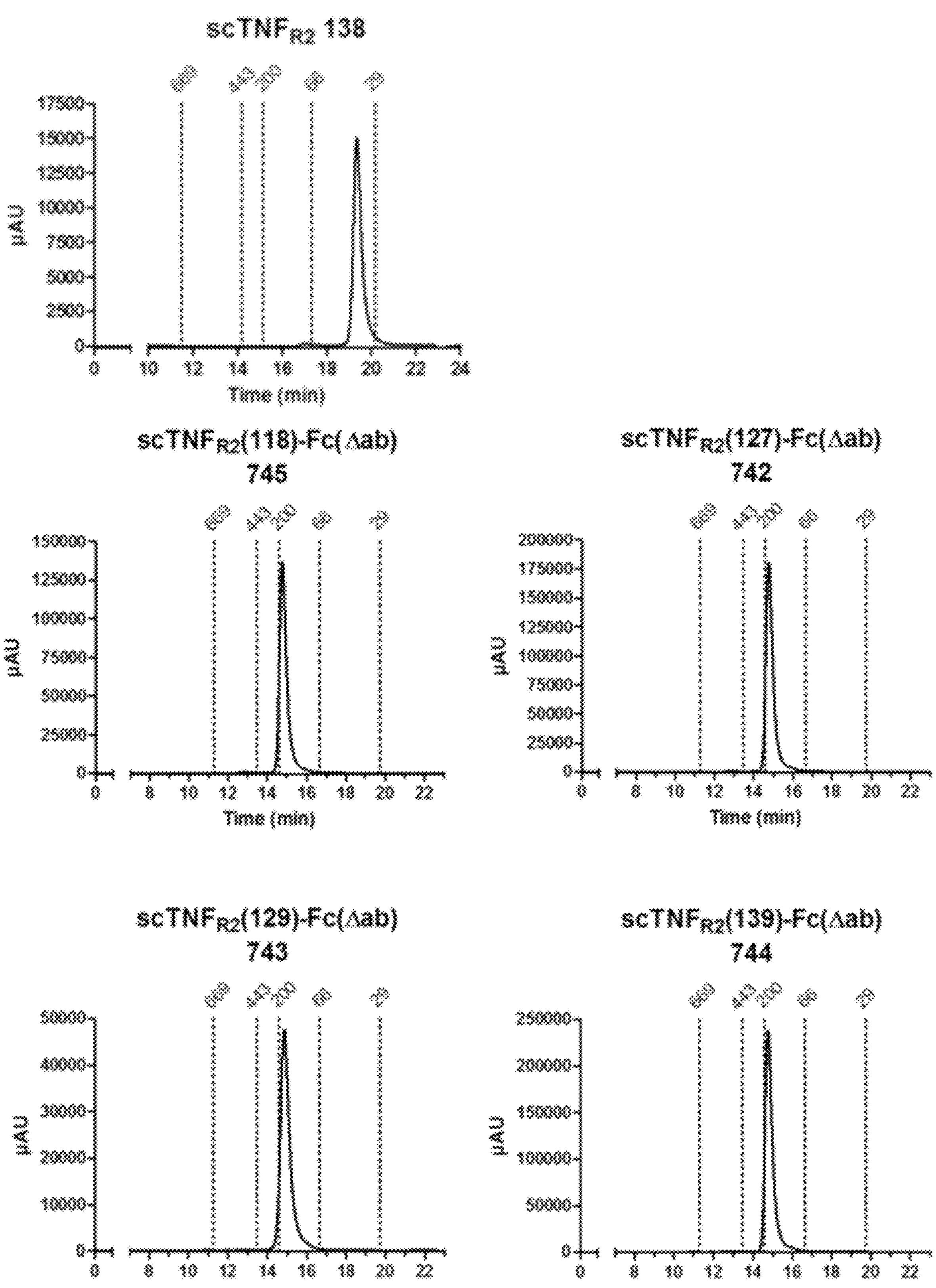

FIG. 3A-3B: Native structure of $scTNF_{R2}$ mutants and dimerized complexes thereof of the present invention. Proteins were analyzed by size-exclusion chromatography using a SuperSW mAb HR, 7.8×300 mm column (Tosoh Bioscience). Positions of used standard proteins are indicated.

Figure 4A:
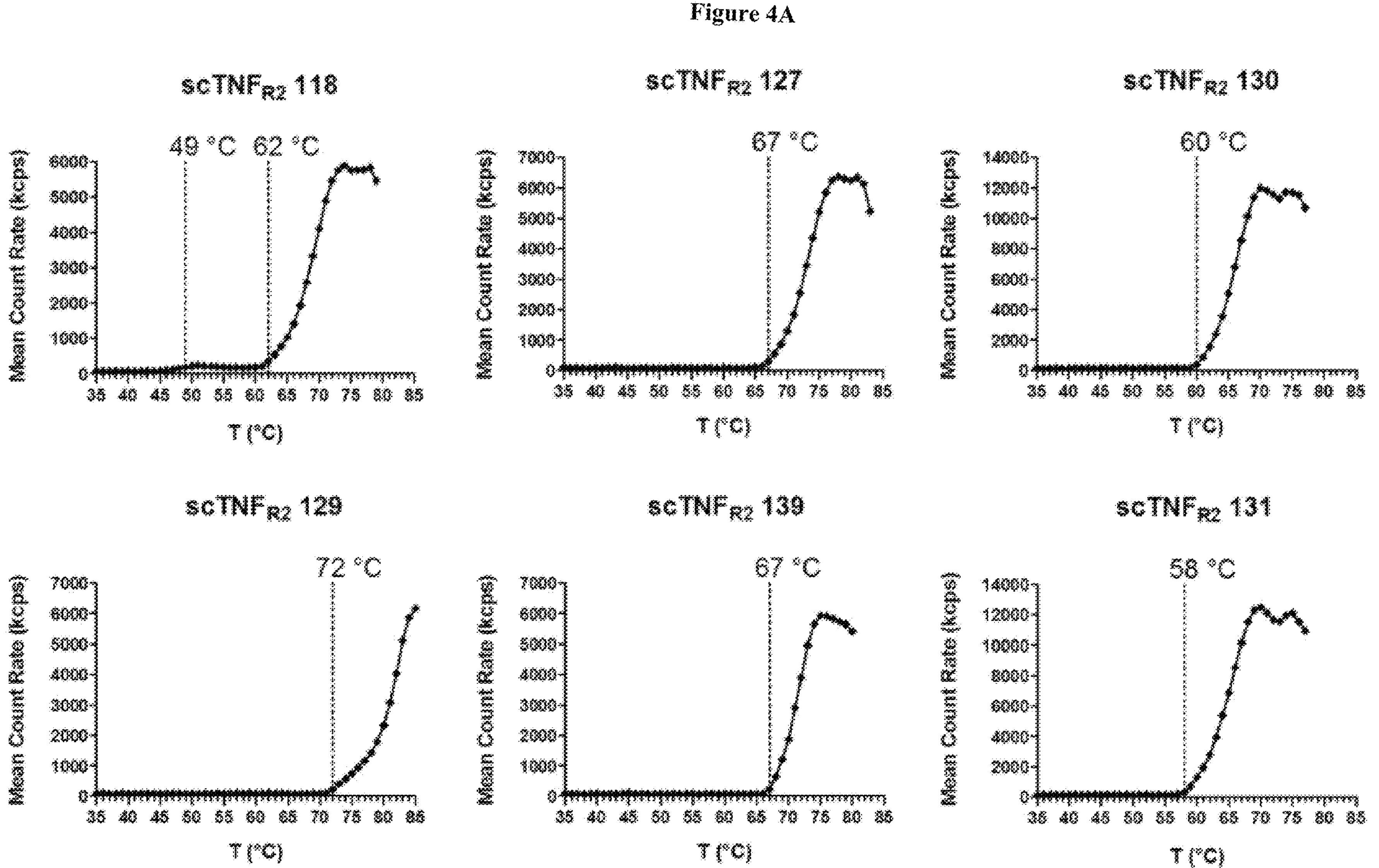
Figure 4B:
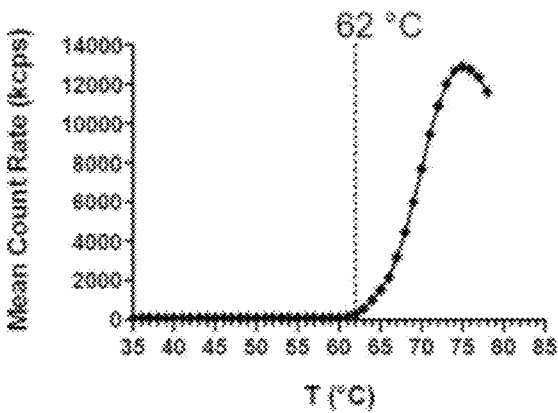
Figure 4B:
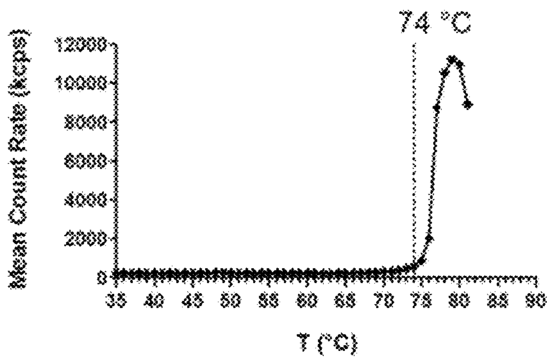
Figure 4B:
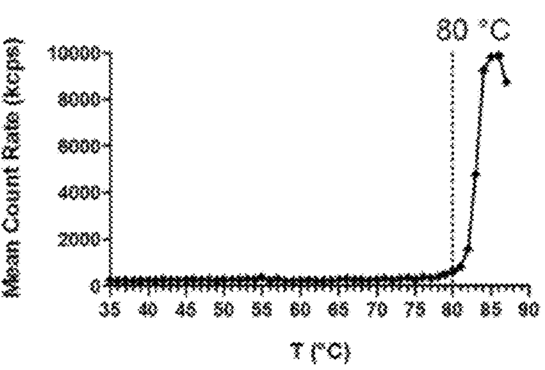
Figure 4B:
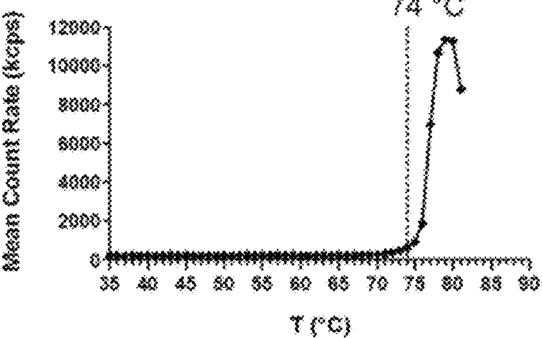

FIG. 4A-B: Thermal stability of $scTNF_{R2}$ mutants and dimerized complexes thereof of the present invention. Proteins were analyzed for their denaturation temperatures by dynamic light scattering. The detected melting points (aggregation points) are indicated by dotted lines.

Figure 5A:
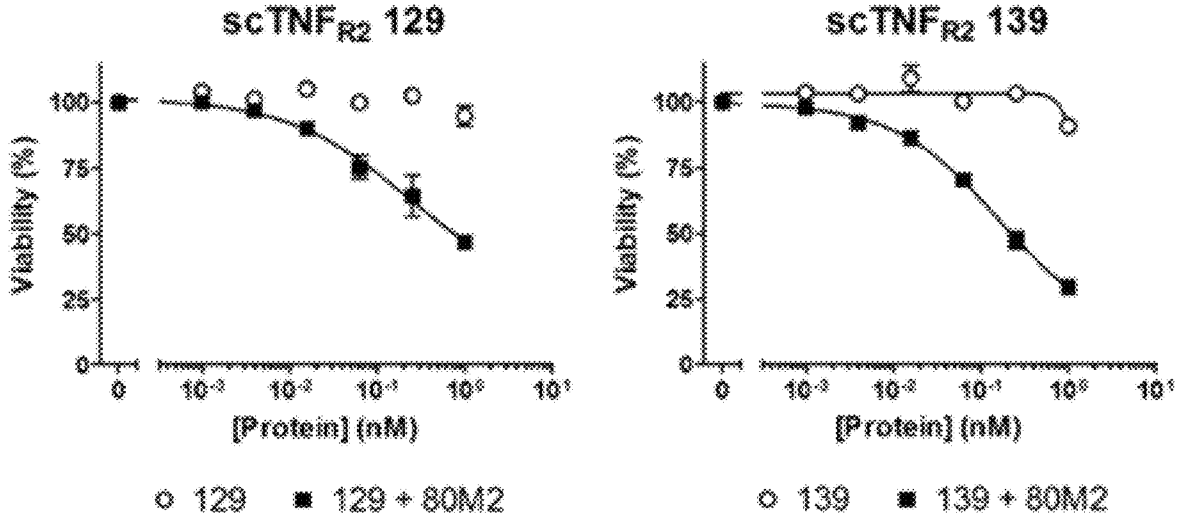
Figure 5B:
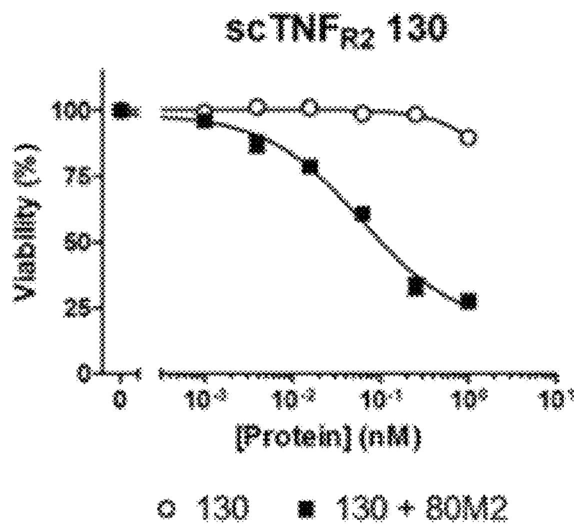

FIG. 5A-B: In vitro bioactivity of $scTNF_{R2}$ mutants on Kym-1 cells. The $ScTNF_{R2}$ mutants were analyzed for their bioactivity on Kym-1 cells in terms of cell death induction. Mechanistically, activation of TNFR2 by $scTNF_{R2}$ mutants, requiring TNFR2 crosslinking by antibody 80M2, leads to expression of trimeric TNF which in turn induces cell death by apoptosis through activation of TNFR1. Kym-1 cells were cultivated for 24 h in presence of serially diluted purified $scTNF_{R2}$ followed by measurement of cell viability using crystal violet staining. In addition, TNF receptor 2 molecules on Kym-1 cells were crosslinked with the 80M2 antibody (1 μg/ml) prior to incubation with the $scTNF_{R2}$ mutants (n=1).

Figure 6:
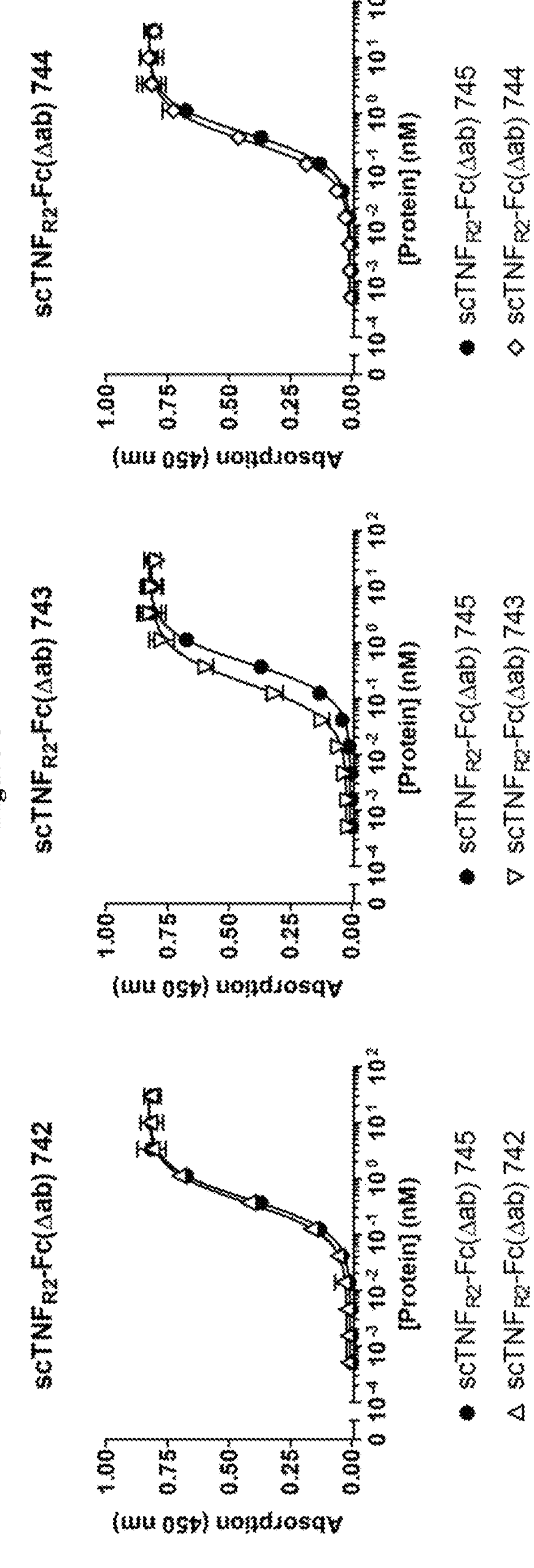

FIG. 6: Binding of $scTNF_{R2}$-Fc(Δab) complexes to TNF-R2. The binding of $SCTNF_{R2}$-Fc(Δab) complexes to TNF-R2-Fc (Etanercept) was tested in ELISA. For reasons of comparison, the binding curve of the state-of-the-art molecule $scTNF_{R2}$-Fc(Δab) 745 was plotted in combination with the proteins of the present invention $scTNF_{R2}$-Fc(Δab) 742, 743 and 744 in individual diagrams (Mean±S.D., n=3).

Figure 7:
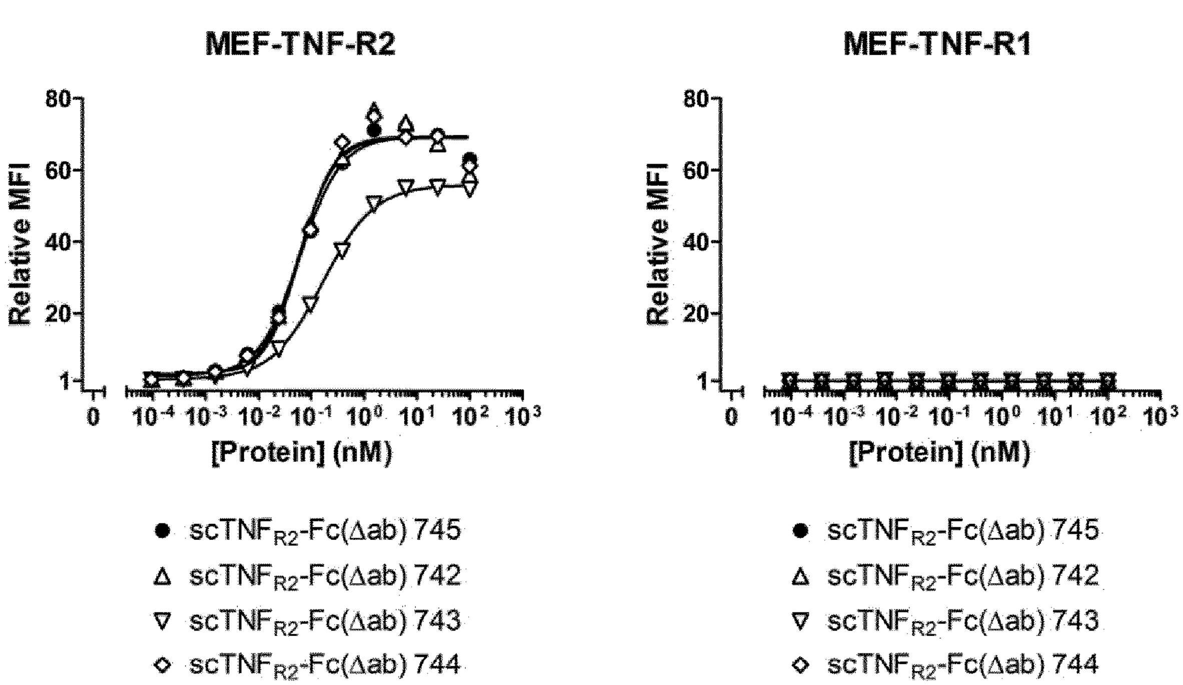

FIG. 7: TNF-R2 selective binding of $scTNF_{R2}$-Fc(Δab) complexes on MEF-TNF-R2. Mouse embryonic fibroblasts stably transfected with either human TNF-R2 (MEF-TNF-R2) or human TNF-R1 (MEF-TNF-R1) were tested for binding of the $scTNF_{R2}$-Fc(Δab) complexes by flow cytometry. The $scTNF_{R2}$-Fc(Δab) complexes bound selectively to MEF-TNF-R2, whereas binding to MEF-TNF-R1 could not be detected (n=1).

Figure 8:
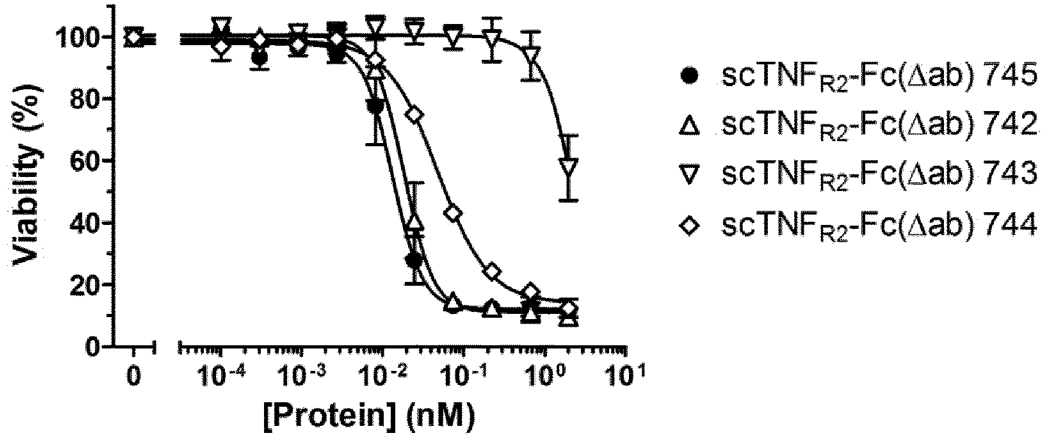

FIG. 8: In vitro bioactivity of $scTNF_{R2}$-Fc(Δab) complexes on Kym-1 cells. The in vitro bioactivity of $scTNF_{R2}$-Fc(Δab) complexes was analyzed on Kym-1 cells. The cells were cultivated for 24 h in presence of serially diluted purified $scTNF_{R2}$-Fc(Δab) complexes followed by measurement of cell viability using crystal violet staining (Mean±S.D., n=3).

Figure 9:
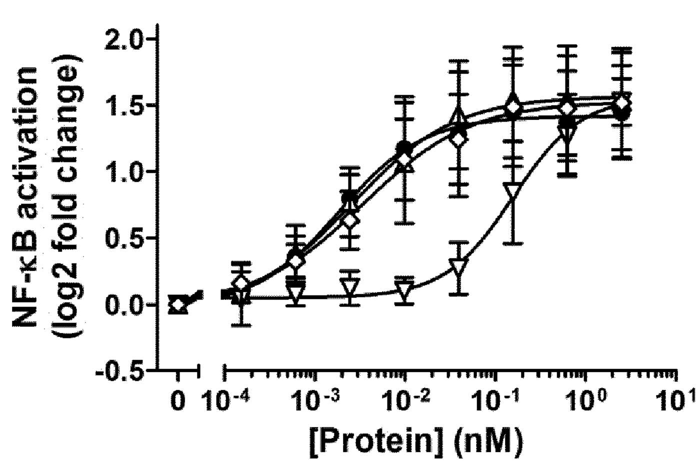

FIG. 9: NF-κB activation by $scTNF_{R2}$-Fc(Δab) complexes. The in vitro NF-κB activation by $scTNF_{R2}$-Fc(Δab) complexes was analyzed in HeLa cells stably transfected with human TNF receptor 2 (HeLa-TNF-R2) using a luciferase reporter assay. 16 h after transfection with experimental and control reporter plasmids, cells were stimulated for 6 h with the serially titrated $scTNF_{R2}$-Fc(Δab) complexes, followed by cell lysis and measurement of luciferase activities (Mean±S.D., n=4).

Figure 10:
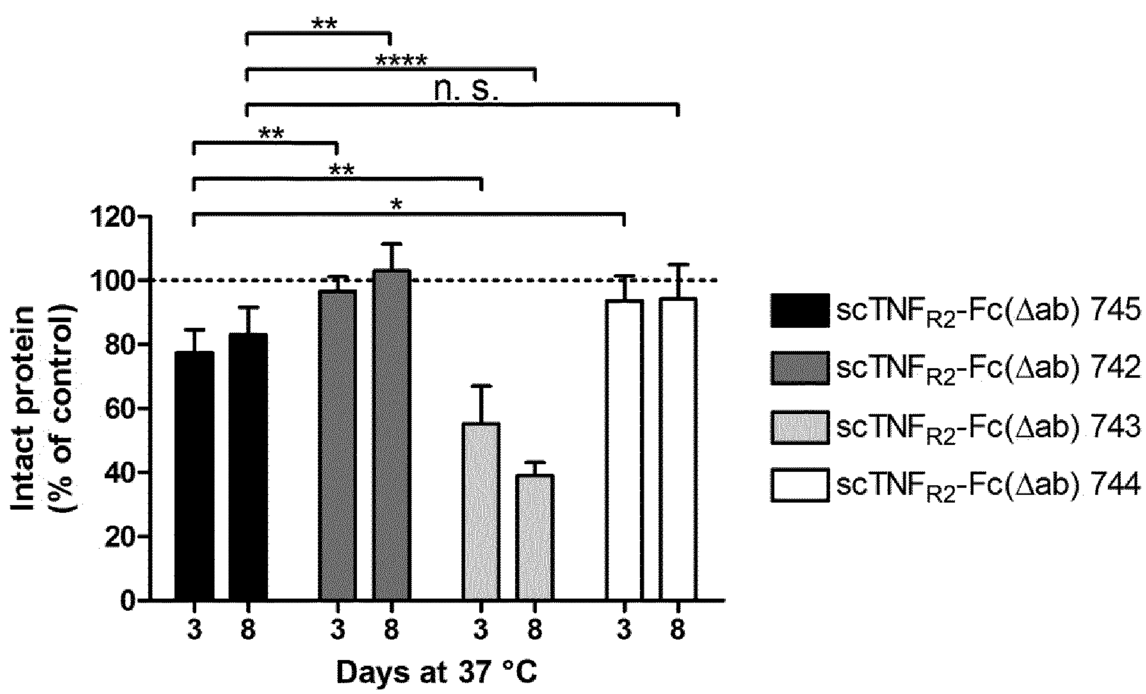

FIG. 10: Stability of $scTNF_{R2}$-Fc(Δab) complexes in human blood plasma. The integrity of the $scTNF_{R2}$-Fc(Δab) complexes after incubation for 0 days (control), 3 days or 8 days in 50% human blood plasma at 37° C. was tested by their ability to bind HeLa-TNF-R2 cells in flow cytometry. The percentage of intact protein (mean #S. D., n=4) was calculated from reciprocals of the $EC_{50}$ values which were normalized to the non-incubated control (100%). Statistical analysis was performed by two-way ANOVA and Dunnett's post-test. Results were summarized as **$p<0.0001$; *$p<0.001$; **$p<0.01$; *$p<0.05$; n.s.=not significant.

Figure 11:
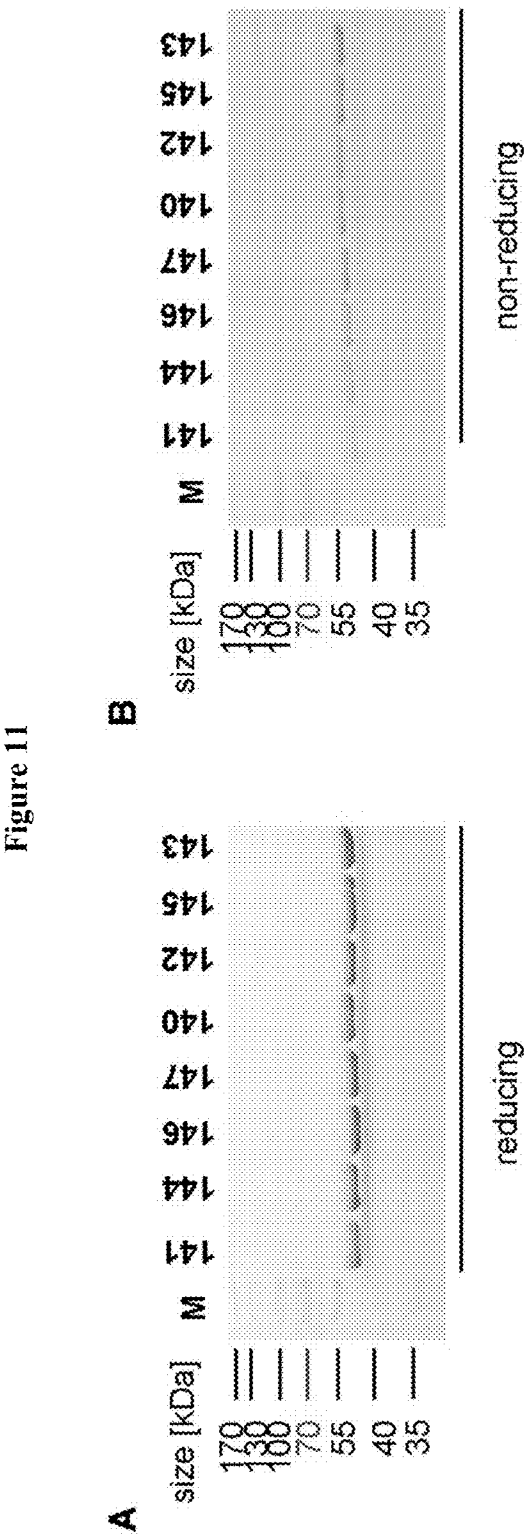

FIG. 11: Comparative SDS-PAGE analysis of $scTNF_{R2}$ variants of example 11. Fusion proteins were produced in HEK293-6E cells and purified by affinity chromatography. $ScTNF_{R2}$ mutants were separated on 10% SDS-PAGE under non-reducing (B) and reducing (A) conditions and stained with Coomassie. M, molecular weight marker.

FIG. 12: Comparative SDS-PAGE analysis of $scTNF_{R2}$-Fc proteins of examples 11. Fusion proteins were produced in HEK293-6E cells and purified by affinity chromatography. $ScTNF_{R2}$-Fc mutants were separated on 10% SDS-PAGE under non-reducing and reducing conditions and stained with Coomassie. M, molecular weight marker.

Figure 13A:
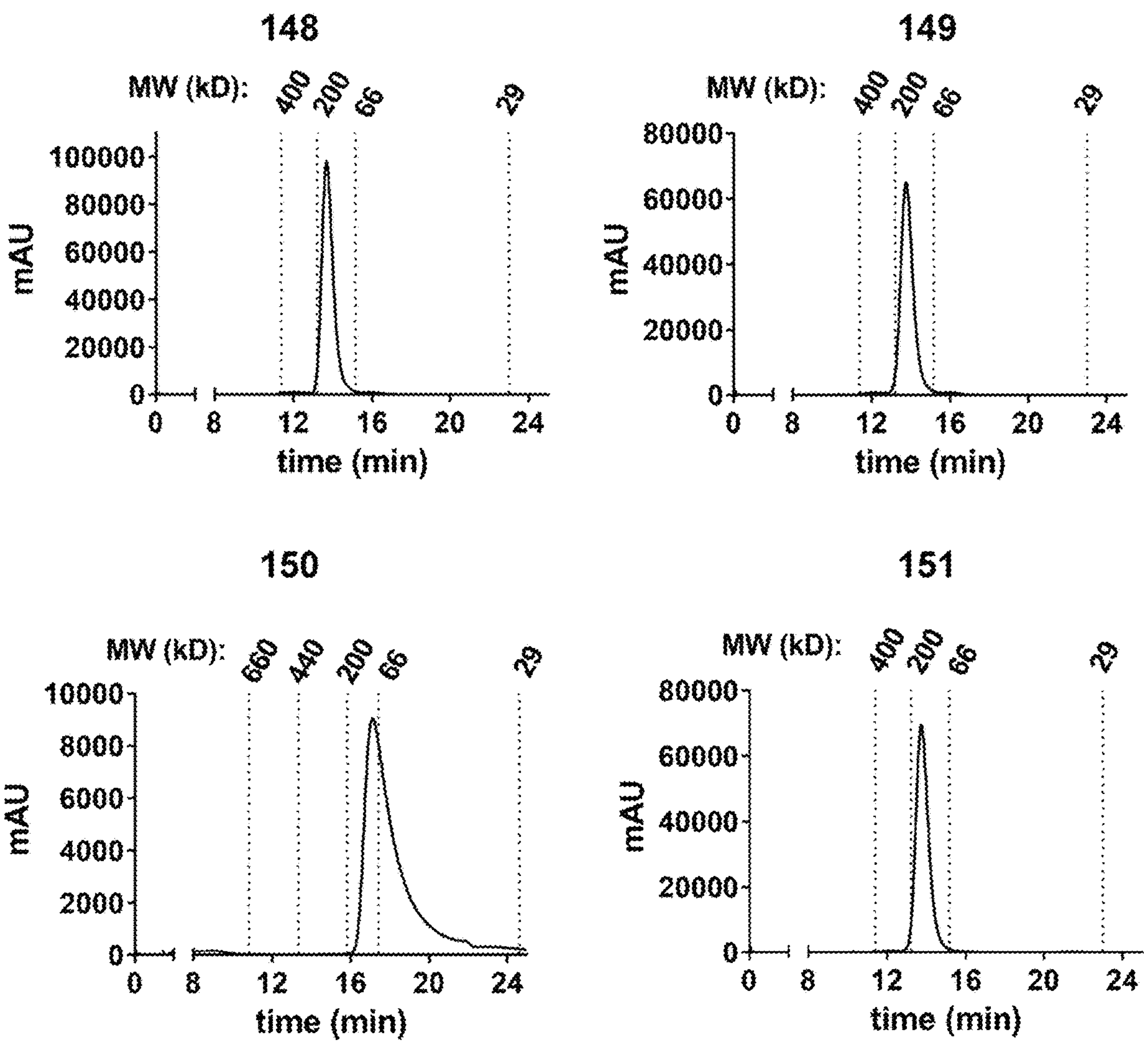
Figure 13B:
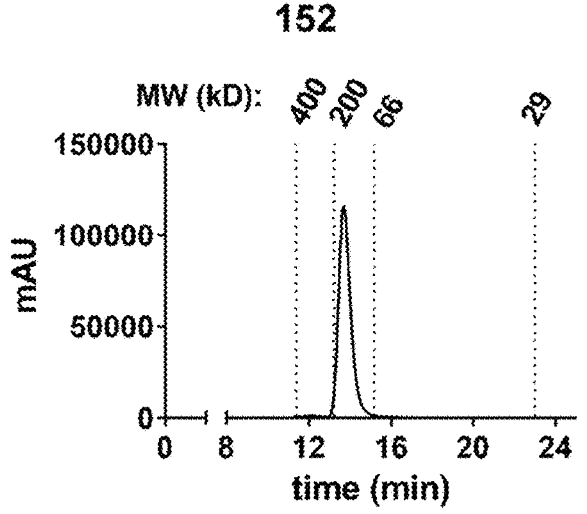
Figure 13B:
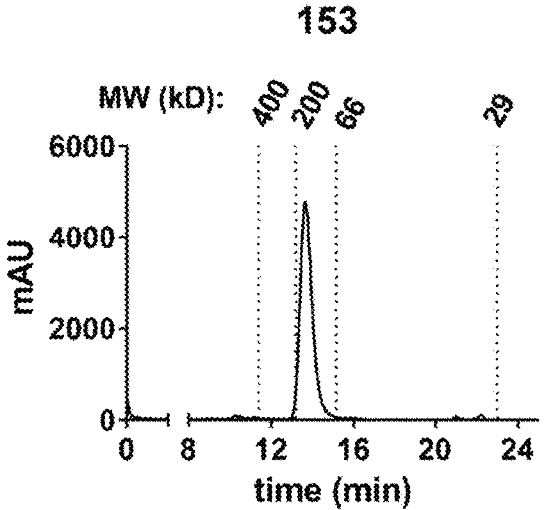
Figure 13B:
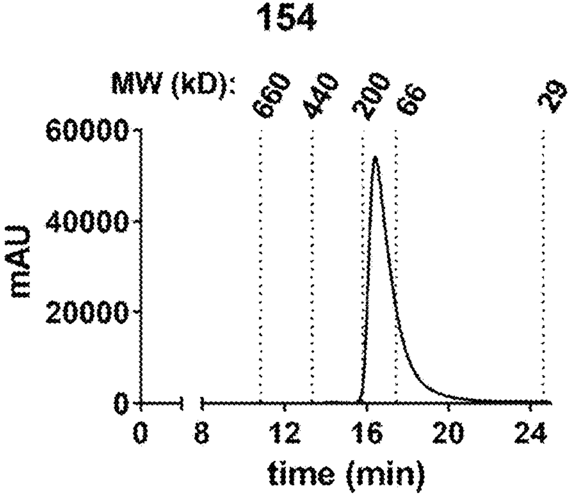

FIG. 13A-13B: Native structure of $scTNF_{R2}$-Fc proteins of examples 11. Proteins were analyzed by size-exclusion chromatography using a SuperSW mAb HR, 7.8×300 mm column (Tosoh Bioscience). Positions of used standard proteins are indicated.

Figure 14A:
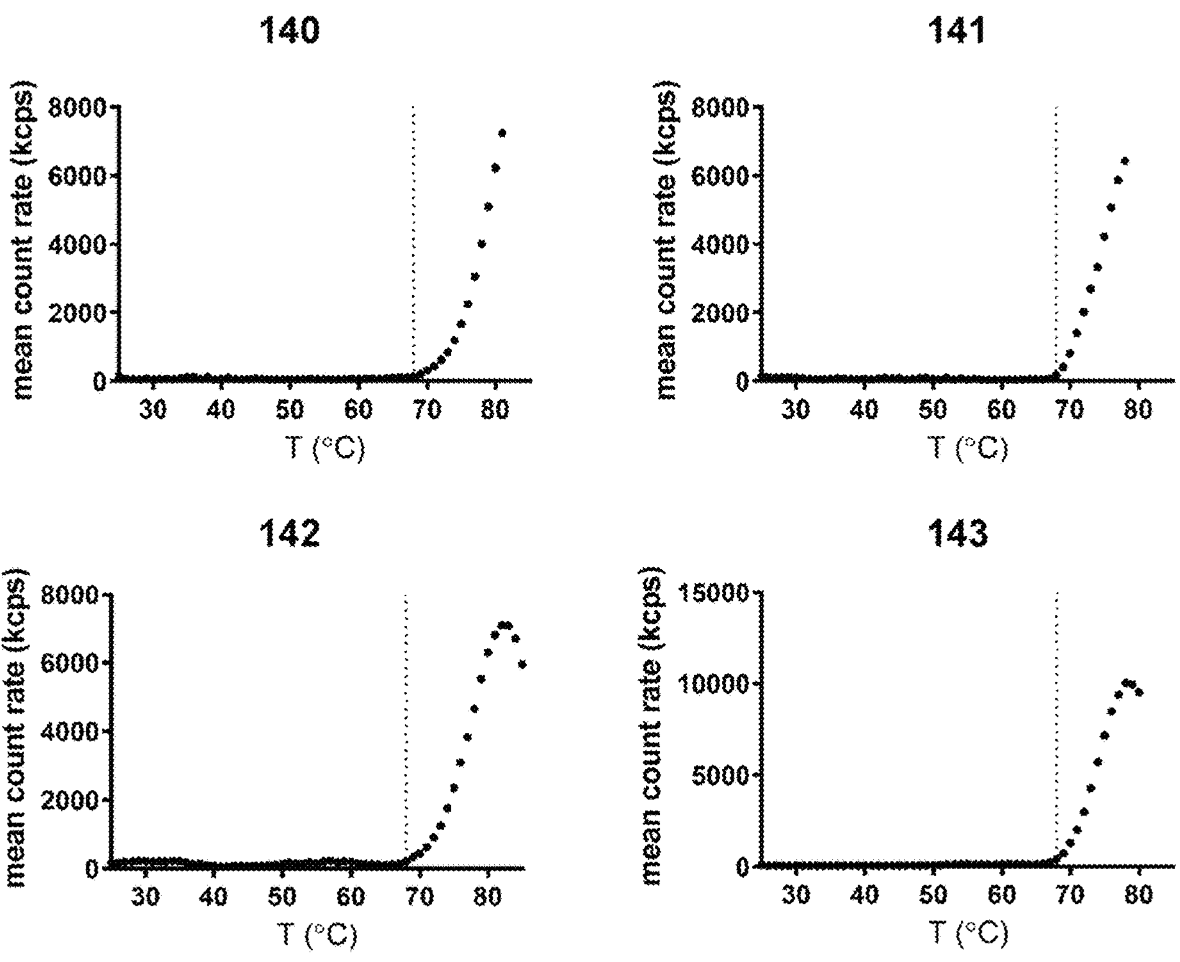
Figure 14B:
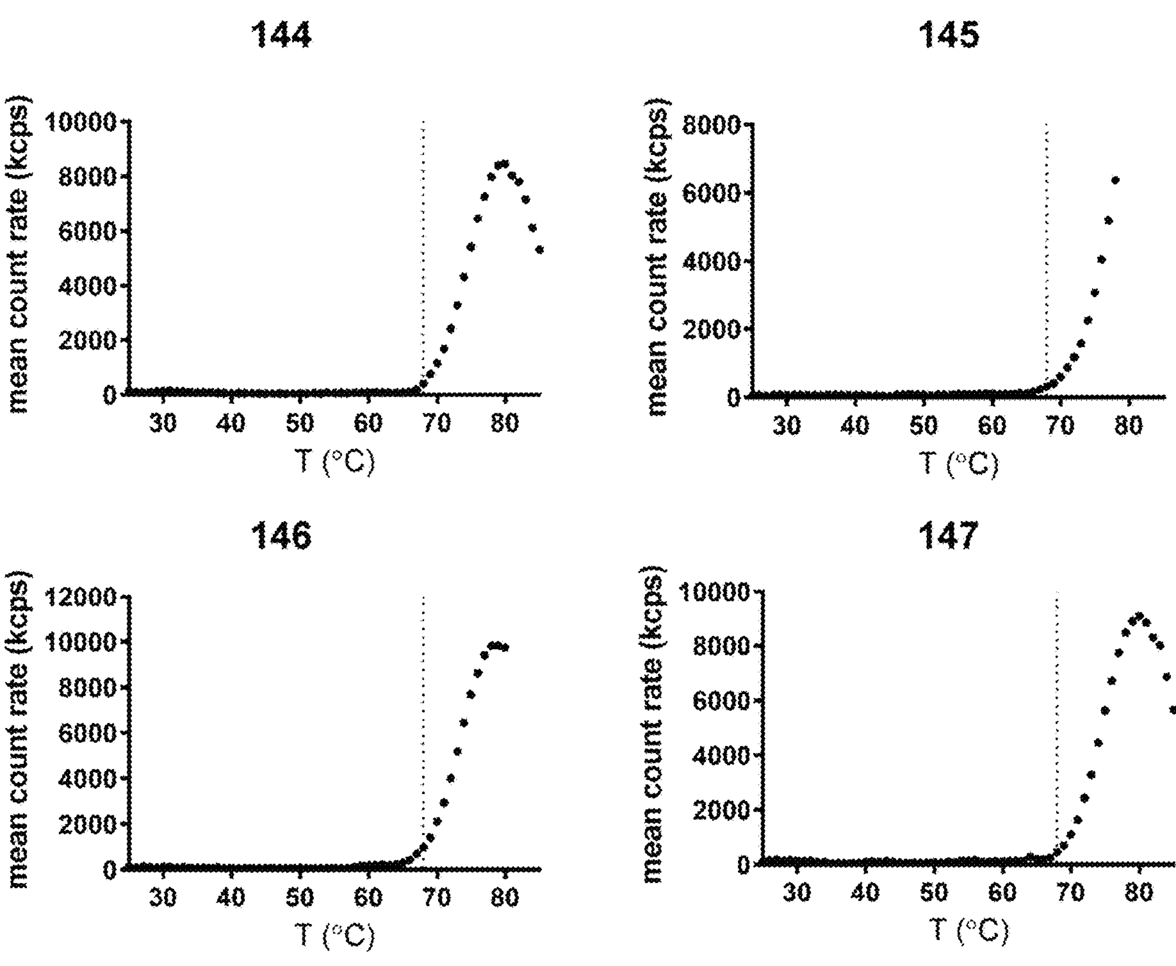

FIG. 14A-14B: Thermal stability of $scTNF_{R2}$ variants of examples 11. Proteins were analyzed for their denaturation temperatures by dynamic light scattering. The detected melting points (aggregation points) are indicated by dotted lines (n=2).

Figure 15A:
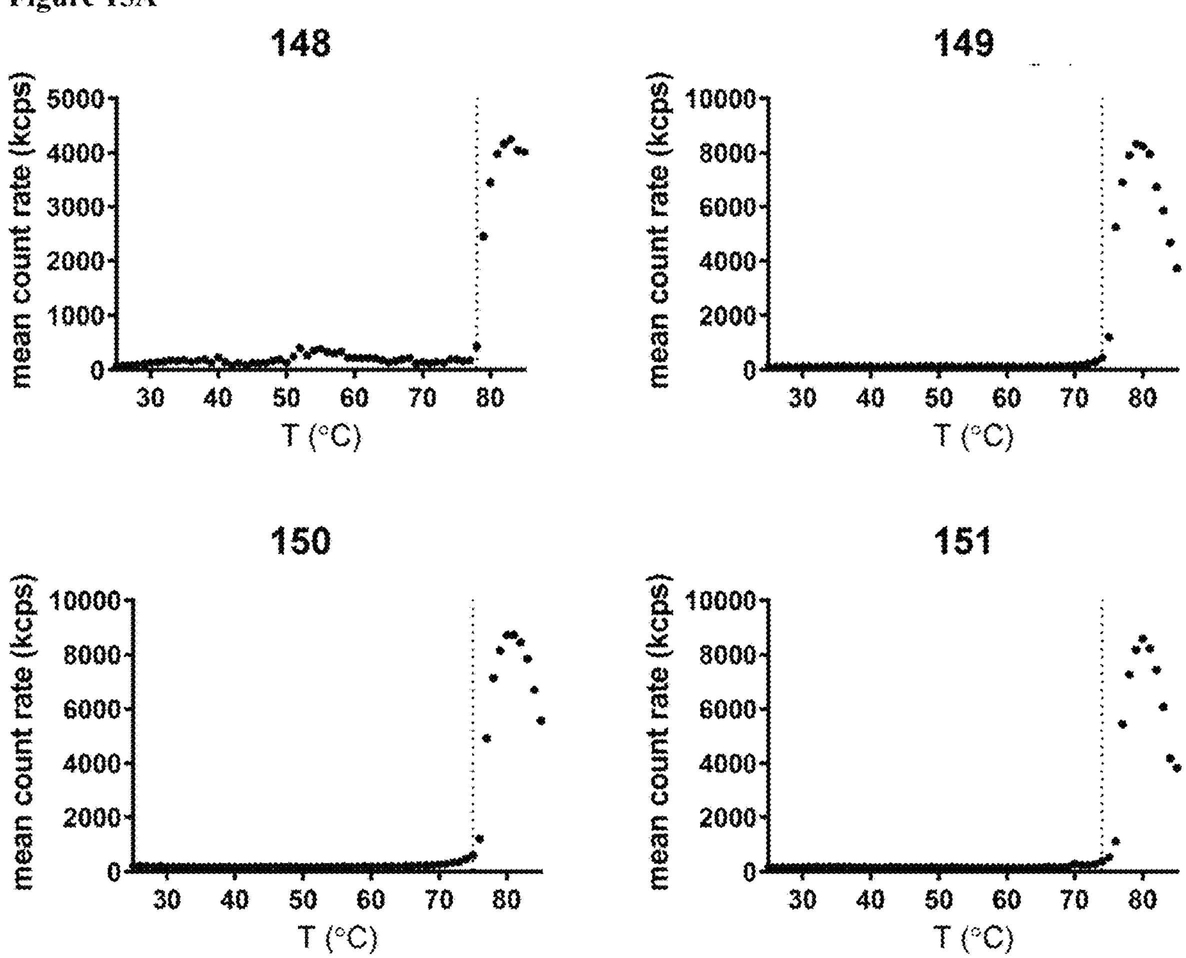
Figure 15B:
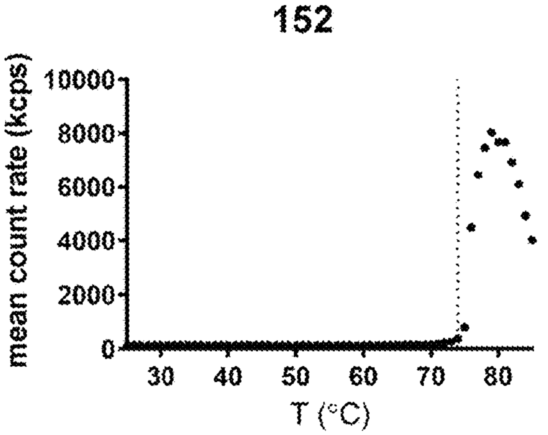
Figure 15B:
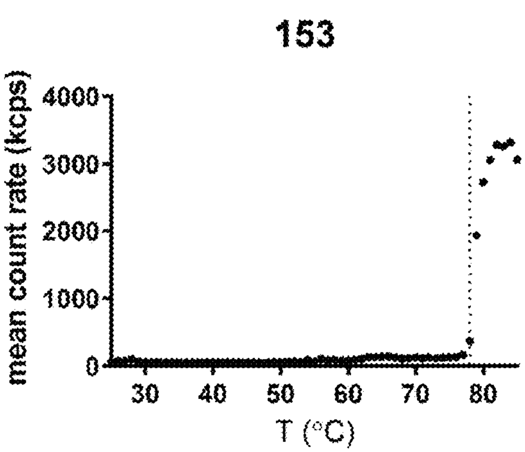
Figure 15B:
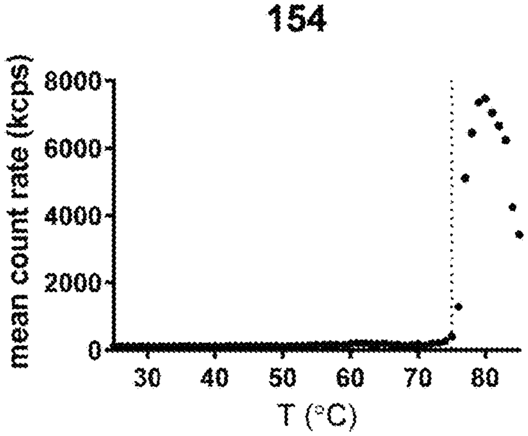

FIG. 15A-15B: Thermal stability of dimeric $scTNF_{R2}$-Fc proteins of examples 11. Proteins were analyzed for their denaturation temperatures by dynamic light scattering. The detected melting points (aggregation points) are indicated by dotted lines (n=1).

Figure 16:
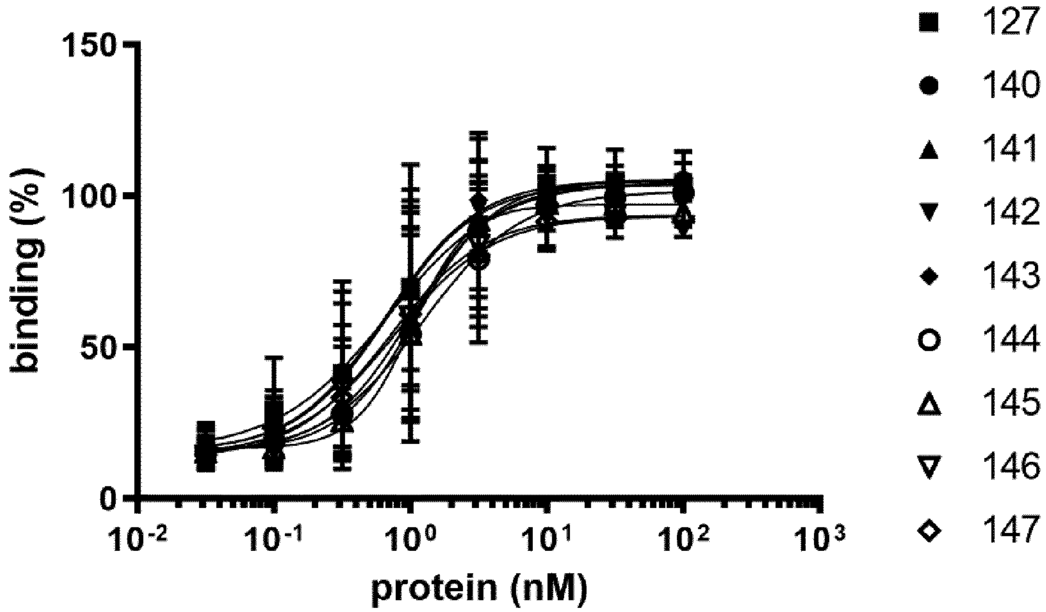

FIG. 16: Binding of $scTNF_{R2}$ variants of example 11 to TNF-R2. The binding of the $scTNF_{R2}$ mutant proteins to TNF-R2-Fc (Etanercept) was tested in ELISA (Mean±range of technical duplicates, n=1).

Figure 17:
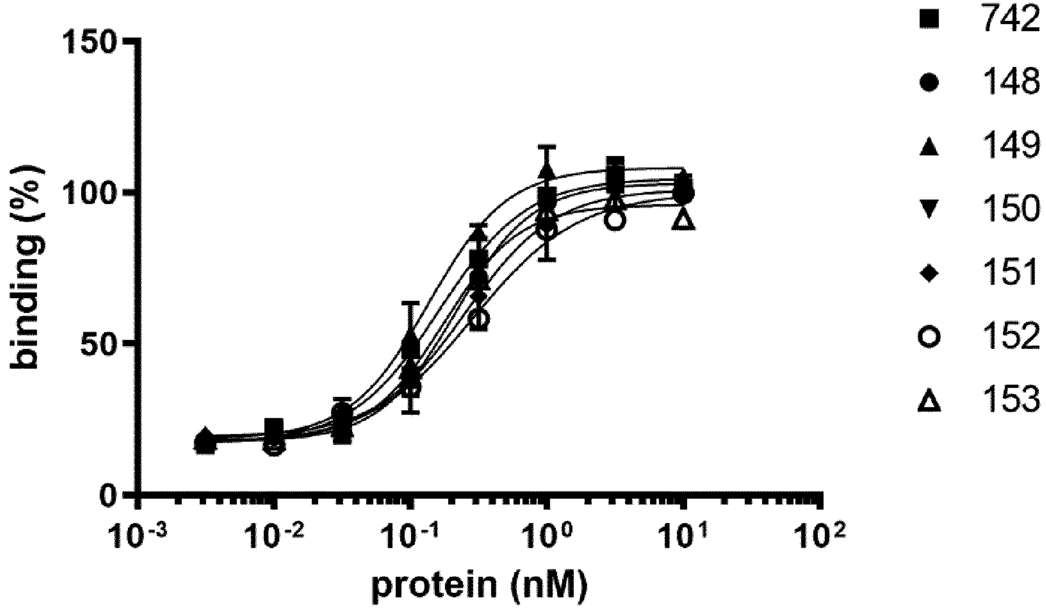

FIG. 17: Binding of $scTNF_{R2}$-Fc proteins of example 11 to TNF-R2. The binding of the $scTNF_{R2}$-Fc mutant proteins to TNF-R2-Fc (Etanercept) was tested in ELISA (Mean±range of technical duplicates, n=1-2).

Figure 18:
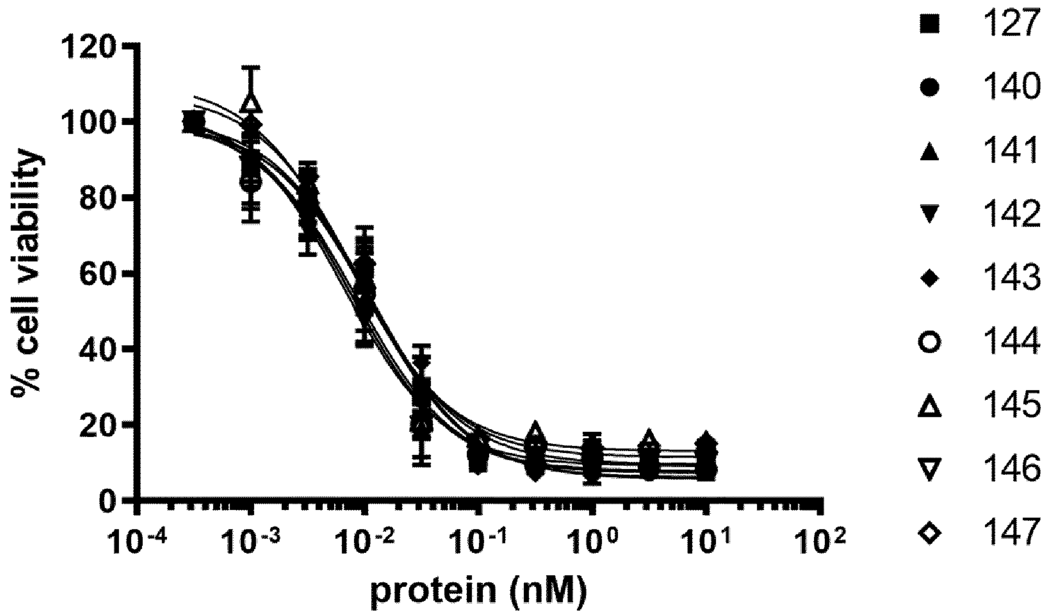

FIG. 18: In vitro bioactivity of $scTNF_{R2}$ variants of example 11 on Kym-1 cells. The $scTNF_{R2}$ mutants were analyzed for their bioactivity on Kym-1 cells in terms of cell death induction. Mechanistically, activation of TNFR2 by $scTNF_{R2}$ mutants, requiring TNFR2 crosslinking by antibody 80M2, leads to expression of trimeric TNF which in turn induces cell death by apoptosis through activation of TNFR1. Kym-1 cells were cultivated for 24 h in presence of serially diluted purified $scTNF_{R2}$ followed by measurement of cell viability using crystal violet staining. In addition, TNF receptor 2 molecules on Kym-1 cells were crosslinked with the 80M2 antibody (1 μg/ml) prior to incubation with the $scTNF_{R2}$ mutants (n=3-8±SD).

Figure 19:
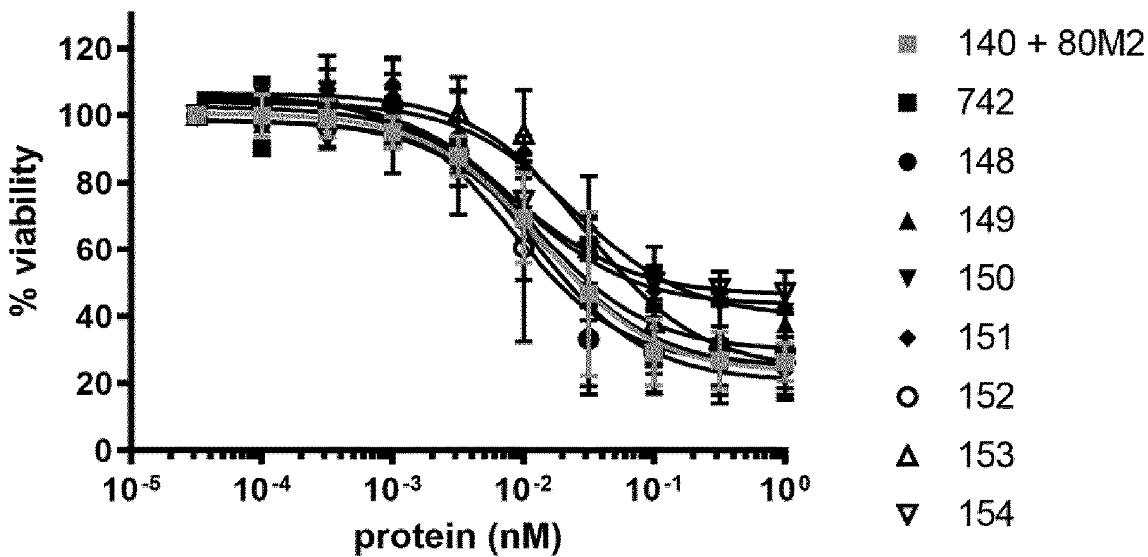

FIG. 19: In vitro bioactivity of dimeric $scTNF_{R2}$-Fc proteins of example 11 on Kym-1 cells. The $scTNF_{R2}$Fc mutants were analyzed for their bioactivity on Kym-1 cells in terms of cell death induction. Mechanistically, activation of TNFR2 by $scTNF_{R2}$-Fc mutants leads to expression of trimeric TNF which in turn induces cell death by apoptosis through activation of TNFR1. Kym-1 cells were cultivated for 24 h in presence of serially diluted purified $scTNF_{R2}$ followed by measurement of cell viability using crystal violet staining. In addition, TNF receptor 2 molecules on Kym-1 cells were crosslinked with the 80M2 antibody (1 μg/ml) prior to incubation with the $scTNF_{R2}$ mutants (n=3-4±SD).

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages, different aspects of the invention are defined in more detail. Each aspect so defined may be combined with any other aspect or aspects unless clearly indicated to the contrary. In particular, any feature indicated as being optional, preferred or advantageous may be combined with any other feature or features indicated as being optional, preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

In the context of the present invention, the term "peptide" refers to a short polymer of amino acids linked by peptide bonds. It has the same chemical (peptide) bonds as proteins but is commonly shorter in length. The shortest peptide is a dipetide consisting of two amino acids joined by a peptide bond. There can also be tripeptides, tetrapeptides, pentapeptides etc. A peptide has an amino end and a carboxyl end, unless it is a cyclic peptide. Peptides usable in the present invention (including peptide derivatives, peptide variants, peptide fragments, peptide segments, peptide epitopes and peptide domains) can be further modified by chemical modification. This means such a chemically modified peptide may comprise other chemical groups than the 20 naturally occurring proteinogenic amino acids. Examples of such other chemical groups include without limitation glycosylated amino acids and phosphorylated amino acids.

Chemical modifications of a peptide may provide advantageous properties as compared to the parent peptide, e.g. one or more of enhanced stability, increased biological half-life, or increased solubility.

The term "polypeptide" refers to any peptide-bond-linked polymer of amino acids. A polypeptide can be one chain or may be composed of more than one chain, which are held together by covalent bonds, e.g. disulphide bonds and/or non-covalent bonds. Modifications of the peptide bonds or of side chains residues are possible, provided the activity of the resulting chemical entity (e.g. component A linked to component B) is not totally lost. The term shall not be construed as limiting the length of the polypeptide.

The term "protein" as used in the context of the present specification refers to a molecule comprising one or more polypeptides that resume a secondary and tertiary structure and additionally refers to a protein that is made up of several polypeptides, i.e. several subunits, forming quaternary structures. The protein has sometimes non-peptide groups attached, which can be called prosthetic groups or cofactors.

The term "C-terminus" (also known as the carboxyl-terminus, carboxy-terminus, C-terminal tail, C-terminal end, or COOH-terminus) as referred to within the context of the present invention is the end of an amino acid chain (protein or polypeptide), terminated by a free carboxyl group (—COOH). When the protein is translated from messenger RNA, it is created from N-terminus to C-terminus. The term "N-terminus" (also known as the amino-terminus, $NH_2$-terminus, N-terminal end or amine-terminus) refers to the start of a protein or polypeptide terminated by an amino acid with a free amine group (—$NH_2$). The convention for writing peptide sequences is to put the N-terminus on the left and write the sequence from N- to C-terminus.

The term "TNF homology domain of TNF-ligand family member proteins" (THD) as used in the present specification refers to a protein domain shared by all tumor necrosis factor (TNF, formerly known as TNFα or TNF alpha) ligand family members. Homology implies evolutionary lineage from a common ancestor. A homology domain is a conserved part of a given protein sequence and (tertiary) structure that can evolve, function, and exist independently of the rest of the protein chain. It is a structural feature shared by all members of a certain protein family. Each domain forms a compact three-dimensional structure and often can be independently stable, folded and critical for biological activity. The C-terminus of a THD within the meaning of the present invention is defined by the C-terminal consensus sequence: V-F/Y-F-G-A/I-$X_1$ (SEQ ID NO: 1) and the N-terminus is defined by the N-terminal consensus sequences: P-V/A-A-H-V/L (SEQ ID NO: 2), wherein $X_1$ is a non-polar/hydrophobic or polar/neutral amino acid, preferably selected from the group consisting of F and I. On the basis of a given TNF-ligand family member protein sequence and using above defined C-terminal and N-terminal homology sequences the skilled person can determine for the given TNF-ligand family member protein the THD. Among the members of the TNF family, the position and length of individual THDs vary considerably, but can be defined by the occurrence of conserved amino acid residues as identified by multiple sequence alignments using appropriate software tools (Bodmer et al., 2002). More importantly, crystal structures can reveal distinct interactions between amino acid residues involved in, for example, homotrimerization of TNF family ligands. Informations of such kind can be helpful to refine THDs for given members of the TNF superfamily as described in Bodmer et al., 2002. Furthermore, functional aspects like protein solubility or bioactivity, such as receptor binding and activation, of engineered protein variants can provide important hints regarding crucial amino acid residues or the minimal length of individual THDs. The term THDs comprises polypeptides based on naturally occurring TNF-ligand family member protein sequences as well as variants thereof, which retain the ability to bind specifically to the receptor of the respective TNF-ligand family member. Preferably such THD variants have an affinity of at least 50% of the wild type THD, more preferably at least 60%, 70%, 80%, 90% and most preferably at least 99%.

TNF-ligand family member proteins comprise a group of multifunctional cytokines that can cause, e.g. programmed cell death (apoptosis), differentiation, cell survival, and immune regulation. TNF is a monocyte-derived cytokine that has been implicated in tumor regression, septic shock, and cachexia which is recognized by its specific receptor. Nineteen proteins have been identified as part of the TNF-ligand family on the basis of sequence, functional, and structural similarities. All these cytokines seem to form homotrimeric (or heterotrimeric in the case of LT-alpha/beta) complexes that are recognized by their specific receptors. The following proteins are members of the TNF-ligand family: TNF-related apoptosis inducing ligand (TRAIL; TNFSF10), a cytokine that induces apoptosis; CD40L (TNFSF5=tumor necrosis factor superfamily member 5), a cytokine that seems to be important in B-cell development and activation; CD27L (TNFSF7), a cytokine that plays a role in T-cell activation which induces the proliferation of co-stimulated T cells and enhances the generation of cytolytic T cells; CD30L (TNFSF8), a cytokine that induces proliferation of T cells; FasL (TNFSF6), a cell surface protein involved in cell death; 4-1BBL (TNFSF9), an inducible T cell surface molecule that contributes to T-cell stimulation; OX40L (TNFSF4), a cell surface protein that co-stimulates T cell proliferation and cytokine production; LTA (TNFSF1), a protein with anti-proliferative activity and an important role in immune regulation. Further members of the TNF-ligand family members comprise EDA; LTB (TNFSF3); CD153 (TNFSF8); RANKL (TNFSF11); TWEAK (TNFSF12); APRIL (TNFSF13); BAFF (TNFSF13B); LIGHT (TNFSF14); VEGI (TNFSF15); GITRL (TNFSF18). More information about the sequences of TNF-ligand family members may be obtained for example from publicly accessible databases such as Genbank. TNF-ligand family members interact with their cognate receptors, e.g. TNF with TNFR1 and TNFR2, TRAIL with TRAILR1 (DR4), TRAILR2 (DR5), TRAILR3 (DcR1), TRAILR4 (DcR2) and OPG. The ligands mediate oligomerization and activation of their respective receptors. The interaction of members of the TNF receptor family with its ligands is characterized by binding of the receptors at the space between two of the three TNF-ligand family member protein monomers of the TNF-ligand family member protein homotrimer, the biological active form of TNF and other members of the TNF-ligand family.

The term "consensus sequence" as used within this specification refers to a calculated order of most frequent residues, either nucleotide or amino acid, found at each position in a sequence alignment between two or more sequences. It represents the results of a multiple sequence alignment in which related sequences are compared to each other and similar sequence motifs are calculated. Conserved sequence motifs are depicted as consensus sequences, which indicate identical amino acids, i.e. amino acids identical among the compared sequences, conserved amino acids, i.e. amino acids which vary among the compared amino acid sequence but wherein all amino acids belong to a certain functional or structural group of amino acids, e.g. polar or neutral, and variable amino acids, i.e. amino acids which show no apparent relatedness among the compared sequence.

The consensus sequence of the C-terminus and N-terminus of the THD is a sequence that is located within the TNF-ligand family member sequence, respectively, and is particularly conserved among TNF-ligand family members. These sequences delineate the part of the TNF-ligand family member participating in the trimerization. Accordingly, the two consensus sequences serve as C-terminal and N-terminal reference points within a given TNF-ligand family member, which may comprise additional N- or C-terminal amino acids that may not be present in other TNF-ligand family members. Thus, the use of consensus sequences allows to refer to the same region of different TNF-ligand family member without referring to a specific position as the N-terminal and C-terminal end of the fragment of the TNF-ligand family member present in the polypeptides of the invention.

The term "multimerization domain" as used herein refers to a protein or polypeptide, a fragment or part of a protein or polypeptide which mediates a close proximity between at least two identical or different protein or polypeptide molecules (monomers) of the invention and thus, enables protein-protein interaction which allows multimerization of multiple structurally similar or different monomers joined by non-covalent or covalent bonds. The multimerization leads to the formation of a macromolecular complex formed by multiple, covalently or non-covalently bound, macromolecules such as proteins. Multimerization domains that allow the multimerization of two, three or four polypeptide molecules of the invention are referred to as dimerization, trimerization or tetramerization domains, respectively.

An "amino acid linker" in the context of the present invention refers to an amino acid sequence which sterically separates two parts or moieties of a complex, e.g. a polypeptide and a multimerization domain. Typically such linker consists of between 1 and 100 amino acids having a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. The indicated preferred minimum and maximum lengths of the peptide linker according to the present invention may be combined, if such a combination makes mathematically sense, e.g. such linker may consist of 1-15, 1-30, 1-60, 6-30, 7-15, 12-40, or 25-75, or 1-100 amino acids. Amino acid linkers may also provide flexibility among the two proteins that are linked together. Such flexibility is generally increased if the amino acids are small. Accordingly, flexible amino acid linkers comprise an increased content of small amino acids, in particular of glycines and/or alanines, and/or hydrophilic amino acids such as serines, threonines, asparagines and glutamines. Preferably, more than 20%, 30%, 40%, 50%, 60%, 70% or 80% or more of the amino acids of the peptide linker are small amino acids. Amino acid linkers may also include N-glycosylation consensus sequences. Glycosylation of amino acid linkers is known to increase the stability of those linkers (Imperialia and O'Connor, Curr Opin Chem Biol. 1999 December; 3 (6): 643-9). Preferably the consensus sequence is Asn-X-Ser/Thr or Asn-X-Cys, whereby X is in both cases any amino acid except for Pro, more preferably the consensus sequence is Asn-X-Ser/Thr. Further amino acid linkers are known in the art that can be used in the polypeptide multimers of the present invention. Such suitable linkers can be found in Chen et al (Adv Drug Deliv Rev. 2013 October; 65 (10): 1357-69) and Klein et al (Protein Eng Des Sel. 2014 October; 27 (10): 325-30).

In the context of the present invention the term "half-life-extension domain" refers to a binding moiety which prolongs the serum/plasma half-life of a pharmaceutically active moiety, i.e. a pharmaceutically active moiety exhibits a prolonged serum/plasma half-life when being part of the half-life-extension domain. The binding moiety may be but is not limited to a polypeptide or protein.

The term "target" or "target molecule" as used in the present invention refers to a natural existing cellular or molecular structure towards which other molecules have a certain binding affinity or to which other molecules specifically bind. "Specific binding" means that a binding moiety (e.g. a polypeptide or polypeptide multimer of the present invention or an antibody) binds stronger to a target, such as a receptor or an epitope, for which it is specific compared to the binding to another target if it binds to the first target with a dissociation constant ($K_d$) which is lower than the dissociation constant for the second target. Targets can be recognized by their ligands which bind with a certain affinity to their targets and thus, the ligand binding to its respective target results in a biological effect. Preferably the dissociation constant ($K_d$) for the target to which the binding moiety binds specifically is more than 10-fold, preferably more than 20-fold, more preferably more than 50-fold, even more preferably more than 100-fold, 200-fold, 500-fold, 1000-fold, 5000-fold or 10.000-fold lower than the dissociation constant ($K_d$) for the target to which the binding moiety does not bind specifically.

As used herein, the term "$K_d$" (measured in "mol/L", sometimes abbreviated as "M") is intended to refer to the dissociation equilibrium constant of the particular interaction between a binding moiety (e.g. a polypeptide or polypeptide multimer of the present invention) and a target molecule (e.g. a receptor). Such affinity is preferably measured at 37° C. Suitable assays include surface plasmon resonance measurements (e.g. Biacore), quartz crystal microbalance measurements (e.g. Attana), biolayer interferometry (e.g. Octet), and competition assays.

As used herein, the term "variant" is to be understood as a peptide or protein which differs in comparison to the peptide or protein from which it is derived by one or more changes in its length or sequence. The polypeptide from which a protein variant is derived is also known as the parent or parental polypeptide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are posttranslational modifications of the parent proteins (e.g. glycosylation, biotinylation, phosphorylation, ubiquitinylation, palmitoylation, or proteolysis). Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

The term "antibody" typically refers to a glycoprotein belonging to the immunoglobulin superfamily comprising at least two heavy (H) chains and two light (L) chains interconnected by disulfide bonds, or an antigen-binding portion thereof. Each heavy chain is comprised of a heavy chain variable region (abbreviated herein as VH or VH) and a heavy chain constant region (abbreviated herein as CH or CH). The heavy chain constant region can be further subdivided into three parts, referred to as CH1, CH2, and CH3 (or CH1, CH2, and CH3). The Fc- (Fragment crystallisable) region comprises two heavy chain constant regions, whereas the Fab (fragment, antigen-binding) region comprises one constant and one variable domain from each heavy and light chain of the antibody. Each light chain is comprised of a light chain variable region (abbreviated herein as VL or VL) and a light chain constant region (abbreviated herein as CL or CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody fragment" as used herein, refers to one or more fragments of an antibody that retain the ability to specifically bind to an antigen. Examples of binding fragments encompassed within the term "antibody fragment" include a fragment antigen binding (Fab) fragment, a Fab' fragment, a $F(ab')_2$ fragment, a heavy chain antibody, a single-domain antibody (sdAb), a single-chain fragment variable (scFv), a fragment variable (Fv), a $V_H$ domain, a $V_L$ domain, a single domain antibody, a nanobody, an IgNAR (immunoglobulin new antigen receptor), a di-scFv, a bispecific T-cell engager (BITEs), a dual affinity re-targeting (DART) molecule, a triple body, an alternative scaffold protein, and a fusion protein thereof.

The terms "$V_L$ region" and "$V_H$ region" refers to $V_L$ and $V_H$ regions of an antibody; i.e. the N-terminal variable region of the light chain of an immunoglobulin and the N-terminal variable region of the heavy chain of an immunoglobulin, respectively. The individual $V_L$ and $V_H$ regions are each composed of three hypervariable regions (complementary determining region (CDR)1, CDR2 and CDR3) and four framework regions (framework (FR) region 1, FR2, FR3, FR4). Identifying the respective subregions within a given sequence is routine in the art and may for example be accomplished by IgBlast of the NCBI. The variable regions of the heavy and the light chain form together the binding region of an antibody. In immunoglobulins, the $V_L$ and the $V_H$ regions are located on different polypeptide chains, but they can be located on the same chain in recombinant antibody derivatives. Interactions of a $V_L$ and a $V_H$ region allows the polypeptide of the present invention to interact with its respective target antigen.

The term "diabody" as used within this specification refers to a fusion protein or a bivalent antibody which can bind different antigens. A diabody is composed of two single protein chains which comprise fragments of an antibody, namely variable fragments. Diabodies comprise a heavy chain variable domain ($V_H$) connected to a light-chain variable domain ($V_L$) on the same polypeptide chain ($V_H$-$V_L$, or $V_L$-$V_H$). By using a short peptide connecting the two variable domains, the domains are forced to pair with the complementary domain of another chain and thus, create two antigen-binding sites. Diabodies can target the same (monospecific) or different antigens (bispecific).

As used in this specification the term "nucleic acid" comprises polymeric or oligomeric macromolecules, or large biological molecules, essential for all known forms of life. Nucleic acids, which include DNA (deoxyribonucleic acid) and RNA (ribonucleic acid), are made from monomers known as nucleotides. Most naturally occurring DNA molecules consist of two complementary biopolymer strands coiled around each other to form a double helix. The DNA strand is also known as polynucleotides consisting of nucleotides. Each nucleotide is composed of a nitrogen-containing nucleobase as well as a monosaccharide sugar called deoxyribose or ribose and a phosphate group. Naturally occurring nucleobases comprise guanine (G), adenine (A), thymine (T), uracil (U) or cytosine (C). The nucleotides are joined to one another in a chain by covalent bonds between the sugar of one nucleotide and the phosphate of the next, resulting in an alternating sugar-phosphate backbone. If the sugar is desoxyribose, the polymer is DNA.

If the sugar is ribose, the polymer is RNA. Typically, a polynucleotide is formed through phosphodiester bonds between the individual nucleotide monomers. In the context of the present invention the term "nucleic acid" includes but is not limited to ribonucleic acid (RNA), deoxyribonucleic acid (DNA), and mixtures thereof such as e.g. RNA-DNA hybrids (within one strand), as well as cDNA, genomic DNA, recombinant DNA, CRNA and mRNA. A nucleic acid may consist of an entire gene, or a portion thereof, the nucleic acid may also be a miRNA, siRNA, or a piRNA.

As used in this specification the term "vector", also referred to as an expression construct, is usually a plasmid or virus designed for protein expression in cells. The vector is used to introduce a specific gene into a target cell and can use the cell's mechanism for protein synthesis to produce the protein encoded by the gene. The expression vector is engineered to contain regulatory sequences that act as enhancer and promoter regions and lead to efficient transcription of the gene carried on the expression vector. The goal of a well-designed expression vector is the production of significant amount of stable messenger RNA, and therefore proteins. Examples of suitable vectors include but are not limited to plasmids, cosmids, phages, viruses or artificial chromosomes.

The term "pharmaceutical composition" as used in the present specification refers to a substance and/or a combination of substances being used for the identification, prevention or treatment of a tissue status or disease. The pharmaceutical composition is formulated to be suitable for administration to a patient in order to prevent and/or treat disease. Further a pharmaceutical composition refers to the combination of an active agent with a carrier, inert or active, making the composition suitable for therapeutic use. Pharmaceutical compositions can be formulated for oral, parenteral, topical, inhalative, rectal, sublingual, transdermal, subcutaneous or vaginal application routes according to their chemical and physical properties. Pharmaceutical compositions comprise solid, semisolid, liquid, transdermal therapeutic systems (TTS). Solid compositions are selected from the group consisting of tablets, coated tablets, powder, granulate, pellets, capsules, effervescent tablets or transdermal therapeutic systems. Also comprised are liquid compositions, selected from the group consisting of solutions, syrups, infusions, extracts, solutions for intravenous application, solutions for infusion or solutions of the carrier systems of the present invention. Semisolid compositions that can be used in the context of the invention comprise emulsion, suspension, creams, lotions, gels, globules, buccal tablets and suppositories.

The term "active agent" refers to the substance in a pharmaceutical composition or formulation that is biologically active, i.e. that provides pharmaceutical value. A pharmaceutical composition may comprise one or more active agents which may act in conjunction with or independently of each other. The active agent can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The term "disease" and "disorder" are used interchangeably herein, referring to an abnormal condition, especially an abnormal medical condition such as an illness or injury, wherein a cell, a tissue, an organ, or an individual is not able to efficiently fulfil its function anymore. Typically, but not necessarily, a disease is associated with specific symptoms or signs indicating the presence of such disease. The presence of such symptoms or signs may thus, be indicative for a cell, a tissue, an organ, or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a cell, tissue, organ or individual/patient to fulfil its function efficiently, whereas the "bettering" of a disease is typically characterised by an increase in the ability of a cell, tissue, an organ or an individual/patient to fulfil its function efficiently.

The term "hyperproliferative disorder" as used in the present application refers to disorders wherein the cell division of the cells is increased in relation to normal tissue. Such disorders are characterized by an abnormal proliferation (production) i.e. overproduction of cells. Hyperproliferative disorders comprise tumor diseases. Tumor diseases may comprise benign or malignant tumors wherein malignant tumor diseases are referred to as cancer. The term hyperproliferative disorder comprises cancers as well as pre-cancerous disorders. Cancer comprises proliferative disorders of mesenchymal origin, i.e. connective tissue (sarcomas) and of epithelial tissues (carcinomas). Common examples of sarcomas are osteosarcoma, chondrosarcoma, liposarcoma, leiomyosarcoma, angiosarcoma and fibrosarcoma and sarcomas of the gastrointestinal tract (GIST). Examples for carcinomas are carcinomas of the skin, testis, liver, gastrointestinal tract such as esophagus, stomach, pancreas, and colon, nasopharynx, bladder, cervix, ovarian, urethra, bladder; prostate and other genitourinary carcinomas, lung, kidney, endocrine tissues such as thyroid and pituitary gland, teratocarcinomas, carcinomas of the brain. Malignancies of the hematologic system are classified as lymphoma or leukemia. Inflammation orchestrates the microenvironment around tumors, contributing to proliferation, survival and migration of cancer cells, thus potentially promoting malignant disease.

Inflammation is in principle a protective immunovascular response that involves immune cells, blood vessels, and a plethora of molecular mediators. The purpose of inflammation is to eliminate the initial cause of cell injury, clear out necrotic cells and tissues damaged from the original insult and the inflammatory process, and to initiate tissue repair. The term "inflammatory disorder" as used in the context of the present invention refers to a situation wherein a physiological inflammatory response turns into a potentially harmful effect for the body. Inflammatory disorders causing damage to normal tissues comprise but are not limited to autoimmune disorders and neurodegenerative diseases.

The term "metabolic disorder," as used in the present specification, refers to diseases or disorders which affect how the body processes (i.e. metabolizes) substances needed to carry out physiological functions. Examples of metabolic disorders include, but are not limited to, diabetes, obesity, the metabolic syndrome and cardiovascular diseases.

The term "diabetes" or "diabetic disorder" or "diabetes mellitus," as used interchangeably herein, refers to a disease which is marked by elevated levels of sugar (glucose) in the blood. Diabetes can be caused by too little insulin (a chemical produced by the pancreas to regulate blood sugar), resistance to insulin, or both. In a preferred embodiment the diabetes is a type 2 diabetes mellitus (i.e. resistance to insulin).

The term "obesity" as used in the present specification, refers to a condition in which the subject has an excess of body fat relative to lean body mass. In a preferred embodiment, obesity is defined as a BMI (body mass index) over 30 $kg/m^2$.

The term "metabolic syndrome", as used in the present specification, and according to the WHO occurs in individuals with glucose intolerance, impaired glucose tolerance (IGT) or diabetes mellitus (DM), and/or insulin resistance, together with two or more of the components listed below:

1. Raised arterial pressure, i.e., ≥140/90 mm of Hg
2. Raised plasma triglyceride (≥150 mg/dl) and/or low HDL-C(<35 mg/dl in men and <39 mg/dl in women)
3. Central obesity, i.e., waist/hip ratio (WHR)>0.9 in men and >0.85 in women and/or body mass index (BMI)>30 $kg/m^2$
4. Microalbuminuria, i.e., urinary albumin excretion rate ≥20 μgm/minute or albumin/creatine ratio ≥30 μgm/mg.

The term "cardiovascular disorders", "cardiovascular diseases" and/or "cardiovascular conditions" are used interchangeably herein and as defined herein, include systemic (or essential) hypertension, pulmonary hypertension (e.g. pulmonary arterial hypertension, pulmonary hypertension of the neonate), congestive heart failure, coronary artery disease, atherosclerosis, stroke, thrombosis, conditions of reduced blood vessel patency (for example post percutaneous transluminal coronary angioplasty), peripheral vascular disease, renal disease (especially that occurring with diabetes), angina (including stable, unstable and variant (Prinzmetal) angina), hyperlipidemia, hypertriglyceridemia, hypercholesterolemia, mixed dyslipidemia and any condition where improved blood flow leads to improved end organ function.

The term "neurodegenerative disorders" are used interchangeably herein and as defined herein, include Alzheimer's disease, HIV-associated dementia, migraine, progressive supranuclear palsy, corticobasal degeneration, tauopathy, Pick's disease, Parkinson's disease, neuropathy, dementia with Lewy bodies, multiply system atrophy, Huntington's disease, spinal and bulbar muscular atrophy, Friedreich's ataxia, spinocerebellar ataxia, Creutzfeldt-Jakob disease, Gerstmann-Sträussler-Scheinker syndrome, fatal familial insomnia, kuru, amyotrophic lateral sclerosis, spinal muscular atrophy, and Batten disease, spinal cord injury, traumatic brain injury, neuropathic pain, multiple sclerosis, acute disseminated encephalomyelitis, Balo's Disease, Charcot-Marie-Tooth Disease, Guillain-Barre Syndrome, HTLV-I Associated Myelopathy, Neuromyelitis Optica, ptic nerve atrophy, Non-Arteritic Anterior Ischemic Optic Neuropathy, Schilder's Disease, Transverse Myelitis, transverse myelitis, stroke, epilepsies, diabetic neuropathy.

The "$EC_{50}$" value refers to half maximal effective concentration of a substance and is thus a measure of the concentration of said substance which induces a response halfway between the baseline and maximum after a specified exposure time. The $EC_{50}$ of a graded dose response curve therefore represents the concentration of a substance where 50% of its maximal effect is observed. Typically, the polypeptide and polypeptide multimers of the present invention exhibit an $EC_{50}$ value of binding to the TNFR2 receptor of between 50 nM to 1 pM, more preferably 10 nM to 10 pM, and even more preferably between 1 nM and 50 pM, i.e. 50 nM, 10 nM, 1 nM, 900 pM, 800 pM, 700 pM, 600 pM, 500 pM, 400 pM, 300 pM, 200 pM, 100 pM, 50 pM, or 1 pM.

"Pharmaceutically acceptable" means approved by a regulatory agency of the Federal or a state government or listed in the U.S. Pharmacopeia, European Pharmacopeia (Ph. Eur.) or other generally recognized pharmacopeia for use in animals, and more particularly in humans.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

EMBODIMENTS

In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention provides a polypeptide, comprising a binding domain consisting of three peptide TNF homology domains of TNF-ligand family member proteins (THD) that specifically bind to the extracellular part of TNFR2, wherein the C-terminus of the first and second THD, respectively, which is in each case defined by the C-terminal consensus sequence V-F/Y-F-G-A/I-$X_1$ (SEQ ID NO: 1), is linked to the N-terminus of the second and third THD, respectively, which is in each case defined by the N-terminal consensus sequence P-V/A-A-H-V/L (SEQ ID NO: 2) through a peptide $X_a$, which is in each case independently selected and has a length of 9 to 12 amino acids, preferably 9 to 11, more preferably 9 to 10, preferably wherein $X_a$ does not comprise the amino acid sequence S-S-R-T-P-S-D-K (SEQ ID NO: 10); wherein $X_1$ is a non-polar/hydrophobic or polar/neutral amino acid, preferably selected from the group consisting of F and I.

In the work leading to the present invention, it was shown that shortening of the linking peptide $X_a$ increased thermal stability significantly, while the biological activity was simultaneously dramatically reduced. Surprisingly the inventors identified a narrow range for the size of the peptide $X_a$ that resulted in a significantly increased stability while maintaining biological activity, such as binding to the respective receptor, preferably TNFR2.

Accordingly, it is preferred that the polypeptide of the present invention has a thermal stability, as measured by dynamic light scattering as disclosed herein, of at least 63° C., at least 64° C., at least 65° C., at least 66° C., at least 67° C., more preferably at least 65° C., at least 66° C., most preferably at least 66° C.

It is further preferred that the polypeptides of the present invention have a certain bioactivity with regard to the activation of the TNFR2 receptor. One preferred example of this bioactivity is the activation of the TNFR2 receptor on Kym-1 cells as described in example 5. Preferably the polypeptides of the present invention have an $EC_{50}$ value for the activation of the TNFR2 receptor, preferably on Kym-1 cells with TNFR2 crosslinking with antibody 80M2, of less than 400 pM, less than 350 pM, less than 300 pM, less than 250 pM, more preferably less than 300 pM.

The C-terminal and N-terminal consensus sequences serve the purpose of providing a reference point for the end of the region of the THD of the TNF-family members that are necessarily included in the polypeptide of the present invention. This is exemplarily illustrated by the preferred examples of the TNF-family members TNF-alpha and LT-alpha. In SEQ ID NO 5 the sequence of human TNF-alpha is disclosed. The C-terminal sequence is VYFGII (SEQ ID NO 3) corresponding to amino acids 226 to 231 of SEQ ID NO 5, whereas the N-terminal sequence is PVAHV (SEQ ID NO 4) corresponding to amino acids 88 to 92 of SEQ ID NO 5. In SEQ ID NO 55 the sequence of human LT-alpha is disclosed. The C-terminal sequence is VFFGAF (SEQ ID NO 56) corresponding to amino acids 198 to 203 of SEQ ID NO 55, whereas the N-terminal sequence is PAAHL (SEQ ID NO 57) corresponding to amino acids 63 to 67 of SEQ ID NO 55.

In a preferred embodiment of the first aspect of the present invention, the peptide $X_a$ consists of $X_C$-$X_L$-$X_N$, wherein $X_C$ is selected from the group consisting of A, A-L, L, preferably A and A-L, more preferably A-L;

$X_L$ is absent or is an amino acid linker consisting of 1-11, preferably 1-10, more preferably 1-9 amino acids, most preferably 4 to 8 amino acids;

$X_N$ is absent or selected form the group consisting of K, D-K, S-D-K, P-S-D-K (SEQ ID NO: 6), T-P-S-D-K (SEQ ID NO: 7), R-T-P-S-D-K (SEQ ID NO: 8), S-R-T-P-S-D-K (SEQ ID NO: 9), S-S-R-T-P-S-D-K (SEQ ID NO: 10), T-K, S-T-K, H-S-T-K (SEQ ID NO: 11), A-H-S-T-K (SEQ ID NO: 12), L-A-H-S-T-K (SEQ ID NO: 13), H-L-A-H-S-T-K (SEQ ID NO: 14), L-H-L-A-H-S-T-K (SEQ ID NO: 15), preferably S-S-R-T-P-S-D-K (SEQ ID NO: 10), S-D-K.

In a more preferred embodiment of the first aspect of the present invention, the peptide $X_a$ consists of $X_C$-$X_L$-$X_N$, wherein $X_C$ is selected from the group consisting of A, A-L, L, preferably A and A-L, more preferably A-L;

$X_L$ is absent or is an amino acid linker consisting of 1-11, preferably 1-10, more preferably 1-9 amino acids, most preferably 4 to 8 amino acids;

$X_N$ is absent or selected form the group consisting of K, D-K, S-D-K, P-S-D-K (SEQ ID NO: 6), T-P-S-D-K (SEQ ID NO: 7), R-T-P-S-D-K (SEQ ID NO: 8), S-R-T-P-S-D-K (SEQ ID NO: 9), T-K, S-T-K, H-S-T-K (SEQ ID NO: 11), A-H-S-T-K (SEQ ID NO: 12), L-A-H-S-T-K (SEQ ID NO: 13), H-L-A-H-S-T-K (SEQ ID NO: 14), L-H-L-A-H-S-T-K (SEQ ID NO: 15), preferably S-R-T-P-S-D-K (SEQ ID NO: 9), R-T-P-S-D-K (SEQ ID NO: 8), T-P-S-D-K (SEQ ID NO: 7), P-S-D-K (SEQ ID NO: 6) S-D-K, more preferably R-T-P-S-D-K (SEQ ID NO: 8) and S-R-T-P-S-D-K (SEQ ID NO: 9).

The peptide $X_a$ consists of the three components $X_C$, $X_L$ and $X_N$, whereas $X_L$ and $X_N$ can be present or absent, with the proviso that at least one of the components $X_L$ and $X_N$ is present. $X_C$ contains amino acids originating from the C-terminal end of the TNF-ligand family member. $X_L$ is an amino acid linker. Preferably the amino acid linker is a glycine-serine linker. $X_N$ contains amino acids originating from the N-terminal end of the THD of a TNF-ligand family member, preferably wherein $X_N$ does not comprise the amino acid sequence S-S-R-T-P-S-D-K (SEQ ID NO: 10).

In a preferred embodiment of the first aspect of the invention, the three THDs of the polypeptide of the present invention are identical in their amino acid sequence.

In a preferred embodiment of the first aspect of the present invention, the C-terminus of the first and second THD, respectively, is in each case defined by the C-terminal sequence V-Y-F-G-I-I (SEQ ID NO: 3) and the N-terminus of the second and third THD, respectively, is in each case defined by the N-terminal sequence P-V-A-H-V (SEQ ID NO: 4). These C-terminal and N-terminal sequences originate from human TNF-alpha.

In a preferred embodiment of the first aspect of the present invention, the THD comprises a contiguous amino acid sequence consisting of amino acids 88 to 231 of SEQ ID NO. 5, optionally comprising at least one mutation selected from the group consisting of: D143Y, D143F, D143E, D143N, D143T, D143S, E146Q, E146H, E146K, A145R/S147T, Q88N/T89S/A145S/E146A/S147D, Q88N/A145I/E146G/S147D, A145H/E146S/S147D, A145H/S147D, L29V/A145D/E146D/S147D, A145N/E146D/S147D, A145T/E146S/S147D, A145Q/E146D/S147D, A145T/E146D/S147D, A145D/E146G/S147D, A145D/S147D, A145K/E146D/S147T, A145R/E146T/S147D, A145R/S147T, E146D/S147D, E146N/S147, S95C/G148C, K65A, K65W, Q67K, Q67T, Q67Y, L75H, L75W, D143W, D143V, D143V/F144L/A145S, D143N/A145R, D143V/A145S, L29V, L29T, L29S, L29A, L29G, R31H, R31I, R31L, R32G, R32E, S147L, S147R, S147P S147T, S147A, Q149E, Q149N, E146D, E146N, E146S, E146G, A145R, A145S, A145T, A145H, A145K, A145F, A145D, A145G, A145N, A145P, A145Q, A145Y, A145V and A145W, preferably selected from D143N and A145R.

The mutations disclosed above increase the specificity of binding to the extracellular part of TNFR2. Preferably the mutations decrease binding affinity to TNFR1, while essentially maintaining the affinity for TNFR2, thereby increasing the specificity for TNFR2 (i.e. the Kd for binding to TNFR2 is at least 10-fold, at least 100-fold, at least 1.000-fold, preferably at least 5.000-fold, higher than the Kd for binding to TNFR1).

These mutations are known in the art and are disclosed in Loetscher et al (JBC, vol 268, no 35, pp. 26350-26357, 1993; see Table 1), Abe et al (Biomaterials 32 (2011) 5498-5504; see Table 1), Ando et al (Biochemistry and Biophysics Reports, 7; 2016; 309-315; see Table 2) and Ban et al (Molecular and Cellular Therapies (2015) 3:7). Preferably, the polypeptide comprises 5, 4, 3, 2, or 1, more preferably 2 or 1, most preferably 1 of these mutations.

In a preferred embodiment of the first aspect of the present invention, $X_C$ is selected from A or A-L, $X_L$ is absent or is a glycine and/or serine linker with a length of 1 to 11, preferably 1-10, more preferably 1-9 amino acids, most preferably 4 to 8 amino acids, and $X_N$ is absent or is selected from K, D-K, S-D-K, P-S-D-K (SEQ ID NO: 6), T-P-S-D-K (SEQ ID NO: 7), R-T-P-S-D-K (SEQ ID NO: 8), S-R-T-P-S-D-K (SEQ ID NO: 9) and S-S-R-T-P-S-D-K (SEQ ID NO: 10); more preferably is selected from K, D-K, S-D-K, P-S-D-K (SEQ ID NO: 6), T-P-S-D-K (SEQ ID NO: 7), R-T-P-S-D-K (SEQ ID NO: 8) and S-R-T-P-S-D-K (SEQ ID NO: 9).

In a preferred embodiment of the first aspect of the present invention, $X_C$ is selected from A or A-L, $X_L$ is selected from G, S, G-G, S-G, G-S, G-G-G, S-G-G, G-S-G, G-G-S, G-G-G-G (SEQ ID NO: 16), G-G-G-S(SEQ ID NO: 17), G-G-S-G (SEQ ID NO: 18), G-S-G-G (SEQ ID NO: 19), S-G-G-G (SEQ ID NO: 20), G-G-G-G-G (SEQ ID NO: 21), S-G-G-G-G (SEQ ID NO: 22), G-S-G-G-G (SEQ ID NO: 23), G-G-S-G-G (SEQ ID NO: 24), G-G-G-S-G (SEQ ID NO: 25), G-G-G-G-S(SEQ ID NO: 26), G-G-G-G-G-G (SEQ ID NO: 27), S-G-G-G-G-G (SEQ ID NO: 28), G-S-G-G-G-G (SEQ ID NO: 29), G-G-S-G-G-G (SEQ ID NO: 30), G-G-G-S-G-G (SEQ ID NO: 31), G-G-G-G-S-G (SEQ ID NO: 32), G-G-G-G-G-S(SEQ ID NO: 33), G-G-G-S-G-G-G-S(SEQ ID NO: 34), S-G-G-G-S-G-G-G (SEQ ID NO: 35), G-G-G-G-G-G-G-G (SEQ ID NO: 36), G-S-G-G-G-S-G-G (SEQ ID NO: 37), G-G-S-G-G-G-S-G (SEQ ID NO: 38), S-G-G-G-S-G-G-G-S(SEQ ID NO: 39), G-S-G-G-G-S-G-G-G (SEQ ID NO: 40), G-G-S-G-G-G-S-G-G (SEQ ID NO: 41), G-G-G-S-G-G-G-S-G (SEQ ID NO: 42), S-G-G-G-S-G-G-G-S-G (SEQ ID NO: 43), G-S-G-G-G-S-G-G-G-S(SEQ ID NO: 44), G-G-S-G-G-G-S-G-G-G (SEQ ID NO: 45), G-G-G-S-G-G-G-S-G-G (SEQ ID NO: 46), S-G-G-G-S-G-G-G-S-G-G (SEQ ID NO: 47), G-S-G-G-G-S-G-G-G-S-G (SEQ ID NO: 48), G-G-S-G-G-G-S-G-G-G-S (SEQ ID NO: 49) and G-G-G-S-G-G-G-S-G-G-G (SEQ ID NO: 50), preferably G-G-G-G (SEQ ID NO: 16), G-G-G-G-S(SEQ ID NO: 26) and G-G-

G-S-G-G-G-S(SEQ ID NO: 34), more preferably G-G-G-G (SEQ ID NO: 16) and G-G-G-S-G-G-G-S(SEQ ID NO: 34); and $X_N$ is absent or is selected from K, D-K, S-D-K, P-S-D-K (SEQ ID NO: 6), T-P-S-D-K (SEQ ID NO: 7), R-T-P-S-D-K (SEQ ID NO: 8), S-R-T-P-S-D-K (SEQ ID NO: 9) and S-S-R-T-P-S-D-K (SEQ ID NO: 10); more preferably is selected from K, D-K, S-D-K, P-S-D-K (SEQ ID NO: 6), T-P-S-D-K (SEQ ID NO: 7), R-T-P-S-D-K (SEQ ID NO: 8) and S-R-T-P-S-D-K (SEQ ID NO: 9).

In a preferred embodiment $X_L$ is a glycine/serine linker with a length of 1 to 11, preferably 1-10, more preferably 1-9 amino acids, most preferably 4 to 8 amino acids, and a glycine to serine content of 3:1. In other words for every three glycines one serine is present. Preferably, each serine is separated from another serine by three glycines.

In a preferred embodiment of the first aspect of the present invention, $X_C$ is A-L, $X_L$ is absent and $X_N$ is selected from S-R-T-P-S-D-K (SEQ ID NO: 9), S-S-R-T-P-S-D-K (SEQ ID NO: 10), S-S-S-R-T-P-S-D-K (SEQ ID NO: 51) and R-S-S-S-R-T-P-S-D-K (SEQ ID NO: 52), preferably S-R-T-P-S-D-K (SEQ ID NO: 9) and S-S-R-T-P-S-D-K (SEQ ID NO: 10); more preferably is selected from S-R-T-P-S-D-K (SEQ ID NO: 9).

In a preferred embodiment of the first aspect of the present invention, $X_C$ is A-L, $X_L$ is G-G-G-G (SEQ ID NO: 16) and $X_N$ is selected from S-D-K, P-S-D-K (SEQ ID NO: 6), T-P-S-D-K (SEQ ID NO: 7), R-T-P-S-D-K (SEQ ID NO: 8).

In a preferred embodiment of the first aspect of the present invention, $X_C$ is A-L, $X_L$ is G-G-G-S-G-G-G-S(SEQ ID NO: 34) and $X_N$ is selected from K and D-K.

In a preferred embodiment of the first aspect of the present invention, $X_C$ is A-L, $X_L$ is G and $X_N$ is selected from R-T-P-S-D-K (SEQ ID NO: 8), S-R-T-P-S-D-K (SEQ ID NO: 9), preferably S-R-T-P-S-D-K (SEQ ID NO: 9).

In a preferred embodiment of the first aspect of the present invention, $X_C$ is A-L, $X_L$ is G-G and $X_N$ is selected from T-P-S-D-K (SEQ ID NO: 7), R-T-P-S-D-K (SEQ ID NO: 8), S-R-T-P-S-D-K (SEQ ID NO: 9), preferably R-T-P-S-D-K (SEQ ID NO: 8).

In a preferred embodiment of the first aspect of the present invention, $X_C$ is A-L, $X_L$ is G-G-G and $X_N$ is selected from P-S-D-K (SEQ ID NO: 6), T-P-S-D-K (SEQ ID NO: 7), R-T-P-S-D-K (SEQ ID NO: 8), S-R-T-P-S-D-K (SEQ ID NO: 9), preferably T-P-S-D-K (SEQ ID NO: 7).

In a preferred embodiment of the first aspect of the present invention, $X_C$ is A-L, $X_L$ is G-G-G-G (SEQ ID NO: 16) and $X_N$ is selected from S-D-K, P-S-D-K (SEQ ID NO: 6), T-P-S-D-K (SEQ ID NO: 7), R-T-P-S-D-K (SEQ ID NO: 8) preferably P-S-D-K (SEQ ID NO: 6).

In a preferred embodiment of the first aspect of the present invention, the polypeptide has an onset of aggregation temperature ($T_m$) as determined by dynamic light scattering of more than 62° C., more than 63° C., more than 64° C., more than 65° C., more than 66° C., more than 67° C., more than 68° C., preferably more than 65° C., more than 66° C. or more than 67° C., most preferably more than 66° C. or more than 67° C. The onset of aggregation temperature ($T_m$) is preferably determined by dynamic light scattering as disclosed herein in example 4. The onset of aggregation in response to increased temperatures is an indication for the denaturation of proteins. The higher an onset of aggregation temperature of a protein, such as the polypeptide of the present invention, is the more thermally stable a protein is. The terms 'denaturation temperature' and 'aggregation temperature' are used synonymously herein.

In a second aspect, the present invention provides a polypeptide multimer comprising at least two polypeptides according to the first aspect of the invention that are (a) linked together, preferably linked together by an amino acid linker that has a length of between 1 to 30 amino acids, preferably 7 to 15 amino acids; or (b) linked to a protein, preferably selected from the group consisting of: a multimerization domain, a serum protein, a cytokine, a targeting moiety or a toxine, preferably a multimerization domain;

optionally wherein said polypeptides are linked to said protein by an amino acid linker that has a length of between 1 to 30 amino acids, preferably 7 to 15 amino acids.

In a preferred embodiment of the second aspect of the invention, the polypeptides of the first aspect of the invention are linked together to form a chain-like structure, wherein the polypeptides are linked to each other directly by their amino terminal, or carboxy-terminal end. In case of an amino acid linker present the linker is attached to the amino terminal, or carboxy-terminal end of the polypeptide. In a preferred embodiment the chain like structure further includes a protein bound to at least one polypeptide of the first aspect of the invention. Preferred examples of such proteins are a multimerization domain, a serum protein, a cytokine, a targeting moiety or a toxin.

The polypeptide multimer of the present invention have, like the polypeptides of the present invention, an increased stability, in particular thermal stability, while retaining their biological activity. In the case a linker is absent the polypeptides of the first aspect of the invention are directly linked to the multimerization domain.

Accordingly, it is preferred that the polypeptide multimer of the present invention has a thermal stability ($T_m$), i.e. onset of aggregation temperature, as measured by dynamic light scattering as disclosed herein, of more than 71° C., at least 72° C., at least 73° C., at least 74° C., preferably at least 72° C., at least 73° C., at least 74° C., at least 75° C., at least 76° C., at least 77° C. or at least 78° C., more preferably at least 74° C. The higher the onset of aggregation temperature is, the more thermally stable the polypeptide multimer is.

Another preferred example of the stability of the polypeptide multimer of the present invention is the stability after 3 days of incubation in human plasma at 37° C., as disclosed in example 10. Preferably, the $EC_{50}$ of the polypeptide multimer of the present invention for binding to TNFR2 in HeLa-TNF-R2 cells according to example 10 after 3 days of incubation in human plasma at 37° C., is not decreased by more than 15%, 12%, 10%, preferably 10%, as compared to the $EC_{50}$ before incubation human plasma.

Another preferred example of the stability of the polypeptide multimer of the present invention is the stability after 8 days of incubation in human plasma at 37° C., as disclosed in example 10. Preferably, the $EC_{50}$ of the polypeptide multimer of the present invention for binding to TNFR2 in HeLa-TNF-R2 cells according to example 10 after 3 days of incubation in human plasma at 37° C., is not decreased by more than 15%, 12%, 10%, preferably 10%, as compared to the $EC_{50}$ before incubation human plasma.

It is further preferred that the polypeptide multimers of the present invention have a certain bioactivity regarding the activation of the TNF R2 receptor.

Accordingly, it is preferred that the polypeptide multimer of the present invention has a biological activity as assessed by binding to TNFR2 expressed on mouse embryonic fibroblasts (MEFs) as disclosed in example 7 of less than $EC_{50}$ of 100 pM, preferably less than 80 pM, more preferably less than 70 pM. Preferably, the polypeptide multimers of the present invention do not bind to TNFR1 under the conditions of example 7.

Another preferred example of this bioactivity is the binding to TNFR2 on Kym-1 cells, as disclosed in example 8, wherein the $EC_{50}$ is less than 200 pM, less than 150 pM, less than 100 pM, less than 75 pM, preferably less than 100 pM pr less than 75 pM, more preferably less than 75 pM.

Another preferred example of this bioactivity is the activation of NF-κB in HeLa-TNF-R2 cells as disclosed in example 9, wherein the $EC_{50}$ is less than 30 pM, less than 20 pM, less than 10 pM, less than 5 pM, preferably less than 10 pM or less than 5 pM, more preferably less than 5 pM.

In a preferred embodiment of the second aspect of the invention the amino acid linker that links the polypeptides to the protein, preferably a multimerization domain, has a length of 5 to 50, 5 to 45, 7 to 40, 7 to 35, 7 to 30, 7 to 25, 7 to 20, 7 to 15, 7 to 12, 9 to 11 amino acids, preferably 7 to 15, 7 to 12, 9 to 11 more preferably 7 to 12 or 9 to 11, most preferably 9 to 11 amino acids.

In a preferred embodiment of the second aspect of the invention the amino acid linker that links the polypeptide of the present invention to the protein, preferably a multimerization domain, is a glycine-serine linker.

In a preferred embodiment of the second aspect of the invention the amino acid linker that links the polypeptide of the present invention to the protein, preferably a multimerization domain, is GGSGGGGSGG (SEQ ID NO: 92).

In a preferred embodiment of the second aspect of the invention the amino acid linker that links the polypeptide of the present invention to the protein, preferably a multimerization domain, comprises a consensus sequence for N-glycosylation.

In a preferred embodiment the polypeptide of the present invention is linked to the N-terminal end of the protein, preferably a multimerization domain, optionally by the amino acid linker of the second aspect of the invention.

In a preferred embodiment the polypeptide of the present invention is linked to the C-terminal end of the protein, preferably a multimerization domain, optionally by the amino acid linker of the second aspect of the invention.

In a preferred embodiment at least one polypeptide of the present invention is linked to the N-terminal end of the protein, preferably a multimerization domain, and at least one polypeptide is linked to the C-terminal end of the protein, preferably the multimerization domain, optionally each of these linkages include separately from each other the amino acid linker of the second aspect of the invention.

In a preferred embodiment of the second aspect of the invention, the multimerization domain is a dimerization domain.

Preferred dimerization domains are dimerization domains from an antibody, including but not limited to an antibody, an antibody heavy chain, a Fc region, heavy chain domain 2 (CH2) of IgM (MHD2), heavy chain domain 2 (CH2) of IgE (EHD2), heavy chain domain 3 (CH3) of IgG, heavy chain domain 3 (CH3) of IgA, heavy chain domain 3 (CH3) of IgD, heavy chain domain 4 (CH4) of IgM, heavy chain domain 4 (CH4) of IgE, Fab, $Fab_2$, and the CH1 and CL domain. A preferred dimerization domain from an antibody, is the Fc region, variants or fragments thereof. The Fc region usable as dimerization domain preferably originates from the following isotypes IgA, IgD, IgE, IgG, and IgM Further preferred dimerization domains are the immunoglobulin Fc region mutants without FcR and/or C1q binding. Preferred examples of immunoglobulin Fc region mutants without FcR and/or C1q binding are FcΔab, LALA, LALA-GP, IgG2, IgG2σ, aglycosylated IgG1, IgG1 (L234F/L235E/P331S), IgG2m4 and IgG4 ProAlaAla. An even more preferred examples of a Fc region mutant is FcΔab which lacks Fcγ receptor I binding and C1q binding (Armour et al; Eur. J. Immunol. 1999, 29:2613-2624).

Other dimerization or multimerization domains include barnase-barstar, C4 bp, CD59, peptides derived from collagen, leucine zipper motifs, miniantibodies, and ZIP miniantibodies, GST, the α and β subunits of inactive human chorionic gonadotropin, maltose-binding protein (MBP), p53 and fragments thereof, phosphatase, streptavidin, surfactant protein D, tenascin, tetranectin, dock-and-lock (DNL) motifs, and uteroglobin.

In a preferred embodiment of the second aspect of the invention, the multimerization domain is a trimerization domain.

Preferred trimerization domains are tenascin C (TNC), the trimerization region of the C-terminal noncollagenous domain (NC1) of collagen XVIII, Fab3 like molecules, and TriBi-minibodies, more preferably TNC.

In a preferred embodiment of the second aspect of the invention, the multimerization domain is a tetramerization domain.

Preferred tetramerization domains are the tetramerization domain of p53, the tetramerization domain of the general control protein 4 (GCN4), the tetramerization domain of VASP (vasodilator stimulated phosphoprotein), tandem diabodies, and di-diabodies.

In a preferred embodiment of the second aspect of the invention, the protein the polypeptides are linked to is a ligand specific for a tissue, organ or cell-type. Preferably the ligand is a targeting moiety that is specific for an organ, tissue or cell-type. More preferably the targeting moiety is specific for cells of the immune system (e.g. regulatory T cells (Treg); costimulatory ligands), cells of the central nervous system (e.g. microglial cells), cardiac muscle (including cardiac precursor cells), colon, skin, inflamed tissues or pancreatic cells.

In a preferred embodiment of the second aspect of the invention, the polypeptide multimer further comprises a ligand specific for a tissue, organ or cell-type. Preferably the ligand is a targeting moiety that is specific for an organ, tissue or cell-type. More preferably the targeting moiety is specific for cells of the immune system (e.g. regulatory T cells (Treg); costimulatory ligands), cells of the central nervous system (e.g. microglial cells), cardiac muscle (including cardiac precursor cells), colon, skin, inflamed tissues or pancreatic cells. Preferably the targeting moiety is present in the polypeptide multimer in addition to the protein the polypeptides are linked to.

In a preferred embodiment of the second aspect of the invention, the targeting moiety is binding to a target selected from transferrin receptor, CD98, IGF1R, LRP1, insulin receptor, low-density lipoprotein receptors (LDLR), diphtheria toxin receptor, efflux pumps, CD25, CD28, GLUT1, LAT1, TMEM119, PDGFR, VEGFR1, VEGFR3, and receptors for RVG-29.

In a preferred embodiment of the second aspect of the invention, the protein the polypeptides are linked to is a cytokine, preferably IL-2 or TGFβ, or a half-life extension domain, preferably an albumin-binding moiety, an immunoglobulin-binding moiety, a PEG-mimetic polypeptide, PEGylation, or HESylation.

In a preferred embodiment of the second aspect of the invention, the polypeptide multimer further comprises a cytokine, preferably IL-2 or TGFβ, or a half-life extension domain, preferably an albumin-binding moiety, an immunoglobulin-binding moiety, a PEG-mimetic polypeptide, PEGylation, or HESylation. Preferably the cytokine, half-life extension domain or immunoglobulin-binding moiety is present in the polypeptide multimer in addition to the protein the polypeptides are linked to.

In a third aspect, the present invention provides a nucleic acid molecule encoding the polypeptide according to the first aspect of the invention or the polypeptide multimer according to the second aspect of the invention. The nucleic acid may be RNA or DNA or a hybrid thereof. Preferably, the nucleic acid also comprises sequences allowing for the expression of the polypeptide according the first and second aspect of the present invention in a suitable expression system. The nucleic acid can be codon optimized for the respective expression system.

In a fourth aspect, the present invention provides a vector encoding the nucleic acid molecule according to the third aspect of the invention. It is preferred that the polypeptide or polypeptide multimer of the present invention is encoded by the introduced nucleic acid molecule according to the third aspect of the invention are expressed within a cell upon introduction of the vector or vectors. Preferably, the vector provides for transcription and expression of the polypeptide encoded by the nucleic acid in a suitable host cell system. Preferably, the expression vector is selected from the group consisting of a bacterial, yeast, baculovirus, plant, viral and mammalian expression vector, more preferably the expression vector is a bacterial expression vector or a cell-free expression vector.

In a fifth aspect, the present invention provides a polypeptide according to the first aspect of the invention, a polypeptide multimer according to the second aspect of the invention, a nucleic acid according to the third aspect of the invention or a vector according to the fourth aspect of the invention for use as a medicament.

In a sixth aspect, the present invention provides a pharmaceutical composition comprising as an active agent a polypeptide according to the first aspect of the invention, a polypeptide multimer according to the second aspect of the invention, a nucleic acid according to the third aspect of the invention or a vector according to the fourth aspect of the invention. The pharmaceutical composition preferably further comprises pharmaceutical acceptable carriers and/or suitable excipients. The pharmaceutical composition is selected from the group consisting of solid, liquid, semi-solid or transdermal therapeutic systems. It is envisioned that the pharmaceutical compositions of the invention comprise one or more polypeptides of the first and/or polypeptide multimers of the second aspect of the invention.

In a seventh aspect, the present invention provides a polypeptide according to the first aspect of the invention, a polypeptide multimer according to the second aspect of the invention, a nucleic acid according to the third aspect of the invention, a vector according to the fourth aspect of the invention or a pharmaceutical composition according to the fifth aspect of the invention for use in the prophylaxis or treatment of hyperproliferative disorders, inflammatory disorders, autoimmune disorders and metabolic diseases, cardiovascular diseases, neuropathic diseases and neurological insults.

Preferred hyperproliferative diseases are cancer or malignancies of the hematologic system.

Particularly preferred cancers to be prevented or treated by the polypeptide or the polypeptide multimers of the present invention are carcinomas of the gastrointestinal tract, liver, kidney, bladder, prostate, endometrium, ovary, testes, skin, invasive oral cancers, small cell and non-small cell lung carcinomas, hormone-dependent breast cancers, hormone-independent breast cancers, transitional and squamous cell cancers, neurological malignancies including neuroblastoma, gliomas, astrocytomas, osteosarcomas, soft tissue sarcomas, hemangioamas, endocrinological tumors, hematologic neoplasias including leukemias, lymphomas, and other myeloproliferative and lymphoproliferative diseases, carcinomas in situ, hyperplastic lesions, adenomas, fibromas, histiocytosis, chronic inflammatory proliferative diseases, vascular proliferative diseases and virus-induced proliferative diseases, skin diseases characterized by hyperproliferation of keratinocytes and/or T cells. Particular preferred diseases treatable with the compounds of the present invention are solid tumors, in particular lung, breast, pancreas, colorectal, ovarian, prostatic and gastric cancers and adenocarcinomas.

Preferred inflammatory diseases to be prevented or treated by the polypeptide or the polypeptide multimers of the present invention include but are not limited to Acute disseminated encephalomyelitis (ADEM), Addison's disease, Agammaglobulinemia, Alopecia areata, Amyotrophic lateral sclerosis (Also Lou Gehrig's disease; Motor Neuron Disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopeniaurpura, Autoimmune urticarial, Autoimmune uveitis, Balo disease/Balo concentric sclerosis, Behçet's disease, Berger's disease, Bickerstaff's encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Dressler's syndrome, Drug-induced lupus, Eczema, Endometriosis, Enthesitis-related arthritis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressive, Fibrosing alveolitis (or Idiopathic pulmonary fibrosis), Gastritis, Gastrointestinal pemphigoid, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenia purpura (See Autoimmune thrombocytopeniaurpura), IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka *Pityriasis lichenoides* et varioliformis *acuta*, Multiple sclerosis, Myasthenia gravis, Myositis, Ménière's disease, Narcolepsy, Neuromyelitis optica (also Devic's disease), Neuromyotonia, Occular cicatricial pemphigoid, Opsoclonus, yoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatic, Polymyositis, Primary biliary cirrhosis, Primary sclerosing cholangitis, Progressive inflammatory neuropathy, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome another form of APS, Schnitzler syndrome, Scleritis, Scleroderma, Serum Sickness, Sjögren's syndrome, Spondyloarthropathy, Stiff person syndrome, Still's disease see Juvenile Rheumatoid Arthritis, Subacute bacterial endocarditis (SBE), Susac's syndrome, Sweet's syndrome, Sydenham chorea, Sympathetic ophthalmia, Systemic lupus erythematosus see Lupus erythematosus, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), undifferentiated connective tissue disease different from Mixed connective tissue disease, undifferentiated spondyloarthropathy, Urticarial vasculitis, Vasculitis, Vitiligo, and Wegener's granulomatosis. Hypersensitivity includes but is not limited to allergy, such as asthma, anaphylaxis or atopy; cytotoxic-antibody-dependent diseases such as autoimmune hemolytic anemia, thrombocytopenia, rheumatic heart disease, erythroblastosis fetal, Goodpasture's syndrome, membranous nephropathy, Graves' disease, myasthenia gravis; immune complex diseases such as serum sickness, arthus reaction, rheumatoid arthritis, post streptococcal glomerulo nephritis, lupus nephritis systemic lupus erythematosus, extrinsic allergic alveolitis (hypersensitivity pneumonitis), cell-mediated immune response such as contact dermatitis, Mantoux test, chronic transplant rejection, and multiple sclerosis.

Particularly preferred neurodegenerative disorders to be prevented or treated by the polypeptide or the polypeptide multimer of the present invention include Alzheimer's disease, HIV-associated dementia, migraine, progressive supranuclear palsy, corticobasal degeneration, tauopathy, Pick's disease, Parkinson's disease, neuropathy, dementia with Lewy bodies, multiply system atrophy, Huntington's disease, spinal and bulbar muscular atrophy, Friedreich's ataxia, spinocerebellar ataxia, Creutzfeldt-Jakob disease, Gerstmann-Sträussler-Scheinker syndrome, fatal familial insomnia, kuru, amyotrophic lateral sclerosis, spinal muscular atrophy, and Batten disease, spinal cord injury, traumatic brain injury, neuropathic pain, multiple sclerosis, acute disseminated encephalomyelitis, Balo's Disease, Charcot-Marie-Tooth Disease, Guillain-Barre Syndrome, HTLV-I Associated Myelopathy, Neuromyelitis Optica, ptic nerve atrophy, Non-Arteritic Anterior Ischemic Optic Neuropathy, Schilder's Disease, Transverse Myelitis, transverse myelitis, stroke, epilepsies, diabetic neuropathy.

Particularly preferred cardiovascular diseases to be prevented or treated by the polypeptide or the polypeptide multimer of the present invention include but are not limited to hyperlipidemia, hypertriglyceridemia, hypercholesterolemia, mixed dyslipidemia, coronary heart disease, atherosclerosis, peripheral vascular disease, cardiomyopathy, vasculitis, inflammatory heart disease, ischemic heart disease, congestive heart failure, valvular heart disease, hypertension, myocardial infarction, diabetic cardiac conditions, embolism, aneurysm, hypertensive heart disease, pseudoaneurysm, stroke and arrhythmia.

Particularly preferred metabolic diseases to be prevented or treated by the polypeptide or the polypeptide multimer of the present invention include but are not limited to diabetes, obesity, the metabolic syndrome and insulin resistance.

EXAMPLES

Example 1: Genetic Engineering of Proteins of the Present Invention

Human TNFR2-selective TNF ($TNF_{R2}$) mutant domains were designed from the ectodomain of human TNF comprising the mutations D143N/A145R, which exhibit an exclusive specificity for TNFR2 and, thus restrict the bioactivity of the molecules to TNF receptor 2 (Loetscher et al., 1993, J. Biol. Chem. 268, 26350-26357). The TNFR2-selective TNF ($TNF_{R2}$) mutant domains used to generate scTNF derivatives are characterized by different lengths due to variable N-terminal start positions. In detail, the proteins of the present invention comprise human $TNF_{R2}$ mutant domains with N-terminal start positions at aa residues 80, 82, 84, 85, 86 and 88, respectively, and ending with aa 233 (C-terminus) (see Table 1; human TNF sequence derived from UniPRotKB entry P01375). Single-chain derivatives ($scTNF_{R2}$) of these domains were generated by fusing three $TNF_{R2}$ mutant domains into one polypeptide chain. This genetic fusion was accomplished either by the use of two peptide linkers to connect the three TNF domains, or by fusing the TNF domains directly without the use of peptide linkers. An N-terminal start position of the $TNF_{R2}$ mutant at aa position 80 in combination with a glycine-serine peptide linker L1 consisting of 5 aa residues (GGGGS) (SEQ ID NO: 26), as present in the reference molecule 118, is considered as state-of-the-art (Fischer et al., 2011, PLOS One, e27621). In detail, the TNF domains of the $scTNF_{R2}$ mutants were fused with peptide linkers L1 consisting of GGGGS (SEQ ID NO: 26) (variant 118 [SEQ ID NO: 65], starting with aa 80 of TNF), GGGG (SEQ ID NO: 16) (variant 139 [SEQ ID NO: 68], starting with aa 85 of TNF) or GGGSGGGS (SEQ ID NO: 34) (variant 138 [SEQ ID NO: 69], starting with aa 88 of TNF). In contrast, in the $scTNF_{R2}$ mutants 127 [SEQ ID NO: 66], 130 [SEQ ID NO: 70], 129 [SEQ ID NO: 67] and 131 [SEQ ID NO: 71], the three TNFR2-specific TNF domains of different lengths (see Table 1, FIG. 1) were directly fused without connecting peptide linkers (variant 127 starting with aa 80 of TNF, variant 130 starting with aa 82 of TNF, variant 129 starting with aa 84 of TNF, variant 131 starting with aa 86 of TNF). The TNF-R2-selective human scTNF$_{R2}$ mutants represent a trivalent arrangement of the three TNF THD, i.e. forming three TNFR2 binding sites.

The state-of-the-art scTNF$_{R2}$ mutant variant 118 and selected scTNF$_{R2}$ mutant variants (127, 129, 139) were connected via a peptide linker L2 consisting of GGSGGGGSGG (SEQ ID NO: 92) to the N-terminus of the Fc(Δab) dimerization region (this Fc region comprises mutations for deletion of Fc effector functions, such as binding to Fcγ receptors and complement component C1; Armour et al., 1999, Eur. J. Immunol. 29, 2613-2624). These hexavalent fusion proteins, i.e. proteins exhibiting six TNFR2-binding sites, are denoted scTNF$_{R2}$(118)-Fc(Δab) (745) [SEQ ID NO: 72], scTNF$_{R2}$(127)-Fc(Δab) (742) [SEQ ID NO: 73], scTNF$_{R2}$(129)-Fc(Δab) (743) [SEQ ID NO: 74] and scTNF$_{R2}$(139)-Fc(Δab) (744) [SEQ ID NO: 75] (see Table 2, FIG. 1).

The overall codon usage of scTNF$_{R2}$ and all complexes was adapted for expression in mammalian cells. An Igκ leader sequence was fused to the N-terminal end of the constructs to facilitate secretion of the proteins into the supernatant. To facilitate purification of the proteins, an N-terminal His-tag was introduced in the scTNF$_{R2}$ mutants, but was omitted in the scTNF$_{R2}$-Fc(Δab) complexes. In detail, coding DNA sequences of scTNF$_{R2}$ mutants and scTNF$_{R2}$-Fc(Δab) mutants were cloned into mammalian expression vectors allowing for recombinant production as sole 6×His-tagged single-chain protein 6×His-scTNF$_{R2}$ (pTT5 vector) or non-tagged Fc fusion protein scTNF$_{R2}$-Fc (Δab) (pSecTag vector).

Example 2: Production and Purification of Proteins of the Present Invention

All proteins (see example 1) were produced in HEK293-6E cells (NRC-BRI), grown in F17 medium (Life Technologies) at 37° C., 5% $CO_2$ under shaking conditions, which were transiently transfected with plasmid DNA using polyethyleneimine (Polysciences). The day after, 0.5% Tryptone N1 (Organotechnie) was added to the cell culture and cells were cultivated for additional 5 days. Then, supernatants were collected, centrifuged cell-free and recombinant proteins were isolated therefrom.

6×His-scTNF$_{R2}$ mutants were purified via immobilized metal ion chromatography (IMAC). In brief, supernatant was batch-incubated on a roller mixer at 4° C. for 16 h with Ni-NTA agarose (Macherey-Nagel), followed by collection in chromatography columns. Unbound proteins were removed using IMAC wash buffer (50 mM sodium phosphate buffer, pH 7.5). Bound proteins were eluted with IMAC elution buffer (50 mM sodium phosphate buffer, 250 mM imidazole, pH 7.5) and dialyzed (membrane cut-off 14 kDa, Roth) against PBS buffer (pH 7.4) overnight at 4° C.

ScTNF$_{R2}$-Fc(Δab) complexes were purified by Protein A affinity chromatography. Supernatants were batch-incubated with Protein A Sepharose 4 Fast Flow (GE Healthcare) or Toyopearl AF-rProtein A-650F (Tosoh) on a roller mixer at 4° C. for 16 h and collected in chromatography columns. Unbound proteins were removed using PBS, pH 7.4. Bound proteins were eluted with Protein A elution buffer (100 mM glycine-HCl, pH 3.5), neutralized immediately by adding 1 M Tris-HCl, pH 9.0 and dialyzed (membrane cut-off 14 kDa, Roth) against PBS buffer (pH 7.4) overnight at 4° C. Table 3 shows examples of protein amounts of the proteins described in example 1 yielded after affinity chromatography steps.

Dialyzed proteins were further purified by gel filtration (size-exclusion chromatography). The protein preparations were separated on a Superdex 200 10/300 GL column (GE Healthcare) using an ÄKTA FPLC device (GE Healthcare) and eluted with PBS, pH 7.4. Protein concentration was determined spectrophotometrically at 280 nm and calculated using the individual extinction coefficients.

Protein preparations were analyzed by SDS-PAGE and subsequent Coomassie staining (FIG. 2). Five ug or 3 μg of

TABLE 1

State-of-the-art molecule scTNF$_{R2}$ 118 and scTNFR2 proteins of the present invention.

| | Sequence human scTNF$_{R2}$ | | | huTNF$_{R2}$ |
|---|---|---|---|---|
| scTNF$_{R2}$ mutant | C-terminus TNF$_{R2}$ domain | Peptide linker | N-terminus TNF$_{R2}$ domain | subunit aa positions |
| 118 | . . . GIIAL | GGGGS | SSRTPSDKPVAHV (SIN: 58) | 80-233 |
| 127 | . . . GIIAL | | SSRTPSDKPVAHV (SIN: 59) | 80-233 |
| 130 | . . . GIIAL | | RTPSDKPVAHV (SIN: 60) | 82-233 |
| 129 | . . . GIIAL | | PSDKPVAHV (SIN: 61) | 84-233 |
| 139 | . . . GIIAL | GGGG | SDKPVAVH (SIN: 62) | 85-233 |
| 131 | . . . GIIAL | | DKPVAVH (SIN: 63) | 86-233 |
| 138 | . . . GIIAL | GGGSGGGS | PVAHV (SIN: 64) | 88-233 |

TABLE 2 nomenclature of scTNF-Fc (Δab) fusion proteins comprising the reference scTNF module (#118) and of scTNF$_{R2}$-Fc molecules of the present invention.

| scTNF$_{R2}$-Fc(Δab) | scTNF$_{R2}$ mutant |
|---|---|
| 745 | 118 |
| 742 | 127 |
| 743 | 129 |
| 744 | 139 |

the purified proteins according to Example 1 were denatured in Laemmli buffer (50 mM Tris pH 6.8, 4 M urea, 1% SDS, 15% glycerol, 0.01% bromphenol blue) under reducing conditions (in the presence of 5% 2-mercaptoethanol) and non-reducing conditions (in the absence of 2-mercaptoethanol) and separated by 10% or 12% SDS-PAGE. For visualization of proteins, the SDS-PAGE gels were incubated in InstantBlue stain (Expedion).

TABLE 3

Yields of $scTNF_{R2}$ mutants and $scTNF_{R2}$-Fc(Δab) molecules after recombinant expression and affinity purification.

| 6xHis-$scTNF_{R2}$ clone # | Yield[1] (mg/L sup.) 6xHis-$scTNF_{R2}$ | $scTNF_{R2}$-Fc(Δab) clone # | Yield[2] (mg/L sup.) $scTNF_{R2}$-Fc(Δab) |
|---|---|---|---|
| 118 | 4.5 | 745 | 33.4 |
| 127 | 7.8 | 742 | 25 |
| 130 | 4.8 | — | — |
| 129 | 9.3 | 743 | 10.4 |
| 139 | 10.5 | 744 | 31.9 |
| 131 | 5.0 | — | — |
| 138 | 3.0 | — | — |

[1]after Ni-NTA IMAC
[2]after Protein A affinity chromatography

Example 3: Molecular Integrity and Purity of Proteins of the Present Invention Under Native Conditions The purity and oligomerization state of the proteins according to example 1 was further characterized by HPLC size-exclusion chromatography (SEC). Approx. 20 μg protein were applied to a SuperSW mAb HR, 7.8×300 mm column (Tosoh Bioscience) equilibrated with SEC buffer (0.1 M $Na_2HPO_4/NaH_2PO_4$, 0.1 M $Na_2SO_4$, pH 6.7) and eluted at a flow rate of 0.5 ml/min. $ScTNF_{R2}$ and the complexes eluted at the expected sizes as single major peaks, indicating the correct assembly and high purity of the proteins (see FIG. 3).

Example 4: Thermal Stability of Proteins of the Present Invention

The thermal stability of the proteins according to example 1 was analyzed by dynamic light scattering using a Malvern Zetasizer instrument. Proteins were diluted to 150 μg/ml in PBS (1.1 ml total volume) and transferred into a quartz cuvette. The previously reported reference variant $SCTNF_{R2}$ 118 showed a denaturation (onset of aggregation) temperature of 62° C. (see FIG. 4, Table 4). In addition, a first partial denaturation of that protein was already observed at a temperature of 49° C. In contrast, the modified $scTNF_{R2}$ mutants 127, 129 and 139 showed considerably increased melting points of 67° C. (127, 139), 72° C. (129), respectively. The melting point of the $scTNF_{R2}$ mutant 138 remained unchanged compared to the reference variant (62° C.) and the $scTNF_{R2}$ mutants 130 and 131 showed a slightly reduced thermal stability.

After fusion of the $scTNF_{R2}$ variants to an Fc(Δab) region, the variant 745 comprising the reference $scTNF_{R2}$ mutant 118 showed a melting point of 71° C. (FIG. 4, Table 5). Notably, the $scTNF_{R2}$-Fc(Δab) complexes 742, 743 and 744 comprising $scTNF_{R2}$ mutants with increased thermal stability (127, 129 and 139) showed clearly higher melting points compared to the variant 745. For example, both $scTNF_{R2}$-Fc(Δab) variant 742 comprising $scTNF_{R2}$ variant 127 and $scTNF_{R2}$-Fc(Δab) variant 744 comprising $scTNF_{R2}$ variant 139 exhibited a melting temperature of 74° C. In summary, the higher thermal stability of particular $scTNF_{R2}$ mutants (e.g. variants 127 and 139) translated in a higher overall thermal stability of the $scTNF_{R2}$-Fc(Δab) complexes.

Proteins:

$SCTNF_{R2}$ molecules 118, 127, 129, 130, 131, 138 and 139 were purified by Ni-NTA-IMAC and gel filtration and eluted in 1×PBS buffer (8 mM $Na_2HPO_4$, 1.8 mM $KH_2PO_4$, 2.7 mM KCl, 137 mM NaCl, pH 7.4). The proteins were present in 1×PBS at the following concentrations: 230 μg/ml (118), 300 μg/ml (127), 480 μg/ml (129), 230 μg/ml (130), 260 μg/ml (131), 110 μg/ml (138) and 450 μg/ml (139).

$SCTNF_{R2}$-Fc(Δab) fusion proteins 745, 742, 743 and 744 were purified by Protein A affinity chromatography and gel filtration and eluted in 1×PBS buffer. The proteins were present in 1×PBS at the following concentrations: 800 μg/ml (745), 1200 μg/ml (742), 320 μg/ml (743) and 1700 μg/ml (744).

DLS Measurement:

For analysis of the aggregation temperatures by dynamic light scattering, the proteins were diluted to a concentration of 150 μg/ml with DPBS w/o calcium, w/o magnesium (Gibco, catalog number 14190144; 8.06 mM $Na_2HPO_4$×$7H_2O$, 1.47 mM $KH_2PO_4$, 2.67 mM KCl, 137.9 mM NaCl, pH 7.0-7.3). The protein 138 was analyzed undiluted. 1.1 ml of the diluted protein solution was filtered particle-free through an Acrodisc 13 mm syringe filter, 0.2 μm (Pall Corporation, part number 4602), which was beforehand equilibrated with 5×1 ml DPBS and transferred to a PCS8501 glass cuvette with round aperture (Malvern Panalytical), which was beforehand cleaned with 1 M NaOH and washed thoroughly with deionized water and DPBS. The cuvette was then placed in the measurement chamber of a preheated Zetasizer Nano-ZS ZEN3600, serial number MAL501015 (Malvern Panalytical), controlled by Dispersion Technology Software 5.00. The measurements were done in the manual mode with the following software settings:

Material: Protein, RI 1.45; Absorption, 0.00

Dispersant: ICN PBS Tablets; Temperature, 25° C.; Viscosity, 0.8882 cP; RI, 1.33

Cell type: PCS8501

Trend sequence: Start temperature, 25° C.; End temperature, 85° C.; Temperature interval, 1.0° C.; no check for melting point Size measurement: Equilibration time, 2 min; Number of measurements, 2; Delay between measurements, 0 sec.; no optimization of measurement settings; Measurement duration, Automatic; Advanced, Positioning method automatic attenuation selection; Data processing, Analysis model multiple narrow modes (high resolution)

The mean of the two measured kcps values at each temperature was calculated and plotted over temperature using GraphPad Prism 4.0 (GraphPad Software Inc.). The aggregation temperature was defined as the temperature T where the quotient $kcp_{ST}/kcps_{(T-5)}$ reached at least a factor 2.0.

TABLE 4

Denaturation temperatures of $scTNF_{R2}$ mutants as determined by dynamic light scattering.

| $6xHis\text{-}scTNF_{R2}$ | Aggregation temperature (° C.) |
|---|---|
| 118 | 62 |
| 127 | 67 |
| 130 | 60 |
| 129 | 72 |
| 139 | 67 |
| 131 | 58 |
| 138 | 62 |

TABLE 5

Denaturation temperatures of $scTNF_{R2}$-Fc(Δab) complexes as determined by dynamic light scattering.

| $scTNF_{R2}$-Fc(Δab) | Aggregation temperature (° C.) |
|---|---|
| 745 | 71 |
| 742 | 74 |
| 743 | 80 |
| 744 | 74 |

TABLE 6

DLS measurements for 6xHis-$scTNF_{R2}$ 118
6xHis-$scTNF_{R2}$ 118

| T (° C.) | Measurement 1 (kcps) | Measurement 2 (kcps) | Mean (kcps) | $kcps_T/kcps_{(T-5)}$ |
|---|---|---|---|---|
| 35 | 73.9 | 74.2 | 74.05 | |
| 36 | 74.1 | 74.5 | 74.3 | |
| 37 | 74.5 | 73.7 | 74.1 | |
| 38 | 72.8 | 72.4 | 72.6 | |
| 39 | 77.8 | 71.8 | 74.8 | |
| 40 | 71.6 | 73.1 | 72.35 | 0.98 |
| 41 | 73.1 | 71.9 | 72.5 | 0.98 |
| 42 | 73.2 | 72.5 | 72.85 | 0.98 |
| 43 | 75.9 | 78.8 | 77.35 | 1.07 |
| 44 | 76.7 | 79.2 | 77.95 | 1.04 |
| 45 | 76.3 | 74.7 | 75.5 | 1.04 |
| 46 | 84.2 | 96.4 | 90.3 | 1.25 |
| 47 | 102.3 | 108.9 | 105.6 | 1.45 |
| 48 | 135.1 | 151.9 | 143.5 | 1.86 |
| 49 | 176.6 | 183.6 | 180.1 | 2.31 |
| 50 | 211.2 | 211.2 | 211.2 | 2.80 |
| 51 | 222.3 | 217.9 | 220.1 | 2.44 |
| 52 | 218.4 | 208.7 | 213.55 | 2.02 |
| 53 | 207.1 | 198.3 | 202.7 | 1.41 |
| 54 | 194.7 | 188 | 191.35 | 1.06 |
| 55 | 185.1 | 182.2 | 183.65 | 0.87 |
| 56 | 172.8 | 169 | 170.9 | 0.78 |
| 57 | 171.1 | 173.3 | 172.2 | 0.81 |
| 58 | 168.9 | 168.4 | 168.65 | 0.83 |
| 59 | 173.1 | 169.7 | 171.4 | 0.90 |
| 60 | 177.7 | 179.7 | 178.7 | 0.97 |
| 61 | 192.6 | 225.7 | 209.15 | 1.22 |
| 62 | 323.6 | 395 | 359.3 | 2.09 |
| 63 | 507.6 | 590.3 | 548.95 | 3.25 |
| 64 | 729.6 | 832.5 | 781.05 | 4.56 |
| 65 | 964.1 | 1096.7 | 1030.4 | 5.77 |
| 66 | 1330.1 | 1492.7 | 1411.4 | 6.75 |
| 67 | 1792.3 | 2089.1 | 1940.7 | 5.40 |
| 68 | 2437.9 | 2753.9 | 2595.9 | 4.73 |
| 69 | 3183.4 | 3501.2 | 3342.3 | 4.28 |
| 70 | 3911.4 | 4319.3 | 4115.35 | 3.99 |
| 71 | 4747.5 | 5022.8 | 4885.15 | 3.46 |
| 72 | 5342.6 | 5582.6 | 5462.6 | 2.81 |
| 73 | 5768.3 | 5755.9 | 5762.1 | 2.22 |
| 74 | 5944 | 5839 | 5891.5 | 1.76 |

TABLE 6-continued

DLS measurements for 6xHis-$scTNF_{R2}$ 118
6xHis-$scTNF_{R2}$ 118

| T (° C.) | Measurement 1 (kcps) | Measurement 2 (kcps) | Mean (kcps) | $kcps_T/kcps_{(T-5)}$ |
|---|---|---|---|---|
| 75 | 5876.9 | 5642.1 | 5759.5 | 1.40 |
| 76 | 5771.7 | 5760.1 | 5765.9 | 1.18 |
| 77 | 5718.4 | 5827.4 | 5772.9 | 1.06 |
| 78 | 5984.5 | 5711.9 | 5848.2 | 1.01 |
| 79 | 5504.7 | 5430.5 | 5467.6 | 0.93 |

TABLE 7

DLS measurements for 6xHis-$scTNF_{R2}$ 127
6xHis-$scTNF_{R2}$ 127

| T (° C.) | Measurement 1 (kcps) | Measurement 2 (kcps) | Mean (kcps) | $kcps_T/kcps_{(T-5)}$ |
|---|---|---|---|---|
| 35 | 85.4 | 90.7 | 88.05 | |
| 36 | 75.8 | 77.2 | 76.5 | |
| 37 | 73 | 69.4 | 71.2 | |
| 38 | 80.8 | 73.7 | 77.25 | |
| 39 | 72.7 | 70.7 | 71.7 | |
| 40 | 78.9 | 76.2 | 77.55 | 0.88 |
| 41 | 73.1 | 72.1 | 72.6 | 0.95 |
| 42 | 83 | 92 | 87.5 | 1.23 |
| 43 | 84.3 | 95.5 | 89.9 | 1.16 |
| 44 | 79.7 | 83.1 | 81.4 | 1.14 |
| 45 | 74.9 | 75.1 | 75 | 0.97 |
| 46 | 71.7 | 71.8 | 71.75 | 0.99 |
| 47 | 72.7 | 76.2 | 74.45 | 0.85 |
| 48 | 76.5 | 78.9 | 77.7 | 0.86 |
| 49 | 77 | 74.2 | 75.6 | 0.93 |
| 50 | 72.4 | 71.9 | 72.15 | 0.96 |
| 51 | 74.6 | 76.8 | 75.7 | 1.06 |
| 52 | 81.4 | 94.8 | 88.1 | 1.18 |
| 53 | 74 | 77.7 | 75.85 | 0.98 |
| 54 | 78.8 | 76.2 | 77.5 | 1.03 |
| 55 | 83.9 | 82.6 | 83.25 | 1.15 |
| 56 | 73.7 | 71.5 | 72.6 | 0.96 |
| 57 | 82.1 | 82.3 | 82.2 | 0.93 |
| 58 | 74 | 77.6 | 75.8 | 1.00 |
| 59 | 75.4 | 70.7 | 73.05 | 0.94 |
| 60 | 81.7 | 80.4 | 81.05 | 0.97 |
| 61 | 81.4 | 75.6 | 78.5 | 1.08 |
| 62 | 72.6 | 74.7 | 73.65 | 0.90 |
| 63 | 76.1 | 74.4 | 75.25 | 0.99 |
| 64 | 80 | 79.9 | 79.95 | 1.09 |
| 65 | 92.9 | 95.8 | 94.35 | 1.16 |
| 66 | 120 | 134.2 | 127.1 | 1.62 |
| 67 | 253.2 | 316.4 | 284.8 | 3.87 |
| 68 | 481.5 | 609.3 | 545.4 | 7.25 |
| 69 | 789.8 | 947 | 868.4 | 10.86 |
| 70 | 1177.1 | 1398.1 | 1287.6 | 13.65 |
| 71 | 1723.4 | 1951.6 | 1837.5 | 14.46 |
| 72 | 2430 | 2688 | 2559 | 8.99 |
| 73 | 3292.7 | 3615.4 | 3454.05 | 6.33 |
| 74 | 4191.2 | 4517.6 | 4354.4 | 5.01 |
| 75 | 5078.5 | 5320.5 | 5199.5 | 4.04 |
| 76 | 5765.7 | 5934.4 | 5850.05 | 3.18 |
| 77 | 6205.4 | 6293.3 | 6249.35 | 2.44 |
| 78 | 6388 | 6362.5 | 6375.25 | 1.85 |
| 79 | 6257.8 | 6323.6 | 6290.7 | 1.44 |
| 80 | 6278.4 | 6191 | 6234.7 | 1.20 |
| 81 | 6355.1 | 6294 | 6324.55 | 1.08 |
| 82 | 6223.2 | 6016.7 | 6119.95 | 0.98 |
| 83 | 5213.2 | 5252.1 | 5232.65 | 0.82 |

TABLE 8

DLS measurements for 6xHis-scTNF$_{R2}$ 129
6xHis-scTNF$_{R2}$ 129

| T (° C.) | Measurement 1 (kcps) | Measurement 2 (kcps) | Mean (kcps) | kcps$_T$/kcps$_{(T-5)}$ |
|---|---|---|---|---|
| 35 | 100.4 | 104.9 | 102.65 | |
| 36 | 91.9 | 87.7 | 89.8 | |
| 37 | 73 | 78.9 | 75.95 | |
| 38 | 83.4 | 87.8 | 85.6 | |
| 39 | 94.1 | 96 | 95.05 | |
| 40 | 79.1 | 73 | 76.05 | 0.74 |
| 41 | 86.2 | 85 | 85.6 | 0.95 |
| 42 | 77.1 | 91.5 | 84.3 | 1.11 |
| 43 | 76.1 | 77.3 | 76.7 | 0.90 |
| 44 | 80.9 | 79.7 | 80.3 | 0.84 |
| 45 | 83.3 | 76 | 79.65 | 1.05 |
| 46 | 87.3 | 86 | 86.65 | 1.01 |
| 47 | 90 | 90.3 | 90.15 | 1.07 |
| 48 | 96.4 | 101.3 | 98.85 | 1.29 |
| 49 | 91.3 | 83.4 | 87.35 | 1.09 |
| 50 | 72.3 | 76.3 | 74.3 | 0.93 |
| 51 | 72.4 | 72.9 | 72.65 | 0.84 |
| 52 | 87.3 | 99.7 | 93.5 | 1.04 |
| 53 | 80.7 | 85.8 | 83.25 | 0.84 |
| 54 | 76.9 | 77.4 | 77.15 | 0.88 |
| 55 | 74.3 | 78.9 | 76.6 | 1.03 |
| 56 | 86.7 | 88.6 | 87.65 | 1.21 |
| 57 | 82.6 | 93.5 | 88.05 | 0.94 |
| 58 | 81.8 | 86.3 | 84.05 | 1.01 |
| 59 | 98.7 | 107.4 | 103.05 | 1.34 |
| 60 | 80.5 | 76.3 | 78.4 | 1.02 |
| 61 | 82.9 | 99.4 | 91.15 | 1.04 |
| 62 | 99.9 | 117.8 | 108.85 | 1.24 |
| 63 | 106.5 | 109.2 | 107.85 | 1.28 |
| 64 | 91 | 82.6 | 86.8 | 0.84 |
| 65 | 80.6 | 83.8 | 82.2 | 1.05 |
| 66 | 69.3 | 71.1 | 70.2 | 0.77 |
| 67 | 66.9 | 66.4 | 66.65 | 0.61 |
| 68 | 81 | 81.9 | 81.45 | 0.76 |
| 69 | 78 | 87.3 | 82.65 | 0.95 |
| 70 | 87 | 82.1 | 84.55 | 1.03 |
| 71 | 92.4 | 106.6 | 99.5 | 1.42 |
| 72 | 182.3 | 233.6 | 207.95 | 3.12 |
| 73 | 362.1 | 411.7 | 386.9 | 4.75 |
| 74 | 524.9 | 591.7 | 558.3 | 6.75 |
| 75 | 712.5 | 744.5 | 728.5 | 8.62 |
| 76 | 897.5 | 963.5 | 930.5 | 9.35 |
| 77 | 1114 | 1193.6 | 1153.8 | 5.55 |
| 78 | 1369.6 | 1469.3 | 1419.45 | 3.67 |
| 79 | 1718.1 | 1869.4 | 1793.75 | 3.21 |
| 80 | 2218.8 | 2433.1 | 2325.95 | 3.19 |
| 81 | 2935.9 | 3230.9 | 3083.4 | 3.31 |
| 82 | 3822.8 | 4249.1 | 4035.95 | 3.50 |
| 83 | 4978.9 | 5246.9 | 5112.9 | 3.60 |
| 84 | 5790.5 | 5911.5 | 5851 | 3.26 |
| 85 | 6181.1 | 6161.5 | 6171.3 | 2.65 |

TABLE 9

DLS measurements for 6xHis-scTNF$_{R2}$ 130
6xHis-scTNF$_{R2}$ 130

| T (° C.) | Measurement 1 (kcps) | Measurement 2 (kcps) | Mean (kcps) | kcps$_T$/kcps$_{(T-5)}$ |
|---|---|---|---|---|
| 35 | 127.3 | 127.1 | 127.2 | |
| 36 | 124.5 | 126.3 | 125.4 | |
| 37 | 125.8 | 126.9 | 126.35 | |
| 38 | 133 | 130.4 | 131.7 | |
| 39 | 126.7 | 129.1 | 127.9 | |
| 40 | 130.4 | 135.7 | 133.05 | 1.05 |
| 41 | 129.2 | 128.9 | 129.05 | 1.03 |
| 42 | 139 | 145.5 | 142.25 | 1.13 |
| 43 | 136.2 | 133.4 | 134.8 | 1.02 |
| 44 | 134.3 | 138.9 | 136.6 | 1.07 |
| 45 | 135.4 | 134.1 | 134.75 | 1.01 |

TABLE 9-continued

DLS measurements for 6xHis-scTNF$_{R2}$ 130
6xHis-scTNF$_{R2}$ 130

| T (° C.) | Measurement 1 (kcps) | Measurement 2 (kcps) | Mean (kcps) | kcps$_T$/kcps$_{(T-5)}$ |
|---|---|---|---|---|
| 46 | 138 | 137.9 | 137.95 | 1.07 |
| 47 | 146.1 | 147.8 | 146.95 | 1.03 |
| 48 | 151 | 145.4 | 148.2 | 1.10 |
| 49 | 155.2 | 152.4 | 153.8 | 1.13 |
| 50 | 148.7 | 150 | 149.35 | 1.11 |
| 51 | 146 | 147.4 | 146.7 | 1.06 |
| 52 | 151.4 | 150.4 | 150.9 | 1.03 |
| 53 | 135.3 | 134.6 | 134.95 | 0.91 |
| 54 | 145.7 | 139 | 142.35 | 0.93 |
| 55 | 139.5 | 138.3 | 138.9 | 0.93 |
| 56 | 145 | 142.1 | 143.55 | 0.98 |
| 57 | 158.5 | 162.3 | 160.4 | 1.06 |
| 58 | 141.3 | 153.6 | 147.45 | 1.09 |
| 59 | 150.4 | 162.5 | 156.45 | 1.10 |
| 60 | 315.7 | 407.2 | 361.45 | 2.60 |
| 61 | 800.8 | 939.6 | 870.2 | 6.06 |
| 62 | 1469.4 | 1656.7 | 1563.05 | 9.74 |
| 63 | 2246 | 2531.8 | 2388.9 | 16.20 |
| 64 | 3291.2 | 3775 | 3533.1 | 22.58 |
| 65 | 4696.7 | 5399.5 | 5048.1 | 13.97 |
| 66 | 6423.7 | 7201.7 | 6812.7 | 7.83 |
| 67 | 8262.4 | 8866.1 | 8564.25 | 5.48 |
| 68 | 9911.3 | 10398.2 | 10154.75 | 4.25 |
| 69 | 11260.9 | 11475.6 | 11368.25 | 3.22 |
| 70 | 11990.5 | 11988.6 | 11989.55 | 2.38 |
| 71 | 11828.1 | 11773.9 | 11801 | 1.73 |
| 72 | 11543.4 | 11568.8 | 11556.1 | 1.35 |
| 73 | 11286.3 | 11271.3 | 11278.8 | 1.11 |
| 74 | 11688.4 | 11739.9 | 11714.15 | 1.03 |
| 75 | 11696.4 | 11662.5 | 11679.45 | 0.97 |
| 76 | 11473.3 | 11549.6 | 11511.45 | 0.98 |
| 77 | 10768.4 | 10649.7 | 10709.05 | 0.93 |

TABLE 10

DLS measurements for 6xHis-scTNF$_{R2}$ 131
6xHis-scTNF$_{R2}$ 131

| T (° C.) | Measurement 1 (kcps) | Measurement 2 (kcps) | Mean (kcps) | kcps$_T$/kcps$_{(T-5)}$ |
|---|---|---|---|---|
| 35 | 138.8 | 143.7 | 141.25 | |
| 36 | 142.6 | 139.9 | 141.25 | |
| 37 | 140.1 | 151.2 | 145.65 | |
| 38 | 159.6 | 164.7 | 162.15 | |
| 39 | 150.9 | 149.7 | 150.3 | |
| 40 | 147.6 | 147.1 | 147.35 | 1.04 |
| 41 | 171 | 153.2 | 162.1 | 1.15 |
| 42 | 145.4 | 142.7 | 144.05 | 0.99 |
| 43 | 152.3 | 150.4 | 151.35 | 0.93 |
| 44 | 143.4 | 142.5 | 142.95 | 0.95 |
| 45 | 142.7 | 140 | 141.35 | 0.96 |
| 46 | 170.5 | 156.9 | 163.7 | 1.01 |
| 47 | 156 | 159.8 | 157.9 | 1.10 |
| 48 | 147.6 | 147 | 147.3 | 0.97 |
| 49 | 136.8 | 135.7 | 136.25 | 0.95 |
| 50 | 141.6 | 142 | 141.8 | 1.00 |
| 51 | 133.9 | 137.6 | 135.75 | 0.83 |
| 52 | 136.4 | 137.5 | 136.95 | 0.87 |
| 53 | 137.7 | 138.7 | 138.2 | 0.94 |
| 54 | 144 | 139.1 | 141.55 | 1.04 |
| 55 | 143.8 | 144.1 | 143.95 | 1.02 |
| 56 | 138.4 | 140.9 | 139.65 | 1.03 |
| 57 | 188.2 | 205.5 | 196.85 | 1.44 |
| 58 | 320.2 | 373.5 | 346.85 | 2.51 |
| 59 | 675.8 | 775.4 | 725.6 | 5.13 |
| 60 | 1199.8 | 1352 | 1275.9 | 8.86 |
| 61 | 1810.6 | 2018 | 1914.3 | 13.71 |
| 62 | 2656.1 | 2932.8 | 2794.45 | 14.20 |
| 63 | 3701.3 | 4175.7 | 3938.5 | 11.36 |
| 64 | 5084.1 | 5638.9 | 5361.5 | 7.39 |

TABLE 10-continued

| DLS measurements for 6xHis-scTNF$_{R2}$ 131 6xHis-scTNF$_{R2}$ 131 | | | | |
|---|---|---|---|---|
| T (° C.) | Measurement 1 (kcps) | Measurement 2 (kcps) | Mean (kcps) | kcps$_T$/kcps$_{(T-5)}$ |
| 65 | 6532.8 | 7214.1 | 6873.45 | 5.39 |
| 66 | 8169.4 | 8901.2 | 8535.3 | 4.46 |
| 67 | 9877.8 | 10442.1 | 10159.95 | 3.64 |
| 68 | 11274.5 | 11761.1 | 11517.8 | 2.92 |
| 69 | 12108.4 | 12494 | 12301.2 | 2.29 |
| 70 | 12531.3 | 12397.9 | 12464.6 | 1.81 |
| 71 | 12212.5 | 11976.2 | 12094.35 | 1.42 |
| 72 | 11688.5 | 11632.9 | 11660.7 | 1.15 |
| 73 | 11490.4 | 11594 | 11542.2 | 1.00 |
| 74 | 11910.7 | 11954.5 | 11932.6 | 0.97 |
| 75 | 12147.3 | 12055.7 | 12101.5 | 0.97 |
| 76 | 11557.8 | 11483.8 | 11520.8 | 0.95 |
| 77 | 11068.4 | 10791.5 | 10929.95 | 0.94 |

TABLE 11

| DLS measurements for 6xHis-scTNF$_{R2}$ 138 6xHis-scTNF$_{R2}$ 138 | | | | |
|---|---|---|---|---|
| T (° C.) | Measurement 1 (kcps) | Measurement 2 (kcps) | Mean (kcps) | kcps$_T$/kcps$_{(T-5)}$ |
| 35 | 108.8 | 114.9 | 111.85 | |
| 36 | 103.1 | 100.6 | 101.85 | |
| 37 | 100.5 | 99.2 | 99.85 | |
| 38 | 111.3 | 119 | 115.15 | |
| 39 | 98.6 | 97.3 | 97.95 | |
| 40 | 102.5 | 107.6 | 105.05 | 0.94 |
| 41 | 103 | 102.7 | 102.85 | 1.01 |
| 42 | 102.9 | 105.7 | 104.3 | 1.04 |
| 43 | 107.4 | 117.9 | 112.65 | 0.98 |
| 44 | 103.6 | 105.2 | 104.4 | 1.07 |
| 45 | 96.6 | 98.3 | 97.45 | 0.93 |
| 46 | 97.1 | 96.1 | 96.6 | 0.94 |
| 47 | 97.4 | 99.9 | 98.65 | 0.95 |
| 48 | 100.1 | 99.7 | 99.9 | 0.89 |
| 49 | 95.9 | 98.9 | 97.4 | 0.93 |
| 50 | 94.8 | 95.7 | 95.25 | 0.98 |
| 51 | 100.3 | 103.3 | 101.8 | 1.05 |
| 52 | 99.3 | 99.9 | 99.6 | 1.01 |
| 53 | 97.6 | 98.6 | 98.1 | 0.98 |
| 54 | 99.6 | 101.5 | 100.55 | 1.03 |
| 55 | 96.2 | 112.6 | 104.4 | 1.10 |
| 56 | 99.3 | 108.4 | 103.85 | 1.02 |
| 57 | 100.2 | 109.3 | 104.75 | 1.05 |
| 58 | 100.7 | 101.9 | 101.3 | 1.03 |
| 59 | 96.9 | 96.8 | 96.85 | 0.96 |
| 60 | 99 | 96.2 | 97.6 | 0.93 |
| 61 | 123.7 | 146.9 | 135.3 | 1.30 |
| 62 | 239.7 | 329.5 | 284.6 | 2.72 |
| 63 | 489.1 | 622.8 | 555.95 | 5.49 |
| 64 | 882.6 | 1079.6 | 981.1 | 10.13 |
| 65 | 1385.4 | 1637.2 | 1511.3 | 15.48 |
| 66 | 2003.4 | 2310 | 2156.7 | 15.94 |
| 67 | 2910.1 | 3444.5 | 3177.3 | 11.16 |
| 68 | 4129.6 | 4746.1 | 4437.85 | 7.98 |
| 69 | 5682.7 | 6303.6 | 5993.15 | 6.11 |
| 70 | 7365.1 | 7975.6 | 7670.35 | 5.08 |
| 71 | 9084.5 | 9809.5 | 9447 | 4.38 |
| 72 | 10713.8 | 11056.2 | 10885 | 3.43 |
| 73 | 11935.1 | 12107.4 | 12021.25 | 2.71 |
| 74 | 12537.5 | 12840.3 | 12688.9 | 2.12 |
| 75 | 12962.3 | 12801.1 | 12881.7 | 1.68 |
| 76 | 12761.9 | 12755.5 | 12758.7 | 1.35 |
| 77 | 12391.2 | 12314.3 | 12352.75 | 1.13 |
| 78 | 11929.7 | 11318.1 | 11623.9 | 0.97 |

TABLE 12

| DLS measurements for 6xHis-scTNF$_{R2}$ 139 6xHis-scTNF$_{R2}$ 139 | | | | |
|---|---|---|---|---|
| T (° C.) | Measurement 1 (kcps) | Measurement 2 (kcps) | Mean (kcps) | kcps$_T$/kcps$_{(T-5)}$ |
| 35 | 74.9 | 78.5 | 76.7 | |
| 36 | 67.1 | 70.9 | 69 | |
| 37 | 63.2 | 66.3 | 64.75 | |
| 38 | 71.1 | 78.3 | 74.7 | |
| 39 | 65.5 | 66.8 | 66.15 | |
| 40 | 83.1 | 83.2 | 83.15 | 1.08 |
| 41 | 67.9 | 70.7 | 69.3 | 1.00 |
| 42 | 69.3 | 67.9 | 68.6 | 1.06 |
| 43 | 78.8 | 77.9 | 78.35 | 1.05 |
| 44 | 78.8 | 70.6 | 74.7 | 1.13 |
| 45 | 91.7 | 99.7 | 95.7 | 1.15 |
| 46 | 79.5 | 79.7 | 79.6 | 1.15 |
| 47 | 77.4 | 72.2 | 74.8 | 1.09 |
| 48 | 82.4 | 81.7 | 82.05 | 1.05 |
| 49 | 73 | 74.7 | 73.85 | 0.99 |
| 50 | 64.1 | 62.7 | 63.4 | 0.66 |
| 51 | 64.6 | 66.7 | 65.65 | 0.82 |
| 52 | 81.2 | 83.4 | 82.3 | 1.10 |
| 53 | 69.1 | 67.6 | 68.35 | 0.83 |
| 54 | 65.1 | 64.6 | 64.85 | 0.88 |
| 55 | 71.2 | 70.5 | 70.85 | 1.12 |
| 56 | 70.6 | 68.5 | 69.55 | 1.06 |
| 57 | 80.7 | 76.5 | 78.6 | 0.96 |
| 58 | 63.3 | 66.7 | 65 | 0.95 |
| 59 | 62.9 | 63.4 | 63.15 | 0.97 |
| 60 | 73.2 | 65 | 69.1 | 0.98 |
| 61 | 68.6 | 67.8 | 68.2 | 0.98 |
| 62 | 64.7 | 69.4 | 67.05 | 0.85 |
| 63 | 69.6 | 76.3 | 72.95 | 1.12 |
| 64 | 68.6 | 80.1 | 74.35 | 1.18 |
| 65 | 67.5 | 72.1 | 69.8 | 1.01 |
| 66 | 73.7 | 83.5 | 78.6 | 1.15 |
| 67 | 155.4 | 291.1 | 223.25 | 3.33 |
| 68 | 504.7 | 757.4 | 631.05 | 8.65 |
| 69 | 1052.6 | 1352.8 | 1202.7 | 16.18 |
| 70 | 1715.7 | 2025.2 | 1870.45 | 26.80 |
| 71 | 2703.7 | 3083.7 | 2893.7 | 36.82 |
| 72 | 3729.4 | 4068.3 | 3898.85 | 17.46 |
| 73 | 4798.4 | 5122.2 | 4960.3 | 7.86 |
| 74 | 5534.1 | 5741.8 | 5637.95 | 4.69 |
| 75 | 5881.8 | 5973 | 5927.4 | 3.17 |
| 76 | 5952.9 | 5877.1 | 5915 | 2.04 |
| 77 | 5840.9 | 5809.9 | 5825.4 | 1.49 |
| 78 | 5749.5 | 5728.7 | 5739.1 | 1.16 |
| 79 | 5609.2 | 5673.7 | 5641.45 | 1.00 |
| 80 | 5475.2 | 5328.3 | 5401.75 | 0.91 |

TABLE 13

| DLS measurements for scTNF$_{R2}$ -Fc(Δab) 745 scTNF$_{R2}$ -Fc(Δab) 745 | | | | |
|---|---|---|---|---|
| T (° C.) | Measurement 1 (kcps) | Measurement 2 (kcps) | Mean (kcps) | kcps$_T$/kcps$_{(T-5)}$ |
| 35 | 236.3 | 241.2 | 238.75 | |
| 36 | 253.3 | 251 | 252.15 | |
| 37 | 259.9 | 259.8 | 259.85 | |
| 38 | 243.8 | 243.4 | 243.6 | |
| 39 | 271.8 | 290.8 | 281.3 | |
| 40 | 246.8 | 248 | 247.4 | 1.04 |
| 41 | 254.2 | 264.8 | 259.5 | 1.03 |
| 42 | 247.6 | 251.9 | 249.75 | 0.96 |
| 43 | 258.1 | 256.2 | 257.15 | 1.06 |
| 44 | 250.9 | 249.6 | 250.25 | 0.89 |
| 45 | 249.6 | 244.5 | 247.05 | 1.00 |
| 46 | 254 | 258.4 | 256.2 | 0.99 |
| 47 | 248.1 | 244.9 | 246.5 | 0.99 |
| 48 | 246.2 | 254 | 250.1 | 0.97 |
| 49 | 245.2 | 244.3 | 244.75 | 0.98 |
| 50 | 242.7 | 245.5 | 244.1 | 0.99 |

TABLE 13-continued

| DLS measurements for scTNF$_{R2}$ -Fc(Δab) 745 scTNF$_{R2}$ -Fc(Δab) 745 | | | | |
|---|---|---|---|---|
| T (° C.) | Measurement 1 (kcps) | Measurement 2 (kcps) | Mean (kcps) | kcps$_T$/ kcps$_{(T-5)}$ |
| 51 | 249.5 | 249.7 | 249.6 | 0.97 |
| 52 | 245.7 | 245.2 | 245.45 | 1.00 |
| 53 | 251.3 | 249 | 250.15 | 1.00 |
| 54 | 251.3 | 244.4 | 247.85 | 1.01 |
| 55 | 247.3 | 257.4 | 252.35 | 1.03 |
| 56 | 272.3 | 257.7 | 265 | 1.06 |
| 57 | 249.8 | 252.3 | 251.05 | 1.02 |
| 58 | 290.2 | 282.6 | 286.4 | 1.14 |
| 59 | 290.6 | 272.3 | 281.45 | 1.14 |
| 60 | 248 | 252 | 250 | 0.99 |
| 61 | 275.3 | 283.2 | 279.25 | 1.05 |
| 62 | 297 | 289.5 | 293.25 | 1.17 |
| 63 | 283.3 | 284.4 | 283.85 | 0.99 |
| 64 | 296.1 | 294.5 | 295.3 | 1.05 |
| 65 | 327.3 | 346.3 | 336.8 | 1.35 |
| 66 | 343 | 358.3 | 350.65 | 1.26 |
| 67 | 325.4 | 326.8 | 326.1 | 1.11 |
| 68 | 358.6 | 372 | 365.3 | 1.29 |
| 69 | 440.5 | 487.9 | 464.2 | 1.57 |
| 70 | 604 | 656.4 | 630.2 | 1.87 |
| 71 | 758.7 | 858 | 808.35 | 2.31 |
| 72 | 1244.3 | 1489.8 | 1367.05 | 4.19 |
| 73 | 2655.6 | 3687 | 3171.3 | 8.68 |
| 74 | 9042.4 | 10023.8 | 9533.1 | 20.54 |
| 75 | 10560.5 | 10706.4 | 10633.45 | 16.87 |
| 76 | 10973.7 | 10977.9 | 10975.8 | 13.58 |
| 77 | 10872.5 | 10784.6 | 10828.55 | 7.92 |
| 78 | 9747.7 | 8522.8 | 9135.25 | 2.88 |

TABLE 14

| DLS measurements for scTNF$_{R2}$ -Fc(Δab) 742 scTNF$_{R2}$ -Fc(Δab) 742 | | | | |
|---|---|---|---|---|
| T (° C.) | Measurement 1 (kcps) | Measurement 2 (kcps) | Mean (kcps) | kcps$_T$/ kcps$_{(T-5)}$ |
| 35 | 226 | 223.3 | 224.65 | |
| 36 | 225.3 | 227.5 | 226.4 | |
| 37 | 226 | 224.6 | 225.3 | |
| 38 | 224.6 | 225.2 | 224.9 | |
| 39 | 219.9 | 220.4 | 220.15 | |
| 40 | 221.3 | 219 | 220.15 | 0.98 |
| 41 | 226.3 | 220.7 | 223.5 | 0.99 |
| 42 | 223.3 | 222.2 | 222.75 | 0.99 |
| 43 | 217.6 | 221.6 | 219.6 | 0.98 |
| 44 | 216.8 | 217.7 | 217.25 | 0.99 |
| 45 | 227.5 | 222.4 | 224.95 | 1.02 |
| 46 | 246.7 | 240.4 | 243.55 | 1.09 |
| 47 | 239.4 | 247.5 | 243.45 | 1.09 |
| 48 | 250.4 | 258.9 | 254.65 | 1.16 |
| 49 | 245.5 | 249.7 | 247.6 | 1.14 |
| 50 | 237.2 | 240.2 | 238.7 | 1.06 |
| 51 | 226.3 | 221.4 | 223.85 | 0.92 |
| 52 | 216.9 | 214.5 | 215.7 | 0.89 |
| 53 | 215.7 | 216.8 | 216.25 | 0.85 |
| 54 | 217.8 | 226.7 | 222.25 | 0.90 |
| 55 | 226.3 | 226.4 | 226.35 | 0.95 |
| 56 | 233.1 | 228.6 | 230.85 | 1.03 |
| 57 | 232.8 | 226.6 | 229.7 | 1.06 |
| 58 | 226.6 | 227.9 | 227.25 | 1.05 |
| 59 | 227.7 | 231 | 229.35 | 1.03 |
| 60 | 225 | 223.7 | 224.35 | 0.99 |
| 61 | 216.8 | 222.1 | 219.45 | 0.95 |
| 62 | 213.4 | 211.5 | 212.45 | 0.92 |
| 63 | 212.9 | 211.8 | 212.35 | 0.93 |
| 64 | 216.7 | 216 | 216.35 | 0.94 |
| 65 | 217.9 | 221.3 | 219.6 | 0.98 |
| 66 | 225 | 228.6 | 226.8 | 1.03 |
| 67 | 238.3 | 234 | 236.15 | 1.11 |
| 68 | 251.8 | 251.9 | 251.85 | 1.19 |

TABLE 14-continued

| DLS measurements for scTNF$_{R2}$ -Fc(Δab) 742 scTNF$_{R2}$ -Fc(Δab) 742 | | | | |
|---|---|---|---|---|
| T (° C.) | Measurement 1 (kcps) | Measurement 2 (kcps) | Mean (kcps) | kcps$_T$/ kcps$_{(T-5)}$ |
| 69 | 267.5 | 275.6 | 271.55 | 1.26 |
| 70 | 300.1 | 302.2 | 301.15 | 1.37 |
| 71 | 312.9 | 326.1 | 319.5 | 1.41 |
| 72 | 349.5 | 360.4 | 354.95 | 1.50 |
| 73 | 416.3 | 444.1 | 430.2 | 1.71 |
| 74 | 535.2 | 597.9 | 566.55 | 2.09 |
| 75 | 786.7 | 930.5 | 858.6 | 2.85 |
| 76 | 1635.9 | 2371.1 | 2003.5 | 6.27 |
| 77 | 8018.5 | 9399.3 | 8708.9 | 24.54 |
| 78 | 10361.2 | 10635 | 10498.1 | 24.40 |
| 79 | 11152.4 | 11268.7 | 11210.55 | 19.79 |
| 80 | 10973 | 10888.1 | 10930.55 | 12.73 |
| 81 | 9341 | 8454 | 8897.5 | 4.44 |

TABLE 15

| DLS measurements for scTNF$_{R2}$ -Fc(Δab) 743 scTNF$_{R2}$ -Fc(Δab) 743 | | | | |
|---|---|---|---|---|
| T (° C.) | Measurement 1 (kcps) | Measurement 2 (kcps) | Mean (kcps) | kcps$_T$/ kcps$_{(T-5)}$ |
| 35 | 223.9 | 235 | 229.45 | |
| 36 | 227.7 | 217.7 | 222.7 | |
| 37 | 216.7 | 210.5 | 213.6 | |
| 38 | 218.7 | 216.1 | 217.4 | |
| 39 | 223.7 | 218.4 | 221.05 | |
| 40 | 238.7 | 248.5 | 243.6 | 1.06 |
| 41 | 223.2 | 219.2 | 221.2 | 0.99 |
| 42 | 257.1 | 264.1 | 260.6 | 1.22 |
| 43 | 246.1 | 235.5 | 240.8 | 1.11 |
| 44 | 246.8 | 233.1 | 239.95 | 1.09 |
| 45 | 259.9 | 251.2 | 255.55 | 1.05 |
| 46 | 261.7 | 253.1 | 257.4 | 1.16 |
| 47 | 242.8 | 239.1 | 240.95 | 0.92 |
| 48 | 246.3 | 249.1 | 247.7 | 1.03 |
| 49 | 223.8 | 220.4 | 222.1 | 0.93 |
| 50 | 240.5 | 261.7 | 251.1 | 0.98 |
| 51 | 258.6 | 291.5 | 275.05 | 1.07 |
| 52 | 259.7 | 242.9 | 251.3 | 1.04 |
| 53 | 310.9 | 288.3 | 299.6 | 1.21 |
| 54 | 258.9 | 256 | 257.45 | 1.16 |
| 55 | 363.1 | 370.1 | 366.6 | 1.46 |
| 56 | 214.3 | 221.3 | 217.8 | 0.79 |
| 57 | 313.5 | 274.1 | 293.8 | 1.17 |
| 58 | 217.5 | 204.8 | 211.15 | 0.70 |
| 59 | 211.6 | 209.6 | 210.6 | 0.82 |
| 60 | 230.3 | 227.8 | 229.05 | 0.62 |
| 61 | 249.8 | 232.9 | 241.35 | 1.11 |
| 62 | 230.9 | 226.1 | 228.5 | 0.78 |
| 63 | 233 | 215.7 | 224.35 | 1.06 |
| 64 | 234.9 | 231.4 | 233.15 | 1.11 |
| 65 | 275.8 | 274.1 | 274.95 | 1.20 |
| 66 | 296.9 | 303.2 | 300.05 | 1.24 |
| 67 | 250.1 | 271.1 | 260.6 | 1.14 |
| 68 | 258.7 | 263.3 | 261 | 1.16 |
| 69 | 237.8 | 236.5 | 237.15 | 1.02 |
| 70 | 262.5 | 257.5 | 260 | 0.95 |
| 71 | 300.3 | 310 | 305.15 | 1.02 |
| 72 | 262 | 267.8 | 264.9 | 1.02 |
| 73 | 290.6 | 291.6 | 291.1 | 1.12 |
| 74 | 345.9 | 348.7 | 347.3 | 1.46 |
| 75 | 265.5 | 272.3 | 268.9 | 1.03 |
| 76 | 357 | 372.8 | 364.9 | 1.20 |
| 77 | 336.6 | 337.4 | 337 | 1.27 |
| 78 | 366.9 | 384.8 | 375.85 | 1.29 |
| 79 | 487.7 | 504.8 | 496.25 | 1.43 |
| 80 | 598.3 | 627.8 | 613.05 | 2.28 |
| 81 | 766.2 | 886.1 | 826.15 | 2.26 |
| 82 | 1376.3 | 1780 | 1578.15 | 4.68 |
| 83 | 3925.6 | 5593.6 | 4759.6 | 12.66 |

TABLE 15-continued

DLS measurements for $scTNF_{R2}$ -Fc(Δab) 743
$scTNF_{R2}$ -Fc(Δab) 743

| T (° C.) | Measurement 1 (kcps) | Measurement 2 (kcps) | Mean (kcps) | $kcps_T/kcps_{(T-5)}$ |
|---|---|---|---|---|
| 84 | 8995.5 | 9427.9 | 9211.7 | 18.56 |
| 85 | 9757.7 | 9866 | 9811.85 | 16.00 |
| 86 | 9959.2 | 9798.1 | 9878.65 | 11.96 |
| 87 | 8953.9 | 8505.6 | 8729.75 | 5.53 |

TABLE 16

DLS measurements for $scTNF_{R2}$ -Fc(Δab) 744
$scTNF_{R2}$ -Fc(Δab) 744

| T (° C.) | Measurement 1 (kcps) | Measurement 2 (kcps) | Mean (kcps) | $kcps_T/kcps(_{T-5})$ |
|---|---|---|---|---|
| 35 | 216 | 217.6 | 216.8 | |
| 36 | 216.4 | 213.8 | 215.1 | |
| 37 | 210 | 211.4 | 210.7 | |
| 38 | 226.6 | 224.9 | 225.75 | |
| 39 | 208 | 207.5 | 207.75 | |
| 40 | 230.3 | 225.3 | 227.8 | 1.05 |
| 41 | 212.3 | 213.1 | 212.7 | 0.99 |
| 42 | 226.4 | 220.5 | 223.45 | 1.06 |
| 43 | 211.9 | 215.7 | 213.8 | 0.95 |
| 44 | 215 | 219.7 | 217.35 | 1.05 |
| 45 | 215.2 | 215 | 215.1 | 0.94 |
| 46 | 211.4 | 210.4 | 210.9 | 0.99 |
| 47 | 210.8 | 210.3 | 210.55 | 0.94 |
| 48 | 209.7 | 209.3 | 209.5 | 0.98 |
| 49 | 209.6 | 211.1 | 210.35 | 0.97 |
| 50 | 213 | 217.2 | 215.1 | 1.00 |
| 51 | 212.7 | 209.5 | 211.1 | 1.00 |
| 52 | 217.8 | 220.7 | 219.25 | 1.04 |
| 53 | 224.8 | 221.9 | 223.35 | 1.07 |
| 54 | 214.5 | 216 | 215.25 | 1.02 |
| 55 | 233.7 | 237.3 | 235.5 | 1.09 |
| 56 | 224.3 | 227.2 | 225.75 | 1.07 |
| 57 | 219.1 | 221.7 | 220.4 | 1.01 |
| 58 | 224.5 | 224.6 | 224.55 | 1.01 |
| 59 | 217.2 | 214.5 | 215.85 | 1.00 |
| 60 | 206.3 | 206.9 | 206.6 | 0.88 |
| 61 | 208.9 | 212.5 | 210.7 | 0.93 |
| 62 | 228.5 | 226.3 | 227.4 | 1.03 |
| 63 | 220 | 218.5 | 219.25 | 0.98 |
| 64 | 209.1 | 209.7 | 209.4 | 0.97 |
| 65 | 217.9 | 220.4 | 219.15 | 1.06 |
| 66 | 219.2 | 220.3 | 219.75 | 1.04 |
| 67 | 224.6 | 227.8 | 226.2 | 0.99 |
| 68 | 242.6 | 254.1 | 248.35 | 1.13 |
| 69 | 250.4 | 255 | 252.7 | 1.21 |
| 70 | 276.5 | 283.2 | 279.85 | 1.28 |
| 71 | 312.9 | 323.5 | 318.2 | 1.45 |
| 72 | 368.1 | 389.1 | 378.6 | 1.67 |
| 73 | 445.5 | 475.8 | 460.65 | 1.85 |
| 74 | 571.2 | 628.8 | 600 | 2.37 |
| 75 | 849.1 | 987.9 | 918.5 | 3.28 |
| 76 | 1598.1 | 2136.1 | 1867.1 | 5.87 |
| 77 | 5595.3 | 8356.8 | 6976.05 | 18.43 |
| 78 | 10540 | 10726.3 | 10633.15 | 23.08 |
| 79 | 11272.5 | 11419.5 | 11346 | 18.91 |
| 80 | 11385.4 | 11100 | 11242.7 | 12.24 |
| 81 | 9549.7 | 7969.2 | 8759.45 | 4.69 |

Figure 5B:
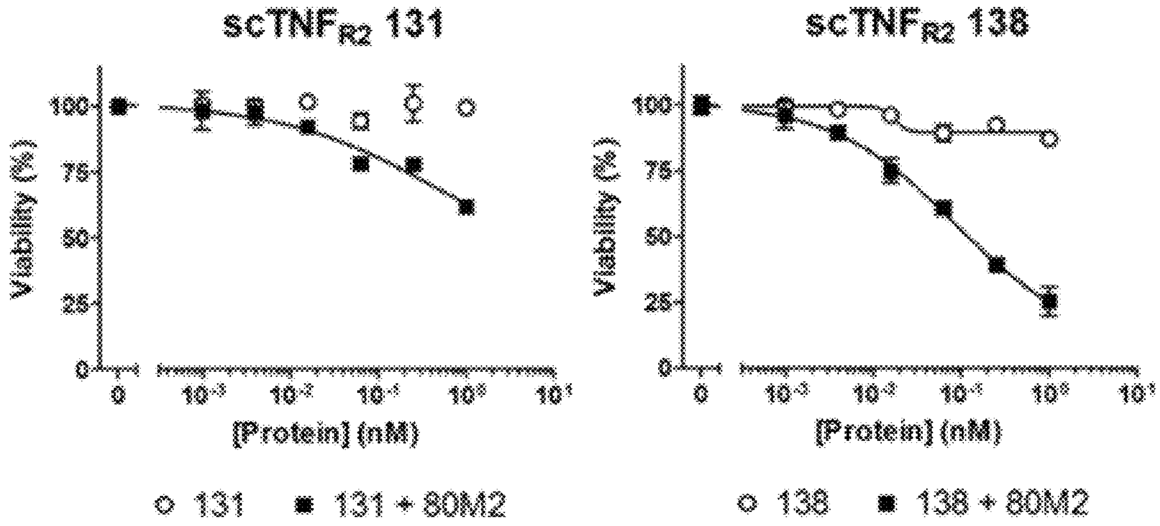

Example 5: In Vitro Bioactivity of $scTNF_{R2}$ Mutants on Kym-1 Cells with and without TNF-R2 coactivation using 80M2 antibody The basic bioactivity of $scTNF_{R2}$ mutants was analyzed in an in vitro assay using Kym-1 cells. The stimulation of TNFR2 on Kym-1 leads to expression of endogenous TNF, which induces apoptosis of the cells via activation of TNFR1-mediated signaling. Of note, pure trivalent $scTNF_{R2}$ has been shown to be nearly inactive in terms of TNFR2 activation and requires, in addition, TNFR2 crosslinking for bioactivity, for instance by using the anti-TNFR2 antibody 80M2, which by itself is non-agonistic. For the experiment, 15,000 Kym-1 cells/well were seeded in 96-well plates, cultivated for 24 h at 37° C. and 5% $CO_2$ and incubated with serially diluted proteins in triplicates for another 24 h. Under conditions of TNFR2 crosslinking, 1 μg/ml 80M2 antibody (Hycult Biotech) was added to the cells 30 min before addition of the proteins titrated in duplicates. The cell viability was determined by crystal violet staining. The data was normalized to untreated control and positive control (1% Triton X-100). In combination with 80M2, all $scTNF_{R2}$ variants induced cell death of Kym-1 cells. However, some mutants, e.g. 129, showed reduced activity compared with the reference $scTNF_{R2}$ 118 (FIG. 5, Table 17).

TABLE 17

$EC_{50}$ values of bioactivity of $scTNF_{R2}$ mutants on Kym-1 cells in combination with TNF-R2 crosslinking with antibody 80M2.

| 6xHis-$scTNF_{R2}$ | $EC_{50}$ (+80M2) on Kym-1 (pM) |
|---|---|
| 118 | 130 |
| 127 | 151 |
| 130 | 100 |
| 129 | 759 |
| 139 | 224 |
| 131 | — |
| 138 | 119 |

Example 6: Binding of $scTNF_{R2}$-Fc(Δab) Complexes to Immobilized TNF-R2

The binding of the $scTNF_{R2}$-Fc(Δab) complexes to TNFR2-Fc (etanercept) was analyzed by ELISA. 96-well ELISA plates were coated with 200 ng/well etanercept in coating buffer (0.1 M sodium carbonate, pH 9.5) overnight at 4° C., blocked with 2% skim milk in PBS (MPBS) and washed with washing buffer PBST (PBS, 0.05% Tween 20). $ScTNF_{R2}$-Fc(Δab) complexes were titrated in duplicates and incubated on the plates for 2 h at room temperature, followed by washing with PBST. Receptor-bound complexes were detected with mouse anti-huTNFα F6C5 (Novus, 1 μg/ml) and goat anti-mouse IgG (Fc)-HRP (Sigma-Aldrich, 1:10,000), followed by extensive washing with PBST each. The $scTNF_{R2}$-Fc(Δab) complexes showed a dose-dependent binding to TNF-R2-Fc with $EC_{50}$ values in the sub-nanomolar range (FIG. 6, Table 18). $ScTNF_{R2}$-Fc(Δab) 742, 743 and 744 showed a binding behavior comparable to the $SCTNF_{R2}$-Fc(Δab) 745 variant comprising the state-of-the-art $scTNF_{R2}$ molecule 118.

TABLE 18

$EC_{50}$ values of binding of $scTNF_{R2}$-Fc(Δab) complexes to TNF-R2-Fc (Mean ± S.D, n = 3).

| $scTNF_{R2}$-Fc(Δab) | $EC_{50}$ on TNFR2-Fc (pM) |
|---|---|
| 745 | 419 ± 14 |
| 742 | 365 ± 31 |
| 743 | 180 ± 11 |
| 744 | 309 ± 15 |

Example 7: TNF-R2 Selective Binding of $scTNF_{R2}$-Fc(Δab) Complexes on Cells

The binding of the $scTNF_{R2}$-Fc(Δab) complexes to mouse embryonic fibroblasts (MEFs) stably transfected with human TNFR1 (MEF-TNFR1) or human TNFR2 (MEF-TNFR2) (Krippner-Heidenreich et al., 2002, J. Biol. Chem. 277, 44155-44163) was analyzed by flow cytometry. To this, cells were trypsinized and washed once in ice-cold FACS buffer (PBS, 2% FBS, 0.05% sodium azide). 200,000 cells per sample were incubated with serially diluted $scTNF_{R2}$-Fc(Δab) complexes in 100 μl FACS buffer for 2 h at 4° C. Next, unbound proteins were removed by two washing steps with FACS buffer, followed by detection with Anti-Human IgG (γ-chain specific)-R-Phycoerythrin antibody (Sigma-Aldrich, 1:500) for 1 h at 4° C. After two final washing steps with FACS buffer, cells were analyzed with a MACSQuant® Analyzer 10 equipped with a 585/40 nm filter. All $scTNF_{R2}$-Fc(Δab) molecules (745, 742, 743 and 744) showed a dose-dependent binding on MEF-TNFR2 (FIG. 7, Table 19). However, while the $SCTNF_{R2}$-Fc(Δab) complexes 742 and 744 showed a $EC_{50}$ values identical to that of the $SCTNF_{R2}$-Fc(Δab) 745 variant comprising the state-of-the-art $scTNF_{R2}$ molecule 118 (with $EC_{50}$ values of around 60 μM), the molecule $scTNF_{R2}$-Fc(Δab) 743 showed weaker (approx. 2.8-fold reduced) binding to MEF-TNFR2 ($EC_{50}$ value of 168 μM). Furthermore, on MEF-TNFR1 no binding of the $scTNF_{R2}$-Fc(Δab) complexes could be detected, demonstrating the selectivity of the molecules for TNFR2.

TABLE 19

$EC_{50}$ values of binding of $scTNF_{R2}$-Fc(Δab) complexes to MEF-TNFR2-Fc.

| $scTNF_{R2}$-Fc(Δab) | $EC_{50}$ on MEF-TNFR2 (pM) |
|---|---|
| 745 | 62 |
| 742 | 59 |
| 743 | 168 |
| 744 | 62 |

Example 8: In Vitro Bioactivity of $scTNF_{R2}$-Fc (Δab) Complexes on Kym-1 Cells The in vitro bioactivity of $scTNF_{R2}$-Fc(Δab) complexes was analyzed on Kym-1 cells in a similar experimental setting described in example 5, with the exception that TNFR2 crosslinking by addition of antibody 80M2 was omitted (the hexavalent $scTNF_{R2}$-Fc(Δab) proteins do not require TNFR2 cross-linking) (FIG. 8, Table 20). On Kym-1 cells, $scTNF_{R2}$-Fc(Δab) 742 showed a bioactivity comparable to the reference molecule $scTNF_{R2}$-Fc(Δab) 745 comprising the state-of-the-art $scTNF_{R2}$ variant 118. $ScTNF_{R2}$-Fc(Δab) 744 showed a reduced bioactivity (approx. 4-fold). However, the bioactivity of $scTNF_{R2}$-Fc(Δab) 743 was strongly reduced compared to $scTNF_{R2}$-Fc(Δab) 745 (approx. 228-fold). These findings indicate that structural properties due to too short peptide linkers have a negative impact on protein folding and therefore receptor activation.

TABLE 20

$EC_{50}$ values of bioactivity of $scTNF_{R2}$-Fc(Δab) complexes on Kym-1 cells (Mean ± S.D., n = 3).

| $scTNF_{R2}$-Fc(Δab) | $EC_{50}$ on Kym-1 (pM) |
|---|---|
| 745 | 14.9 ± 3.3 |
| 742 | 20.5 ± 4.5 |
| 743 | ~3,400 |
| 744 | 59.5 ± 3.8 |

Example 9: NF-κB Activation by $scTNF_{R2}$-Fc (ΔAb) Complexes in HeLa-TNF-R2 Cells The in vitro NF-κB activation by $scTNF_{R2}$-Fc(Δab) complexes was analyzed in Hela cells stably transfected with human TNF receptor 2 (HeLa-TNF-R2) using a luciferase reporter assay. To this, 15,000 cells per 96-well were seeded and cultivated at 37° C. and 5% $CO_2$. After 24 h, culture medium (RPMI/10% FBS, PenStrep) was renewed and cells were transiently transfected with pNF-κB Luc firefly luciferase experimental reporter plasmid (66 ng/well) (Agilent Technologies) and pRL-TK *Renilla* luciferase control plasmid (33 ng/well) (Promega) using Lipofectamine 2000 (Thermo, 4 μl/1 μg of DNA). After 16 h of cultivation, transfected cells were stimulated with the $scTNF_{R2}$-Fc(Δab) proteins titrated in duplicates. After 6 h of stimulation the culture medium was changed to RPMI w/o phenol red/5% FBS (35 μl/well) and luciferase activities were measured with the Dual-Glo® Luciferase Assay System (Promega) in combination with luminescence detection using a Spark® microplate reader (Tecan). The pNF-κB regulated firefly luciferase activity was normalized to the control *Renilla* luciferase activity in each individual well. NF-κB activity in HeLa-TNF-R2 cells showed a sigmoidal dose-response in dependence of the concentration of $scTNF_{R2}$-Fc(Δab) complexes (FIG. 9). The calculated $EC_{50}$ values from four independent experiments (Table 21) reflecting the bioactivity of the $scTNF_{R2}$-Fc(Δab) complexes showed no statistically significant difference for the proteins 745, 742 and 744 (P>0.05, One-way ANOVA with Tukey's post test). However, $scTNF_{R2}$-Fc(Δab) 743 showed lower bioactivity in terms of NF-κB activation compared with the state-of-the-art protein 745 (approx. 95-fold reduced) with statistical significance (p<0.01).

TABLE 21

$EC_{50}$ values of NF-κB activation of $scTNF_{R2}$-Fc(Δab) complexes on HeLa-TNF-R2 cells (Mean ± S.D., n = 3).

| $scTNF_{R2}$-Fc(Δab) | $EC_{50}$ on HeLa-TNF-R2 (pM) |
|---|---|
| 745 | 2.1 ± 0.8 |
| 742 | 3.1 ± 1.2 |
| 743 | 199 ± 110 |
| 744 | 3.4 ± 0.4 |

Example 10: Stability of $scTNF_{R2}$-Fc(ΔAb) Proteins in Human Blood Plasma

The stability of the $scTNF_{R2}$-Fc(Δab) proteins in human blood plasma after incubation periods of 3 and 8 days at 37° C. was assayed by binding of protein samples to Hela cells stably overexpressing TNF-R2 (HeLa-TNF-R2, Richter et al., 2012, Mol. Cell Biol. 32, 2515-2529). In detail, the proteins with stock concentrations in 1×PBS (8 mM $Na_2HPO_4$, 1.8 mM $KH_2PO_4$, 2.7 mM KCl, 137 mM NaCl, pH 7.4) of 5.17 μM (745), 8.05 UM (742), 2.11 μM (743) and 11.25 μM (744) were diluted with PBS to a concentration of 400 nM and incubated for 0 days (control), 3 days or 8 days in 50% human blood plasma (final protein conc. 200 nM) at 37° C. After incubation, samples were stored at −80° C. and thawed prior testing the protein integrity by binding to HeLa-TNF-R2 in flow cytometry. To this, HeLa-TNF-R2 cells with a confluency of 50-70% were trypsinized and washed once in ice-cold FACS buffer (1×PBS, 2% FBS, 0.05% sodium azide). 150,000 cells per sample were incubated with in FACS buffer 1:3 serially diluted $scTNF_{R2}$-Fc(Δab) proteins, starting from 30 nM, in 100 μl FACS buffer for 1.5 h at 4° C. in a V-bottom 96-well plate. Next, unbound proteins were removed by two washing steps with FACS buffer. Therefore, the V-bottom 96-well plates were centrifuged at 500×g and the liquid in the wells was removed by a suction system. 180 μl FACS buffer per well was added and gently pipetted up and down to resuspend the cell pellet. Bound protein was detected with goat anti-human IgG Fcγ fragment specific-R-phycoerythrin antibody (Jackson ImmunoResearch, 1:500) for 1 h at 4° C. After two final washing steps with FACS buffer, cells were analyzed with a MACSQuant® VYB flow cytometer equipped with a 586/15 nm filter for detection of phycoerythrin. Binding curves were fitted with GraphPad Prism and $EC_{50}$ values of binding were calculated from four independent experiments. The percentages of intact protein were calculated for each single experiment from reciprocals of values obtained by normalization of the $EC_{50}$ values to the non-incubated control.

No reduction in the amount of intact protein was observed for the $scTNF_{R2}$-Fc(Δab) proteins 742 and 744 while the protein $scTNF_{R2}$-Fc(Δab) protein 745 showed a slight reduction to approximately 80% remaining activity after 3 and 8 days. In contrast, $scTNF_{R2}$-Fc(Δab) 743 showed a strong and time dependent decline in intact protein, with approximately 40% remaining after 8 days. These data confirm that the variants 742 and 744 exhibit, compared to the parental version 745 and the modified version 743, a statistically significant improved stability under physiological conditions.

TABLE 22

$EC_{50}$ values (pM) of binding of $scTNF_{R2}$-Fc(Δab) proteins incubated in 50% human blood plasma to HeLa-TNF-R2 cells.

| $scTNF_{R2}$-Fc(Δab) | Days at 37° C. | Experiment 1 | 2 | 3 | 4 |
|---|---|---|---|---|---|
| 745 | 0 | 73.1 | 52.7 | 55.8 | 85.5 |
| | 3 | 83.4 | 68.5 | 78.4 | 115.5 |
| | 8 | 82.0 | 66.6 | 76.7 | 93.8 |
| 742 | 0 | 70.2 | 53.9 | 64.0 | 80.2 |
| | 3 | 70.9 | 59.6 | 66.2 | 79.8 |
| | 8 | 60.9 | 54.8 | 65.7 | 79.4 |
| 743 | 0 | 542 | 647 | 1250 | 685 |
| | 3 | 960 | 1383 | 2690 | 900 |
| | 8 | 1223 | 1885 | 3311 | 1728 |
| 744 | 0 | 54.8 | 61.8 | 62.9 | 76.5 |
| | 3 | 61.8 | 59.8 | 65.4 | 88.8 |
| | 8 | 57.6 | 56.7 | 74.6 | 86.9 |

Example 11: Further Variants of Proteins of the Present Invention

Further human scTNF derivatives selective for TNFR2 were generated that are characterized by different linker compositions due to variable N-terminal start positions ($X_N$) and linker $X_L$ length. In detail, the proteins comprise human TNFR2 mutant domains with N-terminal start positions at aa residues 81, 82, 83, and 84, respectively, and ending with aa 233 (C-terminus) (see Table 1 and 2; human TNF sequence derived from UniPRotKB entry P01375). Single-chain derivatives ($scTNF_{R2}$) of these domains were generated by fusing three $TNF_{R2}$ mutant domains into one polypeptide chain. This genetic fusion was accomplished either by the use of two peptide linkers to connect the three TNF domains, or by fusing the TNF domains directly without the use of peptide linkers. In detail, the TNF domains of the $scTNF_{R2}$ mutants were fused either directly (variant 140, SEQ ID NO: 76), or with peptide linkers consisting of one glycine (variant 141, SEQ ID NO: 77; variant 142, SEQ ID NO: 78), with two glycines (variant 144, SEQ ID NO: 80 variant 145, SEQ ID NO: 81), with three glycines (variant 143, SEQ ID NO; 79 variant 146, SEQ ID NO: 82), or with four glycines (variant 147, SEQ ID NO: 83), respectively (Table 23). The TNF-R2-selective human $scTNF_{R2}$ mutants represent a trivalent arrangement of the three TNF THD, i.e. forming three $TNF_{R2}$ binding sites.

Furthermore, the $scTNF_{R2}$ mutant variants were connected via a peptide linker L2 consisting of GGSGGGGSGG (SEQ ID NO: 92) to the N-terminus of the Fc(Δab) dimerization region to generate hexavalent $scTNF_{R2}$-Fc fusion proteins (this Fc region comprises mutations for deletion of Fc effector functions, such as binding to Fcγ receptors and complement component C1; Armour et al., 1999, Eur. J. Immunol. 29, 2613-2624). These hexavalent fusion proteins, i.e. proteins exhibiting six TNFR2-binding sites, are denoted $scTNF_{R2}$(140)-Fc(Δab) (protein 148, SEQ ID NO: 84), $scTNF_{R2}$(141)-Fc(Δab) (protein 149), SEQ ID NO: 85), $scTNF_{R2}$(143)-Fc(Δab) (protein 151, SEQ ID NO: 87), $scTNF_{R2}$(144)-Fc(Δab) (protein 152), SEQ ID NO: 88), and $scTNF_{R2}$(145)-Fc(Δab) (protein 153, SEQ ID NO: 89) (Table 24).

The overall codon usage of $scTNF_{R2}$ and all Fc fusion proteins was adapted for expression in mammalian cells. An Igκ leader sequence was fused to the N-terminal end of the constructs to facilitate secretion of the proteins into the supernatant. To facilitate purification of the proteins, an N-terminal His-tag was introduced in the $scTNF_{R2}$ mutants but was omitted in the $scTNF_{R2}$-Fc(Δab) fusion proteins. In detail, coding DNA sequences of $scTNF_{R2}$ mutants and $scTNF_{R2}$-Fc(Δab) mutants were cloned into mammalian expression vectors allowing for recombinant production as sole 6×His-tagged single-chain protein 6×His-$scTNF_{R2}$ (pTT5 vector) or non-tagged Fc fusion protein $scTNF_{R2}$-Fc(Δab) (pSecTag vector).

TABLE 23

$scTNF_{R2}$ variants of example 11.

| $scTNF_{R2}$ mutant | Sequence human $scTNF_{R2}$: C-termunus $TNF_{R2}$ domain | Peptide linker | N-terminus $TNF_{R2}$ domain | $huTNF_{R2}$ subunit aa positions |
|---|---|---|---|---|
| 141 | . . . GIIAL (SIN: 93) | G | SRTPSDKPVAVH | 81-233 |
| 144 | . . . GIIAL (SIN: 94) | GG | RTPSDKPVAHV | 82-233 |
| 146 | . . . GIIAL (SIN: 95) | GGG | TDSDKPVAHV | 83-233 |

TABLE 23-continued scTNF$_{R2}$ variants of example 11.

| scTNF$_{R2}$ mutant | Sequence human scTNF$_{R2}$: C-termunus TNF$_{R2}$ domain | Peptide linker | N-terminus TNF$_{R2}$ domain | huTNF$_{R2}$ subunit aa positions |
|---|---|---|---|---|
| 147 | . . . GIIAL (SIN: 96) | GGGG | PSDKPVAVH | 84-233 |
| 140 | . . . GIIAL (SIN: 97) | | SRTPSDKPVAH V | 81-233 |
| 142 | . . . GIIAL (SIN: 98) | G | RTPSDKPVAHV | 82-233 |
| 145 | . . . GIIAL (SIN: 99) | GG | TPSDKPVAHV | 83-233 |
| 143 | . . . GIIAL (SIN: 100) | GGG | PSDKPVAVH | 84-233 |

TABLE 24 scTNFR2-Fc variants of example 11.

| scTNF$_{R2}$-Fc mutant | Sequence human scTNF$_{R2}$: C-terminus TNF$_{R2}$ domain | Peptide linker | N-terminus TNF$_{R2}$ domain | huTNF$_{R2}$ subunit aa positions |
|---|---|---|---|---|
| 149 | . . . GIIAL (SIN: 101) | G | SRTPSDKPVAH V | 81-233 |
| 152 | . . . GIIAL (SIN: 102) | GG | RTPSDKPVAHV | 82-233 |
| 154 | . . . GIIAL (SIN: 103) | GGG | TPSDKPVAHV | 83-233 |
| 155 | . . . GIIAL (SIN: 104) | GGGG | PSDKPVAHV | 84-233 |
| 148 | . . . GIIAL (SIN: 105) | | SRTPDSKPVAH V | 81-233 |
| 150 | . . . GIIAL (SIN: 106) | G | RTPSDKPVAHV | 82-233 |
| 153 | . . . GIIAL (SIN: 107) | GG | TPSDKPVAHV | 83-233 |
| 151 | . . . GIIAL (SIN: 108) | GGG | PSDKPVAVH | 84-233 |

Example 12: Production and Purification of Proteins of Example 11

All proteins of example 11 were produced in HEK293-6E cells (NRC-BRI), grown in F17 medium (Life Technologies) at 37° C., 5% $CO_2$ under shaking conditions, which were transiently transfected with plasmid DNA using polyethyleneimine (Polysciences). The day after, 0.5% Tryptone N1 (Organotechnie) was added to the cell culture and cells were cultivated for additional 5 days. Then, supernatants were collected, centrifuged cell-free and recombinant proteins were isolated therefrom.

6×His-scTNF$_{R2}$ mutants were purified via immobilized metal ion chromatography (IMAC). In brief, supernatant was batch-incubated on a roller mixer at 4° C. for 16 h with Ni-NTA agarose (Macherey-Nagel), followed by collection in chromatography columns. Unbound proteins were removed using IMAC wash buffer (50 mM sodium phosphate buffer, pH 7.5). Bound proteins were eluted with IMAC elution buffer (50 mM sodium phosphate buffer, 250 mM imidazole, pH 7.5) and dialyzed (membrane cut-off 14 kDa, Roth) against PBS buffer (pH 7.4) overnight at 4° C.

ScTNF$_{R2}$-Fc(Δab) fusion proteins were purified by Protein A affinity chromatography. Supernatants were batch-incubated with Protein A Sepharose 4 Fast Flow (GE Healthcare) or Toyopearl AF-rProtein A-650F (Tosoh) on a roller mixer at 4° C. for 16 h and collected in chromatography columns. Unbound proteins were removed using PBS, pH 7.4. Bound proteins were eluted with Protein A elution buffer (100 mM glycine-HCl, pH 3.5), neutralized immediately by adding 1 M Tris-HCl, pH 9.0 and dialyzed (membrane cut-off 14 kDa, Roth) against PBS buffer (pH 7.4) overnight at 4° C.

Dialyzed proteins were further purified by preparative size-exclusion chromatography (SEC). The protein preparations were separated on a Superdex 200 10/300 GL column (GE Healthcare) using an ÄKTA FPLC device (GE Healthcare) and eluted with PBS, pH 7.4. Protein concentration was determined spectrophotometrically at 280 nm and calculated using the individual extinction coefficients.

Protein preparations were analyzed by SDS-PAGE and subsequent Coomassie staining (FIGS. 11 and 12). 2.5 μg of the purified proteins according to Example 11 were denatured in Laemmli buffer (50 mM Tris pH 6.8, 4 M urea, 1% SDS, 15% glycerol, 0.01% bromphenol blue) under reducing conditions (in the presence of 5% 2-mercaptoethanol) and non-reducing conditions (in the absence of 2-mercaptoethanol) and separated by 10% or 12% SDS-PAGE. For visualization of proteins, the SDS-PAGE gels were incubated in InstantBlue stain (Expedion).

Example 13: Molecular Integrity and Purity of Proteins of Example 11 Under Native Conditions The purity and oligomerization state of the scTNF$_{R2}$-Fc(Δab) fusion proteins according to example 11 was further characterized by analytical HPLC size-exclusion chromatography (SEC). Approx. 20 μg protein were applied to a SuperSW mAb HR, 7.8×300 mm column (Tosoh Bioscience) equilibrated with SEC buffer (0.1 M $Na_2HPO_4$/$NaH_2PO_4$, 0.1 M $Na_2SO_4$, pH 6.7) and eluted at a flow rate of 0.5 ml/min. The fusion proteins eluted at the expected sizes (with an apparent molecular mass of approximately 160 kDa) as single peaks, indicating the correct assembly and high purity of the proteins (see FIG. 13).

Example 14: Thermal Stability of Proteins of Example 11

The thermal stability of the proteins according to example 11 was analyzed by dynamic light scattering using a Malvern Zetasizer instrument.

ScTNF$_{R2}$ molecules 140, 141, 142, 143, 144, 145, 146, and 147 were present in 1×PBS (8 mM $Na_2HPO_4$, 1.8 mM $KH_2PO_4$, 2.7 mM KCl, 137 mM NaCl, pH 7.4) at the following concentrations: 370 μg/ml (140), 350 μg/ml (141), 450 μg/ml (142), 1.1 mg/ml (143), 430 μg/ml (144), 170 μg/ml (145), 350 μg/ml (146), and 470 μg/ml (147). ScTNF$_{R2}$-Fc(Δab) fusion proteins 148, 149, 150, 151, 152, 153, 154, and 155 were present in 1×PBS at the following concentrations: 1.59 mg/ml (148), 2.35 mg/ml (149), 1.59 mg/ml (151), 1.59 mg/ml (152) and 220 μg/ml (153).

Proteins were diluted to 100 μg/ml in DPBS w/o calcium, w/o magnesium (Gibco, catalog number 14190144; 8.06 mM $Na_2HPO_4 \times 7H_2O$, 1.47 mM $KH_2PO_4$, 2.67 mM KCl, 137.9 mM NaCl, pH 7.0-7.3) in a total volume of 1.1 ml and transferred into a quartz cuvette and analyzed by dynamic light scattering (DLS) as following: 1.1 ml of the diluted protein solution was filtered particle-free through an Acrodisc 13 mm syringe filter, 0.2 μm (Pall Corporation, part number 4602), which was beforehand equilibrated with 5×1 ml DPBS and transferred to a PCS8501 glass cuvette with round aperture (Malvern Panalytical), which was beforehand cleaned with 1 M NaOH and washed thoroughly with deionized water and DPBS. The cuvette was then placed in the measurement chamber of a preheated Zetasizer Nano-ZS ZEN3600, serial number MAL501015 (Malvern Panalytical), controlled by Dispersion Technology Software 5.00. The measurements were done in the manual mode with the following software settings:

- Material: Protein, RI 1.45; Absorption, 0.00
- Dispersant: ICN PBS Tablets; Temperature, 25° C.; Viscosity, 0.8882 cP; RI, 1.33
- Cell type: PCS8501
- Trend sequence: Start temperature, 25° C.; End temperature, 85° C.; Temperature interval, 1.0° C.; no check for melting point
- Size measurement: Equilibration time, 2 min; Number of measurements, 2; Delay between measurements, 0 sec.; no optimization of measurement settings; Measurement duration, Automatic; Advanced, Positioning method automatic attenuation selection; Data processing, Analysis model multiple narrow modes (high resolution)

The mean of the two measured kcps values at each temperature was calculated and plotted over temperature using GraphPad Prism 8 (GraphPad Software Inc.). The aggregation temperature was defined as the temperature T where the quotient $kcps_T/kcps_{(T-5)}$ reached at least a factor 2.0.

Compared to the original variant 118 (see FIG. 1), the modified $scTNF_{R2}$ mutants 140, 141, 142, 143, 144, 145, 146, and 147 showed considerably increased melting points of 67° C. (variants 145, 146), 68° C. (variants 141, 143, 144, 147), and 69° C. (variants 140, 142) respectively (see FIG. 14, Tables 25-33).

The $scTNF_{R2}$-Fc variants with an Xa length of 10 aa showed a melting point of 74° C. (variants 149, 152) and 75° C. (variant 154) (FIG. 15, Tables 34-41), comparable to variant 742 (see FIG. 1). Notably, the $scTNF_{R2}$-Fc(Δab) fusion proteins with a Xa length of 9 aa exhibited an increased thermal stability of 78° C. (variants 148, 153), 76° C. (variant 151) and 75° C. (variant 150). In summary, all $scTNF_{R2}$ variants of example 11 showed increased thermal stability to variant 118 (FIG. 1). The thermal stability of the corresponding $scTNF_{R2}$-Fc variants was significantly increased compared to variant 745 (FIG. 1), with the variants comprising an Xa linker length of 9 aa being more stable that the variants comprising a Xa linker length of 10 aa.

TABLE 25

Denaturation temperatures of $scTNF_{R2}$ mutants as determined by dynamic light scattering.

| 6xHis-$scTNF_{R2}$ | Aggregation temperature (° C.) |
|---|---|
| 140 | 69 |
| 141 | 68 |
| 142 | 69 |
| 143 | 68 |
| 144 | 68 |
| 145 | 67 |
| 140 | 67 |
| 147 | 68 |

TABLE 26

DLS measurements for 6xHis-$scTNF_{R2}$ 140
6x-His-$scTNF_{R2}$ 140

| T (° C.) | Measurement 1 (kcps) | Measurement 2 (kcps) | Mean (kcps) | $kcps_T$/ $kcps_{T-5}$ |
|---|---|---|---|---|
| 25 | 247.2 | 50 | 148.6 | |
| 26 | 88.3 | 53.55 | 70.925 | |
| 27 | 83.5 | 56.6 | 70.05 | |
| 28 | 54.2 | 54.7 | 54.45 | |
| 29 | 98.1 | 60.15 | 79.125 | |
| 30 | 53 | 56.5 | 54.75 | 0.368439 |
| 31 | 78.55 | 55.75 | 67.15 | 0.946775 |
| 32 | 75.85 | 57.5 | 66.675 | 0.95182 |
| 33 | 71.3 | 56.05 | 63.675 | 1.169421 |
| 34 | 121.15 | 56.2 | 88.675 | 1.120695 |
| 35 | 187.1 | 56.6 | 121.85 | 2.225571 |
| 36 | 198.8 | 58.05 | 128.425 | 1.912509 |
| 37 | 78.95 | 57.05 | 68 | 1.019873 |
| 38 | 194.8 | 59.35 | 127.075 | 1.995681 |
| 39 | 48.9 | 54.75 | 51.825 | 0.584438 |
| 40 | 93.2 | 53.55 | 73.375 | 0.602175 |
| 41 | 141.25 | 55.2 | 98.225 | 0.764843 |
| 42 | 70.25 | 55.2 | 62.725 | 0.922426 |
| 43 | 61.95 | 53.35 | 57.65 | 0.453669 |
| 44 | 76.45 | 53.15 | 64.8 | 1.250362 |
| 45 | 109.45 | 53.85 | 81.65 | 1.112777 |
| 46 | 81.6 | 53.7 | 67.65 | 0.688725 |
| 47 | 61.9 | 54.4 | 58.15 | 0.927063 |
| 48 | 65.3 | 54.6 | 59.95 | 1.039896 |
| 49 | 58.25 | 55.15 | 56.7 | 0.875 |
| 50 | 52.55 | 58.8 | 55.675 | 0.681874 |
| 51 | 51.6 | 65.6 | 58.6 | 0.866223 |
| 52 | 54 | 75.15 | 64.575 | 1.11049 |
| 53 | 70.1 | 73.55 | 71.825 | 1.198082 |
| 54 | 55.15 | 69.95 | 62.55 | 1.103175 |
| 55 | 62.1 | 67.2 | 64.65 | 1.161203 |
| 56 | 48.15 | 62.75 | 55.45 | 0.946246 |
| 57 | 49.25 | 63.2 | 56.225 | 0.870693 |
| 58 | 48.65 | 75.7 | 62.175 | 0.865646 |
| 59 | 51.05 | 90.7 | 70.875 | 1.133094 |
| 60 | 48.55 | 94.4 | 71.475 | 1.105568 |
| 61 | 57.7 | 99.25 | 78.475 | 1.415239 |
| 62 | 48.4 | 103.25 | 75.825 | 1.348599 |
| 63 | 51.45 | 108.35 | 79.9 | 1.285082 |
| 64 | 62.55 | 108.2 | 85.375 | 1.204586 |
| 65 | 87 | 109.9 | 98.45 | 1.377405 |
| 66 | 113.8 | 115.25 | 114.525 | 1.459382 |
| 67 | 87.45 | 132.05 | 109.75 | 1.447412 |
| 68 | 70.3 | 214.05 | 142.175 | 1.779412 |
| 69 | 92.4 | 344.9 | 218.65 | 2.561054 |
| 70 | 158.9 | 473 | 315.95 | 3.209243 |
| 71 | 246.75 | 637.65 | 442.2 | 3.861166 |
| 72 | 365.3 | 874.95 | 620.125 | 5.650342 |
| 73 | 526.9 | 1174.85 | 850.875 | 5.984702 |
| 74 | 780.55 | 1611.95 | 1196.25 | 5.471072 |
| 75 | 1137 | 2198 | 1667.5 | 5.277734 |
| 76 | 1607.35 | 2909.15 | 2258.25 | 5.106852 |
| 77 | 2246.2 | 3878.15 | 3062.175 | 4.937996 |
| 78 | 3094.6 | 4920.05 | 4007.325 | 4.709652 |
| 79 | 4033.75 | 6172.8 | 5103.275 | 4.266061 |
| 80 | 5207 | 7257.15 | 6232.075 | 3.737376 |
| 81 | 6358.4 | 8134.35 | 7246.375 | 3.208845 |

TABLE 27

| DLS measurements for 6xHis-scTNF$_{R2}$ 141<br>6x-His-scTNF$_{R2}$ 141 | | | | |
|---|---|---|---|---|
| T (° C.) | Measurement 1 (kcps) | Measurement 2 (kcps) | Mean (kcps) | kcps$_T$/kcps$_{T-5}$ |
| 25 | 152.85 | 154.65 | 153.75 | |
| 26 | 42.2 | 193.3 | 117.75 | |
| 27 | 91.25 | 101.65 | 96.45 | |
| 28 | 35.35 | 184.05 | 109.7 | |
| 29 | 79.65 | 152.5 | 116.075 | |
| 30 | 104.4 | 90 | 97.2 | 0.632195 |
| 31 | 85.95 | 75.2 | 80.575 | 0.684289 |
| 32 | 57.4 | 87.25 | 72.325 | 0.74987 |
| 33 | 42.45 | 81.2 | 61.825 | 0.563582 |
| 34 | 30.65 | 93.5 | 62.075 | 0.534784 |
| 35 | 24.65 | 122.2 | 73.425 | 0.755401 |
| 36 | 31.6 | 139.1 | 85.35 | 1.059262 |
| 37 | 34.6 | 117.05 | 75.825 | 1.048393 |
| 38 | 36.4 | 106.65 | 71.525 | 1.156894 |
| 39 | 42 | 90.55 | 66.275 | 1.06766 |
| 40 | 27.7 | 106 | 66.85 | 0.910453 |
| 41 | 21.45 | 89.85 | 55.65 | 0.652021 |
| 42 | 19.8 | 129.85 | 74.825 | 0.986812 |
| 43 | 17.75 | 175.35 | 96.55 | 1.349878 |
| 44 | 16.3 | 163.85 | 90.075 | 1.35911 |
| 45 | 19.1 | 144.05 | 81.575 | 1.220269 |
| 46 | 16.25 | 94.1 | 55.175 | 0.991465 |
| 47 | 19.25 | 118.2 | 68.725 | 0.918476 |
| 48 | 18.1 | 144.65 | 81.375 | 0.842828 |
| 49 | 20.25 | 170.9 | 95.575 | 1.06106 |
| 50 | 20.1 | 136.35 | 78.225 | 0.958933 |
| 51 | 15.05 | 85 | 50.025 | 0.906661 |
| 52 | 19.7 | 181.15 | 100.425 | 1.461259 |
| 53 | 17.2 | 79.1 | 48.15 | 0.591705 |
| 54 | 27.85 | 122.05 | 74.95 | 0.784201 |
| 55 | 19.4 | 76.95 | 48.175 | 0.615852 |
| 56 | 34.3 | 116.65 | 75.475 | 1.508746 |
| 57 | 24.95 | 76.8 | 50.875 | 0.506597 |
| 58 | 20.75 | 67.45 | 44.1 | 0.915888 |
| 59 | 24.2 | 77.05 | 50.625 | 0.67545 |
| 60 | 27.05 | 63.6 | 45.325 | 0.940841 |
| 61 | 32.45 | 67.3 | 49.875 | 0.660815 |
| 62 | 21.5 | 70.5 | 46 | 0.904177 |
| 63 | 16.95 | 81.85 | 49.4 | 1.120181 |
| 64 | 15.9 | 107.55 | 61.725 | 1.219259 |
| 65 | 15.05 | 108.95 | 62 | 1.367899 |
| 66 | 23.15 | 88.25 | 55.7 | 1.116792 |
| 67 | 56.65 | 94.4 | 75.525 | 1.641848 |
| 68 | 117.2 | 224.05 | 170.625 | 3.453947 |
| 69 | 208.45 | 626.1 | 417.275 | 6.760227 |
| 70 | 327.75 | 1301.8 | 814.775 | 13.14153 |
| 71 | 475.35 | 2344.25 | 1409.8 | 25.31059 |
| 72 | 692.1 | 3334.8 | 2013.45 | 26.65938 |
| 73 | 983.85 | 4428.65 | 2706.25 | 15.86081 |
| 74 | 1364.75 | 5302.2 | 3333.475 | 7.988677 |
| 75 | 1804.65 | 6642.55 | 4223.6 | 5.183762 |
| 76 | 2302.8 | 7853 | 5077.9 | 3.601858 |
| 77 | 2811.7 | 8935.45 | 5873.575 | 2.91717 |
| 78 | 3209.25 | 9666.9 | 6438.075 | 2.378965 |

TABLE 28

| DLS measurements for 6xHis-scTNF$_{R2}$ 142<br>6x-His-scTNF$_{R2}$ 142 | | | | |
|---|---|---|---|---|
| T (° C.) | Measurement 1 (kcps) | Measurement 2 (kcps) | Mean (kcps) | kcps$_T$/kcps$_{T-5}$ |
| 25 | 106.05 | 228.05 | 167.05 | |
| 26 | 77.25 | 269.75 | 173.5 | |
| 27 | 178.9 | 223.25 | 201.075 | |
| 28 | 121.05 | 296.75 | 208.9 | |
| 29 | 172.55 | 295.35 | 233.95 | |
| 30 | 162.85 | 282.95 | 222.9 | 1.334331 |
| 31 | 170.25 | 240.85 | 205.55 | 1.184726 |
| 32 | 188.45 | 238.5 | 213.475 | 1.061669 |
| 33 | 210.6 | 207.25 | 208.925 | 1.00012 |
| 34 | 246.55 | 210 | 228.275 | 0.975743 |
| 35 | 280.95 | 169.35 | 225.15 | 1.010094 |
| 36 | 246.45 | 136.9 | 191.675 | 0.932498 |
| 37 | 198.75 | 60.35 | 129.55 | 0.606863 |
| 38 | 231.85 | 52.85 | 142.35 | 0.681345 |
| 39 | 153.9 | 58.95 | 106.425 | 0.466214 |
| 40 | 177.95 | 17.65 | 97.8 | 0.434377 |
| 41 | 91.55 | 17.05 | 54.3 | 0.283292 |
| 42 | 100.95 | 24.35 | 62.65 | 0.483597 |
| 43 | 130 | 53.5 | 91.75 | 0.644538 |
| 44 | 120.8 | 74.55 | 97.675 | 0.917782 |
| 45 | 82.7 | 71.35 | 77.025 | 0.787577 |
| 46 | 101.05 | 78.2 | 89.625 | 1.650552 |
| 47 | 78.25 | 99.05 | 88.65 | 1.415004 |
| 48 | 87.95 | 124.2 | 106.075 | 1.156131 |
| 49 | 82 | 147.5 | 114.75 | 1.174814 |
| 50 | 81.2 | 198.6 | 139.9 | 1.816293 |
| 51 | 138.95 | 243.6 | 191.275 | 2.13417 |
| 52 | 150.75 | 149 | 149.875 | 1.690637 |
| 53 | 145.4 | 145.2 | 145.3 | 1.369786 |
| 54 | 206 | 185.05 | 195.525 | 1.703922 |
| 55 | 202.7 | 121.15 | 161.925 | 1.157434 |
| 56 | 215.8 | 197.8 | 206.8 | 1.081166 |
| 57 | 315.9 | 158.85 | 237.375 | 1.58382 |
| 58 | 235.9 | 141.95 | 188.925 | 1.300241 |
| 59 | 217.25 | 235.05 | 226.15 | 1.15663 |
| 60 | 247.4 | 159.15 | 203.275 | 1.255365 |
| 61 | 232.8 | 98.1 | 165.45 | 0.800048 |
| 62 | 196.3 | 80.75 | 138.525 | 0.58357 |
| 63 | 197.65 | 64.05 | 130.85 | 0.692603 |
| 64 | 187.85 | 58.8 | 123.325 | 0.545324 |
| 65 | 183.15 | 50.4 | 116.775 | 0.574468 |
| 66 | 187.5 | 57.3 | 122.4 | 0.739801 |
| 67 | 232.3 | 50.6 | 141.45 | 1.021115 |
| 68 | 353.4 | 80.95 | 217.175 | 1.659725 |
| 69 | 547.75 | 137.65 | 342.7 | 2.778836 |
| 70 | 762.05 | 129.7 | 445.875 | 3.81824 |
| 71 | 1087.8 | 173.5 | 630.65 | 5.152369 |
| 72 | 1499.8 | 339.25 | 919.525 | 6.500707 |
| 73 | 2061.05 | 438.6 | 1249.825 | 5.754921 |
| 74 | 2894.75 | 627.3 | 1761.025 | 5.138678 |
| 75 | 3879.95 | 833.25 | 2356.6 | 5.285338 |
| 76 | 5089.75 | 1109.75 | 3099.75 | 4.915167 |
| 77 | 6169.35 | 1503.85 | 3836.6 | 4.172372 |
| 78 | 7405.25 | 1919 | 4662.125 | 3.730222 |
| 79 | 8677.2 | 2386.65 | 5531.925 | 3.14131 |
| 80 | 9695 | 2899.9 | 6297.45 | 2.672261 |
| 81 | 10229.95 | 3378.95 | 6804.45 | 2.195161 |

TABLE 29

| DLS measurements for 6xHis-scTNF$_{R2}$ 143<br>6x-His-scTNF$_{R2}$ 143 | | | | |
|---|---|---|---|---|
| T (° C.) | Measurement 1 (kcps) | Measurement 2 (kcps) | Mean (kcps) | kcps$_T$/kcps$_{T-5}$ |
| 25 | 157.1 | 76.25 | 116.675 | |
| 26 | 74.1 | 67.95 | 71.025 | |
| 27 | 99.05 | 68.7 | 83.875 | |
| 28 | 72 | 62.6 | 67.3 | |
| 29 | 72.2 | 70.6 | 71.4 | |
| 30 | 71.75 | 69.9 | 70.825 | 0.607028 |
| 31 | 70.6 | 69.35 | 69.975 | 0.985216 |
| 32 | 71.25 | 69.45 | 70.35 | 0.838748 |
| 33 | 66.15 | 71.2 | 68.675 | 1.020431 |
| 34 | 67.35 | 57.95 | 62.65 | 0.877451 |
| 35 | 88.2 | 57.65 | 72.925 | 1.029651 |
| 36 | 77.85 | 57.6 | 67.725 | 0.967846 |
| 37 | 76.65 | 57.5 | 67.075 | 0.953447 |

TABLE 29-continued

DLS measurements for 6xHis-scTNF$_{R2}$ 143
6x-His-scTNF$_{R2}$ 143

| T (° C.) | Measurement 1 (kcps) | Measurement 2 (kcps) | Mean (kcps) | $kcps_T/kcps_{T-5}$ |
|---|---|---|---|---|
| 38 | 85.2 | 67 | 76.1 | 1.108118 |
| 39 | 79.55 | 57.1 | 68.325 | 1.090583 |
| 40 | 83.15 | 64.1 | 73.625 | 1.009599 |
| 41 | 92.85 | 67.25 | 80.05 | 1.181986 |
| 42 | 84.85 | 58.55 | 71.7 | 1.068953 |
| 43 | 86.9 | 60.75 | 73.825 | 0.970105 |
| 44 | 103.5 | 66.6 | 85.05 | 1.244786 |
| 45 | 95.55 | 63.85 | 79.7 | 1.082513 |
| 46 | 92.3 | 63.85 | 78.075 | 0.975328 |
| 47 | 110.55 | 64.35 | 87.45 | 1.219665 |
| 48 | 86.5 | 76.45 | 81.475 | 1.103623 |
| 49 | 87.15 | 95.85 | 91.5 | 1.075838 |
| 50 | 78.15 | 115.5 | 96.825 | 1.214868 |
| 51 | 66.8 | 146.7 | 106.75 | 1.367275 |
| 52 | 82.4 | 174.3 | 128.35 | 1.467696 |
| 53 | 76.6 | 203.35 | 139.975 | 1.718012 |
| 54 | 76.85 | 206.25 | 141.55 | 1.546995 |
| 55 | 86.75 | 216 | 151.375 | 1.563388 |
| 56 | 76.5 | 197.25 | 136.875 | 1.282201 |
| 57 | 86.6 | 184.5 | 135.55 | 1.056097 |
| 58 | 79.6 | 182.05 | 130.825 | 0.934631 |
| 59 | 85.9 | 178.6 | 132.25 | 0.934299 |
| 60 | 93.85 | 182.3 | 138.075 | 0.912139 |
| 61 | 126.2 | 174.05 | 150.125 | 1.096804 |
| 62 | 126.6 | 163.3 | 144.95 | 1.069347 |
| 63 | 132.35 | 154.9 | 143.625 | 1.097841 |
| 64 | 146.65 | 144.05 | 145.35 | 1.099055 |
| 65 | 147.95 | 142 | 144.975 | 1.049973 |
| 66 | 173.35 | 160.75 | 167.05 | 1.112739 |
| 67 | 253.75 | 261.75 | 257.75 | 1.778199 |
| 68 | 373.55 | 480.7 | 427.125 | 2.97389 |
| 69 | 685.25 | 807.25 | 746.25 | 5.134159 |
| 70 | 1262.1 | 1339.85 | 1300.975 | 8.973789 |
| 71 | 1980.35 | 2069.6 | 2024.975 | 12.12197 |
| 72 | 2889.1 | 3118.95 | 3004.025 | 11.6548 |
| 73 | 4220.6 | 4357.05 | 4288.825 | 10.04115 |
| 74 | 5715.55 | 5728 | 5721.775 | 7.66737 |
| 75 | 7204.35 | 7133.2 | 7168.775 | 5.51031 |
| 76 | 8570.6 | 8399.15 | 8484.875 | 4.190113 |
| 77 | 9447.75 | 9346.15 | 9396.95 | 3.12812 |
| 78 | 10278.7 | 9815.9 | 10047.3 | 2.34267 |
| 79 | 10009.55 | 9912.4 | 9960.975 | 1.740889 |
| 80 | 9166.7 | 9896.45 | 9531.575 | 1.329596 |

TABLE 30

DLS measurements for 6xHis-scTNF$_{R2}$ 144
6x-His-scTNF$_{R2}$ 1444

| T (° C.) | Measurement 1 (kcps) | Measurement 2 (kcps) | Mean (kcps) | $kcps_T/kcps_{T-5}$ |
|---|---|---|---|---|
| 25 | 206.3 | 45.35 | 125.825 | |
| 26 | 160.45 | 41.7 | 101.075 | |
| 27 | 155.55 | 43.3 | 99.425 | |
| 28 | 141.9 | 46.3 | 94.1 | |
| 29 | 211.85 | 45.2 | 128.525 | |
| 30 | 246.85 | 45.6 | 146.225 | 1.16213 |
| 31 | 249.35 | 51.6 | 150.475 | 1.488746 |
| 32 | 215.35 | 49.45 | 132.4 | 1.331657 |
| 33 | 223 | 41.25 | 132.125 | 1.404091 |
| 34 | 173.2 | 38.8 | 106 | 0.824742 |
| 35 | 137.5 | 40.3 | 88.9 | 0.607967 |
| 36 | 154.95 | 44.25 | 99.6 | 0.661904 |
| 37 | 145 | 38.6 | 91.8 | 0.693353 |
| 38 | 111.85 | 38.55 | 75.2 | 0.569158 |
| 39 | 99.55 | 40.3 | 69.925 | 0.65967 |
| 40 | 79.55 | 46.05 | 62.8 | 0.706412 |
| 41 | 77.15 | 40.9 | 59.025 | 0.59262 |
| 42 | 83.55 | 47.95 | 65.75 | 0.716231 |
| 43 | 70.55 | 47.75 | 59.15 | 0.786569 |

TABLE 30-continued

DLS measurements for 6xHis-scTNF$_{R2}$ 144
6x-His-scTNF$_{R2}$ 1444

| T (° C.) | Measurement 1 (kcps) | Measurement 2 (kcps) | Mean (kcps) | $kcps_T/kcps_{T-5}$ |
|---|---|---|---|---|
| 44 | 66.8 | 46.15 | 56.475 | 0.807651 |
| 45 | 70.5 | 44.2 | 57.35 | 0.913217 |
| 46 | 67.25 | 39.25 | 53.25 | 0.90216 |
| 47 | 64.05 | 37.75 | 50.9 | 0.774144 |
| 48 | 62.2 | 37.45 | 49.825 | 0.84235 |
| 49 | 62.85 | 43.4 | 53.125 | 0.940682 |
| 50 | 64.1 | 43.7 | 53.9 | 0.939843 |
| 51 | 72.55 | 40.9 | 56.725 | 1.065258 |
| 52 | 98 | 42.2 | 70.1 | 1.37721 |
| 53 | 71.1 | 41.55 | 56.325 | 1.130457 |
| 54 | 122.2 | 46.8 | 84.5 | 1.590588 |
| 55 | 93 | 45.15 | 69.075 | 1.28154 |
| 56 | 101.9 | 50.5 | 76.2 | 1.343323 |
| 57 | 102.8 | 39.1 | 70.95 | 1.012126 |
| 58 | 130.35 | 41.55 | 85.95 | 1.525965 |
| 59 | 134.7 | 38.65 | 86.675 | 1.02574 |
| 60 | 140.15 | 43.55 | 91.85 | 1.329714 |
| 61 | 166.05 | 45.7 | 105.875 | 1.389436 |
| 62 | 122.65 | 50.9 | 86.775 | 1.223044 |
| 63 | 124.9 | 49.15 | 87.025 | 1.012507 |
| 64 | 111.05 | 57.85 | 84.45 | 0.974329 |
| 65 | 113.45 | 61.15 | 87.3 | 0.950463 |
| 66 | 145.1 | 80.45 | 112.775 | 1.065171 |
| 67 | 241.3 | 133.9 | 187.6 | 2.161913 |
| 68 | 478.45 | 350.1 | 414.275 | 4.760414 |
| 69 | 885.05 | 616.45 | 750.75 | 8.889876 |
| 70 | 1351.85 | 958.65 | 1155.25 | 13.2331 |
| 71 | 1987.25 | 1360.15 | 1673.7 | 14.84106 |
| 72 | 2848.25 | 1973.65 | 2410.95 | 12.85155 |
| 73 | 3902.05 | 2680.35 | 3291.2 | 7.944481 |
| 74 | 5142.45 | 3495.35 | 4318.9 | 5.752781 |
| 75 | 6553.6 | 4285.9 | 5419.75 | 4.691409 |
| 76 | 7737 | 5174.55 | 6455.775 | 3.857188 |
| 77 | 8655.35 | 5871.25 | 7263.3 | 3.01263 |
| 78 | 9651.15 | 6303.45 | 7977.3 | 2.423827 |
| 79 | 10143.15 | 6650.5 | 8396.825 | 1.944205 |
| 80 | 10354.05 | 6553.45 | 8453.75 | 1.559804 |
| 81 | 10011.45 | 6054.75 | 8033.1 | 1.244328 |
| 82 | 9754.45 | 5843.25 | 7798.85 | 1.073734 |
| 83 | 8709.1 | 5599.8 | 7154.45 | 0.896851 |
| 84 | 7306.55 | 4915.85 | 6111.2 | 0.727799 |
| 85 | 6367.75 | 4281.05 | 5324.4 | 0.629827 |

TABLE 31

DLS measurements for 6xHis-scTNF$_{R2}$ 145
6x-His-scTNF$_{R2}$ 145

| T (° C.) | Measurement 1 (kcps) | Measurement 2 (kcps) | Mean (kcps) | $kcps_T/kcps_{T-5}$ |
|---|---|---|---|---|
| 25 | 86.05 | 65.35 | 75.7 | |
| 26 | 60.05 | 68.95 | 64.5 | |
| 27 | 50 | 59.35 | 54.675 | |
| 28 | 62.35 | 80.45 | 71.4 | |
| 29 | 81.3 | 88.6 | 84.95 | |
| 30 | 75.75 | 64.65 | 70.2 | 0.927345 |
| 31 | 70.8 | 65.9 | 68.35 | 1.05969 |
| 32 | 64.3 | 73.75 | 69.025 | 1.26246 |
| 33 | 57.75 | 81.25 | 69.5 | 0.973389 |
| 34 | 55.35 | 70.2 | 62.775 | 0.738964 |
| 35 | 51.05 | 65.3 | 58.175 | 0.828704 |
| 36 | 52 | 97.8 | 74.9 | 1.09583 |
| 37 | 73.4 | 78.6 | 76 | 1.10105 |
| 38 | 50.9 | 78.7 | 64.8 | 0.932374 |
| 39 | 74.6 | 71.6 | 73.1 | 1.164476 |
| 40 | 61.6 | 60.65 | 61.125 | 1.050709 |
| 41 | 73.75 | 56.5 | 65.125 | 0.869493 |
| 42 | 72.6 | 57.9 | 65.25 | 0.858553 |
| 43 | 58.85 | 53.15 | 56 | 0.864198 |
| 44 | 55.1 | 50.7 | 52.9 | 0.723666 |

TABLE 31-continued

DLS measurements for 6xHis-scTNF$_{R2}$ 145
6x-His-scTNF$_{R2}$ 145

| T (° C.) | Measurement 1 (kcps) | Measurement 2 (kcps) | Mean (kcps) | $kcps_T/kcps_{T-5}$ |
|---|---|---|---|---|
| 45 | 53.75 | 52.45 | 53.1 | 0.868712 |
| 46 | 88.75 | 58.7 | 73.725 | 1.132054 |
| 47 | 111.65 | 57.2 | 84.425 | 1.29387 |
| 48 | 154.7 | 55.15 | 104.925 | 1.873661 |
| 49 | 110.7 | 64.25 | 87.475 | 1.653592 |
| 50 | 83 | 86.6 | 84.8 | 1.596987 |
| 51 | 67.35 | 63.15 | 65.25 | 0.885046 |
| 52 | 79.55 | 82.1 | 80.825 | 0.957359 |
| 53 | 54.1 | 94.5 | 74.3 | 0.708125 |
| 54 | 60.6 | 89.7 | 75.15 | 0.859103 |
| 55 | 65.15 | 150.9 | 108.025 | 1.27388 |
| 56 | 69.7 | 136.9 | 103.3 | 1.583142 |
| 57 | 66.85 | 132.15 | 99.5 | 1.231055 |
| 58 | 63.75 | 171.1 | 117.425 | 1.580417 |
| 59 | 73.15 | 167.55 | 120.35 | 1.601464 |
| 60 | 82.2 | 156 | 119.1 | 1.102523 |
| 61 | 64.45 | 148.2 | 106.325 | 1.029284 |
| 62 | 60.05 | 156.85 | 108.45 | 1.08995 |
| 63 | 65.15 | 157.85 | 111.5 | 0.949542 |
| 64 | 101 | 167.2 | 134.1 | 1.11425 |
| 65 | 59.75 | 187.5 | 123.625 | 1.037993 |
| 66 | 116.6 | 233.55 | 175.075 | 1.646602 |
| 67 | 233.8 | 235.45 | 234.625 | 2.163439 |
| 68 | 350.15 | 301.85 | 326 | 2.923767 |
| 69 | 389.5 | 433.05 | 411.275 | 3.066928 |
| 70 | 623.75 | 578.35 | 601.05 | 4.861881 |
| 71 | 868.7 | 884.25 | 876.475 | 5.006283 |
| 72 | 1213.7 | 1135 | 1174.35 | 5.005221 |
| 73 | 1567.7 | 1591.25 | 1579.475 | 4.845015 |
| 74 | 2260.95 | 2233.05 | 2247 | 5.463498 |
| 75 | 3110.05 | 3051.85 | 3080.95 | 5.125946 |
| 76 | 4120.25 | 3982.65 | 4051.45 | 4.622436 |
| 77 | 5312.75 | 5076.4 | 5194.575 | 4.423362 |
| 78 | 6561.1 | 6180.5 | 6370.8 | 4.033492 |

TABLE 32

DLS measurements for 6xHis-scTNF$_{R2}$ 146
6x-His-scTNF$_{R2}$ 146

| T (° C.) | Measurement 1 (kcps) | Measurement 2 (kcps) | Mean (kcps) | $kcps_T/kcps_{T-5}$ |
|---|---|---|---|---|
| 25 | 192.05 | 189.3 | 192.05 | |
| 26 | 141.4 | 113.7 | 141.4 | |
| 27 | 225.5 | 252.1 | 225.5 | |
| 28 | 153.6 | 135.6 | 153.6 | |
| 29 | 135.85 | 156.2 | 135.85 | |
| 30 | 205.15 | 181.1 | 205.15 | 1.07 |
| 31 | 197.7 | 190.3 | 197.7 | 1.40 |
| 32 | 136.05 | 146.4 | 136.05 | 0.60 |
| 33 | 182.1 | 162.2 | 182.1 | 1.19 |
| 34 | 116.85 | 143.4 | 116.85 | 0.86 |
| 35 | 109.25 | 105.4 | 109.25 | 0.53 |
| 36 | 129.55 | 112 | 129.55 | 0.66 |
| 37 | 86 | 101.1 | 86 | 0.63 |
| 38 | 136.9 | 87.7 | 136.9 | 0.75 |
| 39 | 74.65 | 86.7 | 74.65 | 0.64 |
| 40 | 89.8 | 93.6 | 89.8 | 0.82 |
| 41 | 58.75 | 62.1 | 58.75 | 0.45 |
| 42 | 78.75 | 95.2 | 78.75 | 0.92 |
| 43 | 71.2 | 81.2 | 71.2 | 0.52 |
| 44 | 64.6 | 64.4 | 64.6 | 0.87 |
| 45 | 83.3 | 72.6 | 83.3 | 0.93 |
| 46 | 71.9 | 57.8 | 71.9 | 1.22 |
| 47 | 59.3 | 56.7 | 59.3 | 0.75 |
| 48 | 59.3 | 50.9 | 59.3 | 0.83 |
| 49 | 60.2 | 57.6 | 60.2 | 0.93 |
| 50 | 96.8 | 86.3 | 96.8 | 1.16 |
| 51 | 55.95 | 53.4 | 55.95 | 0.78 |
| 52 | 66.95 | 60.2 | 66.95 | 1.13 |

TABLE 32-continued

DLS measurements for 6xHis-scTNF$_{R2}$ 146
6x-His-scTNF$_{R2}$ 146

| T (° C.) | Measurement 1 (kcps) | Measurement 2 (kcps) | Mean (kcps) | $kcps_T/kcps_{T-5}$ |
|---|---|---|---|---|
| 53 | 62.55 | 66.3 | 62.55 | 1.05 |
| 54 | 59.15 | 53.3 | 59.15 | 0.98 |
| 55 | 68.7 | 62.6 | 68.7 | 0.71 |
| 56 | 67.4 | 80.2 | 67.4 | 1.20 |
| 57 | 84.7 | 75.4 | 84.7 | 1.27 |
| 58 | 58.65 | 59.5 | 58.65 | 0.94 |
| 59 | 67.75 | 63.6 | 67.75 | 1.15 |
| 60 | 79.45 | 71.4 | 79.45 | 1.16 |
| 61 | 101.75 | 115.3 | 101.75 | 1.51 |
| 62 | 114.6 | 88.9 | 114.6 | 1.35 |
| 63 | 89.25 | 103.4 | 89.25 | 1.52 |
| 64 | 76.3 | 62.1 | 76.3 | 1.13 |
| 65 | 70.95 | 71.9 | 70.95 | 0.89 |
| 66 | 150.25 | 133.1 | 150.25 | 1.48 |
| 67 | 368.8 | 327.1 | 368.8 | 3.22 |
| 68 | 600.35 | 566.9 | 600.35 | 6.73 |
| 69 | 871.65 | 839.2 | 871.65 | 11.42 |
| 70 | 1423.6 | 1327.6 | 1423.6 | 20.06 |
| 71 | 2063.2 | 1952 | 2063.2 | 13.73 |
| 72 | 2886.3 | 2741.6 | 2886.3 | 7.83 |
| 73 | 3947.1 | 3786.7 | 3947.1 | 6.57 |
| 74 | 5154.5 | 4875.7 | 5154.5 | 5.91 |
| 75 | 6517.3 | 6282.9 | 6517.3 | 4.58 |
| 76 | 7625.3 | 7436.9 | 7625.3 | 3.70 |
| 77 | 8773.15 | 8597.1 | 8773.15 | 3.04 |
| 78 | 9512.25 | 9347.6 | 9512.25 | 2.41 |
| 79 | 9810.8 | 9715.1 | 9810.8 | 1.90 |
| 80 | 9940 | 9943.8 | 9940 | 1.53 |

TABLE 33

DLS measurements for 6xHis-scTNF$_{R2}$ 147
6x-His-scTNF$_{R2}$ 147

| T (° C.) | Measurement 1 (kcps) | Measurement 2 (kcps) | Mean (kcps) | $kcps_T/kcps_{T-5}$ |
|---|---|---|---|---|
| 25 | 132.05 | 114.1 | 132.05 | |
| 26 | 159.75 | 187.4 | 159.75 | |
| 27 | 177.65 | 157 | 177.65 | |
| 28 | 145.6 | 154 | 145.6 | |
| 29 | 175.6 | 170.2 | 175.6 | |
| 30 | 147.2 | 153.5 | 147.2 | 1.11 |
| 31 | 141.05 | 145.8 | 141.05 | 0.88 |
| 32 | 154 | 120.5 | 154 | 0.87 |
| 33 | 103.25 | 113 | 103.25 | 0.71 |
| 34 | 108.05 | 78.5 | 108.05 | 0.62 |
| 35 | 55.95 | 58.2 | 55.95 | 0.38 |
| 36 | 59.5 | 67.1 | 59.5 | 0.42 |
| 37 | 57.7 | 56.5 | 57.7 | 0.37 |
| 38 | 64.55 | 74.9 | 64.55 | 0.63 |
| 39 | 60.2 | 63.7 | 60.2 | 0.56 |
| 40 | 101.3 | 103.1 | 101.3 | 1.81 |
| 41 | 124.15 | 106 | 124.15 | 2.09 |
| 42 | 114.65 | 99.2 | 114.65 | 1.99 |
| 43 | 134.6 | 130.5 | 134.6 | 2.09 |
| 44 | 97.3 | 89.2 | 97.3 | 1.62 |
| 45 | 81.05 | 90.4 | 81.05 | 0.80 |
| 46 | 70.7 | 81.4 | 70.7 | 0.57 |
| 47 | 82.6 | 88 | 82.6 | 0.72 |
| 48 | 59.95 | 55.2 | 59.95 | 0.45 |
| 49 | 75.9 | 71.8 | 75.9 | 0.78 |
| 50 | 85.2 | 102.6 | 85.2 | 1.05 |
| 51 | 74.8 | 65.6 | 74.8 | 1.06 |
| 52 | 111.3 | 86 | 111.3 | 1.35 |
| 53 | 85.05 | 82.8 | 85.05 | 1.42 |
| 54 | 153.65 | 140 | 153.65 | 2.02 |
| 55 | 142.15 | 161.2 | 142.15 | 1.67 |
| 56 | 177.35 | 184.1 | 177.35 | 2.37 |
| 57 | 110.85 | 110.1 | 110.85 | 1.00 |
| 58 | 114 | 114.1 | 114 | 1.34 |

TABLE 33-continued

DLS measurements for 6xHis-scTNF$_{R2}$ 147
6x-His-scTNF$_{R2}$ 147

| T (° C.) | Measurement 1 (kcps) | Measurement 2 (kcps) | Mean (kcps) | kcps$_T$/ kcps$_{T-5}$ |
|---|---|---|---|---|
| 59 | 132.8 | 142 | 132.8 | 0.86 |
| 60 | 127.6 | 138.7 | 127.6 | 0.90 |
| 61 | 135.85 | 137.1 | 135.85 | 0.77 |
| 62 | 144.1 | 157.4 | 144.1 | 1.30 |
| 63 | 148.3 | 156.1 | 148.3 | 1.30 |
| 64 | 287.05 | 287.8 | 287.05 | 2.16 |
| 65 | 216 | 208.4 | 216 | 1.69 |
| 66 | 196.25 | 204.7 | 196.25 | 1.44 |
| 67 | 257.7 | 233.8 | 257.7 | 1.79 |
| 68 | 461.25 | 404.7 | 461.25 | 3.11 |
| 69 | 697.45 | 654.9 | 697.45 | 2.43 |
| 70 | 1105.15 | 1045.5 | 1105.15 | 5.12 |
| 71 | 1635.9 | 1516.3 | 1635.9 | 8.34 |
| 72 | 2426.35 | 2328.8 | 2426.35 | 9.42 |
| 73 | 3288.05 | 3101.3 | 3288.05 | 7.13 |
| 74 | 4459.9 | 4276.7 | 4459.9 | 6.39 |
| 75 | 5628.45 | 5495.5 | 5628.45 | 5.09 |
| 76 | 6719.65 | 6520.8 | 6719.65 | 4.11 |
| 77 | 7734 | 7639 | 7734 | 3.19 |
| 78 | 8483 | 8359.4 | 8483 | 2.58 |
| 79 | 8899.85 | 8708.4 | 8899.85 | 2.00 |
| 80 | 9083.9 | 9144.6 | 9083.9 | 1.61 |
| 81 | 8844.95 | 8952.6 | 8844.95 | 1.32 |
| 82 | 8302.7 | 8327 | 8302.7 | 1.07 |
| 83 | 8013.8 | 8015.6 | 8013.8 | 0.94 |
| 84 | 6863.7 | 7128.3 | 6863.7 | 0.77 |
| 85 | 5657.15 | 5647.9 | 5657.15 | 0.62 |

TABLE 34

Denaturation temperatures of scTNF$_{R2}$-Fc proteins as determined by dynamic light scattering.

| scTNF$_{R2}$-Fc | Aggregation temperature (° C.) |
|---|---|
| 148 | 78 |
| 149 | 74 |
| 150 | 75 |
| 151 | 76 |
| 152 | 74 |
| 153 | 78 |
| 154 | 75 |

TABLE 35

DLS measurements for scTNF$_{R2}$-Fc 148
scTNF$_{R2}$-Fc 148

| T (° C.) | Measurement 1 (kcps) | Measurement 2 (kcps) | Mean (kcps) | kcps$_T$/ kcps$_{T-5}$ |
|---|---|---|---|---|
| 25 | 88 | 72.6 | 80.3 | |
| 26 | 82.3 | 76.4 | 79.35 | |
| 27 | 86.2 | 86.1 | 86.15 | |
| 28 | 96.9 | 105.8 | 101.35 | |
| 29 | 121.2 | 95.5 | 108.35 | |
| 30 | 119.4 | 142.2 | 130.8 | 1.63 |
| 31 | 149.8 | 133.3 | 141.55 | 1.78 |
| 32 | 160.8 | 143.6 | 152.2 | 1.77 |
| 33 | 176.7 | 175 | 175.85 | 1.74 |
| 34 | 175.6 | 153.6 | 164.6 | 1.52 |
| 35 | 187.7 | 186.5 | 187.1 | 1.43 |
| 36 | 164.7 | 128.5 | 146.6 | 1.04 |
| 37 | 168.3 | 175.2 | 171.75 | 1.13 |
| 38 | 203.3 | 188.2 | 195.75 | 1.11 |
| 39 | 131.7 | 133.2 | 132.45 | 0.80 |
| 40 | 230 | 232.8 | 231.4 | 1.24 |
| 41 | 124.9 | 164.3 | 144.6 | 0.99 |

TABLE 35-continued

DLS measurements for scTNF$_{R2}$-Fc 148
scTNF$_{R2}$-Fc 148

| T (° C.) | Measurement 1 (kcps) | Measurement 2 (kcps) | Mean (kcps) | kcps$_T$/ kcps$_{T-5}$ |
|---|---|---|---|---|
| 42 | 87.1 | 83.5 | 85.3 | 0.50 |
| 43 | 147.6 | 104.9 | 126.25 | 0.64 |
| 44 | 86.1 | 92.1 | 89.1 | 0.67 |
| 45 | 104.1 | 159.2 | 131.65 | 0.57 |
| 46 | 99.1 | 134.7 | 116.9 | 0.81 |
| 47 | 123.6 | 129.6 | 126.6 | 1.48 |
| 48 | 176.7 | 149.2 | 162.95 | 1.29 |
| 49 | 236.3 | 153.9 | 195.1 | 2.19 |
| 50 | 147.4 | 113.8 | 130.6 | 0.99 |
| 51 | 234.3 | 258.1 | 246.2 | 2.11 |
| 52 | 382.8 | 422.3 | 402.55 | 3.18 |
| 53 | 255.5 | 280.4 | 267.95 | 1.64 |
| 54 | 337.4 | 365.9 | 351.65 | 1.80 |
| 55 | 405.2 | 369 | 387.1 | 2.96 |
| 56 | 342.3 | 322.8 | 332.55 | 1.35 |
| 57 | 349 | 258 | 303.5 | 0.75 |
| 58 | 374.1 | 296.9 | 335.5 | 1.25 |
| 59 | 235.4 | 215.6 | 225.5 | 0.64 |
| 60 | 192.9 | 243.3 | 218.1 | 0.56 |
| 61 | 182.5 | 243 | 212.75 | 0.64 |
| 62 | 195.6 | 244.7 | 220.15 | 0.73 |
| 63 | 194.7 | 229.5 | 212.1 | 0.63 |
| 64 | 168.1 | 198 | 183.05 | 0.81 |
| 65 | 134.2 | 141.3 | 137.75 | 0.63 |
| 66 | 147.6 | 170.5 | 159.05 | 0.75 |
| 67 | 175.1 | 215.7 | 195.4 | 0.89 |
| 68 | 237 | 203.6 | 220.3 | 1.04 |
| 69 | 120.9 | 117.8 | 119.35 | 0.65 |
| 70 | 143.9 | 144.9 | 144.4 | 1.05 |
| 71 | 115.5 | 120.5 | 118 | 0.74 |
| 72 | 148.3 | 148 | 148.15 | 0.76 |
| 73 | 132.6 | 131.3 | 131.95 | 0.60 |
| 74 | 190.8 | 208.8 | 199.8 | 1.67 |
| 75 | 166.3 | 217.6 | 191.95 | 1.33 |
| 76 | 148.4 | 169.7 | 159.05 | 1.35 |
| 77 | 169 | 188.3 | 178.65 | 1.21 |
| 78 | 260.6 | 611 | 435.8 | 3.30 |
| 79 | 2167.1 | 2737.1 | 2452.1 | 12.27 |
| 80 | 3329.7 | 3577.5 | 3453.6 | 17.99 |
| 81 | 3949.8 | 4004.7 | 3977.25 | 25.01 |
| 82 | 4148.4 | 4168.9 | 4158.65 | 23.28 |
| 83 | 4246.5 | 4246.3 | 4246.4 | 9.74 |
| 84 | 4056.8 | 4030.7 | 4043.75 | 1.65 |
| 85 | 4050.1 | 3977.3 | 4013.7 | 1.16 |

TABLE 36

DLS measurements for scTNF$_{R2}$-Fc 149
scTNF$_{R2}$-Fc 149

| T (° C.) | Measurement 1 (kcps) | Measurement 2 (kcps) | Mean (kcps) | kcps$_T$/ kcps$_{T-5}$ |
|---|---|---|---|---|
| 25 | 119.3 | 120.5 | 119.9 | |
| 26 | 125.7 | 120.9 | 123.3 | |
| 27 | 122 | 125.4 | 123.7 | |
| 28 | 121 | 121.7 | 121.35 | |
| 29 | 122.6 | 123.1 | 122.85 | |
| 30 | 122.6 | 121.8 | 122.2 | 1.02 |
| 31 | 121.7 | 125.4 | 123.55 | 1.00 |
| 32 | 122 | 126.3 | 124.15 | 1.00 |
| 33 | 122.2 | 121.9 | 122.05 | 1.01 |
| 34 | 124.4 | 127.4 | 125.9 | 1.02 |
| 35 | 126 | 138.8 | 132.4 | 1.08 |
| 36 | 131.9 | 136 | 133.95 | 1.08 |
| 37 | 123.2 | 126.2 | 124.7 | 1.00 |
| 38 | 127.4 | 130.2 | 128.8 | 1.06 |
| 39 | 123.2 | 122.7 | 122.95 | 0.98 |
| 40 | 128.8 | 124.4 | 126.6 | 0.96 |
| 41 | 119.9 | 120.5 | 120.2 | 0.90 |
| 42 | 121.2 | 119.9 | 120.55 | 0.97 |

TABLE 36-continued

| DLS measurements for scTNF$_{R2}$-Fc 149 scTNF$_{R2}$-Fc 149 | | | | |
|---|---|---|---|---|
| T (° C.) | Measurement 1 (kcps) | Measurement 2 (kcps) | Mean (kcps) | kcps$_T$/ kcps$_{T-5}$ |
| 43 | 123.4 | 120.3 | 121.85 | 0.95 |
| 44 | 120.5 | 122.7 | 121.6 | 0.99 |
| 45 | 126.8 | 126.9 | 126.85 | 1.00 |
| 46 | 121.7 | 123.8 | 122.75 | 1.02 |
| 47 | 126.9 | 126 | 126.45 | 1.05 |
| 48 | 121.9 | 133.6 | 127.75 | 1.05 |
| 49 | 135.3 | 151.8 | 143.55 | 1.18 |
| 50 | 132.9 | 129.9 | 131.4 | 1.04 |
| 51 | 127.4 | 124.9 | 126.15 | 1.03 |
| 52 | 120.5 | 124.4 | 122.45 | 0.97 |
| 53 | 125 | 123.1 | 124.05 | 0.97 |
| 54 | 120.8 | 123.7 | 122.25 | 0.85 |
| 55 | 121.1 | 120.3 | 120.7 | 0.92 |
| 56 | 126.5 | 129 | 127.75 | 1.01 |
| 57 | 122.9 | 120.2 | 121.55 | 0.99 |
| 58 | 123.2 | 128.4 | 125.8 | 1.01 |
| 59 | 129.7 | 127.2 | 128.45 | 1.05 |
| 60 | 121.9 | 121.4 | 121.65 | 1.01 |
| 61 | 119.9 | 119.9 | 119.9 | 0.94 |
| 62 | 121.8 | 121.9 | 121.85 | 1.00 |
| 63 | 121.9 | 122.4 | 122.15 | 0.97 |
| 64 | 122.4 | 122.8 | 122.6 | 0.95 |
| 65 | 123.2 | 123.9 | 123.55 | 1.02 |
| 66 | 125.6 | 125.3 | 125.45 | 1.05 |
| 67 | 127.5 | 132.5 | 130 | 1.07 |
| 68 | 133.5 | 136.3 | 134.9 | 1.10 |
| 69 | 144.8 | 150.3 | 147.55 | 1.20 |
| 70 | 164.5 | 169.7 | 167.1 | 1.35 |
| 71 | 182.1 | 195.8 | 188.95 | 1.51 |
| 72 | 224.2 | 238.4 | 231.3 | 1.78 |
| 73 | 280.4 | 310.8 | 295.6 | 2.19 |
| 74 | 406.1 | 486.3 | 446.2 | 3.02 |
| 75 | 871.5 | 1547.6 | 1209.55 | 7.24 |
| 76 | 5009.9 | 5496.9 | 5253.4 | 27.80 |
| 77 | 6691.8 | 7132.8 | 6912.3 | 29.88 |
| 78 | 7783.9 | 8037.4 | 7910.65 | 26.76 |
| 79 | 8297.8 | 8361.8 | 8329.8 | 18.67 |
| 80 | 8199.5 | 8278.1 | 8238.8 | 6.81 |
| 81 | 8140.5 | 7768.4 | 7954.45 | 1.51 |
| 82 | 7006 | 6490.3 | 6748.15 | 0.98 |
| 83 | 6007 | 5694.8 | 5850.9 | 0.74 |
| 84 | 4952.5 | 4389.4 | 4670.95 | 0.56 |
| 85 | 3910.4 | 3563.5 | 3736.95 | 0.45 |

TABLE 37

| DLS measurements for scTNF$_{R2}$-Fc 150 scTNF$_{R2}$-Fc 150 | | | | |
|---|---|---|---|---|
| T (° C.) | Measurement 1 (kcps) | Measurement 2 (kcps) | Mean (kcps) | kcps$_T$/ kcps$_{T-5}$ |
| 25 | 226.5 | 213.7 | 220.1 | |
| 26 | 217.7 | 209.4 | 213.55 | |
| 27 | 206.7 | 210.4 | 208.55 | |
| 28 | 197.6 | 192.8 | 195.2 | |
| 29 | 203.8 | 196.3 | 200.05 | |
| 30 | 194 | 192.4 | 193.2 | 0.88 |
| 31 | 186 | 186.6 | 186.3 | 0.87 |
| 32 | 183.8 | 189.6 | 186.7 | 0.90 |
| 33 | 183 | 186.9 | 184.95 | 0.95 |
| 34 | 184.7 | 182.4 | 183.55 | 0.92 |
| 35 | 180.6 | 177.5 | 179.05 | 0.93 |
| 36 | 180.2 | 180.2 | 180.2 | 0.97 |
| 37 | 180.7 | 179.7 | 180.2 | 0.97 |
| 38 | 188.2 | 183.4 | 185.8 | 1.00 |
| 39 | 187.2 | 180.4 | 183.8 | 1.00 |
| 40 | 183.5 | 179.9 | 181.7 | 1.01 |
| 41 | 177.8 | 175.7 | 176.75 | 0.98 |
| 42 | 187.4 | 178.4 | 182.9 | 1.01 |
| 43 | 184.4 | 189 | 186.7 | 1.00 |

TABLE 37-continued

| DLS measurements for scTNF$_{R2}$-Fc 150 scTNF$_{R2}$-Fc 150 | | | | |
|---|---|---|---|---|
| T (° C.) | Measurement 1 (kcps) | Measurement 2 (kcps) | Mean (kcps) | kcps$_T$/ kcps$_{T-5}$ |
| 44 | 189.1 | 188 | 188.55 | 1.03 |
| 45 | 186.4 | 185.9 | 186.15 | 1.02 |
| 46 | 192.4 | 196.4 | 194.4 | 1.10 |
| 47 | 186.9 | 192.8 | 189.85 | 1.04 |
| 48 | 194.2 | 190 | 192.1 | 1.03 |
| 49 | 186.5 | 187 | 186.75 | 0.99 |
| 50 | 181.2 | 180 | 180.6 | 0.97 |
| 51 | 178.4 | 180.9 | 179.65 | 0.92 |
| 52 | 179 | 181.7 | 180.35 | 0.95 |
| 53 | 183.3 | 184.3 | 183.8 | 0.96 |
| 54 | 182.8 | 192.4 | 187.6 | 1.00 |
| 55 | 189.8 | 190.5 | 190.15 | 1.05 |
| 56 | 189.6 | 194.3 | 191.95 | 1.07 |
| 57 | 189.1 | 190.4 | 189.75 | 1.05 |
| 58 | 196.3 | 202.4 | 199.35 | 1.08 |
| 59 | 200.9 | 202.8 | 201.85 | 1.08 |
| 60 | 198.1 | 197.4 | 197.75 | 1.04 |
| 61 | 201.8 | 198.5 | 200.15 | 1.04 |
| 62 | 202.5 | 197.8 | 200.15 | 1.05 |
| 63 | 201.7 | 203.2 | 202.45 | 1.02 |
| 64 | 205 | 203.8 | 204.4 | 1.01 |
| 65 | 210.4 | 215.1 | 212.75 | 1.08 |
| 66 | 216.4 | 214.9 | 215.65 | 1.08 |
| 67 | 227.6 | 226.3 | 226.95 | 1.13 |
| 68 | 229.9 | 231.2 | 230.55 | 1.14 |
| 69 | 241.6 | 243 | 242.3 | 1.19 |
| 70 | 264.1 | 277.1 | 270.6 | 1.27 |
| 71 | 280.6 | 289.7 | 285.15 | 1.32 |
| 72 | 327.1 | 345.9 | 336.5 | 1.48 |
| 73 | 355.8 | 367.7 | 361.75 | 1.57 |
| 74 | 442.3 | 494.7 | 468.5 | 1.93 |
| 75 | 569 | 647.7 | 608.35 | 2.25 |
| 76 | 1014.2 | 1406.8 | 1210.5 | 4.25 |
| 77 | 4340.6 | 5508.5 | 4924.55 | 14.63 |
| 78 | 6945.5 | 7305.6 | 7125.55 | 19.70 |
| 79 | 7960.7 | 8338.2 | 8149.45 | 17.39 |
| 80 | 8597.8 | 8820 | 8708.9 | 14.32 |
| 81 | 8720.9 | 8726.3 | 8723.6 | 7.21 |
| 82 | 8473 | 8411 | 8442 | 1.71 |
| 83 | 7792.5 | 7897.8 | 7845.15 | 1.10 |
| 84 | 6715.4 | 6690.2 | 6702.8 | 0.82 |
| 85 | 5807.2 | 5335.5 | 5571.35 | 0.64 |

TABLE 38

| DLS measurements for scTNF$_{R2}$-Fc 151 cTNF$_{R2}$-Fc 151 | | | | |
|---|---|---|---|---|
| T (° C.) | Measurement 1 (kcps) | Measurement 2 (kcps) | Mean (kcps) | kcps$_T$/ kcps$_{T-5}$ |
| 25 | 170.2 | 171.5 | 170.85 | |
| 26 | 167.7 | 163.2 | 165.45 | |
| 27 | 172.2 | 179.6 | 175.9 | |
| 28 | 166.2 | 167 | 166.6 | |
| 29 | 173.4 | 168.2 | 170.8 | |
| 30 | 168.8 | 166.2 | 167.5 | 0.98 |
| 31 | 186.5 | 182.1 | 184.3 | 1.11 |
| 32 | 183.4 | 184.1 | 183.75 | 1.04 |
| 33 | 183.1 | 182.6 | 182.85 | 1.10 |
| 34 | 198.5 | 193.5 | 196 | 1.15 |
| 35 | 185.3 | 184.6 | 184.95 | 1.10 |
| 36 | 195.1 | 188.9 | 192 | 1.04 |
| 37 | 181.8 | 191 | 186.4 | 1.01 |
| 38 | 172.5 | 162.6 | 167.55 | 0.92 |
| 39 | 178.4 | 189.7 | 184.05 | 0.94 |
| 40 | 160.6 | 161.2 | 160.9 | 0.87 |
| 41 | 164.6 | 151.5 | 158.05 | 0.82 |
| 42 | 166.3 | 159 | 162.65 | 0.87 |
| 43 | 188.3 | 184.2 | 186.25 | 1.11 |
| 44 | 175.7 | 179.6 | 177.65 | 0.97 |

TABLE 38-continued

DLS measurements for scTNF$_{R2}$-Fc 151
cTNF$_{R2}$-Fc 151

| T (° C.) | Measurement 1 (kcps) | Measurement 2 (kcps) | Mean (kcps) | kcps$_T$/ kcps$_{T-5}$ |
|---|---|---|---|---|
| 45 | 163 | 160.3 | 161.65 | 1.00 |
| 46 | 167.2 | 170.9 | 169.05 | 1.07 |
| 47 | 168.1 | 171.9 | 170 | 1.05 |
| 48 | 164.9 | 166.2 | 165.55 | 0.89 |
| 49 | 176.7 | 175.5 | 176.1 | 0.99 |
| 50 | 156.7 | 161.6 | 159.15 | 0.98 |
| 51 | 162.5 | 169 | 165.75 | 0.98 |
| 52 | 177.6 | 184.7 | 181.15 | 1.07 |
| 53 | 165.8 | 155.3 | 160.55 | 0.97 |
| 54 | 159.6 | 170.3 | 164.95 | 0.94 |
| 55 | 159.3 | 157 | 158.15 | 0.99 |
| 56 | 150.4 | 155.6 | 153 | 0.92 |
| 57 | 157.6 | 151 | 154.3 | 0.85 |
| 58 | 152.2 | 159.6 | 155.9 | 0.97 |
| 59 | 165.2 | 151 | 158.1 | 0.96 |
| 60 | 162.1 | 151.7 | 156.9 | 0.99 |
| 61 | 154.5 | 147.1 | 150.8 | 0.99 |
| 62 | 149 | 150.5 | 149.75 | 0.97 |
| 63 | 159.4 | 158.1 | 158.75 | 1.02 |
| 64 | 147.7 | 152.5 | 150.1 | 0.95 |
| 65 | 158.6 | 161.7 | 160.15 | 1.02 |
| 66 | 192.5 | 180.2 | 186.35 | 1.24 |
| 67 | 173.2 | 178 | 175.6 | 1.17 |
| 68 | 175.1 | 190.8 | 182.95 | 1.15 |
| 69 | 193.7 | 189 | 191.35 | 1.27 |
| 70 | 250.9 | 319.4 | 285.15 | 1.78 |
| 71 | 249.6 | 237 | 243.3 | 1.31 |
| 72 | 242.4 | 257.3 | 249.85 | 1.42 |
| 73 | 273.5 | 293.1 | 283.3 | 1.55 |
| 74 | 366.4 | 414.3 | 390.35 | 2.04 |
| 75 | 510.6 | 554.5 | 532.55 | 1.87 |
| 76 | 932.3 | 1310.3 | 1121.3 | 4.61 |
| 77 | 5016.8 | 5863.7 | 5440.25 | 21.77 |
| 78 | 7105.9 | 7432.4 | 7269.15 | 25.66 |
| 79 | 8027.8 | 8317.1 | 8172.45 | 20.94 |
| 80 | 8563.4 | 8604.6 | 8584 | 16.12 |
| 81 | 8331.4 | 8107.2 | 8219.3 | 7.33 |
| 82 | 7775.2 | 7097.8 | 7436.5 | 1.37 |
| 83 | 6346 | 5816.9 | 6081.45 | 0.84 |
| 84 | 4621.4 | 3747.7 | 4184.55 | 0.51 |
| 85 | 3843.7 | 3813.5 | 3828.6 | 0.45 |

TABLE 39

DLS measurements for scTNF$_{R2}$-Fc 152
scTNF$_{R2}$-Fc 152

| T (° C.) | Measurement 1 (kcps) | Measurement 2 (kcps) | Mean (kcps) | kcps$_T$/ kcps$_{T-5}$ |
|---|---|---|---|---|
| 25 | 139.1 | 140.3 | 139.7 | |
| 26 | 134.5 | 134.3 | 134.4 | |
| 27 | 128.8 | 132.1 | 130.45 | |
| 28 | 130 | 127.8 | 128.9 | |
| 29 | 128.4 | 130.2 | 129.3 | |
| 30 | 132.4 | 132.6 | 132.5 | 0.95 |
| 31 | 129 | 131.9 | 130.45 | 0.97 |
| 32 | 129.1 | 133.9 | 131.5 | 1.01 |
| 33 | 131.3 | 131.1 | 131.2 | 1.02 |
| 34 | 137.7 | 142.9 | 140.3 | 1.09 |
| 35 | 136.4 | 137.3 | 136.85 | 1.03 |
| 36 | 131.7 | 127.8 | 129.75 | 0.99 |
| 37 | 127.5 | 125.2 | 126.35 | 0.96 |
| 38 | 130.3 | 133.1 | 131.7 | 1.00 |
| 39 | 125.5 | 127.6 | 126.55 | 0.90 |
| 40 | 133.9 | 132.3 | 133.1 | 0.97 |
| 41 | 130.1 | 136.1 | 133.1 | 1.03 |
| 42 | 126.4 | 128 | 127.2 | 1.01 |
| 43 | 132.5 | 137.7 | 135.1 | 1.03 |
| 44 | 143.7 | 133.9 | 138.8 | 1.10 |
| 45 | 136.9 | 135.6 | 136.25 | 1.02 |

TABLE 39-continued

DLS measurements for scTNF$_{R2}$-Fc 152
scTNF$_{R2}$-Fc 152

| T (° C.) | Measurement 1 (kcps) | Measurement 2 (kcps) | Mean (kcps) | kcps$_T$/ kcps$_{T-5}$ |
|---|---|---|---|---|
| 46 | 140.6 | 135.4 | 138 | 1.04 |
| 47 | 127 | 124.4 | 125.7 | 0.99 |
| 48 | 125.2 | 123.9 | 124.55 | 0.92 |
| 49 | 127.1 | 137.7 | 132.4 | 0.95 |
| 50 | 130.1 | 127.3 | 128.7 | 0.94 |
| 51 | 126.4 | 129.7 | 128.05 | 0.93 |
| 52 | 127.6 | 130.3 | 128.95 | 1.03 |
| 53 | 127.1 | 133.5 | 130.3 | 1.05 |
| 54 | 122.9 | 122.4 | 122.65 | 0.93 |
| 55 | 135.1 | 131.1 | 133.1 | 1.03 |
| 56 | 125.2 | 127.4 | 126.3 | 0.99 |
| 57 | 128.5 | 127.6 | 128.05 | 0.99 |
| 58 | 126.7 | 126.2 | 126.45 | 0.97 |
| 59 | 124 | 124.2 | 124.1 | 1.01 |
| 60 | 124.5 | 124.8 | 124.65 | 0.94 |
| 61 | 126.1 | 127.7 | 126.9 | 1.00 |
| 62 | 125.9 | 127.7 | 126.8 | 0.99 |
| 63 | 127.8 | 129.2 | 128.5 | 1.02 |
| 64 | 131.3 | 133.1 | 132.2 | 1.07 |
| 65 | 139.7 | 138 | 138.85 | 1.11 |
| 66 | 150 | 151.1 | 150.55 | 1.19 |
| 67 | 150.6 | 149.9 | 150.25 | 1.18 |
| 68 | 140 | 145.6 | 142.8 | 1.11 |
| 69 | 155.2 | 157.3 | 156.25 | 1.18 |
| 70 | 163.8 | 167.3 | 165.55 | 1.19 |
| 71 | 179.2 | 190.4 | 184.8 | 1.23 |
| 72 | 210.6 | 224.6 | 217.6 | 1.45 |
| 73 | 258.9 | 282 | 270.45 | 1.89 |
| 74 | 350.9 | 405.1 | 378 | 2.42 |
| 75 | 643.4 | 950 | 796.7 | 4.81 |
| 76 | 3902.1 | 5065.3 | 4483.7 | 24.26 |
| 77 | 6269.6 | 6646.9 | 6458.25 | 29.68 |
| 78 | 7300.4 | 7622.6 | 7461.5 | 27.59 |
| 79 | 7903.9 | 8156 | 8029.95 | 21.24 |
| 80 | 8157.5 | 7198.8 | 7678.15 | 9.64 |
| 81 | 8043.1 | 7307.8 | 7675.45 | 1.71 |
| 82 | 7445.5 | 6409.3 | 6927.4 | 1.07 |
| 83 | 6494.4 | 5698.9 | 6096.65 | 0.82 |
| 84 | 4917.5 | 4931.4 | 4924.45 | 0.61 |
| 85 | 4180.2 | 3859.1 | 4019.65 | 0.52 |

TABLE 40

DLS measurements for scTNF$_{R2}$-Fc 153
scTNF$_{R2}$-Fc 153

| T (° C.) | Measurement 1 (kcps) | Measurement 2 (kcps) | Mean (kcps) | kcps$_T$/ kcps$_{T-5}$ |
|---|---|---|---|---|
| 25 | 59 | 60.1 | 59.55 | |
| 26 | 60.7 | 91.1 | 75.9 | |
| 27 | 82.2 | 75.5 | 78.85 | |
| 28 | 113.2 | 93.6 | 103.4 | |
| 29 | 76.9 | 62.8 | 69.85 | |
| 30 | 64 | 56.8 | 60.4 | 1.01 |
| 31 | 56.8 | 58 | 57.4 | 0.76 |
| 32 | 56.4 | 57.5 | 56.95 | 0.72 |
| 33 | 53.6 | 56.1 | 54.85 | 0.53 |
| 34 | 56.9 | 59.5 | 58.2 | 0.83 |
| 35 | 56 | 57.3 | 56.65 | 0.94 |
| 36 | 54.7 | 54.2 | 54.45 | 0.95 |
| 37 | 53.7 | 59.5 | 56.6 | 0.99 |
| 38 | 54.2 | 58.6 | 56.4 | 1.03 |
| 39 | 57.9 | 57.4 | 57.65 | 0.99 |
| 40 | 55.2 | 59.7 | 57.45 | 1.01 |
| 41 | 55.3 | 56.4 | 55.85 | 1.03 |
| 42 | 63.8 | 59.7 | 61.75 | 1.09 |
| 43 | 55.4 | 56.1 | 55.75 | 0.99 |
| 44 | 54.4 | 53.2 | 53.8 | 0.93 |
| 45 | 56.1 | 56.8 | 56.45 | 0.98 |
| 46 | 55.4 | 52.9 | 54.15 | 0.97 |

TABLE 40-continued

DLS measurements for scTNF$_{R2}$-Fc 153
scTNF$_{R2}$-Fc 153

| T (° C.) | Measurement 1 (kcps) | Measurement 2 (kcps) | Mean (kcps) | kcps$_T$/ kcps$_{T-5}$ |
|---|---|---|---|---|
| 47 | 53 | 53.5 | 53.25 | 0.86 |
| 48 | 55.5 | 56.7 | 56.1 | 1.01 |
| 49 | 61.4 | 62.6 | 62 | 1.15 |
| 50 | 54.9 | 60.4 | 57.65 | 1.02 |
| 51 | 63.4 | 68.3 | 65.85 | 1.22 |
| 52 | 79.2 | 73.4 | 76.3 | 1.43 |
| 53 | 56.7 | 63.3 | 60 | 1.07 |
| 54 | 93 | 91.3 | 92.15 | 1.49 |
| 55 | 72.8 | 73.6 | 73.2 | 1.27 |
| 56 | 97.2 | 117 | 107.1 | 1.63 |
| 57 | 90.6 | 81.2 | 85.9 | 1.13 |
| 58 | 87.6 | 99 | 93.3 | 1.56 |
| 59 | 88.4 | 81.6 | 85 | 0.92 |
| 60 | 76.8 | 82.6 | 79.7 | 1.09 |
| 61 | 93.6 | 99 | 96.3 | 0.90 |
| 62 | 107 | 112.4 | 109.7 | 1.28 |
| 63 | 130.8 | 138.8 | 134.8 | 1.44 |
| 64 | 133.2 | 134.7 | 133.95 | 1.58 |
| 65 | 143.8 | 142.2 | 143 | 1.79 |
| 66 | 144.2 | 144.4 | 144.3 | 1.50 |
| 67 | 126.7 | 126.8 | 126.75 | 1.16 |
| 68 | 113.5 | 111 | 112.25 | 0.83 |
| 69 | 117.5 | 117.9 | 117.7 | 0.88 |
| 70 | 132.9 | 130.6 | 131.75 | 0.92 |
| 71 | 116.9 | 119 | 117.95 | 0.82 |
| 72 | 132.8 | 125.7 | 129.25 | 1.02 |
| 73 | 117.8 | 122 | 119.9 | 1.07 |
| 74 | 125.2 | 128.1 | 126.65 | 1.08 |
| 75 | 129.5 | 136.2 | 132.85 | 1.01 |
| 76 | 133 | 138.6 | 135.8 | 1.15 |
| 77 | 163.3 | 175 | 169.15 | 1.31 |
| 78 | 240.3 | 510.2 | 375.25 | 3.13 |
| 79 | 1715 | 2155.5 | 1935.25 | 15.28 |
| 80 | 2640.5 | 2822.5 | 2731.5 | 20.56 |
| 81 | 2989 | 3126.9 | 3057.95 | 22.52 |
| 82 | 3262.5 | 3307.1 | 3284.8 | 19.42 |
| 83 | 3295 | 3232.2 | 3263.6 | 8.70 |
| 84 | 3278.9 | 3358.1 | 3318.5 | 1.71 |
| 85 | 3222.7 | 2908.3 | 3065.5 | 1.12 |

TABLE 41

DLS measurements for scTNF$_{R2}$-Fc 154
scTNF$_{R2}$-Fc 154

| T (° C.) | Measurement 1 (kcps) | Measurement 2 (kcps) | Mean (kcps) | kcps$_T$/ kcps$_{T-5}$ |
|---|---|---|---|---|
| 25 | 110.8 | 109.9 | 110.35 | |
| 26 | 107.6 | 109.7 | 108.65 | |
| 27 | 105.4 | 110.4 | 107.9 | |
| 28 | 107 | 110.4 | 108.7 | |
| 29 | 108.3 | 112.7 | 110.5 | |
| 30 | 107.9 | 112.9 | 110.4 | 1.00 |
| 31 | 105.5 | 105.2 | 105.35 | 0.97 |
| 32 | 105.9 | 110.9 | 108.4 | 1.00 |
| 33 | 106.1 | 109.2 | 107.65 | 0.99 |
| 34 | 111.7 | 114.9 | 113.3 | 1.03 |
| 35 | 112 | 116.3 | 114.15 | 1.03 |
| 36 | 118.3 | 118.6 | 118.45 | 1.12 |
| 37 | 106.8 | 115.6 | 111.2 | 1.03 |
| 38 | 110.4 | 109.4 | 109.9 | 1.02 |
| 39 | 109.2 | 111.1 | 110.15 | 0.97 |
| 40 | 112.2 | 117.4 | 114.8 | 1.01 |
| 41 | 106.1 | 106.2 | 106.15 | 0.90 |
| 42 | 122.3 | 130.5 | 126.4 | 1.14 |
| 43 | 114.1 | 131 | 122.55 | 1.12 |
| 44 | 111.9 | 124 | 117.95 | 1.07 |
| 45 | 115.1 | 128.9 | 122 | 1.06 |
| 46 | 112.4 | 124.5 | 118.45 | 1.12 |
| 47 | 112 | 123.4 | 117.7 | 0.93 |

TABLE 41-continued

DLS measurements for scTNF$_{R2}$-Fc 154
scTNF$_{R2}$-Fc 154

| T (° C.) | Measurement 1 (kcps) | Measurement 2 (kcps) | Mean (kcps) | kcps$_T$/ kcps$_{T-5}$ |
|---|---|---|---|---|
| 48 | 118.1 | 127.2 | 122.65 | 1.00 |
| 49 | 117.3 | 127.1 | 122.2 | 1.04 |
| 50 | 107.7 | 108.1 | 107.9 | 0.88 |
| 51 | 112.1 | 133.8 | 122.95 | 1.04 |
| 52 | 124.1 | 121 | 122.55 | 1.04 |
| 53 | 117.3 | 119 | 118.15 | 0.96 |
| 54 | 140.3 | 146.4 | 143.35 | 1.17 |
| 55 | 154.2 | 155.6 | 154.9 | 1.44 |
| 56 | 161.9 | 153.1 | 157.5 | 1.28 |
| 57 | 154 | 156.2 | 155.1 | 1.27 |
| 58 | 156.5 | 153.1 | 154.8 | 1.31 |
| 59 | 165.1 | 154.1 | 159.6 | 1.11 |
| 60 | 191 | 199.6 | 195.3 | 1.26 |
| 61 | 213.1 | 207.7 | 210.4 | 1.34 |
| 62 | 204.3 | 206.1 | 205.2 | 1.32 |
| 63 | 174.6 | 185.9 | 180.25 | 1.16 |
| 64 | 172.2 | 183.5 | 177.85 | 1.11 |
| 65 | 201.5 | 197.1 | 199.3 | 1.02 |
| 66 | 154.3 | 154.1 | 154.2 | 0.73 |
| 67 | 155.2 | 163 | 159.1 | 0.78 |
| 68 | 126.8 | 128.5 | 127.65 | 0.71 |
| 69 | 139.8 | 161.6 | 150.7 | 0.85 |
| 70 | 161.8 | 196.9 | 179.35 | 0.90 |
| 71 | 142.3 | 150.7 | 146.5 | 0.95 |
| 72 | 178.8 | 210.5 | 194.65 | 1.22 |
| 73 | 211.6 | 224.3 | 217.95 | 1.71 |
| 74 | 252.3 | 281.5 | 266.9 | 1.77 |
| 75 | 371.4 | 445.2 | 408.3 | 2.28 |
| 76 | 859.5 | 1701.9 | 1280.7 | 8.74 |
| 77 | 4784.5 | 5430.5 | 5107.5 | 26.24 |
| 78 | 6316.1 | 6588.7 | 6452.4 | 29.60 |
| 79 | 7305.7 | 7403.7 | 7354.7 | 27.56 |
| 80 | 7551.9 | 7393 | 7472.45 | 18.30 |
| 81 | 6908.1 | 7172.3 | 7040.2 | 5.50 |
| 82 | 6460.9 | 6860.8 | 6660.85 | 1.30 |
| 83 | 6340.6 | 6134.8 | 6237.7 | 0.97 |
| 84 | 4305.9 | 4196.2 | 4251.05 | 0.58 |
| 85 | 3532.9 | 3337.2 | 3435.05 | 0.46 |

Example 15: Binding of scTNF$_{R2}$ and scTNF$_{R2}$-Fc (Δab) Proteins to Immobilized TNF-R2

The binding of scTNF$_{R2}$ and the scTNF$_{R2}$-Fc(Δab) proteins to human TNFR2-Fc (etanercept) was analyzed by ELISA. 96-well ELISA plates were coated with 200 ng/well etanercept in coating buffer (0.1 M sodium carbonate, pH 9.5) overnight at 4° C., blocked with 2% skim milk in PBS (MPBS) and washed with washing buffer PBST (PBS, 0.05% Tween 20). ScTNF$_{R2}$ and SCTNF$_{R2}$-Fc(Δab) proteins were titrated in duplicates and incubated on the plates for 2 h at room temperature, followed by washing with PBST. Receptor-bound complexes were detected with mouse anti-huTNFα F6C5 (Novus, 1 μg/ml) and goat anti-mouse IgG (Fc)-HRP (Sigma-Aldrich, 1:10,000), followed by extensive washing with PBST each, before incubation with HRP substrate.

The scTNF$_{R2}$ variants showed a similar dose-dependent binding to TNF$_{R2}$-Fc with $EC_{50}$ values in the low nanomolar range (FIG. 16, Table 42). The scTNF$_{R2}$-Fc(Δab) fusion proteins showed lower $EC_{50}$ values in the sub-nanomolar range (FIG. 17, Table 43), indicating increased binding of the hexavalent Fc fusion proteins due to avidity effects.

TABLE 42

| EC$_{50}$ values of binding of scTNF$_{R2}$ variants to human TNFR2-Fc | |
|---|---|
| scTNF$_{R2}$ variant | EC$_{50}$ (nM) |
| 140 | 1.12 |
| 141 | 1.00 |
| 142 | 0.68 |
| 143 | 0.67 |
| 144 | 1.22 |
| 145 | 1.03 |
| 146 | 0.71 |
| 147 | 0.76 |

TABLE 43

| EC$_{50}$ values of binding of scTNF$_{R2}$-Fc fusion proteins variants to TNFR2-Fc | |
|---|---|
| scTNF$_{R2}$-Fc variant | EC$_{50}$ (nM) |
| 742 | 0.16 |
| 148 | 0.22 |
| 149 | 0.14 |
| 151 | 0.25 |
| 152 | 0.29 |
| 153 | 0.18 |

Example 16: In Vitro Bioactivity of scTNF$_{R2}$ Variants of Example 11 on Kym-1 Cells with TNF-R2 Coactivation Using 80M2 Antibody The basic bioactivity of scTNF$_{R2}$ variants of example 11 was analyzed in an in vitro assay using Kym-1 cells. The stimulation of TNFR2 on Kym-1 leads to expression of endogenous TNF, which induces apoptosis of the cells via activation of TNFR1-mediated signaling. Of note, pure trivalent scTNFR2 has been shown to be nearly inactive in terms of TNFR2 activation and requires, in addition, TNFR2 crosslinking for bioactivity, for instance by using the anti-TNFR2 antibody 80M2, which by itself is non-agonistic. For the experiment, 10,000 Kym-1 cells/well were seeded in 96-well plates, cultivated for 24 h at 37° C. and 5% $CO_2$ and incubated with serially diluted proteins in triplicates for another 24 h. For TNFR2 crosslinking, 1 μg/ml 80M2 antibody (Hycult Biotech) was added to the cells 30 min before addition of the proteins titrated in triplicates. The cell viability was determined by crystal violet staining. The data was normalized to untreated control and positive control (1% Triton X-100). In combination with 80M2, all scTNF$_{R2}$ variants induced cell death of Kym-1 cells in the sub-nanomolar range (FIG. 18, Table 44).

TABLE 44

| EC$_{50}$ values of bioactivity of scTNF$_{R2}$ variants on Kym-1 | |
|---|---|
| scTNF$_{R2}$ | EC$_{50}$ (pM) |
| 140 | 10.84 |
| 141 | 7.44 |
| 142 | 7.77 |
| 143 | 11.93 |
| 144 | 8.43 |
| 145 | 7.49 |
| 146 | 6.55 |
| 147 | 8.58 |

Example 17: In Vitro Bioactivity of scTNF$_{R2}$-Fc (Δab) Proteins of Example 11 on Kym-1 Cells The in vitro bioactivity of scTNF$_{R2}$-Fc(Δab) proteins of example 11 was analyzed on Kym-1 cells in a similar experimental setting described in example 16, with the exception that TNFR2 crosslinking by addition of antibody 80M2 was omitted (the hexavalent scTNF$_{R2}$-Fc(Δab) proteins do not require TNFR2 cross-linking) (FIG. 19, Table 45). Using Kym-1 cells, SCTNF$_{R2}$-Fc(Δab) variants 148, 149, 150, 151, 152, 153 and 154 showed a similar bioactivity to the reference molecules scTNF$_{R2}$-Fc(Δab) 742 alone or scTNF$_{R2}$ 140 in presence of TNFR2-cross-linking antibody 80M2.

TABLE 45

| EC$_{50}$ values of bioactivity of scTNF$_{R2}$-Fc mutants on Kym-1 | |
|---|---|
| SCTNF$_{R2}$-FC | EC$_{50}$ on Kym-1 (pM) |
| 140 [+80M2] | 14.11 |
| 742 | 14.18 |
| 148 | 11.61 |
| 149 | 12.55 |
| 150 | 8.96 |
| 151 | 24.04 |
| 152 | 8.08 |
| 153 | 30.37 |
| 154 | 10.26 |

The present invention also pertains to the following items:

1. A polypeptide, comprising a binding domain consisting of three peptide TNF homology domains of TNF-ligand family member proteins (THD) that specifically bind to the extracellular part of TNFR2, wherein the C-terminus of the first and second THD, respectively, which is in each case defined by the C-terminal consensus sequence (SEQ ID NO: 1)
V-F/Y-F-G-A/I-$X_1$, is linked to the N-terminus of the second and third THD, respectively, which is in each case defined by the N-terminal consensus sequence (SEQ ID NO: 2)
P-V/A-A-H-V/L through a peptide $X_a$, which is in each case independently selected and has a length of 9 to 12 amino acids, preferably 9 to 11, more preferably 9 to 10, wherein $X_a$ does not comprise the amino acid sequence S-S-R-T-P-S-D-K (SEQ ID NO: 10), wherein $X_1$ is a non-polar/hydrophobic or polar/neutral amino acid, preferably selected from the group consisting of F and I.

2. The polypeptide according to item 1, wherein the peptide $X_a$ consists of $X_C$-$X_L$-$X_N$ wherein $X_C$ is selected from the group consisting of A, A-L, L, preferably A and A-L;

$X_L$ is absent or is an amino acid linker consisting of 1-11, preferably 1-10, more preferably 1-9 amino acids;

$X_N$ is absent or selected from the group consisting of K, D-K, S-D-K, P-S-D-K (SEQ ID NO: 6), T-P-S-D-K (SEQ ID NO: 7), R-T-P-S-D-K (SEQ ID NO: 8), S-R-T-P-S-D-K (SEQ ID NO: 9), T-K, S-T-K, H-S-T-K (SEQ ID NO: 11), A-H-S-T-K (SEQ ID NO: 12), L-A-H-S-T-K (SEQ ID NO: 13), H-L-A-H-S-T-K (SEQ ID NO: 14), L-H-L-A-H-S-T-K (SEQ ID NO: 15).

3. The polypeptide according to any one of the preceding items, wherein the three THDs are identical.

4. The polypeptide according to any one of the preceding items, wherein the C-terminus of the first and second THD, respectively, is in each case defined by the C-terminal sequence

```
                                  (SEQ ID NO: 3)
V-Y-F-G-I-I
```

and the N-terminus of the second and third THD, respectively, is in each case defined by the N-terminal sequence

```
                                  (SEQ ID NO: 4)
P-V-A-H-V.
```

5. The polypeptide according to any one of the preceding items wherein the THD comprises a contiguous amino acid sequence consisting of amino acids 88 to 231 of SEQ ID NO. 5, optionally comprising at least one mutation selected from the group consisting of: D143Y, D143F, D143E, D143N, D143T, D143S, E146Q, E146H, E146K, A145R/S147T, Q88N/T89S/A145S/E146A/S147D, Q88N/A145I/E146G/S147D, A145H/E146S/S147D, A145H/S147D, L29V/A145D/E146D/S147D, A145N/E146D/S147D, A145T/E146S/S147D, A145Q/E146D/S147D, A145T/E146D/S147D, A145D/E146G/S147D, A145D/S147D, A145K/E146D/S147T, A145R/E146T/S147D, A145R/S147T, E146D/S147D, E146N/S147, S95C/G148C, K65A, K65W, Q67K, Q67T, Q67Y, L75H, L75W, D143W, D143V, D143V/F144L/A145S, D143N/A145R, D143V/A145S, L29V, L29T, L29S, L29A, L29G, R31H, R31I, R31L, R32G, R32E, S147L, S147R, S147P S147T, S147A, Q149E, Q149N, E146D, E146N, E146S, E146G, A145R, A145S, A145T, A145H, A145K, A145F, A145D, A145G, A145N, A145P, A145Q, A145Y, A145V and A145W, preferably selected from D143N and A145R.

6. The polypeptide according to any one of the preceding items, wherein $X_C$ is selected from A or A-L, $X_L$ is absent or is a glycine and/or serine linker with a length of 1 to 11 amino acids, preferably selected from G, S, G-G, S-G, G-S, G-G-G, S-G-G, G-S-G, G-G-S, G-G-G-G (SEQ ID NO: 16), G-G-G-S(SEQ ID NO: 17), G-G-S-G (SEQ ID NO: 18), G-S-G-G (SEQ ID NO: 19), S-G-G-G (SEQ ID NO: 20), G-G-G-G-G (SEQ ID NO: 21), S-G-G-G-G (SEQ ID NO: 22), G-S-G-G-G (SEQ ID NO: 23), G-G-S-G-G (SEQ ID NO: 24), G-G-G-S-G (SEQ ID NO: 25), G-G-G-G-S(SEQ ID NO: 26), G-G-G-G-G-G (SEQ ID NO: 27), S-G-G-G-G-G (SEQ ID NO: 28), G-S-G-G-G-G (SEQ ID NO: 29), G-G-S-G-G-G (SEQ ID NO: 30), G-G-G-S-G-G (SEQ ID NO: 31), G-G-G-G-S-G (SEQ ID NO: 32), G-G-G-G-G-S(SEQ ID NO: 33), G-G-G-S-G-G-G-S(SEQ ID NO: 34), S-G-G-G-S-G-G-G (SEQ ID NO: 35), G-G-G-G-G-G-G (SEQ ID NO: 36), G-S-G-G-G-S-G-G (SEQ ID NO: 37), G-G-S-G-G-G-S-G (SEQ ID NO: 38), S-G-G-G-S-G-G-G-S(SEQ ID NO: 39), G-S-G-G-G-S-G-G-G (SEQ ID NO: 40), G-G-S-G-G-G-S-G-G (SEQ ID NO: 41), G-G-G-S-G-G-G-S-G (SEQ ID NO: 42), S-G-G-G-S-G-G-G-S-G (SEQ ID NO: 43), G-S-G-G-G-S-G-G-G-S(SEQ ID NO: 44), G-G-S-G-G-G-S-G-G-G (SEQ ID NO: 45), G-G-G-S-G-G-G-S-G-G (SEQ ID NO: 46), S-G-G-G-S-G-G-G-S-G-G (SEQ ID NO: 47), G-S-G-G-G-S-G-G-G-S-G (SEQ ID NO: 48), G-G-S-G-G-G-S-G-G-G-S (SEQ ID NO: 49) and G-G-G-S-G-G-G-S-G-G-G (SEQ ID NO: 50), more preferably G-G-G-G (SEQ ID NO: 16), G-G-G-G-S(SEQ ID NO: 26) and G-G-G-S-G-G-G-S(SEQ ID NO: 34), and $X_N$ is absent or is selected from K, D-K, S-D-K, P-S-D-K (SEQ ID NO: 6), T-P-S-D-K (SEQ ID NO: 7), R-T-P-S-D-K (SEQ ID NO: 8) and S-R-T-P-S-D-K (SEQ ID NO: 9).

7. The polypeptide according to any one of the preceding items, wherein:

(i) $X_C$ is A-L, $X_L$ is absent and $X_N$ is selected from S-R-T-P-S-D-K (SEQ ID NO: 9), (ii) $X_C$ is A-L, $X_L$ is G-G-G-G (SEQ ID NO: 16) and $X_N$ is selected from S-D-K, P-S-D-K (SEQ ID NO: 6), T-P-S-D-K (SEQ ID NO: 7), R-T-P-S-D-K (SEQ ID NO: 8), preferably P-S-D-K (SEQ ID NO: 6);

(iii) $X_C$ is A-L, $X_L$ is G-G-G-S-G-G-G-S(SEQ ID NO: 34) and $X_N$ is selected from K and D-K;

(iv) $X_C$ is A-L, $X_L$ is G and $X_N$ is selected from R-T-P-S-D-K (SEQ ID NO: 8), S-R-T-P-S-D-K (SEQ ID NO: 9), preferably S-R-T-P-S-D-K (SEQ ID NO: 9);

(v) $X_C$ is A-L, $X_L$ is G-G and $X_N$ is selected from T-P-S-D-K (SEQ ID NO: 7), R-T-P-S-D-K (SEQ ID NO: 8), S-R-T-P-S-D-K (SEQ ID NO: 9), preferably R-T-P-S-D-K (SEQ ID NO: 8); or (vi) $X_C$ is A-L, $X_L$ is G-G-G and $X_N$ is selected from P-S-D-K (SEQ ID NO: 6), T-P-S-D-K (SEQ ID NO: 7), R-T-P-S-D-K (SEQ ID NO: 8), S-R-T-P-S-D-K (SEQ ID NO: 9), preferably T-P-S-D-K (SEQ ID NO: 7).

8. The polypeptide according to any one of the preceding items, wherein the polypeptide has an onset of aggregation temperature ($T_m$) of more than 62° C. as determined by dynamic light scattering.

9. A polypeptide multimer comprising at least two polypeptides according to any one of the preceding items that are (a) linked together, preferably linked together by an amino acid linker that has a length of between 1 to 30 amino acids, preferably 7 to 15 amino acids; or (b) linked to a protein, preferably selected from the group consisting of: a multimerization domain, a serum protein, a cytokine, a targeting moiety or a toxin, optionally wherein said polypeptides are linked to said protein by an amino acid linker that has a length of between 1 to 30 amino acids, preferably 7 to 15 amino acids.

10. The polypeptide multimer according to item 9, wherein:

A. the polypeptide multimer has at least one of the following properties:

an onset of aggregation temperature ($T_m$) of at least 72° C., preferably at least 74° C.;

an $EC_{50}$ for binding to TNFR2 in HeLa-TNF-R2 cells that is not decreased by more than 15%, 12%, 10%, preferably 10%, after 8 days of incubation in human plasma at 37° C.;

an $EC_{50}$ for binding to TNFR2 expressed on MEFs of less than 100 μM, preferably less than 80 μM;

an $EC_{50}$ for binding to TNFR2 on Kym-1 cells of less than 200 μM, preferably less than 100 μM;

an $EC_{50}$ for activation of NF-κB in HeLa-TNF-R2 cells of less than 30 μM, preferably less than 10 μM;

and/or

B. the multimerization domain is a dimerization domain, a trimerization domain or a tetramerization domain, preferably wherein the (i) dimerization domain is selected from the group consisting of an antibody, an antibody heavy chain, immunoglobulin Fc region, heavy chain domain 2 (CH2) of IgM (MHD2), heavy chain domain 2 ($CH_2$) of IgE (EHD2), heavy chain domain 3 (CH3) of IgG, heavy chain domain 3 (CH3) of IgA, heavy chain domain 3 (CH3) of IgD, heavy chain domain 4 (CH4) of IgM, heavy chain domain 4 (CH4) of IgE, Fab, Fab2, leucine zipper motifs, barnase-barstar dimers, miniantibodies, and ZIP miniantibodies, preferably immunoglobulin Fc region mutants without FcR and/or C1q binding, more preferably FcΔab, LALA, LALA-GP, IgG2, IgG2σ, aglycosylated IgG1, IgG1 (L234F/L235E/P331S), IgG2m4, IgG4 ProAlaAla, most preferably FcΔab;

(ii) trimerization domain is selected from the group consisting of tenascin C (TNC), the trimerization region of the C-terminal noncollagenous domain (NC1) of collagen XVIII, Fab3 like molecules, and TriBi-minibodies; or (iii) tetramerization domain is selected from the group consisting of the tetramerization domain of p53, the tetramerization domain of the general control protein 4 (GCN4), the tetramerization domain of VASP (vasodilator stimulated phosphoprotein), tandem diabodies, and di-diabodies;

and/or

C. the polypeptide multimer further comprises a ligand specific for an organ, tissue or cell-type, more preferably a targeting moiety binding to a target selected from transferrin receptor, insulin receptor, low-density lipoprotein receptors (LDLR), diphtheria toxin receptor, efflux pumps, CD25, CD28, GLUT1, LAT1, TMEM119, PDGFR, VEGFR1, VEGFR3, and receptors for RVG-29.

11. A nucleic acid molecule encoding the polypeptide according to any one of items 1 to 8 or the polypeptide multimer according to item 9 or 10.

12. A vector encoding the nucleic acid molecule according to item 11.

13. A polypeptide according to items 1 to 8, a polypeptide multimer according to item 9 or 10, a nucleic acid according to item 11 or a vector according to item 12 for use as a medicament.

14. A pharmaceutical composition comprising as an active agent a polypeptide according to items 1 to 8, a polypeptide multimer according to item 9 or 10, a nucleic acid according to item 11 or a vector according to item 12.

15. A polypeptide according to items 1 to 8, a polypeptide multimer according to item 9 or 10, a nucleic acid according to item 11, a vector according to item 12 or a pharmaceutical composition according to item 14 for use in the diagnosis, prophylaxis or treatment of hyperproliferative disorders, inflammatory disorders, neurodegenerative disorders or metabolic disorders, preferably cancer or malignancies of the hematologic system, autoimmune disorders, metabolic syndrome, cardiovascular diseases, neuropathic diseases and neurological insults.

The invention claimed is:

1. A polypeptide, comprising a binding domain consisting of three peptide tumor necrosis factor (TNF) homology domains of TNF-ligand family member proteins (THD) that specifically bind to the extracellular part of TNF receptor 2 (TNFR2), wherein the C-terminus of the first and second THD, respectively, which is in each case defined by the C-terminal sequence

V-Y-F-G-I-I, (SEQ ID NO: 3)

is linked to the N-terminus of the second and third THD, respectively, which is in each case defined by the N-terminal sequence

P-V-A-H-V (SEQ ID NO: 4)

through a peptide $X_a$, which is in each case independently selected and has a length of 9 to 10 amino acids, wherein the peptide $X_a$ consists of $X_C$-$X_L$-$X_N$ wherein $X_C$ is A-L;

$X_L$ is absent or is selected from the group consisting of G, G-G, G-G-G, and G-G-G-G (SEQ ID NO: 16);

$X_N$ is selected from the group consisting of P-S-D-K (SEQ ID NO: 6), T-P-S-D-K (SEQ ID NO: 7), R-T-P-S-D-K (SEQ ID NO: 8), and S-R-T-P-S-D-K (SEQ ID NO: 9), and wherein the THD comprises a contiguous amino acid sequence consisting of amino acids 88 to 231 of full length human TNF alpha of SEQ ID NO: 5, but comprising the mutations D143N and A145R of the ectodomain of human TNF alpha corresponding to D219N and A221R, respectively, relative to SEQ ID NO: 5.

2. The polypeptide according to claim 1, wherein the three THDs are identical.

3. The polypeptide according to claim 2, wherein:

(i) $X_L$ is absent and $X_N$ is S-R-T-P-S-D-K (SEQ ID NO: 9);

(ii) $X_L$ is G-G-G-G (SEQ ID NO: 16) and $X_N$ is P-S-D-K (SEQ ID NO: 6);

(iii) $X_L$ is G and $X_N$ is selected from R-T-P-S-D-K (SEQ ID NO: 8), and S-R-T-P-S-D-K (SEQ ID NO: 9);

(iv) $X_L$ is G-G and $X_N$ is selected from T-P-S-D-K (SEQ ID NO: 7), and R-T-P-S-D-K (SEQ ID NO: 8); or (v) $X_L$ is G-G-G and $X_N$ is selected from P-S-D-K (SEQ ID NO: 6), and T-P-S-D-K (SEQ ID NO: 7).

4. The polypeptide according to claim 1, wherein the polypeptide has an onset of aggregation temperature ($T_m$) of more than 62° C. as determined by dynamic light scattering.

5. A polypeptide multimer comprising at least two polypeptides according to claim 1 that are (a) linked together; or (b) linked to a protein selected from the group consisting of: a multimerization domain, a serum protein, a cytokine, a targeting moiety and a toxin.

6. The polypeptide multimer according to claim 5, wherein:

A. the polypeptide multimer has at least one of the following properties:

(i) an onset of aggregation temperature ($T_m$) of at least 72° C.;

(ii) an $EC_{50}$ for binding to TNFR2 in HeLa-TNF-R2 cells that is not decreased by more than 15%, 12%, or 10%, after 8 days of incubation in human plasma at 37° C.;

(iii) an $EC_{50}$ for binding to TNFR2 expressed on MEFs of less than 100 pM;

(iv) an $EC_{50}$ for binding to TNFR2 on Kym-1 cells of less than 200 pM;

(v) an $EC_{50}$ for activation of NF-κB in HeLa-TNF-R2 cells of less than 30 pM; and/or B. the polypeptide multimer further comprises a ligand specific for an organ, tissue or cell-type.

7. The polypeptide multimer according to claim 5, wherein said polypeptides are:

(a) linked together by an amino acid linker that has a length of between 1 to 30 amino acids or between 7 to 15 amino acids; or (b) linked to said protein by an amino acid linker that has a length of between 1 to 30 amino acids.

8. The polypeptide multimer according to claim 5, wherein the at least two polypeptides are linked to a protein that is a multimerization domain, and wherein the multimerization domain is a dimerization domain, a trimerization domain or a tetramerization domain.

9. The polypeptide multimer according to claim 8, wherein the dimerization domain is selected from the group consisting of an antibody, an antibody heavy chain, immunoglobulin Fc region, heavy chain domain 2 (CH2) of IgM (MHD2), heavy chain domain 2 (CH2) of IgE (EHD2), heavy chain domain 3 (CH3) of IgG, heavy chain domain 3 (CH3) of IgA, heavy chain domain 3 (CH3) of IgD, heavy chain domain 4 (CH4) of IgM, heavy chain domain 4 (CH4) of IgE, Fab, $Fab_2$, leucine zipper motifs, barnase-barstar dimers, miniantibodies, and ZIP miniantibodies.

10. The polypeptide multimer according to claim 8, wherein the (i) the trimerization domain is selected from the group consisting of tenascin C (TNC), the trimerization region of the C-terminal noncollagenous domain (NC1) of collagen XVIII, Fab3 like molecules, and TriBi-minibodies; or (ii) the tetramerization domain is selected from the group consisting of the tetramerization domain of p53, the tetramerization domain of the general control protein 4 (GCN4), the tetramerization domain of VASP (vasodilator stimulated phosphoprotein), tandem diabodies, and di-diabodies.

11. The polypeptide multimer according to claim 8, wherein the dimerization domain is selected from the group consisting of FcΔab, LALA, LALA-GP, IgG2, IgG2σ, aglycosylated IgG1, IgG1 L234F/L235E/P331S, IgG2m4, and IgG4 ProAlaAla.

12. A nucleic acid molecule encoding the polypeptide according to claim 1.

13. A vector comprising the nucleic acid molecule according to claim 12.

14. A pharmaceutical composition comprising as an active agent a polypeptide according to claim 1.

15. A method of treating, hyperproliferative disorders, inflammatory disorders, neurodegenerative disorders, neuropathic diseases, neurological insults autoimmune disorders, or metabolic disorders in a subject, the method comprising: administering to the subject in need thereof an effective amount of a polypeptide according to claim 1 or a nucleic acid molecule encoding the polypeptide according to claim 1.

16. The method of claim 15, wherein the hyperproliferative disorders are cancer or malignancies of the hematologic system, or the metabolic disorders are metabolic syndromes or cardiovascular diseases.

* * * * *

SEQUENCE LISTING

```
<160> NUMBER OF SEQ ID NOS: 108

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: can be F or Y
<220> FEATURE:
<221> NAME/KEY: MISC_FEATURE
<222> LOCATION: (5)..(5)
<223> OTHER INFORMATION: can be A or I
<220> FEATURE:
<221> NAME/KEY: MISC_FEATURE
<222> LOCATION: (6)..(6)
<223> OTHER INFORMATION: can be a non-polar/hydrophobic or polar/neutral
      amino acid

<400> SEQUENCE: 1

Val Xaa Phe Gly Xaa Xaa
1               5


<210> SEQ ID NO 2
<211> LENGTH: 5
<212> TYPE: PRT
<213> ORGANISM: Homo sapiens
```

```
<220> FEATURE:
<221> NAME/KEY: MISC_FEATURE
<222> LOCATION: (2)..(2)
<223> OTHER INFORMATION: can be V or A
<220> FEATURE:
<221> NAME/KEY: MISC_FEATURE
<222> LOCATION: (5)..(5)
<223> OTHER INFORMATION: can be V or L

<400> SEQUENCE: 2

Pro Xaa Ala His Xaa
1               5


<210> SEQ ID NO 3
<211> LENGTH: 6
<212> TYPE: PRT
<213> ORGANISM: Homo sapiens

<400> SEQUENCE: 3

Val Tyr Phe Gly Ile Ile
1               5


<210> SEQ ID NO 4
<211> LENGTH: 5
<212> TYPE: PRT
<213> ORGANISM: Homo sapiens

<400> SEQUENCE: 4

Pro Val Ala His Val
1               5


<210> SEQ ID NO 5
<211> LENGTH: 233
<212> TYPE: PRT
<213> ORGANISM: Homo sapiens

<400> SEQUENCE: 5

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190
```

```
Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230


<210> SEQ ID NO 6
<211> LENGTH: 4
<212> TYPE: PRT
<213> ORGANISM: Homo sapiens

<400> SEQUENCE: 6

Pro Ser Asp Lys
1


<210> SEQ ID NO 7
<211> LENGTH: 5
<212> TYPE: PRT
<213> ORGANISM: Homo sapiens

<400> SEQUENCE: 7

Thr Pro Ser Asp Lys
1               5


<210> SEQ ID NO 8
<211> LENGTH: 6
<212> TYPE: PRT
<213> ORGANISM: Homo sapiens

<400> SEQUENCE: 8

Arg Thr Pro Ser Asp Lys
1               5


<210> SEQ ID NO 9
<211> LENGTH: 7
<212> TYPE: PRT
<213> ORGANISM: Homo sapiens

<400> SEQUENCE: 9

Ser Arg Thr Pro Ser Asp Lys
1               5


<210> SEQ ID NO 10
<211> LENGTH: 8
<212> TYPE: PRT
<213> ORGANISM: Homo sapiens

<400> SEQUENCE: 10

Ser Ser Arg Thr Pro Ser Asp Lys
1               5


<210> SEQ ID NO 11
<211> LENGTH: 4
<212> TYPE: PRT
<213> ORGANISM: Homo sapiens

<400> SEQUENCE: 11

His Ser Thr Lys
1


<210> SEQ ID NO 12
<211> LENGTH: 5
```

<212> TYPE: PRT
<213> ORGANISM: Homo sapiens

<400> SEQUENCE: 12

Ala His Ser Thr Lys
1               5

<210> SEQ ID NO 13
<211> LENGTH: 6
<212> TYPE: PRT
<213> ORGANISM: Homo sapiens

<400> SEQUENCE: 13

Leu Ala His Ser Thr Lys
1               5

<210> SEQ ID NO 14
<211> LENGTH: 7
<212> TYPE: PRT
<213> ORGANISM: Homo sapiens

<400> SEQUENCE: 14

His Leu Ala His Ser Thr Lys
1               5

<210> SEQ ID NO 15
<211> LENGTH: 8
<212> TYPE: PRT
<213> ORGANISM: Homo sapiens

<400> SEQUENCE: 15

Leu His Leu Ala His Ser Thr Lys
1               5

<210> SEQ ID NO 16
<211> LENGTH: 4
<212> TYPE: PRT
<213> ORGANISM: Artificial Sequence
<220> FEATURE:
<223> OTHER INFORMATION: linker

<400> SEQUENCE: 16

Gly Gly Gly Gly
1

<210> SEQ ID NO 17
<211> LENGTH: 4
<212> TYPE: PRT
<213> ORGANISM: Artificial Sequence
<220> FEATURE:
<223> OTHER INFORMATION: linker

<400> SEQUENCE: 17

Gly Gly Gly Ser
1

<210> SEQ ID NO 18
<211> LENGTH: 4
<212> TYPE: PRT
<213> ORGANISM: Artificial Sequence
<220> FEATURE:
<223> OTHER INFORMATION: linker

<400> SEQUENCE: 18

Gly Gly Ser Gly
1

<210> SEQ ID NO 19
<211> LENGTH: 4
<212> TYPE: PRT
<213> ORGANISM: Artificial Sequence
<220> FEATURE:
<223> OTHER INFORMATION: linker

<400> SEQUENCE: 19

Gly Ser Gly Gly
1

<210> SEQ ID NO 20
<211> LENGTH: 4
<212> TYPE: PRT
<213> ORGANISM: Artificial Sequence
<220> FEATURE:
<223> OTHER INFORMATION: linker

<400> SEQUENCE: 20

Ser Gly Gly Gly
1

<210> SEQ ID NO 21
<211> LENGTH: 5
<212> TYPE: PRT
<213> ORGANISM: Artificial Sequence
<220> FEATURE:
<223> OTHER INFORMATION: linker

<400> SEQUENCE: 21

Gly Gly Gly Gly Gly
1               5

<210> SEQ ID NO 22
<211> LENGTH: 5
<212> TYPE: PRT
<213> ORGANISM: Artificial Sequence
<220> FEATURE:
<223> OTHER INFORMATION: linker

<400> SEQUENCE: 22

Ser Gly Gly Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: linker

<400> SEQUENCE: 23

Gly Ser Gly Gly Gly
1               5

<210> SEQ ID NO 24
<211> LENGTH: 5
<212> TYPE: PRT
<213> ORGANISM: Artificial Sequence
<220> FEATURE:
<223> OTHER INFORMATION: linker

<400> SEQUENCE: 24

Gly Gly Ser Gly Gly
1               5

<210> SEQ ID NO 25
<211> LENGTH: 5
<212> TYPE: PRT
<213> ORGANISM: Artificial Sequence
<220> FEATURE:
<223> OTHER INFORMATION: linker

<400> SEQUENCE: 25

Gly Gly Gly Ser Gly
1 5

<210> SEQ ID NO 26
<211> LENGTH: 5
<212> TYPE: PRT
<213> ORGANISM: Artificial Sequence
<220> FEATURE:
<223> OTHER INFORMATION: linker

<400> SEQUENCE: 26

Gly Gly Gly Gly Ser
1 5

<210> SEQ ID NO 27
<211> LENGTH: 6
<212> TYPE: PRT
<213> ORGANISM: Artificial Sequence
<220> FEATURE:
<223> OTHER INFORMATION: linker

<400> SEQUENCE: 27

Gly Gly Gly Gly Gly Gly
1 5

<210> SEQ ID NO 28
<211> LENGTH: 6
<212> TYPE: PRT
<213> ORGANISM: Artificial Sequence
<220> FEATURE:
<223> OTHER INFORMATION: linker

<400> SEQUENCE: 28

Ser Gly Gly Gly Gly Gly
1 5

<210> SEQ ID NO 29
<211> LENGTH: 6
<212> TYPE: PRT
<213> ORGANISM: Artificial Sequence
<220> FEATURE:
<223> OTHER INFORMATION: linker

<400> SEQUENCE: 29

Gly Ser Gly Gly Gly Gly
1 5

<210> SEQ ID NO 30
<211> LENGTH: 6
<212> TYPE: PRT
<213> ORGANISM: Artificial Sequence
<220> FEATURE:
<223> OTHER INFORMATION: linker

<400> SEQUENCE: 30

Gly Gly Ser Gly Gly Gly
1 5

<210> SEQ ID NO 31
<211> LENGTH: 6
<212> TYPE: PRT
<213> ORGANISM: Artificial Sequence
<220> FEATURE:
<223> OTHER INFORMATION: linker

<400> SEQUENCE: 31

Gly Gly Gly Ser Gly Gly
1 5

<210> SEQ ID NO 32
<211> LENGTH: 6
<212> TYPE: PRT
<213> ORGANISM: Artificial Sequence
<220> FEATURE:
<223> OTHER INFORMATION: linker

<400> SEQUENCE: 32

Gly Gly Gly Gly Ser Gly
1 5

<210> SEQ ID NO 33
<211> LENGTH: 6
<212> TYPE: PRT
<213> ORGANISM: Artificial Sequence
<220> FEATURE:
<223> OTHER INFORMATION: linker

<400> SEQUENCE: 33

Gly Gly Gly Gly Gly Ser
1 5

<210> SEQ ID NO 34
<211> LENGTH: 8
<212> TYPE: PRT
<213> ORGANISM: Artificial Sequence
<220> FEATURE:
<223> OTHER INFORMATION: linker

<400> SEQUENCE: 34

Gly Gly Gly Ser Gly Gly Gly Ser
1 5

<210> SEQ ID NO 35
<211> LENGTH: 8
<212> TYPE: PRT
<213> ORGANISM: Artificial Sequence
<220> FEATURE:
<223> OTHER INFORMATION: linker

<400> SEQUENCE: 35

Ser Gly Gly Gly Ser Gly Gly Gly
1 5

<210> SEQ ID NO 36
<211> LENGTH: 8
<212> TYPE: PRT
<213> ORGANISM: Artificial Sequence
<220> FEATURE:
<223> OTHER INFORMATION: linker

<400> SEQUENCE: 36

Gly Gly Gly Gly Gly Gly Gly Gly
1 5

<210> SEQ ID NO 37

<211> LENGTH: 8
<212> TYPE: PRT
<213> ORGANISM: Artificial Sequence
<220> FEATURE:
<223> OTHER INFORMATION: linker

<400> SEQUENCE: 37

Gly Ser Gly Gly Gly Ser Gly Gly
1               5

<210> SEQ ID NO 38
<211> LENGTH: 8
<212> TYPE: PRT
<213> ORGANISM: Artificial Sequence
<220> FEATURE:
<223> OTHER INFORMATION: linker

<400> SEQUENCE: 38

Gly Gly Ser Gly Gly Gly Ser Gly
1               5

<210> SEQ ID NO 39
<211> LENGTH: 9
<212> TYPE: PRT
<213> ORGANISM: Artificial Sequence
<220> FEATURE:
<223> OTHER INFORMATION: linker

<400> SEQUENCE: 39

Ser Gly Gly Gly Ser Gly Gly Gly Ser
1               5

<210> SEQ ID NO 40
<211> LENGTH: 9
<212> TYPE: PRT
<213> ORGANISM: Artificial Sequence
<220> FEATURE:
<223> OTHER INFORMATION: linker

<400> SEQUENCE: 40

Gly Ser Gly Gly Gly Ser Gly Gly Gly
1               5

<210> SEQ ID NO 41
<211> LENGTH: 9
<212> TYPE: PRT
<213> ORGANISM: Artificial Sequence
<220> FEATURE:
<223> OTHER INFORMATION: linker

<400> SEQUENCE: 41

Gly Gly Ser Gly Gly Gly Ser Gly Gly
1               5

<210> SEQ ID NO 42
<211> LENGTH: 9
<212> TYPE: PRT
<213> ORGANISM: Artificial Sequence
<220> FEATURE:
<223> OTHER INFORMATION: linker

<400> SEQUENCE: 42

Gly Gly Gly Ser Gly Gly Gly Ser Gly
1               5

<210> SEQ ID NO 43
<211> LENGTH: 10

<212> TYPE: PRT
<213> ORGANISM: Artificial Sequence
<220> FEATURE:
<223> OTHER INFORMATION: linker

<400> SEQUENCE: 43

Ser Gly Gly Gly Ser Gly Gly Gly Ser Gly
1 5 10

<210> SEQ ID NO 44
<211> LENGTH: 10
<212> TYPE: PRT
<213> ORGANISM: Artificial Sequence
<220> FEATURE:
<223> OTHER INFORMATION: linker

<400> SEQUENCE: 44

Gly Ser Gly Gly Gly Ser Gly Gly Gly Ser
1 5 10

<210> SEQ ID NO 45
<211> LENGTH: 10
<212> TYPE: PRT
<213> ORGANISM: Artificial Sequence
<220> FEATURE:
<223> OTHER INFORMATION: linker

<400> SEQUENCE: 45

Gly Gly Ser Gly Gly Gly Ser Gly Gly Gly
1 5 10

<210> SEQ ID NO 46
<211> LENGTH: 10
<212> TYPE: PRT
<213> ORGANISM: Artificial Sequence
<220> FEATURE:
<223> OTHER INFORMATION: linker

<400> SEQUENCE: 46

Gly Gly Gly Ser Gly Gly Gly Ser Gly Gly
1 5 10

<210> SEQ ID NO 47
<211> LENGTH: 11
<212> TYPE: PRT
<213> ORGANISM: Artificial Sequence
<220> FEATURE:
<223> OTHER INFORMATION: linker

<400> SEQUENCE: 47

Ser Gly Gly Gly Ser Gly Gly Gly Ser Gly Gly
1 5 10

<210> SEQ ID NO 48
<211> LENGTH: 11
<212> TYPE: PRT
<213> ORGANISM: Artificial Sequence
<220> FEATURE:
<223> OTHER INFORMATION: lnker

<400> SEQUENCE: 48

Gly Ser Gly Gly Gly Ser Gly Gly Gly Ser Gly
1 5 10

<210> SEQ ID NO 49
<211> LENGTH: 11
<212> TYPE: PRT

```
<213> ORGANISM: Artificial Sequence
<220> FEATURE:
<223> OTHER INFORMATION: linker

<400> SEQUENCE: 49

Gly Gly Ser Gly Gly Gly Ser Gly Gly Gly Ser
1               5                   10


<210> SEQ ID NO 50
<211> LENGTH: 11
<212> TYPE: PRT
<213> ORGANISM: Artificial Sequence
<220> FEATURE:
<223> OTHER INFORMATION: linker

<400> SEQUENCE: 50

Gly Gly Gly Ser Gly Gly Gly Ser Gly Gly Gly
1               5                   10


<210> SEQ ID NO 51
<211> LENGTH: 9
<212> TYPE: PRT
<213> ORGANISM: Homo sapiens

<400> SEQUENCE: 51

Ser Ser Ser Arg Thr Pro Ser Asp Lys
1               5


<210> SEQ ID NO 52
<211> LENGTH: 10
<212> TYPE: PRT
<213> ORGANISM: Homo sapiens

<400> SEQUENCE: 52

Arg Ser Ser Ser Arg Thr Pro Ser Asp Lys
1               5                   10


<210> SEQ ID NO 53
<211> LENGTH: 12
<212> TYPE: PRT
<213> ORGANISM: Artificial Sequence
<220> FEATURE:
<223> OTHER INFORMATION: linker

<400> SEQUENCE: 53

Gly Gly Gly Ser Gly Gly Gly Ser Gly Gly Gly Ser
1               5                   10


<210> SEQ ID NO 54
<211> LENGTH: 16
<212> TYPE: PRT
<213> ORGANISM: Artificial Sequence
<220> FEATURE:
<223> OTHER INFORMATION: linker

<400> SEQUENCE: 54

Gly Gly Gly Ser Gly Gly Gly Ser Gly Gly Gly Ser Gly Gly Gly Ser
1               5                   10                  15


<210> SEQ ID NO 55
<211> LENGTH: 205
<212> TYPE: PRT
<213> ORGANISM: Homo sapiens

<400> SEQUENCE: 55

Met Thr Pro Pro Glu Arg Leu Phe Leu Pro Arg Val Cys Gly Thr Thr
```

```
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205


<210> SEQ ID NO 56
<211> LENGTH: 6
<212> TYPE: PRT
<213> ORGANISM: Homo sapiens

<400> SEQUENCE: 56

Val Phe Phe Gly Ala Phe
1               5


<210> SEQ ID NO 57
<211> LENGTH: 5
<212> TYPE: PRT
<213> ORGANISM: Homo sapiens

<400> SEQUENCE: 57

Pro Ala Ala His Leu
1               5


<210> SEQ ID NO 58
<211> LENGTH: 23
<212> TYPE: PRT
<213> ORGANISM: Artificial Sequence
<220> FEATURE:
<223> OTHER INFORMATION: scTNFR2 construct

<400> SEQUENCE: 58

Gly Ile Ile Ala Leu Gly Gly Gly Gly Ser Ser Ser Arg Thr Pro Ser
1               5                   10                  15

Asp Lys Pro Val Ala His Val
            20


<210> SEQ ID NO 59
<211> LENGTH: 18
```

<212> TYPE: PRT
<213> ORGANISM: Artificial Sequence
<220> FEATURE:
<223> OTHER INFORMATION: scTNFR2 construct

<400> SEQUENCE: 59

Gly Ile Ile Ala Leu Ser Ser Arg Thr Pro Ser Asp Lys Pro Val Ala
1 5 10 15

His Val

<210> SEQ ID NO 60
<211> LENGTH: 16
<212> TYPE: PRT
<213> ORGANISM: Artificial Sequence
<220> FEATURE:
<223> OTHER INFORMATION: scTNFR2 contruct

<400> SEQUENCE: 60

Gly Ile Ile Ala Leu Arg Thr Pro Ser Asp Lys Pro Val Ala His Val
1 5 10 15

<210> SEQ ID NO 61
<211> LENGTH: 14
<212> TYPE: PRT
<213> ORGANISM: Artificial Sequence
<220> FEATURE:
<223> OTHER INFORMATION: scTNFR2 construct

<400> SEQUENCE: 61

Gly Ile Ile Ala Leu Pro Ser Asp Lys Pro Val Ala His Val
1 5 10

<210> SEQ ID NO 62
<211> LENGTH: 17
<212> TYPE: PRT
<213> ORGANISM: Artificial Sequence
<220> FEATURE:
<223> OTHER INFORMATION: scTNFR2 construct

<400> SEQUENCE: 62

Gly Ile Ile Ala Leu Gly Gly Gly Gly Ser Asp Lys Pro Val Ala His
1 5 10 15

Val

<210> SEQ ID NO 63
<211> LENGTH: 12
<212> TYPE: PRT
<213> ORGANISM: Artificial Sequence
<220> FEATURE:
<223> OTHER INFORMATION: scTNFR2 construct

<400> SEQUENCE: 63

Gly Ile Ile Ala Leu Asp Lys Pro Val Ala His Val
1 5 10

<210> SEQ ID NO 64
<211> LENGTH: 18
<212> TYPE: PRT
<213> ORGANISM: Artificial Sequence
<220> FEATURE:
<223> OTHER INFORMATION: scTNFR2 construct

<400> SEQUENCE: 64

Gly Ile Ile Ala Leu Gly Gly Gly Ser Gly Gly Gly Ser Pro Val Ala
1 5 10 15

His Val

<210> SEQ ID NO 65
<211> LENGTH: 507
<212> TYPE: PRT
<213> ORGANISM: Artificial Sequence
<220> FEATURE:
<223> OTHER INFORMATION: scTNFR2 (118)

<400> SEQUENCE: 65

```
Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Ser Ser Arg Thr Pro Ser Asp Lys Pro Val Ala His Val
        35                  40                  45

Val Ala Asn Pro Gln Ala Glu Gly Gln Leu Gln Trp Leu Asn Arg Arg
    50                  55                  60

Ala Asn Ala Leu Leu Ala Asn Gly Val Glu Leu Arg Asp Asn Gln Leu
65                  70                  75                  80

Val Val Pro Ser Glu Gly Leu Tyr Leu Ile Tyr Ser Gln Val Leu Phe
                85                  90                  95

Lys Gly Gln Gly Cys Pro Ser Thr His Val Leu Leu Thr His Thr Ile
            100                 105                 110

Ser Arg Ile Ala Val Ser Tyr Gln Thr Lys Val Asn Leu Leu Ser Ala
        115                 120                 125

Ile Lys Ser Pro Cys Gln Arg Glu Thr Pro Glu Gly Ala Glu Ala Lys
    130                 135                 140

Pro Trp Tyr Glu Pro Ile Tyr Leu Gly Gly Val Phe Gln Leu Glu Lys
145                 150                 155                 160

Gly Asp Arg Leu Ser Ala Glu Ile Asn Arg Pro Asp Tyr Leu Asn Phe
                165                 170                 175

Arg Glu Ser Gly Gln Val Tyr Phe Gly Ile Ile Ala Leu Gly Gly Gly
            180                 185                 190

Gly Ser Ser Ser Arg Thr Pro Ser Asp Lys Pro Val Ala His Val Val
        195                 200                 205

Ala Asn Pro Gln Ala Glu Gly Gln Leu Gln Trp Leu Asn Arg Arg Ala
    210                 215                 220

Asn Ala Leu Leu Ala Asn Gly Val Glu Leu Arg Asp Asn Gln Leu Val
225                 230                 235                 240

Val Pro Ser Glu Gly Leu Tyr Leu Ile Tyr Ser Gln Val Leu Phe Lys
                245                 250                 255

Gly Gln Gly Cys Pro Ser Thr His Val Leu Leu Thr His Thr Ile Ser
            260                 265                 270

Arg Ile Ala Val Ser Tyr Gln Thr Lys Val Asn Leu Leu Ser Ala Ile
        275                 280                 285

Lys Ser Pro Cys Gln Arg Glu Thr Pro Glu Gly Ala Glu Ala Lys Pro
    290                 295                 300

Trp Tyr Glu Pro Ile Tyr Leu Gly Gly Val Phe Gln Leu Glu Lys Gly
305                 310                 315                 320

Asp Arg Leu Ser Ala Glu Ile Asn Arg Pro Asp Tyr Leu Asn Phe Arg
                325                 330                 335

Glu Ser Gly Gln Val Tyr Phe Gly Ile Ile Ala Leu Gly Gly Gly Gly
            340                 345                 350

Ser Ser Ser Arg Thr Pro Ser Asp Lys Pro Val Ala His Val Val Ala
```

```
        355                 360                 365

Asn Pro Gln Ala Glu Gly Gln Leu Gln Trp Leu Asn Arg Arg Ala Asn
    370                 375                 380

Ala Leu Leu Ala Asn Gly Val Glu Leu Arg Asp Asn Gln Leu Val Val
385                 390                 395                 400

Pro Ser Glu Gly Leu Tyr Leu Ile Tyr Ser Gln Val Leu Phe Lys Gly
                405                 410                 415

Gln Gly Cys Pro Ser Thr His Val Leu Leu Thr His Thr Ile Ser Arg
            420                 425                 430

Ile Ala Val Ser Tyr Gln Thr Lys Val Asn Leu Leu Ser Ala Ile Lys
        435                 440                 445

Ser Pro Cys Gln Arg Glu Thr Pro Glu Gly Ala Glu Ala Lys Pro Trp
    450                 455                 460

Tyr Glu Pro Ile Tyr Leu Gly Gly Val Phe Gln Leu Glu Lys Gly Asp
465                 470                 475                 480

Arg Leu Ser Ala Glu Ile Asn Arg Pro Asp Tyr Leu Asn Phe Arg Glu
                485                 490                 495

Ser Gly Gln Val Tyr Phe Gly Ile Ile Ala Leu
            500                 505
```

```
<210> SEQ ID NO 66
<211> LENGTH: 497
<212> TYPE: PRT
<213> ORGANISM: Artificial Sequence
<220> FEATURE:
<223> OTHER INFORMATION: scTNFR2 (127)

<400> SEQUENCE: 66

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Ser Ser Arg Thr Pro Ser Asp Lys Pro Val Ala His Val
        35                  40                  45

Val Ala Asn Pro Gln Ala Glu Gly Gln Leu Gln Trp Leu Asn Arg Arg
    50                  55                  60

Ala Asn Ala Leu Leu Ala Asn Gly Val Glu Leu Arg Asp Asn Gln Leu
65                  70                  75                  80

Val Val Pro Ser Glu Gly Leu Tyr Leu Ile Tyr Ser Gln Val Leu Phe
                85                  90                  95

Lys Gly Gln Gly Cys Pro Ser Thr His Val Leu Leu Thr His Thr Ile
            100                 105                 110

Ser Arg Ile Ala Val Ser Tyr Gln Thr Lys Val Asn Leu Leu Ser Ala
        115                 120                 125

Ile Lys Ser Pro Cys Gln Arg Glu Thr Pro Glu Gly Ala Glu Ala Lys
    130                 135                 140

Pro Trp Tyr Glu Pro Ile Tyr Leu Gly Gly Val Phe Gln Leu Glu Lys
145                 150                 155                 160

Gly Asp Arg Leu Ser Ala Glu Ile Asn Arg Pro Asp Tyr Leu Asn Phe
                165                 170                 175

Arg Glu Ser Gly Gln Val Tyr Phe Gly Ile Ile Ala Leu Ser Ser Arg
            180                 185                 190

Thr Pro Ser Asp Lys Pro Val Ala His Val Val Ala Asn Pro Gln Ala
        195                 200                 205

Glu Gly Gln Leu Gln Trp Leu Asn Arg Arg Ala Asn Ala Leu Leu Ala
```

```
    210                 215                 220

Asn Gly Val Glu Leu Arg Asp Asn Gln Leu Val Val Pro Ser Glu Gly
225                 230                 235                 240

Leu Tyr Leu Ile Tyr Ser Gln Val Leu Phe Lys Gly Gln Gly Cys Pro
                245                 250                 255

Ser Thr His Val Leu Leu Thr His Thr Ile Ser Arg Ile Ala Val Ser
            260                 265                 270

Tyr Gln Thr Lys Val Asn Leu Leu Ser Ala Ile Lys Ser Pro Cys Gln
        275                 280                 285

Arg Glu Thr Pro Glu Gly Ala Glu Ala Lys Pro Trp Tyr Glu Pro Ile
    290                 295                 300

Tyr Leu Gly Gly Val Phe Gln Leu Glu Lys Gly Asp Arg Leu Ser Ala
305                 310                 315                 320

Glu Ile Asn Arg Pro Asp Tyr Leu Asn Phe Arg Glu Ser Gly Gln Val
                325                 330                 335

Tyr Phe Gly Ile Ile Ala Leu Ser Ser Arg Thr Pro Ser Asp Lys Pro
            340                 345                 350

Val Ala His Val Val Ala Asn Pro Gln Ala Glu Gly Gln Leu Gln Trp
        355                 360                 365

Leu Asn Arg Arg Ala Asn Ala Leu Leu Ala Asn Gly Val Glu Leu Arg
    370                 375                 380

Asp Asn Gln Leu Val Val Pro Ser Glu Gly Leu Tyr Leu Ile Tyr Ser
385                 390                 395                 400

Gln Val Leu Phe Lys Gly Gln Gly Cys Pro Ser Thr His Val Leu Leu
                405                 410                 415

Thr His Thr Ile Ser Arg Ile Ala Val Ser Tyr Gln Thr Lys Val Asn
            420                 425                 430

Leu Leu Ser Ala Ile Lys Ser Pro Cys Gln Arg Glu Thr Pro Glu Gly
        435                 440                 445

Ala Glu Ala Lys Pro Trp Tyr Glu Pro Ile Tyr Leu Gly Gly Val Phe
    450                 455                 460

Gln Leu Glu Lys Gly Asp Arg Leu Ser Ala Glu Ile Asn Arg Pro Asp
465                 470                 475                 480

Tyr Leu Asn Phe Arg Glu Ser Gly Gln Val Tyr Phe Gly Ile Ile Ala
                485                 490                 495

Leu


<210> SEQ ID NO 67
<211> LENGTH: 485
<212> TYPE: PRT
<213> ORGANISM: Artificial Sequence
<220> FEATURE:
<223> OTHER INFORMATION: scTNFR2 (129)

<400> SEQUENCE: 67

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Pro Ser Asp Lys Pro Val Ala His Val Val Ala Asn Pro
        35                  40                  45

Gln Ala Glu Gly Gln Leu Gln Trp Leu Asn Arg Arg Ala Asn Ala Leu
    50                  55                  60

Leu Ala Asn Gly Val Glu Leu Arg Asp Asn Gln Leu Val Val Pro Ser
65                  70                  75                  80
```

```
Glu Gly Leu Tyr Leu Ile Tyr Ser Gln Val Leu Phe Lys Gly Gln Gly
                85                  90                  95

Cys Pro Ser Thr His Val Leu Leu Thr His Thr Ile Ser Arg Ile Ala
            100                 105                 110

Val Ser Tyr Gln Thr Lys Val Asn Leu Leu Ser Ala Ile Lys Ser Pro
        115                 120                 125

Cys Gln Arg Glu Thr Pro Glu Gly Ala Glu Ala Lys Pro Trp Tyr Glu
    130                 135                 140

Pro Ile Tyr Leu Gly Gly Val Phe Gln Leu Glu Lys Gly Asp Arg Leu
145                 150                 155                 160

Ser Ala Glu Ile Asn Arg Pro Asp Tyr Leu Asn Phe Arg Glu Ser Gly
                165                 170                 175

Gln Val Tyr Phe Gly Ile Ile Ala Leu Pro Ser Asp Lys Pro Val Ala
            180                 185                 190

His Val Val Ala Asn Pro Gln Ala Glu Gly Gln Leu Gln Trp Leu Asn
        195                 200                 205

Arg Arg Ala Asn Ala Leu Leu Ala Asn Gly Val Glu Leu Arg Asp Asn
    210                 215                 220

Gln Leu Val Val Pro Ser Glu Gly Leu Tyr Leu Ile Tyr Ser Gln Val
225                 230                 235                 240

Leu Phe Lys Gly Gln Gly Cys Pro Ser Thr His Val Leu Leu Thr His
                245                 250                 255

Thr Ile Ser Arg Ile Ala Val Ser Tyr Gln Thr Lys Val Asn Leu Leu
            260                 265                 270

Ser Ala Ile Lys Ser Pro Cys Gln Arg Glu Thr Pro Glu Gly Ala Glu
        275                 280                 285

Ala Lys Pro Trp Tyr Glu Pro Ile Tyr Leu Gly Gly Val Phe Gln Leu
    290                 295                 300

Glu Lys Gly Asp Arg Leu Ser Ala Glu Ile Asn Arg Pro Asp Tyr Leu
305                 310                 315                 320

Asn Phe Arg Glu Ser Gly Gln Val Tyr Phe Gly Ile Ile Ala Leu Pro
                325                 330                 335

Ser Asp Lys Pro Val Ala His Val Val Ala Asn Pro Gln Ala Glu Gly
            340                 345                 350

Gln Leu Gln Trp Leu Asn Arg Arg Ala Asn Ala Leu Leu Ala Asn Gly
        355                 360                 365

Val Glu Leu Arg Asp Asn Gln Leu Val Val Pro Ser Glu Gly Leu Tyr
    370                 375                 380

Leu Ile Tyr Ser Gln Val Leu Phe Lys Gly Gln Gly Cys Pro Ser Thr
385                 390                 395                 400

His Val Leu Leu Thr His Thr Ile Ser Arg Ile Ala Val Ser Tyr Gln
                405                 410                 415

Thr Lys Val Asn Leu Leu Ser Ala Ile Lys Ser Pro Cys Gln Arg Glu
            420                 425                 430

Thr Pro Glu Gly Ala Glu Ala Lys Pro Trp Tyr Glu Pro Ile Tyr Leu
        435                 440                 445

Gly Gly Val Phe Gln Leu Glu Lys Gly Asp Arg Leu Ser Ala Glu Ile
    450                 455                 460

Asn Arg Pro Asp Tyr Leu Asn Phe Arg Glu Ser Gly Gln Val Tyr Phe
465                 470                 475                 480

Gly Ile Ile Ala Leu
                485
```

```
<210> SEQ ID NO 68
<211> LENGTH: 490
<212> TYPE: PRT
<213> ORGANISM: Artificial Sequence
<220> FEATURE:
<223> OTHER INFORMATION: scTNFR2 (139)

<400> SEQUENCE: 68

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Ser Asp Lys Pro Val Ala His Val Val Ala Asn Pro Gln
        35                  40                  45

Ala Glu Gly Gln Leu Gln Trp Leu Asn Arg Arg Ala Asn Ala Leu Leu
    50                  55                  60

Ala Asn Gly Val Glu Leu Arg Asp Asn Gln Leu Val Val Pro Ser Glu
65                  70                  75                  80

Gly Leu Tyr Leu Ile Tyr Ser Gln Val Leu Phe Lys Gly Gln Gly Cys
                85                  90                  95

Pro Ser Thr His Val Leu Leu Thr His Thr Ile Ser Arg Ile Ala Val
            100                 105                 110

Ser Tyr Gln Thr Lys Val Asn Leu Leu Ser Ala Ile Lys Ser Pro Cys
        115                 120                 125

Gln Arg Glu Thr Pro Glu Gly Ala Glu Ala Lys Pro Trp Tyr Glu Pro
    130                 135                 140

Ile Tyr Leu Gly Gly Val Phe Gln Leu Glu Lys Gly Asp Arg Leu Ser
145                 150                 155                 160

Ala Glu Ile Asn Arg Pro Asp Tyr Leu Asn Phe Arg Glu Ser Gly Gln
                165                 170                 175

Val Tyr Phe Gly Ile Ile Ala Leu Gly Gly Gly Gly Ser Asp Lys Pro
            180                 185                 190

Val Ala His Val Val Ala Asn Pro Gln Ala Glu Gly Gln Leu Gln Trp
        195                 200                 205

Leu Asn Arg Arg Ala Asn Ala Leu Leu Ala Asn Gly Val Glu Leu Arg
    210                 215                 220

Asp Asn Gln Leu Val Val Pro Ser Glu Gly Leu Tyr Leu Ile Tyr Ser
225                 230                 235                 240

Gln Val Leu Phe Lys Gly Gln Gly Cys Pro Ser Thr His Val Leu Leu
                245                 250                 255

Thr His Thr Ile Ser Arg Ile Ala Val Ser Tyr Gln Thr Lys Val Asn
            260                 265                 270

Leu Leu Ser Ala Ile Lys Ser Pro Cys Gln Arg Glu Thr Pro Glu Gly
        275                 280                 285

Ala Glu Ala Lys Pro Trp Tyr Glu Pro Ile Tyr Leu Gly Gly Val Phe
    290                 295                 300

Gln Leu Glu Lys Gly Asp Arg Leu Ser Ala Glu Ile Asn Arg Pro Asp
305                 310                 315                 320

Tyr Leu Asn Phe Arg Glu Ser Gly Gln Val Tyr Phe Gly Ile Ile Ala
                325                 330                 335

Leu Gly Gly Gly Gly Ser Asp Lys Pro Val Ala His Val Val Ala Asn
            340                 345                 350

Pro Gln Ala Glu Gly Gln Leu Gln Trp Leu Asn Arg Arg Ala Asn Ala
        355                 360                 365
```

```
Leu Leu Ala Asn Gly Val Glu Leu Arg Asp Asn Gln Leu Val Val Pro
    370                 375                 380

Ser Glu Gly Leu Tyr Leu Ile Tyr Ser Gln Val Leu Phe Lys Gly Gln
385                 390                 395                 400

Gly Cys Pro Ser Thr His Val Leu Leu Thr His Thr Ile Ser Arg Ile
                405                 410                 415

Ala Val Ser Tyr Gln Thr Lys Val Asn Leu Leu Ser Ala Ile Lys Ser
            420                 425                 430

Pro Cys Gln Arg Glu Thr Pro Glu Gly Ala Glu Ala Lys Pro Trp Tyr
        435                 440                 445

Glu Pro Ile Tyr Leu Gly Gly Val Phe Gln Leu Glu Lys Gly Asp Arg
    450                 455                 460

Leu Ser Ala Glu Ile Asn Arg Pro Asp Tyr Leu Asn Phe Arg Glu Ser
465                 470                 475                 480

Gly Gln Val Tyr Phe Gly Ile Ile Ala Leu
                485                 490


<210> SEQ ID NO 69
<211> LENGTH: 489
<212> TYPE: PRT
<213> ORGANISM: Artificial Sequence
<220> FEATURE:
<223> OTHER INFORMATION: scTNFR2 (138)

<400> SEQUENCE: 69

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Pro Val Ala His Val Val Ala Asn Pro Gln Ala Glu Gly
        35                  40                  45

Gln Leu Gln Trp Leu Asn Arg Arg Ala Asn Ala Leu Leu Ala Asn Gly
    50                  55                  60

Val Glu Leu Arg Asp Asn Gln Leu Val Val Pro Ser Glu Gly Leu Tyr
65                  70                  75                  80

Leu Ile Tyr Ser Gln Val Leu Phe Lys Gly Gln Gly Cys Pro Ser Thr
                85                  90                  95

His Val Leu Leu Thr His Thr Ile Ser Arg Ile Ala Val Ser Tyr Gln
            100                 105                 110

Thr Lys Val Asn Leu Leu Ser Ala Ile Lys Ser Pro Cys Gln Arg Glu
        115                 120                 125

Thr Pro Glu Gly Ala Glu Ala Lys Pro Trp Tyr Glu Pro Ile Tyr Leu
    130                 135                 140

Gly Gly Val Phe Gln Leu Glu Lys Gly Asp Arg Leu Ser Ala Glu Ile
145                 150                 155                 160

Asn Arg Pro Asp Tyr Leu Asn Phe Arg Glu Ser Gly Gln Val Tyr Phe
                165                 170                 175

Gly Ile Ile Ala Leu Gly Gly Gly Ser Gly Gly Gly Ser Pro Val Ala
            180                 185                 190

His Val Val Ala Asn Pro Gln Ala Glu Gly Gln Leu Gln Trp Leu Asn
        195                 200                 205

Arg Arg Ala Asn Ala Leu Leu Ala Asn Gly Val Glu Leu Arg Asp Asn
    210                 215                 220

Gln Leu Val Val Pro Ser Glu Gly Leu Tyr Leu Ile Tyr Ser Gln Val
225                 230                 235                 240
```

```
Leu Phe Lys Gly Gln Gly Cys Pro Ser Thr His Val Leu Leu Thr His
                245                 250                 255

Thr Ile Ser Arg Ile Ala Val Ser Tyr Gln Thr Lys Val Asn Leu Leu
            260                 265                 270

Ser Ala Ile Lys Ser Pro Cys Gln Arg Glu Thr Pro Glu Gly Ala Glu
        275                 280                 285

Ala Lys Pro Trp Tyr Glu Pro Ile Tyr Leu Gly Gly Val Phe Gln Leu
    290                 295                 300

Glu Lys Gly Asp Arg Leu Ser Ala Glu Ile Asn Arg Pro Asp Tyr Leu
305                 310                 315                 320

Asn Phe Arg Glu Ser Gly Gln Val Tyr Phe Gly Ile Ile Ala Leu Gly
                325                 330                 335

Gly Gly Ser Gly Gly Gly Ser Pro Val Ala His Val Val Ala Asn Pro
            340                 345                 350

Gln Ala Glu Gly Gln Leu Gln Trp Leu Asn Arg Arg Ala Asn Ala Leu
        355                 360                 365

Leu Ala Asn Gly Val Glu Leu Arg Asp Asn Gln Leu Val Val Pro Ser
    370                 375                 380

Glu Gly Leu Tyr Leu Ile Tyr Ser Gln Val Leu Phe Lys Gly Gln Gly
385                 390                 395                 400

Cys Pro Ser Thr His Val Leu Leu Thr His Thr Ile Ser Arg Ile Ala
                405                 410                 415

Val Ser Tyr Gln Thr Lys Val Asn Leu Leu Ser Ala Ile Lys Ser Pro
            420                 425                 430

Cys Gln Arg Glu Thr Pro Glu Gly Ala Glu Ala Lys Pro Trp Tyr Glu
        435                 440                 445

Pro Ile Tyr Leu Gly Gly Val Phe Gln Leu Glu Lys Gly Asp Arg Leu
    450                 455                 460

Ser Ala Glu Ile Asn Arg Pro Asp Tyr Leu Asn Phe Arg Glu Ser Gly
465                 470                 475                 480

Gln Val Tyr Phe Gly Ile Ile Ala Leu
                485


<210> SEQ ID NO 70
<211> LENGTH: 491
<212> TYPE: PRT
<213> ORGANISM: Artificial Sequence
<220> FEATURE:
<223> OTHER INFORMATION: scTNFR2 (130)

<400> SEQUENCE: 70

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Arg Thr Pro Ser Asp Lys Pro Val Ala His Val Val Ala
        35                  40                  45

Asn Pro Gln Ala Glu Gly Gln Leu Gln Trp Leu Asn Arg Arg Ala Asn
    50                  55                  60

Ala Leu Leu Ala Asn Gly Val Glu Leu Arg Asp Asn Gln Leu Val Val
65                  70                  75                  80

Pro Ser Glu Gly Leu Tyr Leu Ile Tyr Ser Gln Val Leu Phe Lys Gly
                85                  90                  95

Gln Gly Cys Pro Ser Thr His Val Leu Leu Thr His Thr Ile Ser Arg
            100                 105                 110
```

```
Ile Ala Val Ser Tyr Gln Thr Lys Val Asn Leu Leu Ser Ala Ile Lys
        115                 120                 125

Ser Pro Cys Gln Arg Glu Thr Pro Glu Gly Ala Glu Ala Lys Pro Trp
    130                 135                 140

Tyr Glu Pro Ile Tyr Leu Gly Gly Val Phe Gln Leu Glu Lys Gly Asp
145                 150                 155                 160

Arg Leu Ser Ala Glu Ile Asn Arg Pro Asp Tyr Leu Asn Phe Arg Glu
                165                 170                 175

Ser Gly Gln Val Tyr Phe Gly Ile Ile Ala Leu Arg Thr Pro Ser Asp
            180                 185                 190

Lys Pro Val Ala His Val Val Ala Asn Pro Gln Ala Glu Gly Gln Leu
        195                 200                 205

Gln Trp Leu Asn Arg Arg Ala Asn Ala Leu Leu Ala Asn Gly Val Glu
    210                 215                 220

Leu Arg Asp Asn Gln Leu Val Val Pro Ser Glu Gly Leu Tyr Leu Ile
225                 230                 235                 240

Tyr Ser Gln Val Leu Phe Lys Gly Gln Gly Cys Pro Ser Thr His Val
                245                 250                 255

Leu Leu Thr His Thr Ile Ser Arg Ile Ala Val Ser Tyr Gln Thr Lys
            260                 265                 270

Val Asn Leu Leu Ser Ala Ile Lys Ser Pro Cys Gln Arg Glu Thr Pro
        275                 280                 285

Glu Gly Ala Glu Ala Lys Pro Trp Tyr Glu Pro Ile Tyr Leu Gly Gly
    290                 295                 300

Val Phe Gln Leu Glu Lys Gly Asp Arg Leu Ser Ala Glu Ile Asn Arg
305                 310                 315                 320

Pro Asp Tyr Leu Asn Phe Arg Glu Ser Gly Gln Val Tyr Phe Gly Ile
                325                 330                 335

Ile Ala Leu Arg Thr Pro Ser Asp Lys Pro Val Ala His Val Val Ala
            340                 345                 350

Asn Pro Gln Ala Glu Gly Gln Leu Gln Trp Leu Asn Arg Arg Ala Asn
        355                 360                 365

Ala Leu Leu Ala Asn Gly Val Glu Leu Arg Asp Asn Gln Leu Val Val
    370                 375                 380

Pro Ser Glu Gly Leu Tyr Leu Ile Tyr Ser Gln Val Leu Phe Lys Gly
385                 390                 395                 400

Gln Gly Cys Pro Ser Thr His Val Leu Leu Thr His Thr Ile Ser Arg
                405                 410                 415

Ile Ala Val Ser Tyr Gln Thr Lys Val Asn Leu Leu Ser Ala Ile Lys
            420                 425                 430

Ser Pro Cys Gln Arg Glu Thr Pro Glu Gly Ala Glu Ala Lys Pro Trp
        435                 440                 445

Tyr Glu Pro Ile Tyr Leu Gly Gly Val Phe Gln Leu Glu Lys Gly Asp
    450                 455                 460

Arg Leu Ser Ala Glu Ile Asn Arg Pro Asp Tyr Leu Asn Phe Arg Glu
465                 470                 475                 480

Ser Gly Gln Val Tyr Phe Gly Ile Ile Ala Leu
                485                 490


<210> SEQ ID NO 71
<211> LENGTH: 479
<212> TYPE: PRT
<213> ORGANISM: Artificial Sequence
<220> FEATURE:
<223> OTHER INFORMATION: scTNFR2 (131)
```

<400> SEQUENCE: 71

```
Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Asp Lys Pro Val Ala His Val Val Ala Asn Pro Gln Ala
        35                  40                  45

Glu Gly Gln Leu Gln Trp Leu Asn Arg Arg Ala Asn Ala Leu Leu Ala
    50                  55                  60

Asn Gly Val Glu Leu Arg Asp Asn Gln Leu Val Val Pro Ser Glu Gly
65                  70                  75                  80

Leu Tyr Leu Ile Tyr Ser Gln Val Leu Phe Lys Gly Gln Gly Cys Pro
                85                  90                  95

Ser Thr His Val Leu Leu Thr His Thr Ile Ser Arg Ile Ala Val Ser
            100                 105                 110

Tyr Gln Thr Lys Val Asn Leu Leu Ser Ala Ile Lys Ser Pro Cys Gln
        115                 120                 125

Arg Glu Thr Pro Glu Gly Ala Glu Ala Lys Pro Trp Tyr Glu Pro Ile
    130                 135                 140

Tyr Leu Gly Gly Val Phe Gln Leu Glu Lys Gly Asp Arg Leu Ser Ala
145                 150                 155                 160

Glu Ile Asn Arg Pro Asp Tyr Leu Asn Phe Arg Glu Ser Gly Gln Val
                165                 170                 175

Tyr Phe Gly Ile Ile Ala Leu Asp Lys Pro Val Ala His Val Val Ala
            180                 185                 190

Asn Pro Gln Ala Glu Gly Gln Leu Gln Trp Leu Asn Arg Arg Ala Asn
        195                 200                 205

Ala Leu Leu Ala Asn Gly Val Glu Leu Arg Asp Asn Gln Leu Val Val
    210                 215                 220

Pro Ser Glu Gly Leu Tyr Leu Ile Tyr Ser Gln Val Leu Phe Lys Gly
225                 230                 235                 240

Gln Gly Cys Pro Ser Thr His Val Leu Leu Thr His Thr Ile Ser Arg
                245                 250                 255

Ile Ala Val Ser Tyr Gln Thr Lys Val Asn Leu Leu Ser Ala Ile Lys
            260                 265                 270

Ser Pro Cys Gln Arg Glu Thr Pro Glu Gly Ala Glu Ala Lys Pro Trp
        275                 280                 285

Tyr Glu Pro Ile Tyr Leu Gly Gly Val Phe Gln Leu Glu Lys Gly Asp
    290                 295                 300

Arg Leu Ser Ala Glu Ile Asn Arg Pro Asp Tyr Leu Asn Phe Arg Glu
305                 310                 315                 320

Ser Gly Gln Val Tyr Phe Gly Ile Ile Ala Leu Asp Lys Pro Val Ala
                325                 330                 335

His Val Val Ala Asn Pro Gln Ala Glu Gly Gln Leu Gln Trp Leu Asn
            340                 345                 350

Arg Arg Ala Asn Ala Leu Leu Ala Asn Gly Val Glu Leu Arg Asp Asn
        355                 360                 365

Gln Leu Val Val Pro Ser Glu Gly Leu Tyr Leu Ile Tyr Ser Gln Val
    370                 375                 380

Leu Phe Lys Gly Gln Gly Cys Pro Ser Thr His Val Leu Leu Thr His
385                 390                 395                 400

Thr Ile Ser Arg Ile Ala Val Ser Tyr Gln Thr Lys Val Asn Leu Leu
```

```
                405                 410                 415

Ser Ala Ile Lys Ser Pro Cys Gln Arg Glu Thr Pro Glu Gly Ala Glu
            420                 425                 430

Ala Lys Pro Trp Tyr Glu Pro Ile Tyr Leu Gly Gly Val Phe Gln Leu
        435                 440                 445

Glu Lys Gly Asp Arg Leu Ser Ala Glu Ile Asn Arg Pro Asp Tyr Leu
    450                 455                 460

Asn Phe Arg Glu Ser Gly Gln Val Tyr Phe Gly Ile Ile Ala Leu
465                 470                 475


<210> SEQ ID NO 72
<211> LENGTH: 728
<212> TYPE: PRT
<213> ORGANISM: Artificial Sequence
<220> FEATURE:
<223> OTHER INFORMATION: scTNFR2(118)-Fc(dab) 745

<400> SEQUENCE: 72

Met Glu Thr Asp Thr Leu Leu Leu Trp Val Leu Leu Leu Trp Val Pro
1               5                   10                  15

Gly Ser Thr Gly Ser Ser Arg Thr Pro Ser Asp Lys Pro Val Ala His
            20                  25                  30

Val Val Ala Asn Pro Gln Ala Glu Gly Gln Leu Gln Trp Leu Asn Arg
        35                  40                  45

Arg Ala Asn Ala Leu Leu Ala Asn Gly Val Glu Leu Arg Asp Asn Gln
    50                  55                  60

Leu Val Val Pro Ser Glu Gly Leu Tyr Leu Ile Tyr Ser Gln Val Leu
65                  70                  75                  80

Phe Lys Gly Gln Gly Cys Pro Ser Thr His Val Leu Leu Thr His Thr
                85                  90                  95

Ile Ser Arg Ile Ala Val Ser Tyr Gln Thr Lys Val Asn Leu Leu Ser
            100                 105                 110

Ala Ile Lys Ser Pro Cys Gln Arg Glu Thr Pro Glu Gly Ala Glu Ala
        115                 120                 125

Lys Pro Trp Tyr Glu Pro Ile Tyr Leu Gly Gly Val Phe Gln Leu Glu
    130                 135                 140

Lys Gly Asp Arg Leu Ser Ala Glu Ile Asn Arg Pro Asp Tyr Leu Asn
145                 150                 155                 160

Phe Arg Glu Ser Gly Gln Val Tyr Phe Gly Ile Ile Ala Leu Gly Gly
                165                 170                 175

Gly Gly Ser Ser Ser Arg Thr Pro Ser Asp Lys Pro Val Ala His Val
            180                 185                 190

Val Ala Asn Pro Gln Ala Glu Gly Gln Leu Gln Trp Leu Asn Arg Arg
        195                 200                 205

Ala Asn Ala Leu Leu Ala Asn Gly Val Glu Leu Arg Asp Asn Gln Leu
    210                 215                 220

Val Val Pro Ser Glu Gly Leu Tyr Leu Ile Tyr Ser Gln Val Leu Phe
225                 230                 235                 240

Lys Gly Gln Gly Cys Pro Ser Thr His Val Leu Leu Thr His Thr Ile
                245                 250                 255

Ser Arg Ile Ala Val Ser Tyr Gln Thr Lys Val Asn Leu Leu Ser Ala
            260                 265                 270

Ile Lys Ser Pro Cys Gln Arg Glu Thr Pro Glu Gly Ala Glu Ala Lys
        275                 280                 285

Pro Trp Tyr Glu Pro Ile Tyr Leu Gly Gly Val Phe Gln Leu Glu Lys
```

```
    290                 295                 300

Gly Asp Arg Leu Ser Ala Glu Ile Asn Arg Pro Asp Tyr Leu Asn Phe
305                 310                 315                 320

Arg Glu Ser Gly Gln Val Tyr Phe Gly Ile Ile Ala Leu Gly Gly Gly
                325                 330                 335

Gly Ser Ser Ser Arg Thr Pro Ser Asp Lys Pro Val Ala His Val Val
            340                 345                 350

Ala Asn Pro Gln Ala Glu Gly Gln Leu Gln Trp Leu Asn Arg Arg Ala
        355                 360                 365

Asn Ala Leu Leu Ala Asn Gly Val Glu Leu Arg Asp Asn Gln Leu Val
    370                 375                 380

Val Pro Ser Glu Gly Leu Tyr Leu Ile Tyr Ser Gln Val Leu Phe Lys
385                 390                 395                 400

Gly Gln Gly Cys Pro Ser Thr His Val Leu Leu Thr His Thr Ile Ser
                405                 410                 415

Arg Ile Ala Val Ser Tyr Gln Thr Lys Val Asn Leu Leu Ser Ala Ile
            420                 425                 430

Lys Ser Pro Cys Gln Arg Glu Thr Pro Glu Gly Ala Glu Ala Lys Pro
        435                 440                 445

Trp Tyr Glu Pro Ile Tyr Leu Gly Gly Val Phe Gln Leu Glu Lys Gly
    450                 455                 460

Asp Arg Leu Ser Ala Glu Ile Asn Arg Pro Asp Tyr Leu Asn Phe Arg
465                 470                 475                 480

Glu Ser Gly Gln Val Tyr Phe Gly Ile Ile Ala Leu Gly Gly Ser Gly
                485                 490                 495

Gly Gly Gly Ser Gly Gly Asp Lys Thr His Thr Cys Pro Pro Cys Pro
            500                 505                 510

Ala Pro Pro Val Ala Gly Pro Ser Val Phe Leu Phe Pro Pro Lys Pro
        515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Gly
        595                 600                 605

Leu Pro Ser Ser Ile Glu Lys Thr Ile Ser Lys Ala Lys Gly Gln Pro
    610                 615                 620

Arg Glu Pro Gln Val Tyr Thr Leu Pro Pro Ser Arg Asp Glu Leu Thr
625                 630                 635                 640

Lys Asn Gln Val Ser Leu Thr Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
        675                 680                 685

Ser Lys Leu Thr Val Asp Lys Ser Arg Trp Gln Gln Gly Asn Val Phe
    690                 695                 700

Ser Cys Ser Val Met His Glu Ala Leu His Asn His Tyr Thr Gln Lys
705                 710                 715                 720
```

```
Ser Leu Ser Leu Ser Pro Gly Lys
                725


<210> SEQ ID NO 73
<211> LENGTH: 718
<212> TYPE: PRT
<213> ORGANISM: Artificial Sequence
<220> FEATURE:
<223> OTHER INFORMATION: scTNFR2(127)-Fc(dab) 742

<400> SEQUENCE: 73

Met Glu Thr Asp Thr Leu Leu Leu Trp Val Leu Leu Leu Trp Val Pro
1               5                   10                  15

Gly Ser Thr Gly Ser Ser Arg Thr Pro Ser Asp Lys Pro Val Ala His
            20                  25                  30

Val Val Ala Asn Pro Gln Ala Glu Gly Gln Leu Gln Trp Leu Asn Arg
        35                  40                  45

Arg Ala Asn Ala Leu Leu Ala Asn Gly Val Glu Leu Arg Asp Asn Gln
    50                  55                  60

Leu Val Val Pro Ser Glu Gly Leu Tyr Leu Ile Tyr Ser Gln Val Leu
65                  70                  75                  80

Phe Lys Gly Gln Gly Cys Pro Ser Thr His Val Leu Leu Thr His Thr
                85                  90                  95

Ile Ser Arg Ile Ala Val Ser Tyr Gln Thr Lys Val Asn Leu Leu Ser
            100                 105                 110

Ala Ile Lys Ser Pro Cys Gln Arg Glu Thr Pro Glu Gly Ala Glu Ala
        115                 120                 125

Lys Pro Trp Tyr Glu Pro Ile Tyr Leu Gly Gly Val Phe Gln Leu Glu
    130                 135                 140

Lys Gly Asp Arg Leu Ser Ala Glu Ile Asn Arg Pro Asp Tyr Leu Asn
145                 150                 155                 160

Phe Arg Glu Ser Gly Gln Val Tyr Phe Gly Ile Ile Ala Leu Ser Ser
                165                 170                 175

Arg Thr Pro Ser Asp Lys Pro Val Ala His Val Val Ala Asn Pro Gln
            180                 185                 190

Ala Glu Gly Gln Leu Gln Trp Leu Asn Arg Arg Ala Asn Ala Leu Leu
        195                 200                 205

Ala Asn Gly Val Glu Leu Arg Asp Asn Gln Leu Val Val Pro Ser Glu
    210                 215                 220

Gly Leu Tyr Leu Ile Tyr Ser Gln Val Leu Phe Lys Gly Gln Gly Cys
225                 230                 235                 240

Pro Ser Thr His Val Leu Leu Thr His Thr Ile Ser Arg Ile Ala Val
                245                 250                 255

Ser Tyr Gln Thr Lys Val Asn Leu Leu Ser Ala Ile Lys Ser Pro Cys
            260                 265                 270

Gln Arg Glu Thr Pro Glu Gly Ala Glu Ala Lys Pro Trp Tyr Glu Pro
        275                 280                 285

Ile Tyr Leu Gly Gly Val Phe Gln Leu Glu Lys Gly Asp Arg Leu Ser
    290                 295                 300

Ala Glu Ile Asn Arg Pro Asp Tyr Leu Asn Phe Arg Glu Ser Gly Gln
305                 310                 315                 320

Val Tyr Phe Gly Ile Ile Ala Leu Ser Ser Arg Thr Pro Ser Asp Lys
                325                 330                 335

Pro Val Ala His Val Val Ala Asn Pro Gln Ala Glu Gly Gln Leu Gln
            340                 345                 350
```

```
Trp Leu Asn Arg Arg Ala Asn Ala Leu Leu Ala Asn Gly Val Glu Leu
        355                 360                 365

Arg Asp Asn Gln Leu Val Val Pro Ser Glu Gly Leu Tyr Leu Ile Tyr
    370                 375                 380

Ser Gln Val Leu Phe Lys Gly Gln Gly Cys Pro Ser Thr His Val Leu
385                 390                 395                 400

Leu Thr His Thr Ile Ser Arg Ile Ala Val Ser Tyr Gln Thr Lys Val
                405                 410                 415

Asn Leu Leu Ser Ala Ile Lys Ser Pro Cys Gln Arg Glu Thr Pro Glu
            420                 425                 430

Gly Ala Glu Ala Lys Pro Trp Tyr Glu Pro Ile Tyr Leu Gly Gly Val
        435                 440                 445

Phe Gln Leu Glu Lys Gly Asp Arg Leu Ser Ala Glu Ile Asn Arg Pro
    450                 455                 460

Asp Tyr Leu Asn Phe Arg Glu Ser Gly Gln Val Tyr Phe Gly Ile Ile
465                 470                 475                 480

Ala Leu Gly Gly Ser Gly Gly Gly Gly Ser Gly Gly Asp Lys Thr His
                485                 490                 495

Thr Cys Pro Pro Cys Pro Ala Pro Pro Val Ala Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Gly Leu Pro Ser Ser Ile Glu Lys Thr Ile Ser
        595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly Lys
705                 710                 715
```

<210> SEQ ID NO 74
<211> LENGTH: 706
<212> TYPE: PRT
<213> ORGANISM: Artificial Sequence
<220> FEATURE:
<223> OTHER INFORMATION: scTNFR2(129)-Fc(dab) 743

<400> SEQUENCE: 74

```
Met Glu Thr Asp Thr Leu Leu Leu Trp Val Leu Leu Leu Trp Val Pro
1               5                   10                  15

Gly Ser Thr Gly Pro Ser Asp Lys Pro Val Ala His Val Val Ala Asn
            20                  25                  30

Pro Gln Ala Glu Gly Gln Leu Gln Trp Leu Asn Arg Arg Ala Asn Ala
        35                  40                  45

Leu Leu Ala Asn Gly Val Glu Leu Arg Asp Asn Gln Leu Val Val Pro
    50                  55                  60

Ser Glu Gly Leu Tyr Leu Ile Tyr Ser Gln Val Leu Phe Lys Gly Gln
65                  70                  75                  80

Gly Cys Pro Ser Thr His Val Leu Leu Thr His Thr Ile Ser Arg Ile
                85                  90                  95

Ala Val Ser Tyr Gln Thr Lys Val Asn Leu Leu Ser Ala Ile Lys Ser
            100                 105                 110

Pro Cys Gln Arg Glu Thr Pro Glu Gly Ala Glu Ala Lys Pro Trp Tyr
        115                 120                 125

Glu Pro Ile Tyr Leu Gly Gly Val Phe Gln Leu Glu Lys Gly Asp Arg
    130                 135                 140

Leu Ser Ala Glu Ile Asn Arg Pro Asp Tyr Leu Asn Phe Arg Glu Ser
145                 150                 155                 160

Gly Gln Val Tyr Phe Gly Ile Ile Ala Leu Pro Ser Asp Lys Pro Val
                165                 170                 175

Ala His Val Val Ala Asn Pro Gln Ala Glu Gly Gln Leu Gln Trp Leu
            180                 185                 190

Asn Arg Arg Ala Asn Ala Leu Leu Ala Asn Gly Val Glu Leu Arg Asp
        195                 200                 205

Asn Gln Leu Val Val Pro Ser Glu Gly Leu Tyr Leu Ile Tyr Ser Gln
    210                 215                 220

Val Leu Phe Lys Gly Gln Gly Cys Pro Ser Thr His Val Leu Leu Thr
225                 230                 235                 240

His Thr Ile Ser Arg Ile Ala Val Ser Tyr Gln Thr Lys Val Asn Leu
                245                 250                 255

Leu Ser Ala Ile Lys Ser Pro Cys Gln Arg Glu Thr Pro Glu Gly Ala
            260                 265                 270

Glu Ala Lys Pro Trp Tyr Glu Pro Ile Tyr Leu Gly Gly Val Phe Gln
        275                 280                 285

Leu Glu Lys Gly Asp Arg Leu Ser Ala Glu Ile Asn Arg Pro Asp Tyr
    290                 295                 300

Leu Asn Phe Arg Glu Ser Gly Gln Val Tyr Phe Gly Ile Ile Ala Leu
305                 310                 315                 320

Pro Ser Asp Lys Pro Val Ala His Val Val Ala Asn Pro Gln Ala Glu
                325                 330                 335

Gly Gln Leu Gln Trp Leu Asn Arg Arg Ala Asn Ala Leu Leu Ala Asn
            340                 345                 350

Gly Val Glu Leu Arg Asp Asn Gln Leu Val Val Pro Ser Glu Gly Leu
        355                 360                 365

Tyr Leu Ile Tyr Ser Gln Val Leu Phe Lys Gly Gln Gly Cys Pro Ser
    370                 375                 380

Thr His Val Leu Leu Thr His Thr Ile Ser Arg Ile Ala Val Ser Tyr
385                 390                 395                 400

Gln Thr Lys Val Asn Leu Leu Ser Ala Ile Lys Ser Pro Cys Gln Arg
                405                 410                 415
```

```
Glu Thr Pro Glu Gly Ala Glu Ala Lys Pro Trp Tyr Glu Pro Ile Tyr
            420                 425                 430

Leu Gly Gly Val Phe Gln Leu Glu Lys Gly Asp Arg Leu Ser Ala Glu
        435                 440                 445

Ile Asn Arg Pro Asp Tyr Leu Asn Phe Arg Glu Ser Gly Gln Val Tyr
    450                 455                 460

Phe Gly Ile Ile Ala Leu Gly Gly Ser Gly Gly Gly Gly Ser Gly Gly
465                 470                 475                 480

Asp Lys Thr His Thr Cys Pro Pro Cys Pro Ala Pro Pro Val Ala Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Gly Leu Pro Ser Ser Ile Glu
            580                 585                 590

Lys Thr Ile Ser Lys Ala Lys Gly Gln Pro Arg Glu Pro Gln Val Tyr
        595                 600                 605

Thr Leu Pro Pro Ser Arg Asp Glu Leu Thr Lys Asn Gln Val Ser Leu
    610                 615                 620

Thr Cys Leu Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
    690                 695                 700

Gly Lys
705


<210> SEQ ID NO 75
<211> LENGTH: 711
<212> TYPE: PRT
<213> ORGANISM: Artificial Sequence
<220> FEATURE:
<223> OTHER INFORMATION: scTNFR2(139)-Fc(dab) 744

<400> SEQUENCE: 75

Met Glu Thr Asp Thr Leu Leu Leu Trp Val Leu Leu Leu Trp Val Pro
1               5                   10                  15

Gly Ser Thr Gly Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60
```

```
Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140

Ser Ala Glu Ile Asn Arg Pro Asp Tyr Leu Asn Phe Arg Glu Ser Gly
145                 150                 155                 160

Gln Val Tyr Phe Gly Ile Ile Ala Leu Gly Gly Gly Gly Ser Asp Lys
                165                 170                 175

Pro Val Ala His Val Val Ala Asn Pro Gln Ala Glu Gly Gln Leu Gln
            180                 185                 190

Trp Leu Asn Arg Arg Ala Asn Ala Leu Leu Ala Asn Gly Val Glu Leu
        195                 200                 205

Arg Asp Asn Gln Leu Val Val Pro Ser Glu Gly Leu Tyr Leu Ile Tyr
    210                 215                 220

Ser Gln Val Leu Phe Lys Gly Gln Gly Cys Pro Ser Thr His Val Leu
225                 230                 235                 240

Leu Thr His Thr Ile Ser Arg Ile Ala Val Ser Tyr Gln Thr Lys Val
                245                 250                 255

Asn Leu Leu Ser Ala Ile Lys Ser Pro Cys Gln Arg Glu Thr Pro Glu
            260                 265                 270

Gly Ala Glu Ala Lys Pro Trp Tyr Glu Pro Ile Tyr Leu Gly Gly Val
        275                 280                 285

Phe Gln Leu Glu Lys Gly Asp Arg Leu Ser Ala Glu Ile Asn Arg Pro
    290                 295                 300

Asp Tyr Leu Asn Phe Arg Glu Ser Gly Gln Val Tyr Phe Gly Ile Ile
305                 310                 315                 320

Ala Leu Gly Gly Gly Gly Ser Asp Lys Pro Val Ala His Val Val Ala
                325                 330                 335

Asn Pro Gln Ala Glu Gly Gln Leu Gln Trp Leu Asn Arg Arg Ala Asn
            340                 345                 350

Ala Leu Leu Ala Asn Gly Val Glu Leu Arg Asp Asn Gln Leu Val Val
        355                 360                 365

Pro Ser Glu Gly Leu Tyr Leu Ile Tyr Ser Gln Val Leu Phe Lys Gly
    370                 375                 380

Gln Gly Cys Pro Ser Thr His Val Leu Leu Thr His Thr Ile Ser Arg
385                 390                 395                 400

Ile Ala Val Ser Tyr Gln Thr Lys Val Asn Leu Leu Ser Ala Ile Lys
                405                 410                 415

Ser Pro Cys Gln Arg Glu Thr Pro Glu Gly Ala Glu Ala Lys Pro Trp
            420                 425                 430

Tyr Glu Pro Ile Tyr Leu Gly Gly Val Phe Gln Leu Glu Lys Gly Asp
        435                 440                 445

Arg Leu Ser Ala Glu Ile Asn Arg Pro Asp Tyr Leu Asn Phe Arg Glu
    450                 455                 460

Ser Gly Gln Val Tyr Phe Gly Ile Ile Ala Leu Gly Gly Ser Gly Gly
465                 470                 475                 480

Gly Gly Ser Gly Gly Asp Lys Thr His Thr Cys Pro Pro Cys Pro Ala
```

485 490 495

Pro Pro Val Ala Gly Pro Ser Val Phe Leu Phe Pro Pro Lys Pro Lys
500 505 510

Asp Thr Leu Met Ile Ser Arg Thr Pro Glu Val Thr Cys Val Val Val
515 520 525

Asp Val Ser His Glu Asp Pro Glu Val Lys Phe Asn Trp Tyr Val Asp
530 535 540

Gly Val Glu Val His Asn Ala Lys Thr Lys Pro Arg Glu Glu Gln Tyr
545 550 555 560

Asn Ser Thr Tyr Arg Val Val Ser Val Leu Thr Val Leu His Gln Asp
565 570 575

Trp Leu Asn Gly Lys Glu Tyr Lys Cys Lys Val Ser Asn Lys Gly Leu
580 585 590

Pro Ser Ser Ile Glu Lys Thr Ile Ser Lys Ala Lys Gly Gln Pro Arg
595 600 605

Glu Pro Gln Val Tyr Thr Leu Pro Pro Ser Arg Asp Glu Leu Thr Lys
610 615 620

Asn Gln Val Ser Leu Thr Cys Leu Val Lys Gly Phe Tyr Pro Ser Asp
625 630 635 640

Ile Ala Val Glu Trp Glu Ser Asn Gly Gln Pro Glu Asn Asn Tyr Lys
645 650 655

Thr Thr Pro Pro Val Leu Asp Ser Asp Gly Ser Phe Phe Leu Tyr Ser
660 665 670

Lys Leu Thr Val Asp Lys Ser Arg Trp Gln Gln Gly Asn Val Phe Ser
675 680 685

Cys Ser Val Met His Glu Ala Leu His Asn His Tyr Thr Gln Lys Ser
690 695 700

Leu Ser Leu Ser Pro Gly Lys
705 710

<210> SEQ ID NO 76
<211> LENGTH: 495
<212> TYPE: PRT
<213> ORGANISM: Artificial Sequence
<220> FEATURE:
<223> OTHER INFORMATION: variant 140

<400> SEQUENCE: 76

Met Glu Thr Asp Thr Leu Leu Leu Trp Val Leu Leu Leu Trp Val Pro
1 5 10 15

Gly Ser Thr Gly Met Cys Gly Ser His His His His His His Ser Gly
20 25 30

Ile Pro Ala Ser Ser Arg Thr Pro Ser Asp Lys Pro Val Ala His Val
35 40 45

Val Ala Asn Pro Gln Ala Glu Gly Gln Leu Gln Trp Leu Asn Arg Arg
50 55 60

Ala Asn Ala Leu Leu Ala Asn Gly Val Glu Leu Arg Asp Asn Gln Leu
65 70 75 80

Val Val Pro Ser Glu Gly Leu Tyr Leu Ile Tyr Ser Gln Val Leu Phe
85 90 95

Lys Gly Gln Gly Cys Pro Ser Thr His Val Leu Leu Thr His Thr Ile
100 105 110

Ser Arg Ile Ala Val Ser Tyr Gln Thr Lys Val Asn Leu Leu Ser Ala
115 120 125

Ile Lys Ser Pro Cys Gln Arg Glu Thr Pro Glu Gly Ala Glu Ala Lys

```
    130                 135                 140

Pro Trp Tyr Glu Pro Ile Tyr Leu Gly Gly Val Phe Gln Leu Glu Lys
145                 150                 155                 160

Gly Asp Arg Leu Ser Ala Glu Ile Asn Arg Pro Asp Tyr Leu Asn Phe
                165                 170                 175

Arg Glu Ser Gly Gln Val Tyr Phe Gly Ile Ile Ala Leu Ser Arg Thr
            180                 185                 190

Pro Ser Asp Lys Pro Val Ala His Val Val Ala Asn Pro Gln Ala Glu
        195                 200                 205

Gly Gln Leu Gln Trp Leu Asn Arg Arg Ala Asn Ala Leu Leu Ala Asn
    210                 215                 220

Gly Val Glu Leu Arg Asp Asn Gln Leu Val Val Pro Ser Glu Gly Leu
225                 230                 235                 240

Tyr Leu Ile Tyr Ser Gln Val Leu Phe Lys Gly Gln Gly Cys Pro Ser
                245                 250                 255

Thr His Val Leu Leu Thr His Thr Ile Ser Arg Ile Ala Val Ser Tyr
            260                 265                 270

Gln Thr Lys Val Asn Leu Leu Ser Ala Ile Lys Ser Pro Cys Gln Arg
        275                 280                 285

Glu Thr Pro Glu Gly Ala Glu Ala Lys Pro Trp Tyr Glu Pro Ile Tyr
    290                 295                 300

Leu Gly Gly Val Phe Gln Leu Glu Lys Gly Asp Arg Leu Ser Ala Glu
305                 310                 315                 320

Ile Asn Arg Pro Asp Tyr Leu Asn Phe Arg Glu Ser Gly Gln Val Tyr
                325                 330                 335

Phe Gly Ile Ile Ala Leu Ser Arg Thr Pro Ser Asp Lys Pro Val Ala
            340                 345                 350

His Val Val Ala Asn Pro Gln Ala Glu Gly Gln Leu Gln Trp Leu Asn
        355                 360                 365

Arg Arg Ala Asn Ala Leu Leu Ala Asn Gly Val Glu Leu Arg Asp Asn
    370                 375                 380

Gln Leu Val Val Pro Ser Glu Gly Leu Tyr Leu Ile Tyr Ser Gln Val
385                 390                 395                 400

Leu Phe Lys Gly Gln Gly Cys Pro Ser Thr His Val Leu Leu Thr His
                405                 410                 415

Thr Ile Ser Arg Ile Ala Val Ser Tyr Gln Thr Lys Val Asn Leu Leu
            420                 425                 430

Ser Ala Ile Lys Ser Pro Cys Gln Arg Glu Thr Pro Glu Gly Ala Glu
        435                 440                 445

Ala Lys Pro Trp Tyr Glu Pro Ile Tyr Leu Gly Gly Val Phe Gln Leu
    450                 455                 460

Glu Lys Gly Asp Arg Leu Ser Ala Glu Ile Asn Arg Pro Asp Tyr Leu
465                 470                 475                 480

Asn Phe Arg Glu Ser Gly Gln Val Tyr Phe Gly Ile Ile Ala Leu
                485                 490                 495
```

<210> SEQ ID NO 77
<211> LENGTH: 497
<212> TYPE: PRT
<213> ORGANISM: Artificial Sequence
<220> FEATURE:
<223> OTHER INFORMATION: variant 141

<400> SEQUENCE: 77

```
Met Glu Thr Asp Thr Leu Leu Leu Trp Val Leu Leu Leu Trp Val Pro
```

```
1               5                   10                  15

Gly Ser Thr Gly Met Cys Gly Ser His His His His His His Ser Gly
            20                  25                  30

Ile Pro Ala Ser Ser Arg Thr Pro Ser Asp Lys Pro Val Ala His Val
        35                  40                  45

Val Ala Asn Pro Gln Ala Glu Gly Gln Leu Gln Trp Leu Asn Arg Arg
    50                  55                  60

Ala Asn Ala Leu Leu Ala Asn Gly Val Glu Leu Arg Asp Asn Gln Leu
65                  70                  75                  80

Val Val Pro Ser Glu Gly Leu Tyr Leu Ile Tyr Ser Gln Val Leu Phe
                85                  90                  95

Lys Gly Gln Gly Cys Pro Ser Thr His Val Leu Leu Thr His Thr Ile
            100                 105                 110

Ser Arg Ile Ala Val Ser Tyr Gln Thr Lys Val Asn Leu Leu Ser Ala
        115                 120                 125

Ile Lys Ser Pro Cys Gln Arg Glu Thr Pro Glu Gly Ala Glu Ala Lys
    130                 135                 140

Pro Trp Tyr Glu Pro Ile Tyr Leu Gly Gly Val Phe Gln Leu Glu Lys
145                 150                 155                 160

Gly Asp Arg Leu Ser Ala Glu Ile Asn Arg Pro Asp Tyr Leu Asn Phe
                165                 170                 175

Arg Glu Ser Gly Gln Val Tyr Phe Gly Ile Ile Ala Leu Gly Ser Arg
            180                 185                 190

Thr Pro Ser Asp Lys Pro Val Ala His Val Val Ala Asn Pro Gln Ala
        195                 200                 205

Glu Gly Gln Leu Gln Trp Leu Asn Arg Arg Ala Asn Ala Leu Leu Ala
    210                 215                 220

Asn Gly Val Glu Leu Arg Asp Asn Gln Leu Val Val Pro Ser Glu Gly
225                 230                 235                 240

Leu Tyr Leu Ile Tyr Ser Gln Val Leu Phe Lys Gly Gln Gly Cys Pro
                245                 250                 255

Ser Thr His Val Leu Leu Thr His Thr Ile Ser Arg Ile Ala Val Ser
            260                 265                 270

Tyr Gln Thr Lys Val Asn Leu Leu Ser Ala Ile Lys Ser Pro Cys Gln
        275                 280                 285

Arg Glu Thr Pro Glu Gly Ala Glu Ala Lys Pro Trp Tyr Glu Pro Ile
    290                 295                 300

Tyr Leu Gly Gly Val Phe Gln Leu Glu Lys Gly Asp Arg Leu Ser Ala
305                 310                 315                 320

Glu Ile Asn Arg Pro Asp Tyr Leu Asn Phe Arg Glu Ser Gly Gln Val
                325                 330                 335

Tyr Phe Gly Ile Ile Ala Leu Gly Ser Arg Thr Pro Ser Asp Lys Pro
            340                 345                 350

Val Ala His Val Val Ala Asn Pro Gln Ala Glu Gly Gln Leu Gln Trp
        355                 360                 365

Leu Asn Arg Arg Ala Asn Ala Leu Leu Ala Asn Gly Val Glu Leu Arg
    370                 375                 380

Asp Asn Gln Leu Val Val Pro Ser Glu Gly Leu Tyr Leu Ile Tyr Ser
385                 390                 395                 400

Gln Val Leu Phe Lys Gly Gln Gly Cys Pro Ser Thr His Val Leu Leu
                405                 410                 415

Thr His Thr Ile Ser Arg Ile Ala Val Ser Tyr Gln Thr Lys Val Asn
            420                 425                 430
```

```
Leu Leu Ser Ala Ile Lys Ser Pro Cys Gln Arg Glu Thr Pro Glu Gly
        435                 440                 445

Ala Glu Ala Lys Pro Trp Tyr Glu Pro Ile Tyr Leu Gly Gly Val Phe
    450                 455                 460

Gln Leu Glu Lys Gly Asp Arg Leu Ser Ala Glu Ile Asn Arg Pro Asp
465                 470                 475                 480

Tyr Leu Asn Phe Arg Glu Ser Gly Gln Val Tyr Phe Gly Ile Ile Ala
                485                 490                 495

Leu


<210> SEQ ID NO 78
<211> LENGTH: 495
<212> TYPE: PRT
<213> ORGANISM: Artificial Sequence
<220> FEATURE:
<223> OTHER INFORMATION: variant 142

<400> SEQUENCE: 78

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Ser Ser Arg Thr Pro Ser Asp Lys Pro Val Ala His Val
        35                  40                  45

Val Ala Asn Pro Gln Ala Glu Gly Gln Leu Gln Trp Leu Asn Arg Arg
    50                  55                  60

Ala Asn Ala Leu Leu Ala Asn Gly Val Glu Leu Arg Asp Asn Gln Leu
65                  70                  75                  80

Val Val Pro Ser Glu Gly Leu Tyr Leu Ile Tyr Ser Gln Val Leu Phe
                85                  90                  95

Lys Gly Gln Gly Cys Pro Ser Thr His Val Leu Leu Thr His Thr Ile
            100                 105                 110

Ser Arg Ile Ala Val Ser Tyr Gln Thr Lys Val Asn Leu Leu Ser Ala
        115                 120                 125

Ile Lys Ser Pro Cys Gln Arg Glu Thr Pro Glu Gly Ala Glu Ala Lys
    130                 135                 140

Pro Trp Tyr Glu Pro Ile Tyr Leu Gly Gly Val Phe Gln Leu Glu Lys
145                 150                 155                 160

Gly Asp Arg Leu Ser Ala Glu Ile Asn Arg Pro Asp Tyr Leu Asn Phe
                165                 170                 175

Arg Glu Ser Gly Gln Val Tyr Phe Gly Ile Ile Ala Leu Gly Arg Thr
            180                 185                 190

Pro Ser Asp Lys Pro Val Ala His Val Val Ala Asn Pro Gln Ala Glu
        195                 200                 205

Gly Gln Leu Gln Trp Leu Asn Arg Arg Ala Asn Ala Leu Leu Ala Asn
    210                 215                 220

Gly Val Glu Leu Arg Asp Asn Gln Leu Val Val Pro Ser Glu Gly Leu
225                 230                 235                 240

Tyr Leu Ile Tyr Ser Gln Val Leu Phe Lys Gly Gln Gly Cys Pro Ser
                245                 250                 255

Thr His Val Leu Leu Thr His Thr Ile Ser Arg Ile Ala Val Ser Tyr
            260                 265                 270

Gln Thr Lys Val Asn Leu Leu Ser Ala Ile Lys Ser Pro Cys Gln Arg
        275                 280                 285
```

```
Glu Thr Pro Glu Gly Ala Glu Ala Lys Pro Trp Tyr Glu Pro Ile Tyr
    290                 295                 300

Leu Gly Gly Val Phe Gln Leu Glu Lys Gly Asp Arg Leu Ser Ala Glu
305                 310                 315                 320

Ile Asn Arg Pro Asp Tyr Leu Asn Phe Arg Glu Ser Gly Gln Val Tyr
                325                 330                 335

Phe Gly Ile Ile Ala Leu Gly Arg Thr Pro Ser Asp Lys Pro Val Ala
            340                 345                 350

His Val Val Ala Asn Pro Gln Ala Glu Gly Gln Leu Gln Trp Leu Asn
        355                 360                 365

Arg Arg Ala Asn Ala Leu Leu Ala Asn Gly Val Glu Leu Arg Asp Asn
    370                 375                 380

Gln Leu Val Val Pro Ser Glu Gly Leu Tyr Leu Ile Tyr Ser Gln Val
385                 390                 395                 400

Leu Phe Lys Gly Gln Gly Cys Pro Ser Thr His Val Leu Leu Thr His
                405                 410                 415

Thr Ile Ser Arg Ile Ala Val Ser Tyr Gln Thr Lys Val Asn Leu Leu
            420                 425                 430

Ser Ala Ile Lys Ser Pro Cys Gln Arg Glu Thr Pro Glu Gly Ala Glu
        435                 440                 445

Ala Lys Pro Trp Tyr Glu Pro Ile Tyr Leu Gly Gly Val Phe Gln Leu
    450                 455                 460

Glu Lys Gly Asp Arg Leu Ser Ala Glu Ile Asn Arg Pro Asp Tyr Leu
465                 470                 475                 480

Asn Phe Arg Glu Ser Gly Gln Val Tyr Phe Gly Ile Ile Ala Leu
                485                 490                 495


<210> SEQ ID NO 79
<211> LENGTH: 490
<212> TYPE: PRT
<213> ORGANISM: Artificial Sequence
<220> FEATURE:
<223> OTHER INFORMATION: variant 143

<400> SEQUENCE: 79

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Ser Asp Lys Pro Val Ala His Val Val Ala Asn Pro Gln
        35                  40                  45

Ala Glu Gly Gln Leu Gln Trp Leu Asn Arg Arg Ala Asn Ala Leu Leu
    50                  55                  60

Ala Asn Gly Val Glu Leu Arg Asp Asn Gln Leu Val Val Pro Ser Glu
65                  70                  75                  80

Gly Leu Tyr Leu Ile Tyr Ser Gln Val Leu Phe Lys Gly Gln Gly Cys
                85                  90                  95

Pro Ser Thr His Val Leu Leu Thr His Thr Ile Ser Arg Ile Ala Val
            100                 105                 110

Ser Tyr Gln Thr Lys Val Asn Leu Leu Ser Ala Ile Lys Ser Pro Cys
        115                 120                 125

Gln Arg Glu Thr Pro Glu Gly Ala Glu Ala Lys Pro Trp Tyr Glu Pro
    130                 135                 140

Ile Tyr Leu Gly Gly Val Phe Gln Leu Glu Lys Gly Asp Arg Leu Ser
145                 150                 155                 160
```

```
Ala Glu Ile Asn Arg Pro Asp Tyr Leu Asn Phe Arg Glu Ser Gly Gln
                165                 170                 175

Val Tyr Phe Gly Ile Ile Ala Leu Gly Gly Gly Pro Ser Asp Lys Pro
            180                 185                 190

Val Ala His Val Val Ala Asn Pro Gln Ala Glu Gly Gln Leu Gln Trp
        195                 200                 205

Leu Asn Arg Arg Ala Asn Ala Leu Leu Ala Asn Gly Val Glu Leu Arg
    210                 215                 220

Asp Asn Gln Leu Val Val Pro Ser Glu Gly Leu Tyr Leu Ile Tyr Ser
225                 230                 235                 240

Gln Val Leu Phe Lys Gly Gln Gly Cys Pro Ser Thr His Val Leu Leu
                245                 250                 255

Thr His Thr Ile Ser Arg Ile Ala Val Ser Tyr Gln Thr Lys Val Asn
            260                 265                 270

Leu Leu Ser Ala Ile Lys Ser Pro Cys Gln Arg Glu Thr Pro Glu Gly
        275                 280                 285

Ala Glu Ala Lys Pro Trp Tyr Glu Pro Ile Tyr Leu Gly Gly Val Phe
    290                 295                 300

Gln Leu Glu Lys Gly Asp Arg Leu Ser Ala Glu Ile Asn Arg Pro Asp
305                 310                 315                 320

Tyr Leu Asn Phe Arg Glu Ser Gly Gln Val Tyr Phe Gly Ile Ile Ala
                325                 330                 335

Leu Gly Gly Gly Pro Ser Asp Lys Pro Val Ala His Val Val Ala Asn
            340                 345                 350

Pro Gln Ala Glu Gly Gln Leu Gln Trp Leu Asn Arg Arg Ala Asn Ala
        355                 360                 365

Leu Leu Ala Asn Gly Val Glu Leu Arg Asp Asn Gln Leu Val Val Pro
    370                 375                 380

Ser Glu Gly Leu Tyr Leu Ile Tyr Ser Gln Val Leu Phe Lys Gly Gln
385                 390                 395                 400

Gly Cys Pro Ser Thr His Val Leu Leu Thr His Thr Ile Ser Arg Ile
                405                 410                 415

Ala Val Ser Tyr Gln Thr Lys Val Asn Leu Leu Ser Ala Ile Lys Ser
            420                 425                 430

Pro Cys Gln Arg Glu Thr Pro Glu Gly Ala Glu Ala Lys Pro Trp Tyr
        435                 440                 445

Glu Pro Ile Tyr Leu Gly Gly Val Phe Gln Leu Glu Lys Gly Asp Arg
    450                 455                 460

Leu Ser Ala Glu Ile Asn Arg Pro Asp Tyr Leu Asn Phe Arg Glu Ser
465                 470                 475                 480

Gly Gln Val Tyr Phe Gly Ile Ile Ala Leu
                485                 490


<210> SEQ ID NO 80
<211> LENGTH: 497
<212> TYPE: PRT
<213> ORGANISM: Artificial Sequence
<220> FEATURE:
<223> OTHER INFORMATION: variant 144

<400> SEQUENCE: 80

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30
```

```
Ile Pro Ala Ser Ser Arg Thr Pro Ser Asp Lys Pro Val Ala His Val
        35                  40                  45

Val Ala Asn Pro Gln Ala Glu Gly Gln Leu Gln Trp Leu Asn Arg Arg
    50                  55                  60

Ala Asn Ala Leu Leu Ala Asn Gly Val Glu Leu Arg Asp Asn Gln Leu
65                  70                  75                  80

Val Val Pro Ser Glu Gly Leu Tyr Leu Ile Tyr Ser Gln Val Leu Phe
                85                  90                  95

Lys Gly Gln Gly Cys Pro Ser Thr His Val Leu Leu Thr His Thr Ile
            100                 105                 110

Ser Arg Ile Ala Val Ser Tyr Gln Thr Lys Val Asn Leu Leu Ser Ala
        115                 120                 125

Ile Lys Ser Pro Cys Gln Arg Glu Thr Pro Glu Gly Ala Glu Ala Lys
    130                 135                 140

Pro Trp Tyr Glu Pro Ile Tyr Leu Gly Gly Val Phe Gln Leu Glu Lys
145                 150                 155                 160

Gly Asp Arg Leu Ser Ala Glu Ile Asn Arg Pro Asp Tyr Leu Asn Phe
                165                 170                 175

Arg Glu Ser Gly Gln Val Tyr Phe Gly Ile Ile Ala Leu Gly Gly Arg
            180                 185                 190

Thr Pro Ser Asp Lys Pro Val Ala His Val Val Ala Asn Pro Gln Ala
        195                 200                 205

Glu Gly Gln Leu Gln Trp Leu Asn Arg Arg Ala Asn Ala Leu Leu Ala
    210                 215                 220

Asn Gly Val Glu Leu Arg Asp Asn Gln Leu Val Val Pro Ser Glu Gly
225                 230                 235                 240

Leu Tyr Leu Ile Tyr Ser Gln Val Leu Phe Lys Gly Gln Gly Cys Pro
                245                 250                 255

Ser Thr His Val Leu Leu Thr His Thr Ile Ser Arg Ile Ala Val Ser
            260                 265                 270

Tyr Gln Thr Lys Val Asn Leu Leu Ser Ala Ile Lys Ser Pro Cys Gln
        275                 280                 285

Arg Glu Thr Pro Glu Gly Ala Glu Ala Lys Pro Trp Tyr Glu Pro Ile
    290                 295                 300

Tyr Leu Gly Gly Val Phe Gln Leu Glu Lys Gly Asp Arg Leu Ser Ala
305                 310                 315                 320

Glu Ile Asn Arg Pro Asp Tyr Leu Asn Phe Arg Glu Ser Gly Gln Val
                325                 330                 335

Tyr Phe Gly Ile Ile Ala Leu Gly Gly Arg Thr Pro Ser Asp Lys Pro
            340                 345                 350

Val Ala His Val Val Ala Asn Pro Gln Ala Glu Gly Gln Leu Gln Trp
        355                 360                 365

Leu Asn Arg Arg Ala Asn Ala Leu Leu Ala Asn Gly Val Glu Leu Arg
    370                 375                 380

Asp Asn Gln Leu Val Val Pro Ser Glu Gly Leu Tyr Leu Ile Tyr Ser
385                 390                 395                 400

Gln Val Leu Phe Lys Gly Gln Gly Cys Pro Ser Thr His Val Leu Leu
                405                 410                 415

Thr His Thr Ile Ser Arg Ile Ala Val Ser Tyr Gln Thr Lys Val Asn
            420                 425                 430

Leu Leu Ser Ala Ile Lys Ser Pro Cys Gln Arg Glu Thr Pro Glu Gly
        435                 440                 445

Ala Glu Ala Lys Pro Trp Tyr Glu Pro Ile Tyr Leu Gly Gly Val Phe
```

```
    450                 455                 460

Gln Leu Glu Lys Gly Asp Arg Leu Ser Ala Glu Ile Asn Arg Pro Asp
465                 470                 475                 480

Tyr Leu Asn Phe Arg Glu Ser Gly Gln Val Tyr Phe Gly Ile Ile Ala
                485                 490                 495

Leu


<210> SEQ ID NO 81
<211> LENGTH: 493
<212> TYPE: PRT
<213> ORGANISM: Artificial Sequence
<220> FEATURE:
<223> OTHER INFORMATION: variant 145

<400> SEQUENCE: 81

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Arg Thr Pro Ser Asp Lys Pro Val Ala His Val Val Ala
        35                  40                  45

Asn Pro Gln Ala Glu Gly Gln Leu Gln Trp Leu Asn Arg Arg Ala Asn
    50                  55                  60

Ala Leu Leu Ala Asn Gly Val Glu Leu Arg Asp Asn Gln Leu Val Val
65                  70                  75                  80

Pro Ser Glu Gly Leu Tyr Leu Ile Tyr Ser Gln Val Leu Phe Lys Gly
                85                  90                  95

Gln Gly Cys Pro Ser Thr His Val Leu Leu Thr His Thr Ile Ser Arg
            100                 105                 110

Ile Ala Val Ser Tyr Gln Thr Lys Val Asn Leu Leu Ser Ala Ile Lys
        115                 120                 125

Ser Pro Cys Gln Arg Glu Thr Pro Glu Gly Ala Glu Ala Lys Pro Trp
    130                 135                 140

Tyr Glu Pro Ile Tyr Leu Gly Gly Val Phe Gln Leu Glu Lys Gly Asp
145                 150                 155                 160

Arg Leu Ser Ala Glu Ile Asn Arg Pro Asp Tyr Leu Asn Phe Arg Glu
                165                 170                 175

Ser Gly Gln Val Tyr Phe Gly Ile Ile Ala Leu Gly Gly Thr Pro Ser
            180                 185                 190

Asp Lys Pro Val Ala His Val Val Ala Asn Pro Gln Ala Glu Gly Gln
        195                 200                 205

Leu Gln Trp Leu Asn Arg Arg Ala Asn Ala Leu Leu Ala Asn Gly Val
    210                 215                 220

Glu Leu Arg Asp Asn Gln Leu Val Val Pro Ser Glu Gly Leu Tyr Leu
225                 230                 235                 240

Ile Tyr Ser Gln Val Leu Phe Lys Gly Gln Gly Cys Pro Ser Thr His
                245                 250                 255

Val Leu Leu Thr His Thr Ile Ser Arg Ile Ala Val Ser Tyr Gln Thr
            260                 265                 270

Lys Val Asn Leu Leu Ser Ala Ile Lys Ser Pro Cys Gln Arg Glu Thr
        275                 280                 285

Pro Glu Gly Ala Glu Ala Lys Pro Trp Tyr Glu Pro Ile Tyr Leu Gly
    290                 295                 300

Gly Val Phe Gln Leu Glu Lys Gly Asp Arg Leu Ser Ala Glu Ile Asn
305                 310                 315                 320
```

```
Arg Pro Asp Tyr Leu Asn Phe Arg Glu Ser Gly Gln Val Tyr Phe Gly
                325                 330                 335

Ile Ile Ala Leu Gly Gly Thr Pro Ser Asp Lys Pro Val Ala His Val
            340                 345                 350

Val Ala Asn Pro Gln Ala Glu Gly Gln Leu Gln Trp Leu Asn Arg Arg
        355                 360                 365

Ala Asn Ala Leu Leu Ala Asn Gly Val Glu Leu Arg Asp Asn Gln Leu
    370                 375                 380

Val Val Pro Ser Glu Gly Leu Tyr Leu Ile Tyr Ser Gln Val Leu Phe
385                 390                 395                 400

Lys Gly Gln Gly Cys Pro Ser Thr His Val Leu Leu Thr His Thr Ile
                405                 410                 415

Ser Arg Ile Ala Val Ser Tyr Gln Thr Lys Val Asn Leu Leu Ser Ala
            420                 425                 430

Ile Lys Ser Pro Cys Gln Arg Glu Thr Pro Glu Gly Ala Glu Ala Lys
        435                 440                 445

Pro Trp Tyr Glu Pro Ile Tyr Leu Gly Gly Val Phe Gln Leu Glu Lys
    450                 455                 460

Gly Asp Arg Leu Ser Ala Glu Ile Asn Arg Pro Asp Tyr Leu Asn Phe
465                 470                 475                 480

Arg Glu Ser Gly Gln Val Tyr Phe Gly Ile Ile Ala Leu
                485                 490


<210> SEQ ID NO 82
<211> LENGTH: 492
<212> TYPE: PRT
<213> ORGANISM: Artificial Sequence
<220> FEATURE:
<223> OTHER INFORMATION: variant 146

<400> SEQUENCE: 82

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Ser Asp Lys Pro Val Ala His Val Val Ala Asn Pro Gln
        35                  40                  45

Ala Glu Gly Gln Leu Gln Trp Leu Asn Arg Arg Ala Asn Ala Leu Leu
    50                  55                  60

Ala Asn Gly Val Glu Leu Arg Asp Asn Gln Leu Val Val Pro Ser Glu
65                  70                  75                  80

Gly Leu Tyr Leu Ile Tyr Ser Gln Val Leu Phe Lys Gly Gln Gly Cys
                85                  90                  95

Pro Ser Thr His Val Leu Leu Thr His Thr Ile Ser Arg Ile Ala Val
            100                 105                 110

Ser Tyr Gln Thr Lys Val Asn Leu Leu Ser Ala Ile Lys Ser Pro Cys
        115                 120                 125

Gln Arg Glu Thr Pro Glu Gly Ala Glu Ala Lys Pro Trp Tyr Glu Pro
    130                 135                 140

Ile Tyr Leu Gly Gly Val Phe Gln Leu Glu Lys Gly Asp Arg Leu Ser
145                 150                 155                 160

Ala Glu Ile Asn Arg Pro Asp Tyr Leu Asn Phe Arg Glu Ser Gly Gln
                165                 170                 175

Val Tyr Phe Gly Ile Ile Ala Leu Gly Gly Gly Thr Pro Ser Asp Lys
            180                 185                 190
```

```
Pro Val Ala His Val Val Ala Asn Pro Gln Ala Glu Gly Gln Leu Gln
        195                 200                 205

Trp Leu Asn Arg Arg Ala Asn Ala Leu Leu Ala Asn Gly Val Glu Leu
    210                 215                 220

Arg Asp Asn Gln Leu Val Val Pro Ser Glu Gly Leu Tyr Leu Ile Tyr
225                 230                 235                 240

Ser Gln Val Leu Phe Lys Gly Gln Gly Cys Pro Ser Thr His Val Leu
                245                 250                 255

Leu Thr His Thr Ile Ser Arg Ile Ala Val Ser Tyr Gln Thr Lys Val
            260                 265                 270

Asn Leu Leu Ser Ala Ile Lys Ser Pro Cys Gln Arg Glu Thr Pro Glu
        275                 280                 285

Gly Ala Glu Ala Lys Pro Trp Tyr Glu Pro Ile Tyr Leu Gly Gly Val
    290                 295                 300

Phe Gln Leu Glu Lys Gly Asp Arg Leu Ser Ala Glu Ile Asn Arg Pro
305                 310                 315                 320

Asp Tyr Leu Asn Phe Arg Glu Ser Gly Gln Val Tyr Phe Gly Ile Ile
                325                 330                 335

Ala Leu Gly Gly Gly Thr Pro Ser Asp Lys Pro Val Ala His Val Val
            340                 345                 350

Ala Asn Pro Gln Ala Glu Gly Gln Leu Gln Trp Leu Asn Arg Arg Ala
        355                 360                 365

Asn Ala Leu Leu Ala Asn Gly Val Glu Leu Arg Asp Asn Gln Leu Val
    370                 375                 380

Val Pro Ser Glu Gly Leu Tyr Leu Ile Tyr Ser Gln Val Leu Phe Lys
385                 390                 395                 400

Gly Gln Gly Cys Pro Ser Thr His Val Leu Leu Thr His Thr Ile Ser
                405                 410                 415

Arg Ile Ala Val Ser Tyr Gln Thr Lys Val Asn Leu Leu Ser Ala Ile
            420                 425                 430

Lys Ser Pro Cys Gln Arg Glu Thr Pro Glu Gly Ala Glu Ala Lys Pro
        435                 440                 445

Trp Tyr Glu Pro Ile Tyr Leu Gly Gly Val Phe Gln Leu Glu Lys Gly
    450                 455                 460

Asp Arg Leu Ser Ala Glu Ile Asn Arg Pro Asp Tyr Leu Asn Phe Arg
465                 470                 475                 480

Glu Ser Gly Gln Val Tyr Phe Gly Ile Ile Ala Leu
                485                 490


<210> SEQ ID NO 83
<211> LENGTH: 492
<212> TYPE: PRT
<213> ORGANISM: Artificial Sequence
<220> FEATURE:
<223> OTHER INFORMATION: variant 147

<400> SEQUENCE: 83

Met Glu Thr Asp Thr Leu Leu Leu Trp Val Leu Leu Leu Trp Val Pro
1               5                   10                  15

Gly Ser Thr Gly Met Cys Gly Ser His His His His His His Ser Gly
            20                  25                  30

Ile Pro Ala Ser Asp Lys Pro Val Ala His Val Val Ala Asn Pro Gln
        35                  40                  45

Ala Glu Gly Gln Leu Gln Trp Leu Asn Arg Arg Ala Asn Ala Leu Leu
    50                  55                  60
```

```
Ala Asn Gly Val Glu Leu Arg Asp Asn Gln Leu Val Val Pro Ser Glu
65                  70                  75                  80

Gly Leu Tyr Leu Ile Tyr Ser Gln Val Leu Phe Lys Gly Gln Gly Cys
                85                  90                  95

Pro Ser Thr His Val Leu Leu Thr His Thr Ile Ser Arg Ile Ala Val
            100                 105                 110

Ser Tyr Gln Thr Lys Val Asn Leu Leu Ser Ala Ile Lys Ser Pro Cys
        115                 120                 125

Gln Arg Glu Thr Pro Glu Gly Ala Glu Ala Lys Pro Trp Tyr Glu Pro
    130                 135                 140

Ile Tyr Leu Gly Gly Val Phe Gln Leu Glu Lys Gly Asp Arg Leu Ser
145                 150                 155                 160

Ala Glu Ile Asn Arg Pro Asp Tyr Leu Asn Phe Arg Glu Ser Gly Gln
                165                 170                 175

Val Tyr Phe Gly Ile Ile Ala Leu Gly Gly Gly Gly Pro Ser Asp Lys
            180                 185                 190

Pro Val Ala His Val Val Ala Asn Pro Gln Ala Glu Gly Gln Leu Gln
        195                 200                 205

Trp Leu Asn Arg Arg Ala Asn Ala Leu Leu Ala Asn Gly Val Glu Leu
    210                 215                 220

Arg Asp Asn Gln Leu Val Val Pro Ser Glu Gly Leu Tyr Leu Ile Tyr
225                 230                 235                 240

Ser Gln Val Leu Phe Lys Gly Gln Gly Cys Pro Ser Thr His Val Leu
                245                 250                 255

Leu Thr His Thr Ile Ser Arg Ile Ala Val Ser Tyr Gln Thr Lys Val
            260                 265                 270

Asn Leu Leu Ser Ala Ile Lys Ser Pro Cys Gln Arg Glu Thr Pro Glu
        275                 280                 285

Gly Ala Glu Ala Lys Pro Trp Tyr Glu Pro Ile Tyr Leu Gly Gly Val
    290                 295                 300

Phe Gln Leu Glu Lys Gly Asp Arg Leu Ser Ala Glu Ile Asn Arg Pro
305                 310                 315                 320

Asp Tyr Leu Asn Phe Arg Glu Ser Gly Gln Val Tyr Phe Gly Ile Ile
                325                 330                 335

Ala Leu Gly Gly Gly Gly Pro Ser Asp Lys Pro Val Ala His Val Val
            340                 345                 350

Ala Asn Pro Gln Ala Glu Gly Gln Leu Gln Trp Leu Asn Arg Arg Ala
        355                 360                 365

Asn Ala Leu Leu Ala Asn Gly Val Glu Leu Arg Asp Asn Gln Leu Val
    370                 375                 380

Val Pro Ser Glu Gly Leu Tyr Leu Ile Tyr Ser Gln Val Leu Phe Lys
385                 390                 395                 400

Gly Gln Gly Cys Pro Ser Thr His Val Leu Leu Thr His Thr Ile Ser
                405                 410                 415

Arg Ile Ala Val Ser Tyr Gln Thr Lys Val Asn Leu Leu Ser Ala Ile
            420                 425                 430

Lys Ser Pro Cys Gln Arg Glu Thr Pro Glu Gly Ala Glu Ala Lys Pro
        435                 440                 445

Trp Tyr Glu Pro Ile Tyr Leu Gly Gly Val Phe Gln Leu Glu Lys Gly
    450                 455                 460

Asp Arg Leu Ser Ala Glu Ile Asn Arg Pro Asp Tyr Leu Asn Phe Arg
465                 470                 475                 480
```

```
Glu Ser Gly Gln Val Tyr Phe Gly Ile Ile Ala Leu
                485                 490


<210> SEQ ID NO 84
<211> LENGTH: 716
<212> TYPE: PRT
<213> ORGANISM: Artificial Sequence
<220> FEATURE:
<223> OTHER INFORMATION: variant 148

<400> SEQUENCE: 84

Met Glu Thr Asp Thr Leu Leu Leu Trp Val Leu Leu Leu Trp Val Pro
1               5                   10                  15

Gly Ser Thr Gly Ser Ser Arg Thr Pro Ser Asp Lys Pro Val Ala His
            20                  25                  30

Val Val Ala Asn Pro Gln Ala Glu Gly Gln Leu Gln Trp Leu Asn Arg
        35                  40                  45

Arg Ala Asn Ala Leu Leu Ala Asn Gly Val Glu Leu Arg Asp Asn Gln
    50                  55                  60

Leu Val Val Pro Ser Glu Gly Leu Tyr Leu Ile Tyr Ser Gln Val Leu
65                  70                  75                  80

Phe Lys Gly Gln Gly Cys Pro Ser Thr His Val Leu Leu Thr His Thr
                85                  90                  95

Ile Ser Arg Ile Ala Val Ser Tyr Gln Thr Lys Val Asn Leu Leu Ser
            100                 105                 110

Ala Ile Lys Ser Pro Cys Gln Arg Glu Thr Pro Glu Gly Ala Glu Ala
        115                 120                 125

Lys Pro Trp Tyr Glu Pro Ile Tyr Leu Gly Gly Val Phe Gln Leu Glu
    130                 135                 140

Lys Gly Asp Arg Leu Ser Ala Glu Ile Asn Arg Pro Asp Tyr Leu Asn
145                 150                 155                 160

Phe Arg Glu Ser Gly Gln Val Tyr Phe Gly Ile Ile Ala Leu Ser Arg
                165                 170                 175

Thr Pro Ser Asp Lys Pro Val Ala His Val Val Ala Asn Pro Gln Ala
            180                 185                 190

Glu Gly Gln Leu Gln Trp Leu Asn Arg Arg Ala Asn Ala Leu Leu Ala
        195                 200                 205

Asn Gly Val Glu Leu Arg Asp Asn Gln Leu Val Val Pro Ser Glu Gly
    210                 215                 220

Leu Tyr Leu Ile Tyr Ser Gln Val Leu Phe Lys Gly Gln Gly Cys Pro
225                 230                 235                 240

Ser Thr His Val Leu Leu Thr His Thr Ile Ser Arg Ile Ala Val Ser
                245                 250                 255

Tyr Gln Thr Lys Val Asn Leu Leu Ser Ala Ile Lys Ser Pro Cys Gln
            260                 265                 270

Arg Glu Thr Pro Glu Gly Ala Glu Ala Lys Pro Trp Tyr Glu Pro Ile
        275                 280                 285

Tyr Leu Gly Gly Val Phe Gln Leu Glu Lys Gly Asp Arg Leu Ser Ala
    290                 295                 300

Glu Ile Asn Arg Pro Asp Tyr Leu Asn Phe Arg Glu Ser Gly Gln Val
305                 310                 315                 320

Tyr Phe Gly Ile Ile Ala Leu Ser Arg Thr Pro Ser Asp Lys Pro Val
                325                 330                 335

Ala His Val Val Ala Asn Pro Gln Ala Glu Gly Gln Leu Gln Trp Leu
            340                 345                 350
```

```
Asn Arg Arg Ala Asn Ala Leu Leu Ala Asn Gly Val Glu Leu Arg Asp
        355                 360                 365

Asn Gln Leu Val Val Pro Ser Glu Gly Leu Tyr Leu Ile Tyr Ser Gln
    370                 375                 380

Val Leu Phe Lys Gly Gln Gly Cys Pro Ser Thr His Val Leu Leu Thr
385                 390                 395                 400

His Thr Ile Ser Arg Ile Ala Val Ser Tyr Gln Thr Lys Val Asn Leu
                405                 410                 415

Leu Ser Ala Ile Lys Ser Pro Cys Gln Arg Glu Thr Pro Glu Gly Ala
            420                 425                 430

Glu Ala Lys Pro Trp Tyr Glu Pro Ile Tyr Leu Gly Gly Val Phe Gln
        435                 440                 445

Leu Glu Lys Gly Asp Arg Leu Ser Ala Glu Ile Asn Arg Pro Asp Tyr
    450                 455                 460

Leu Asn Phe Arg Glu Ser Gly Gln Val Tyr Phe Gly Ile Ile Ala Leu
465                 470                 475                 480

Gly Gly Ser Gly Gly Gly Gly Ser Gly Gly Asp Lys Thr His Thr Cys
                485                 490                 495

Pro Pro Cys Pro Ala Pro Pro Val Ala Gly Pro Ser Val Phe Leu Phe
            500                 505                 510

Pro Pro Lys Pro Lys Asp Thr Leu Met Ile Ser Arg Thr Pro Glu Val
        515                 520                 525

Thr Cys Val Val Val Asp Val Ser His Glu Asp Pro Glu Val Lys Phe
    530                 535                 540

Asn Trp Tyr Val Asp Gly Val Glu Val His Asn Ala Lys Thr Lys Pro
545                 550                 555                 560

Arg Glu Glu Gln Tyr Asn Ser Thr Tyr Arg Val Val Ser Val Leu Thr
                565                 570                 575

Val Leu His Gln Asp Trp Leu Asn Gly Lys Glu Tyr Lys Cys Lys Val
            580                 585                 590

Ser Asn Lys Gly Leu Pro Ser Ser Ile Glu Lys Thr Ile Ser Lys Ala
        595                 600                 605

Lys Gly Gln Pro Arg Glu Pro Gln Val Tyr Thr Leu Pro Pro Ser Arg
    610                 615                 620

Asp Glu Leu Thr Lys Asn Gln Val Ser Leu Thr Cys Leu Val Lys Gly
625                 630                 635                 640

Phe Tyr Pro Ser Asp Ile Ala Val Glu Trp Glu Ser Asn Gly Gln Pro
                645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
        675                 680                 685

Gly Asn Val Phe Ser Cys Ser Val Met His Glu Ala Leu His Asn His
    690                 695                 700

Tyr Thr Gln Lys Ser Leu Ser Leu Ser Pro Gly Lys
705                 710                 715
```

<210> SEQ ID NO 85
<211> LENGTH: 718
<212> TYPE: PRT
<213> ORGANISM: Artificial Sequence
<220> FEATURE:
<223> OTHER INFORMATION: variant 149

<400> SEQUENCE: 85

```
Met Glu Thr Asp Thr Leu Leu Leu Trp Val Leu Leu Leu Trp Val Pro
1               5                   10                  15

Gly Ser Thr Gly Ser Ser Arg Thr Pro Ser Asp Lys Pro Val Ala His
            20                  25                  30

Val Val Ala Asn Pro Gln Ala Glu Gly Gln Leu Gln Trp Leu Asn Arg
        35                  40                  45

Arg Ala Asn Ala Leu Leu Ala Asn Gly Val Glu Leu Arg Asp Asn Gln
    50                  55                  60

Leu Val Val Pro Ser Glu Gly Leu Tyr Leu Ile Tyr Ser Gln Val Leu
65                  70                  75                  80

Phe Lys Gly Gln Gly Cys Pro Ser Thr His Val Leu Leu Thr His Thr
                85                  90                  95

Ile Ser Arg Ile Ala Val Ser Tyr Gln Thr Lys Val Asn Leu Leu Ser
            100                 105                 110

Ala Ile Lys Ser Pro Cys Gln Arg Glu Thr Pro Glu Gly Ala Glu Ala
        115                 120                 125

Lys Pro Trp Tyr Glu Pro Ile Tyr Leu Gly Gly Val Phe Gln Leu Glu
    130                 135                 140

Lys Gly Asp Arg Leu Ser Ala Glu Ile Asn Arg Pro Asp Tyr Leu Asn
145                 150                 155                 160

Phe Arg Glu Ser Gly Gln Val Tyr Phe Gly Ile Ile Ala Leu Gly Ser
                165                 170                 175

Arg Thr Pro Ser Asp Lys Pro Val Ala His Val Val Ala Asn Pro Gln
            180                 185                 190

Ala Glu Gly Gln Leu Gln Trp Leu Asn Arg Arg Ala Asn Ala Leu Leu
        195                 200                 205

Ala Asn Gly Val Glu Leu Arg Asp Asn Gln Leu Val Val Pro Ser Glu
    210                 215                 220

Gly Leu Tyr Leu Ile Tyr Ser Gln Val Leu Phe Lys Gly Gln Gly Cys
225                 230                 235                 240

Pro Ser Thr His Val Leu Leu Thr His Thr Ile Ser Arg Ile Ala Val
                245                 250                 255

Ser Tyr Gln Thr Lys Val Asn Leu Leu Ser Ala Ile Lys Ser Pro Cys
            260                 265                 270

Gln Arg Glu Thr Pro Glu Gly Ala Glu Ala Lys Pro Trp Tyr Glu Pro
        275                 280                 285

Ile Tyr Leu Gly Gly Val Phe Gln Leu Glu Lys Gly Asp Arg Leu Ser
    290                 295                 300

Ala Glu Ile Asn Arg Pro Asp Tyr Leu Asn Phe Arg Glu Ser Gly Gln
305                 310                 315                 320

Val Tyr Phe Gly Ile Ile Ala Leu Gly Ser Arg Thr Pro Ser Asp Lys
                325                 330                 335

Pro Val Ala His Val Val Ala Asn Pro Gln Ala Glu Gly Gln Leu Gln
            340                 345                 350

Trp Leu Asn Arg Arg Ala Asn Ala Leu Leu Ala Asn Gly Val Glu Leu
        355                 360                 365

Arg Asp Asn Gln Leu Val Val Pro Ser Glu Gly Leu Tyr Leu Ile Tyr
    370                 375                 380

Ser Gln Val Leu Phe Lys Gly Gln Gly Cys Pro Ser Thr His Val Leu
385                 390                 395                 400

Leu Thr His Thr Ile Ser Arg Ile Ala Val Ser Tyr Gln Thr Lys Val
                405                 410                 415

Asn Leu Leu Ser Ala Ile Lys Ser Pro Cys Gln Arg Glu Thr Pro Glu
```

```
            420                 425                 430

Gly Ala Glu Ala Lys Pro Trp Tyr Glu Pro Ile Tyr Leu Gly Gly Val
        435                 440                 445

Phe Gln Leu Glu Lys Gly Asp Arg Leu Ser Ala Glu Ile Asn Arg Pro
    450                 455                 460

Asp Tyr Leu Asn Phe Arg Glu Ser Gly Gln Val Tyr Phe Gly Ile Ile
465                 470                 475                 480

Ala Leu Gly Gly Ser Gly Gly Gly Gly Ser Gly Gly Asp Lys Thr His
                485                 490                 495

Thr Cys Pro Pro Cys Pro Ala Pro Pro Val Ala Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Gly Leu Pro Ser Ser Ile Glu Lys Thr Ile Ser
        595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly Lys
705                 710                 715


<210> SEQ ID NO 86
<211> LENGTH: 711
<212> TYPE: PRT
<213> ORGANISM: Artificial Sequence
<220> FEATURE:
<223> OTHER INFORMATION: variant 150

<400> SEQUENCE: 86

Met Glu Thr Asp Thr Leu Leu Leu Trp Val Leu Leu Leu Trp Val Pro
1               5                   10                  15

Gly Ser Thr Gly Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
```

-continued

```
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140

Ser Ala Glu Ile Asn Arg Pro Asp Tyr Leu Asn Phe Arg Glu Ser Gly
145                 150                 155                 160

Gln Val Tyr Phe Gly Ile Ile Ala Leu Gly Arg Thr Pro Ser Asp Lys
                165                 170                 175

Pro Val Ala His Val Val Ala Asn Pro Gln Ala Glu Gly Gln Leu Gln
            180                 185                 190

Trp Leu Asn Arg Arg Ala Asn Ala Leu Leu Ala Asn Gly Val Glu Leu
        195                 200                 205

Arg Asp Asn Gln Leu Val Val Pro Ser Glu Gly Leu Tyr Leu Ile Tyr
    210                 215                 220

Ser Gln Val Leu Phe Lys Gly Gln Gly Cys Pro Ser Thr His Val Leu
225                 230                 235                 240

Leu Thr His Thr Ile Ser Arg Ile Ala Val Ser Tyr Gln Thr Lys Val
                245                 250                 255

Asn Leu Leu Ser Ala Ile Lys Ser Pro Cys Gln Arg Glu Thr Pro Glu
            260                 265                 270

Gly Ala Glu Ala Lys Pro Trp Tyr Glu Pro Ile Tyr Leu Gly Gly Val
        275                 280                 285

Phe Gln Leu Glu Lys Gly Asp Arg Leu Ser Ala Glu Ile Asn Arg Pro
    290                 295                 300

Asp Tyr Leu Asn Phe Arg Glu Ser Gly Gln Val Tyr Phe Gly Ile Ile
305                 310                 315                 320

Ala Leu Gly Arg Thr Pro Ser Asp Lys Pro Val Ala His Val Val Ala
                325                 330                 335

Asn Pro Gln Ala Glu Gly Gln Leu Gln Trp Leu Asn Arg Arg Ala Asn
            340                 345                 350

Ala Leu Leu Ala Asn Gly Val Glu Leu Arg Asp Asn Gln Leu Val Val
        355                 360                 365

Pro Ser Glu Gly Leu Tyr Leu Ile Tyr Ser Gln Val Leu Phe Lys Gly
    370                 375                 380

Gln Gly Cys Pro Ser Thr His Val Leu Leu Thr His Thr Ile Ser Arg
385                 390                 395                 400

Ile Ala Val Ser Tyr Gln Thr Lys Val Asn Leu Leu Ser Ala Ile Lys
                405                 410                 415

Ser Pro Cys Gln Arg Glu Thr Pro Glu Gly Ala Glu Ala Lys Pro Trp
            420                 425                 430

Tyr Glu Pro Ile Tyr Leu Gly Gly Val Phe Gln Leu Glu Lys Gly Asp
        435                 440                 445

Arg Leu Ser Ala Glu Ile Asn Arg Pro Asp Tyr Leu Asn Phe Arg Glu
    450                 455                 460

Ser Gly Gln Val Tyr Phe Gly Ile Ile Ala Leu Gly Gly Ser Gly Gly
465                 470                 475                 480

Gly Gly Ser Gly Gly Asp Lys Thr His Thr Cys Pro Pro Cys Pro Ala
                485                 490                 495
```

```
Pro Pro Val Ala Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Gly Leu
            580                 585                 590

Pro Ser Ser Ile Glu Lys Thr Ile Ser Lys Ala Lys Gly Gln Pro Arg
        595                 600                 605

Glu Pro Gln Val Tyr Thr Leu Pro Pro Ser Arg Asp Glu Leu Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn His Tyr Thr Gln Lys Ser
    690                 695                 700

Leu Ser Leu Ser Pro Gly Lys
705                 710


<210> SEQ ID NO 87
<211> LENGTH: 711
<212> TYPE: PRT
<213> ORGANISM: Artificial Sequence
<220> FEATURE:
<223> OTHER INFORMATION: variant 151

<400> SEQUENCE: 87

Met Glu Thr Asp Thr Leu Leu Leu Trp Val Leu Leu Leu Trp Val Pro
1               5                   10                  15

Gly Ser Thr Gly Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140
```

-continued

```
Ser Ala Glu Ile Asn Arg Pro Asp Tyr Leu Asn Phe Arg Glu Ser Gly
145                 150                 155                 160

Gln Val Tyr Phe Gly Ile Ile Ala Leu Gly Gly Gly Pro Ser Asp Lys
                165                 170                 175

Pro Val Ala His Val Val Ala Asn Pro Gln Ala Glu Gly Gln Leu Gln
            180                 185                 190

Trp Leu Asn Arg Arg Ala Asn Ala Leu Leu Ala Asn Gly Val Glu Leu
        195                 200                 205

Arg Asp Asn Gln Leu Val Val Pro Ser Glu Gly Leu Tyr Leu Ile Tyr
    210                 215                 220

Ser Gln Val Leu Phe Lys Gly Gln Gly Cys Pro Ser Thr His Val Leu
225                 230                 235                 240

Leu Thr His Thr Ile Ser Arg Ile Ala Val Ser Tyr Gln Thr Lys Val
                245                 250                 255

Asn Leu Leu Ser Ala Ile Lys Ser Pro Cys Gln Arg Glu Thr Pro Glu
            260                 265                 270

Gly Ala Glu Ala Lys Pro Trp Tyr Glu Pro Ile Tyr Leu Gly Gly Val
        275                 280                 285

Phe Gln Leu Glu Lys Gly Asp Arg Leu Ser Ala Glu Ile Asn Arg Pro
    290                 295                 300

Asp Tyr Leu Asn Phe Arg Glu Ser Gly Gln Val Tyr Phe Gly Ile Ile
305                 310                 315                 320

Ala Leu Gly Gly Gly Pro Ser Asp Lys Pro Val Ala His Val Val Ala
                325                 330                 335

Asn Pro Gln Ala Glu Gly Gln Leu Gln Trp Leu Asn Arg Arg Ala Asn
            340                 345                 350

Ala Leu Leu Ala Asn Gly Val Glu Leu Arg Asp Asn Gln Leu Val Val
        355                 360                 365

Pro Ser Glu Gly Leu Tyr Leu Ile Tyr Ser Gln Val Leu Phe Lys Gly
    370                 375                 380

Gln Gly Cys Pro Ser Thr His Val Leu Leu Thr His Thr Ile Ser Arg
385                 390                 395                 400

Ile Ala Val Ser Tyr Gln Thr Lys Val Asn Leu Leu Ser Ala Ile Lys
                405                 410                 415

Ser Pro Cys Gln Arg Glu Thr Pro Glu Gly Ala Glu Ala Lys Pro Trp
            420                 425                 430

Tyr Glu Pro Ile Tyr Leu Gly Gly Val Phe Gln Leu Glu Lys Gly Asp
        435                 440                 445

Arg Leu Ser Ala Glu Ile Asn Arg Pro Asp Tyr Leu Asn Phe Arg Glu
    450                 455                 460

Ser Gly Gln Val Tyr Phe Gly Ile Ile Ala Leu Gly Gly Ser Gly Gly
465                 470                 475                 480

Gly Gly Ser Gly Gly Asp Lys Thr His Thr Cys Pro Pro Cys Pro Ala
                485                 490                 495

Pro Pro Val Ala Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560
```

```
Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Gly Leu
            580                 585                 590

Pro Ser Ser Ile Glu Lys Thr Ile Ser Lys Ala Lys Gly Gln Pro Arg
        595                 600                 605

Glu Pro Gln Val Tyr Thr Leu Pro Pro Ser Arg Asp Glu Leu Thr Lys
    610                 615                 620

Asn Gln Val Ser Leu Thr Cys Leu Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Tyr Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn His Tyr Thr Gln Lys Ser
    690                 695                 700

Leu Ser Leu Ser Pro Gly Lys
705                 710


<210> SEQ ID NO 88
<211> LENGTH: 718
<212> TYPE: PRT
<213> ORGANISM: Artificial Sequence
<220> FEATURE:
<223> OTHER INFORMATION: variant 152

<400> SEQUENCE: 88

Met Glu Thr Asp Thr Leu Leu Leu Trp Val Leu Leu Leu Trp Val Pro
1               5                   10                  15

Gly Ser Thr Gly Ser Ser Arg Thr Pro Ser Asp Lys Pro Val Ala His
            20                  25                  30

Val Val Ala Asn Pro Gln Ala Glu Gly Gln Leu Gln Trp Leu Asn Arg
        35                  40                  45

Arg Ala Asn Ala Leu Leu Ala Asn Gly Val Glu Leu Arg Asp Asn Gln
    50                  55                  60

Leu Val Val Pro Ser Glu Gly Leu Tyr Leu Ile Tyr Ser Gln Val Leu
65                  70                  75                  80

Phe Lys Gly Gln Gly Cys Pro Ser Thr His Val Leu Leu Thr His Thr
                85                  90                  95

Ile Ser Arg Ile Ala Val Ser Tyr Gln Thr Lys Val Asn Leu Leu Ser
            100                 105                 110

Ala Ile Lys Ser Pro Cys Gln Arg Glu Thr Pro Glu Gly Ala Glu Ala
        115                 120                 125

Lys Pro Trp Tyr Glu Pro Ile Tyr Leu Gly Gly Val Phe Gln Leu Glu
    130                 135                 140

Lys Gly Asp Arg Leu Ser Ala Glu Ile Asn Arg Pro Asp Tyr Leu Asn
145                 150                 155                 160

Phe Arg Glu Ser Gly Gln Val Tyr Phe Gly Ile Ile Ala Leu Gly Gly
                165                 170                 175

Arg Thr Pro Ser Asp Lys Pro Val Ala His Val Val Ala Asn Pro Gln
            180                 185                 190

Ala Glu Gly Gln Leu Gln Trp Leu Asn Arg Arg Ala Asn Ala Leu Leu
        195                 200                 205
```

```
Ala Asn Gly Val Glu Leu Arg Asp Asn Gln Leu Val Val Pro Ser Glu
    210                 215                 220

Gly Leu Tyr Leu Ile Tyr Ser Gln Val Leu Phe Lys Gly Gln Gly Cys
225                 230                 235                 240

Pro Ser Thr His Val Leu Leu Thr His Thr Ile Ser Arg Ile Ala Val
                245                 250                 255

Ser Tyr Gln Thr Lys Val Asn Leu Leu Ser Ala Ile Lys Ser Pro Cys
            260                 265                 270

Gln Arg Glu Thr Pro Glu Gly Ala Glu Ala Lys Pro Trp Tyr Glu Pro
        275                 280                 285

Ile Tyr Leu Gly Gly Val Phe Gln Leu Glu Lys Gly Asp Arg Leu Ser
    290                 295                 300

Ala Glu Ile Asn Arg Pro Asp Tyr Leu Asn Phe Arg Glu Ser Gly Gln
305                 310                 315                 320

Val Tyr Phe Gly Ile Ile Ala Leu Gly Gly Arg Thr Pro Ser Asp Lys
                325                 330                 335

Pro Val Ala His Val Val Ala Asn Pro Gln Ala Glu Gly Gln Leu Gln
            340                 345                 350

Trp Leu Asn Arg Arg Ala Asn Ala Leu Leu Ala Asn Gly Val Glu Leu
        355                 360                 365

Arg Asp Asn Gln Leu Val Val Pro Ser Glu Gly Leu Tyr Leu Ile Tyr
    370                 375                 380

Ser Gln Val Leu Phe Lys Gly Gln Gly Cys Pro Ser Thr His Val Leu
385                 390                 395                 400

Leu Thr His Thr Ile Ser Arg Ile Ala Val Ser Tyr Gln Thr Lys Val
                405                 410                 415

Asn Leu Leu Ser Ala Ile Lys Ser Pro Cys Gln Arg Glu Thr Pro Glu
            420                 425                 430

Gly Ala Glu Ala Lys Pro Trp Tyr Glu Pro Ile Tyr Leu Gly Gly Val
        435                 440                 445

Phe Gln Leu Glu Lys Gly Asp Arg Leu Ser Ala Glu Ile Asn Arg Pro
    450                 455                 460

Asp Tyr Leu Asn Phe Arg Glu Ser Gly Gln Val Tyr Phe Gly Ile Ile
465                 470                 475                 480

Ala Leu Gly Gly Ser Gly Gly Gly Gly Ser Gly Gly Asp Lys Thr His
                485                 490                 495

Thr Cys Pro Pro Cys Pro Ala Pro Pro Val Ala Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Gly Leu Pro Ser Ser Ile Glu Lys Thr Ile Ser
        595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
```

```
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly Lys
705                 710                 715


<210> SEQ ID NO 89
<211> LENGTH: 714
<212> TYPE: PRT
<213> ORGANISM: Artificial Sequence
<220> FEATURE:
<223> OTHER INFORMATION: variant 153

<400> SEQUENCE: 89

Met Glu Thr Asp Thr Leu Leu Leu Trp Val Leu Leu Leu Trp Val Pro
1               5                   10                  15

Gly Ser Thr Gly Arg Thr Pro Ser Asp Lys Pro Val Ala His Val Val
            20                  25                  30

Ala Asn Pro Gln Ala Glu Gly Gln Leu Gln Trp Leu Asn Arg Arg Ala
        35                  40                  45

Asn Ala Leu Leu Ala Asn Gly Val Glu Leu Arg Asp Asn Gln Leu Val
    50                  55                  60

Val Pro Ser Glu Gly Leu Tyr Leu Ile Tyr Ser Gln Val Leu Phe Lys
65                  70                  75                  80

Gly Gln Gly Cys Pro Ser Thr His Val Leu Leu Thr His Thr Ile Ser
                85                  90                  95

Arg Ile Ala Val Ser Tyr Gln Thr Lys Val Asn Leu Leu Ser Ala Ile
            100                 105                 110

Lys Ser Pro Cys Gln Arg Glu Thr Pro Glu Gly Ala Glu Ala Lys Pro
        115                 120                 125

Trp Tyr Glu Pro Ile Tyr Leu Gly Gly Val Phe Gln Leu Glu Lys Gly
    130                 135                 140

Asp Arg Leu Ser Ala Glu Ile Asn Arg Pro Asp Tyr Leu Asn Phe Arg
145                 150                 155                 160

Glu Ser Gly Gln Val Tyr Phe Gly Ile Ile Ala Leu Gly Gly Thr Pro
                165                 170                 175

Ser Asp Lys Pro Val Ala His Val Val Ala Asn Pro Gln Ala Glu Gly
            180                 185                 190

Gln Leu Gln Trp Leu Asn Arg Arg Ala Asn Ala Leu Leu Ala Asn Gly
        195                 200                 205

Val Glu Leu Arg Asp Asn Gln Leu Val Val Pro Ser Glu Gly Leu Tyr
    210                 215                 220

Leu Ile Tyr Ser Gln Val Leu Phe Lys Gly Gln Gly Cys Pro Ser Thr
225                 230                 235                 240

His Val Leu Leu Thr His Thr Ile Ser Arg Ile Ala Val Ser Tyr Gln
                245                 250                 255

Thr Lys Val Asn Leu Leu Ser Ala Ile Lys Ser Pro Cys Gln Arg Glu
            260                 265                 270

Thr Pro Glu Gly Ala Glu Ala Lys Pro Trp Tyr Glu Pro Ile Tyr Leu
```

```
        275                 280                 285

Gly Gly Val Phe Gln Leu Glu Lys Gly Asp Arg Leu Ser Ala Glu Ile
    290                 295                 300

Asn Arg Pro Asp Tyr Leu Asn Phe Arg Glu Ser Gly Gln Val Tyr Phe
305                 310                 315                 320

Gly Ile Ile Ala Leu Gly Gly Thr Pro Ser Asp Lys Pro Val Ala His
                325                 330                 335

Val Val Ala Asn Pro Gln Ala Glu Gly Gln Leu Gln Trp Leu Asn Arg
            340                 345                 350

Arg Ala Asn Ala Leu Leu Ala Asn Gly Val Glu Leu Arg Asp Asn Gln
        355                 360                 365

Leu Val Val Pro Ser Glu Gly Leu Tyr Leu Ile Tyr Ser Gln Val Leu
    370                 375                 380

Phe Lys Gly Gln Gly Cys Pro Ser Thr His Val Leu Leu Thr His Thr
385                 390                 395                 400

Ile Ser Arg Ile Ala Val Ser Tyr Gln Thr Lys Val Asn Leu Leu Ser
                405                 410                 415

Ala Ile Lys Ser Pro Cys Gln Arg Glu Thr Pro Glu Gly Ala Glu Ala
            420                 425                 430

Lys Pro Trp Tyr Glu Pro Ile Tyr Leu Gly Gly Val Phe Gln Leu Glu
        435                 440                 445

Lys Gly Asp Arg Leu Ser Ala Glu Ile Asn Arg Pro Asp Tyr Leu Asn
    450                 455                 460

Phe Arg Glu Ser Gly Gln Val Tyr Phe Gly Ile Ile Ala Leu Gly Gly
465                 470                 475                 480

Ser Gly Gly Gly Gly Ser Gly Gly Asp Lys Thr His Thr Cys Pro Pro
                485                 490                 495

Cys Pro Ala Pro Pro Val Ala Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Gly Leu Pro Ser Ser Ile Glu Lys Thr Ile Ser Lys Ala Lys Gly
        595                 600                 605

Gln Pro Arg Glu Pro Gln Val Tyr Thr Leu Pro Pro Ser Arg Asp Glu
    610                 615                 620

Leu Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700
```

```
Gln Lys Ser Leu Ser Leu Ser Pro Gly Lys
705                 710


<210> SEQ ID NO 90
<211> LENGTH: 713
<212> TYPE: PRT
<213> ORGANISM: Artificial Sequence
<220> FEATURE:
<223> OTHER INFORMATION: variant 154

<400> SEQUENCE: 90

Met Glu Thr Asp Thr Leu Leu Leu Trp Val Leu Leu Leu Trp Val Pro
1               5                   10                  15

Gly Ser Thr Gly Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140

Ser Ala Glu Ile Asn Arg Pro Asp Tyr Leu Asn Phe Arg Glu Ser Gly
145                 150                 155                 160

Gln Val Tyr Phe Gly Ile Ile Ala Leu Gly Gly Gly Thr Pro Ser Asp
                165                 170                 175

Lys Pro Val Ala His Val Val Ala Asn Pro Gln Ala Glu Gly Gln Leu
            180                 185                 190

Gln Trp Leu Asn Arg Arg Ala Asn Ala Leu Leu Ala Asn Gly Val Glu
        195                 200                 205

Leu Arg Asp Asn Gln Leu Val Val Pro Ser Glu Gly Leu Tyr Leu Ile
    210                 215                 220

Tyr Ser Gln Val Leu Phe Lys Gly Gln Gly Cys Pro Ser Thr His Val
225                 230                 235                 240

Leu Leu Thr His Thr Ile Ser Arg Ile Ala Val Ser Tyr Gln Thr Lys
                245                 250                 255

Val Asn Leu Leu Ser Ala Ile Lys Ser Pro Cys Gln Arg Glu Thr Pro
            260                 265                 270

Glu Gly Ala Glu Ala Lys Pro Trp Tyr Glu Pro Ile Tyr Leu Gly Gly
        275                 280                 285

Val Phe Gln Leu Glu Lys Gly Asp Arg Leu Ser Ala Glu Ile Asn Arg
    290                 295                 300

Pro Asp Tyr Leu Asn Phe Arg Glu Ser Gly Gln Val Tyr Phe Gly Ile
305                 310                 315                 320

Ile Ala Leu Gly Gly Gly Thr Pro Ser Asp Lys Pro Val Ala His Val
                325                 330                 335

Val Ala Asn Pro Gln Ala Glu Gly Gln Leu Gln Trp Leu Asn Arg Arg
            340                 345                 350
```

```
Ala Asn Ala Leu Leu Ala Asn Gly Val Glu Leu Arg Asp Asn Gln Leu
        355                 360                 365

Val Val Pro Ser Glu Gly Leu Tyr Leu Ile Tyr Ser Gln Val Leu Phe
    370                 375                 380

Lys Gly Gln Gly Cys Pro Ser Thr His Val Leu Leu Thr His Thr Ile
385                 390                 395                 400

Ser Arg Ile Ala Val Ser Tyr Gln Thr Lys Val Asn Leu Leu Ser Ala
                405                 410                 415

Ile Lys Ser Pro Cys Gln Arg Glu Thr Pro Glu Gly Ala Glu Ala Lys
            420                 425                 430

Pro Trp Tyr Glu Pro Ile Tyr Leu Gly Gly Val Phe Gln Leu Glu Lys
        435                 440                 445

Gly Asp Arg Leu Ser Ala Glu Ile Asn Arg Pro Asp Tyr Leu Asn Phe
    450                 455                 460

Arg Glu Ser Gly Gln Val Tyr Phe Gly Ile Ile Ala Leu Gly Gly Ser
465                 470                 475                 480

Gly Gly Gly Gly Ser Gly Gly Asp Lys Thr His Thr Cys Pro Pro Cys
                485                 490                 495

Pro Ala Pro Pro Val Ala Gly Pro Ser Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
    530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Gly Leu Pro Ser Ser Ile Glu Lys Thr Ile Ser Lys Ala Lys Gly Gln
        595                 600                 605

Pro Arg Glu Pro Gln Val Tyr Thr Leu Pro Pro Ser Arg Asp Glu Leu
    610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Ser Leu Ser Pro Gly Lys
705                 710
```

```
<210> SEQ ID NO 91
<211> LENGTH: 713
<212> TYPE: PRT
<213> ORGANISM: Artificial Sequence
<220> FEATURE:
<223> OTHER INFORMATION: variant 155

<400> SEQUENCE: 91
```

```
Met Glu Thr Asp Thr Leu Leu Leu Trp Val Leu Leu Leu Trp Val Pro
1               5                   10                  15

Gly Ser Thr Gly Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140

Ser Ala Glu Ile Asn Arg Pro Asp Tyr Leu Asn Phe Arg Glu Ser Gly
145                 150                 155                 160

Gln Val Tyr Phe Gly Ile Ile Ala Leu Gly Gly Gly Gly Pro Ser Asp
                165                 170                 175

Lys Pro Val Ala His Val Val Ala Asn Pro Gln Ala Glu Gly Gln Leu
            180                 185                 190

Gln Trp Leu Asn Arg Arg Ala Asn Ala Leu Leu Ala Asn Gly Val Glu
        195                 200                 205

Leu Arg Asp Asn Gln Leu Val Val Pro Ser Glu Gly Leu Tyr Leu Ile
    210                 215                 220

Tyr Ser Gln Val Leu Phe Lys Gly Gln Gly Cys Pro Ser Thr His Val
225                 230                 235                 240

Leu Leu Thr His Thr Ile Ser Arg Ile Ala Val Ser Tyr Gln Thr Lys
                245                 250                 255

Val Asn Leu Leu Ser Ala Ile Lys Ser Pro Cys Gln Arg Glu Thr Pro
            260                 265                 270

Glu Gly Ala Glu Ala Lys Pro Trp Tyr Glu Pro Ile Tyr Leu Gly Gly
        275                 280                 285

Val Phe Gln Leu Glu Lys Gly Asp Arg Leu Ser Ala Glu Ile Asn Arg
    290                 295                 300

Pro Asp Tyr Leu Asn Phe Arg Glu Ser Gly Gln Val Tyr Phe Gly Ile
305                 310                 315                 320

Ile Ala Leu Gly Gly Gly Gly Pro Ser Asp Lys Pro Val Ala His Val
                325                 330                 335

Val Ala Asn Pro Gln Ala Glu Gly Gln Leu Gln Trp Leu Asn Arg Arg
            340                 345                 350

Ala Asn Ala Leu Leu Ala Asn Gly Val Glu Leu Arg Asp Asn Gln Leu
        355                 360                 365

Val Val Pro Ser Glu Gly Leu Tyr Leu Ile Tyr Ser Gln Val Leu Phe
    370                 375                 380

Lys Gly Gln Gly Cys Pro Ser Thr His Val Leu Leu Thr His Thr Ile
385                 390                 395                 400

Ser Arg Ile Ala Val Ser Tyr Gln Thr Lys Val Asn Leu Leu Ser Ala
                405                 410                 415
```

```
Ile Lys Ser Pro Cys Gln Arg Glu Thr Pro Glu Gly Ala Glu Ala Lys
            420                 425                 430

Pro Trp Tyr Glu Pro Ile Tyr Leu Gly Gly Val Phe Gln Leu Glu Lys
        435                 440                 445

Gly Asp Arg Leu Ser Ala Glu Ile Asn Arg Pro Asp Tyr Leu Asn Phe
    450                 455                 460

Arg Glu Ser Gly Gln Val Tyr Phe Gly Ile Ile Ala Leu Gly Gly Ser
465                 470                 475                 480

Gly Gly Gly Gly Ser Gly Gly Asp Lys Thr His Thr Cys Pro Pro Cys
                485                 490                 495

Pro Ala Pro Pro Val Ala Gly Pro Ser Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
    530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Gly Leu Pro Ser Ser Ile Glu Lys Thr Ile Ser Lys Ala Lys Gly Gln
        595                 600                 605

Pro Arg Glu Pro Gln Val Tyr Thr Leu Pro Pro Ser Arg Asp Glu Leu
    610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Ser Leu Ser Pro Gly Lys
705                 710


<210> SEQ ID NO 92
<211> LENGTH: 10
<212> TYPE: PRT
<213> ORGANISM: Artificial Sequence
<220> FEATURE:
<223> OTHER INFORMATION: linker

<400> SEQUENCE: 92

Gly Gly Ser Gly Gly Gly Gly Ser Gly Gly
1               5                   10


<210> SEQ ID NO 93
<211> LENGTH: 18
<212> TYPE: PRT
<213> ORGANISM: Artificial Sequence
<220> FEATURE:
<223> OTHER INFORMATION: from variant 141

<400> SEQUENCE: 93
```

```
Gly Ile Ile Ala Leu Gly Ser Arg Thr Pro Ser Asp Lys Pro Val Ala
1               5                   10                  15

His Val


<210> SEQ ID NO 94
<211> LENGTH: 18
<212> TYPE: PRT
<213> ORGANISM: Artificial Sequence
<220> FEATURE:
<223> OTHER INFORMATION: from variant 144

<400> SEQUENCE: 94

Gly Ile Ile Ala Leu Gly Gly Arg Thr Pro Ser Asp Lys Pro Val Ala
1               5                   10                  15

His Val


<210> SEQ ID NO 95
<211> LENGTH: 18
<212> TYPE: PRT
<213> ORGANISM: Artificial Sequence
<220> FEATURE:
<223> OTHER INFORMATION: from variant 146

<400> SEQUENCE: 95

Gly Ile Ile Ala Leu Gly Gly Gly Thr Pro Ser Asp Lys Pro Val Ala
1               5                   10                  15

His Val


<210> SEQ ID NO 96
<211> LENGTH: 18
<212> TYPE: PRT
<213> ORGANISM: Artificial Sequence
<220> FEATURE:
<223> OTHER INFORMATION: from variant 147

<400> SEQUENCE: 96

Gly Ile Ile Ala Leu Gly Gly Gly Gly Pro Ser Asp Lys Pro Val Ala
1               5                   10                  15

His Val


<210> SEQ ID NO 97
<211> LENGTH: 17
<212> TYPE: PRT
<213> ORGANISM: Artificial Sequence
<220> FEATURE:
<223> OTHER INFORMATION: from variant 140

<400> SEQUENCE: 97

Gly Ile Ile Ala Leu Ser Arg Thr Pro Ser Asp Lys Pro Val Ala His
1               5                   10                  15

Val


<210> SEQ ID NO 98
<211> LENGTH: 17
<212> TYPE: PRT
<213> ORGANISM: Artificial Sequence
<220> FEATURE:
<223> OTHER INFORMATION: from variant 142

<400> SEQUENCE: 98

Gly Ile Ile Ala Leu Gly Arg Thr Pro Ser Asp Lys Pro Val Ala His
1               5                   10                  15
```

Val

<210> SEQ ID NO 99
<211> LENGTH: 17
<212> TYPE: PRT
<213> ORGANISM: Artificial Sequence
<220> FEATURE:
<223> OTHER INFORMATION: from variant 145

<400> SEQUENCE: 99

Gly Ile Ile Ala Leu Gly Gly Thr Pro Ser Asp Lys Pro Val Ala His
1 5 10 15

Val

<210> SEQ ID NO 100
<211> LENGTH: 17
<212> TYPE: PRT
<213> ORGANISM: Artificial Sequence
<220> FEATURE:
<223> OTHER INFORMATION: from variant 143

<400> SEQUENCE: 100

Gly Ile Ile Ala Leu Gly Gly Gly Pro Ser Asp Lys Pro Val Ala His
1 5 10 15

Val

<210> SEQ ID NO 101
<211> LENGTH: 18
<212> TYPE: PRT
<213> ORGANISM: Artificial Sequence
<220> FEATURE:
<223> OTHER INFORMATION: from variant 149

<400> SEQUENCE: 101

Gly Ile Ile Ala Leu Gly Ser Arg Thr Pro Ser Asp Lys Pro Val Ala
1 5 10 15

His Val

<210> SEQ ID NO 102
<211> LENGTH: 18
<212> TYPE: PRT
<213> ORGANISM: Artificial Sequence
<220> FEATURE:
<223> OTHER INFORMATION: from variant 152

<400> SEQUENCE: 102

Gly Ile Ile Ala Leu Gly Gly Arg Thr Pro Ser Asp Lys Pro Val Ala
1 5 10 15

His Val

<210> SEQ ID NO 103
<211> LENGTH: 18
<212> TYPE: PRT
<213> ORGANISM: Artificial Sequence
<220> FEATURE:
<223> OTHER INFORMATION: from variant 154

<400> SEQUENCE: 103

Gly Ile Ile Ala Leu Gly Gly Gly Thr Pro Ser Asp Lys Pro Val Ala
1 5 10 15

His Val

<210> SEQ ID NO 104

<211> LENGTH: 18
<212> TYPE: PRT
<213> ORGANISM: Artificial Sequence
<220> FEATURE:
<223> OTHER INFORMATION: from variant 155

<400> SEQUENCE: 104

```
Gly Ile Ile Ala Leu Gly Gly Gly Gly Pro Ser Asp Lys Pro Val Ala
1               5                   10                  15

His Val
```

<210> SEQ ID NO 105
<211> LENGTH: 17
<212> TYPE: PRT
<213> ORGANISM: Artificial Sequence
<220> FEATURE:
<223> OTHER INFORMATION: from variant 148

<400> SEQUENCE: 105

```
Gly Ile Ile Ala Leu Ser Arg Thr Pro Ser Asp Lys Pro Val Ala His
1               5                   10                  15

Val
```

<210> SEQ ID NO 106
<211> LENGTH: 17
<212> TYPE: PRT
<213> ORGANISM: Artificial Sequence
<220> FEATURE:
<223> OTHER INFORMATION: from variant 150

<400> SEQUENCE: 106

```
Gly Ile Ile Ala Leu Gly Arg Thr Pro Ser Asp Lys Pro Val Ala His
1               5                   10                  15

Val
```

<210> SEQ ID NO 107
<211> LENGTH: 17
<212> TYPE: PRT
<213> ORGANISM: Artificial Sequence
<220> FEATURE:
<223> OTHER INFORMATION: from variant 153

<400> SEQUENCE: 107

```
Gly Ile Ile Ala Leu Gly Gly Thr Pro Ser Asp Lys Pro Val Ala His
1               5                   10                  15

Val
```

<210> SEQ ID NO 108
<211> LENGTH: 17
<212> TYPE: PRT
<213> ORGANISM: Artificial Sequence
<220> FEATURE:
<223> OTHER INFORMATION: from variant 151

<400> SEQUENCE: 108

```
Gly Ile Ile Ala Leu Gly Gly Gly Pro Ser Asp Lys Pro Val Ala His
1               5                   10                  15

Val
```